(12) United States Patent
Nguyen et al.

(10) Patent No.: US 12,084,453 B2
(45) Date of Patent: Sep. 10, 2024

(54) BICYCLIC AMINES AS CDK12 INHIBITORS

(71) Applicant: Incyte Corporation, Wilmington, DE (US)

(72) Inventors: Minh Nguyen, Claymont, DE (US); Xin Li, Claymont, DE (US); Oleg Vechorkin, Wilmington, DE (US); Hai Fen Ye, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 18/064,173

(22) Filed: Dec. 9, 2022

(65) Prior Publication Data

US 2023/0183251 A1    Jun. 15, 2023

Related U.S. Application Data

(60) Provisional application No. 63/288,247, filed on Dec. 10, 2021.

(51) Int. Cl.
| C07D 487/04 | (2006.01) |
| A61P 35/00 | (2006.01) |
| C07D 471/04 | (2006.01) |

(52) U.S. Cl.
CPC ............ *C07D 487/04* (2013.01); *A61P 35/00* (2018.01); *C07D 471/04* (2013.01)

(58) Field of Classification Search
None
See application file for complete search history.

(56) References Cited

U.S. PATENT DOCUMENTS

| | | | |
|---|---|---|---|
| 4,820,710 A | 4/1989 | Manoury et al. | |
| 4,912,219 A | 3/1990 | Manoury et al. | |
| 5,521,184 A | 5/1996 | Zimmermann | |
| 6,143,749 A | 11/2000 | Bhagwat et al. | |
| 7,488,802 B2 | 2/2009 | Collins et al. | |
| 7,745,437 B2 | 6/2010 | Ren et al. | |
| 7,759,336 B2 | 7/2010 | Habashita et al. | |
| 7,943,743 B2 | 5/2011 | Korman et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 9,828,373 B2 | 5/2017 | Zhang et al. | |
| 9,670,202 B2 * | 6/2017 | Schirok | A61P 43/00 |
| 10,059,690 B2 | 8/2018 | Ciblat et al. | |
| 10,106,526 B2 | 10/2018 | Sprott et al. | |
| 10,111,875 B2 | 10/2018 | Su et al. | |
| 10,519,135 B2 | 12/2019 | Sprott et al. | |
| 10,550,121 B2 | 2/2020 | Gray et al. | |
| 10,618,916 B2 | 4/2020 | Wu et al. | |
| 10,669,271 B2 | 6/2020 | Wu et al. | |
| 10,696,677 B2 | 6/2020 | Maitra et al. | |
| 10,851,082 B2 | 12/2020 | Schiltz et al. | |
| 10,894,788 B2 | 1/2021 | Kanouni et al. | |
| 10,906,920 B2 | 2/2021 | Wu et al. | |
| 11,248,001 B2 | 2/2022 | Serrano-Wu et al. | |
| 11,325,910 B2 | 5/2022 | Gray et al. | |
| 11,414,433 B2 | 8/2022 | Wu et al. | |
| 11,596,631 B2 | 3/2023 | Hayes et al. | |
| 11,746,151 B2 | 9/2023 | Chinnaiyan et al. | |
| 2004/0224967 A1 | 11/2004 | Chen | |
| 2005/0209284 A1 | 9/2005 | Bentzien et al. | |
| 2005/0228031 A1 | 10/2005 | Bilodeau et al. | |
| 2005/0277655 A1 | 12/2005 | Ding et al. | |
| 2009/0143302 A1 | 6/2009 | Yen et al. | |
| 2011/0306588 A1 | 12/2011 | Allen et al. | |
| 2013/0225552 A1 | 8/2013 | Allen et al. | |
| 2013/0303507 A1 | 11/2013 | Antonios-Mccrea et al. | |
| 2018/0177784 A1 | 6/2018 | Wu et al. | |
| 2018/0177870 A1 | 6/2018 | Liu et al. | |
| 2018/0179179 A1 | 6/2018 | Wu et al. | |
| 2018/0179197 A1 | 6/2018 | Wu et al. | |
| 2018/0179201 A1 | 6/2018 | Wu et al. | |
| 2018/0179202 A1 | 6/2018 | Wu et al. | |
| 2018/0334461 A1 | 11/2018 | Hu et al. | |
| 2020/0248271 A1 | 8/2020 | Kong et al. | |
| 2021/0128565 A1 | 5/2021 | Alexander et al. | |
| 2023/0203010 A1 | 6/2023 | Li et al. | |

FOREIGN PATENT DOCUMENTS

| CN | 103864792 | 6/2014 |
|---|---|---|
| CN | 105294737 | 2/2016 |
| CN | 105384695 | 3/2016 |
| CN | 105712998 | 6/2016 |
| CN | 106336398 | 1/2017 |
| CN | 106831605 | 6/2017 |
| CN | 107625766 | 1/2018 |
| CN | 110003171 | 7/2019 |
| CN | 110835320 | 2/2020 |
| CN | 111269217 | 6/2020 |

(Continued)

OTHER PUBLICATIONS

Atzrodt et al., "The Renaissance of H/D Exchange," Angew. Chem. Int. Ed., 2007, 46:7744-7765.
Bajrami et al., "Genome-wide Profiling of Genetic Synthetic Lethality Identifies CDK12 as a Novel Determinant of PARP1/2 Inhibitor Sensitivity," Cancer Res., 2014, 74(1):287-297.
Bartkowiak et al., "CDK12 is a transcription elongation-associated CTD kinase, the metazoan ortholog of yeast Ctk1," Genes & Dev., 2010, 24(20):2303-2316.
Bayles et al., "Ex vivo screen identifies CDK12 as a metastatic vulnerability in osteosarcoma," JCI, 2019, 129(10):4377-4392.
Blazek et al., "The Cyclin K/Cdk12 complex maintains genomic stability via regulation of expression of DNA damage response genes," Genes & Dev., 2011, 25(20):2158-2172.
Blom et al., "Optimizing Preparative LC-MS Configurations and Methods for Parallel Synthesis Purification," J. Combi. Chem., 2003, 5:670-683.

(Continued)

*Primary Examiner* — Joseph R Kosack
*Assistant Examiner* — Quincy A McKoy
(74) *Attorney, Agent, or Firm* — Fish & Richardson P.C.

(57) ABSTRACT

The present application provides bicyclic amines that are inhibitors of cyclin-dependent kinase 12 (CDK12), as well as pharmaceutical compositions thereof, and methods of treating cancer using the same.

59 Claims, No Drawings
Specification includes a Sequence Listing.

(56) References Cited

FOREIGN PATENT DOCUMENTS

| | | |
|---|---|---|
| CN | 111393415 | 7/2020 |
| EP | 2489663 | 8/2012 |
| EP | 3126352 | 2/2017 |
| JP | 6594949 | 10/2019 |
| KR | 20120018236 | 3/2012 |
| KR | 20160020616 | 2/2016 |
| KR | 20200029949 | 3/2020 |
| WO | WO 2000009495 | 2/2000 |
| WO | WO 2000053595 | 9/2000 |
| WO | WO 2001014402 | 3/2001 |
| WO | WO 2001019817 | 3/2001 |
| WO | WO 2001055143 | 8/2001 |
| WO | WO 2001064655 | 9/2001 |
| WO | WO 2002000196 | 1/2002 |
| WO | WO 2002046172 | 6/2002 |
| WO | WO 2002081443 | 10/2002 |
| WO | WO 2002094831 | 11/2002 |
| WO | WO 2002096905 | 12/2002 |
| WO | WO 2003024967 | 3/2003 |
| WO | WO 2003037347 | 5/2003 |
| WO | WO 2003042402 | 5/2003 |
| WO | WO 2003051886 | 6/2003 |
| WO | WO 2003055489 | 7/2003 |
| WO | WO 2003062236 | 7/2003 |
| WO | WO 2003082855 | 10/2003 |
| WO | WO 2003091245 | 11/2003 |
| WO | WO 2003099771 | 12/2003 |
| WO | WO 2004002964 | 1/2004 |
| WO | WO 2004005281 | 1/2004 |
| WO | WO 2004032882 | 4/2004 |
| WO | WO 2004037814 | 5/2004 |
| WO | WO 2004041813 | 5/2004 |
| WO | WO 2004043913 | 5/2004 |
| WO | WO 2004043962 | 5/2004 |
| WO | WO 2004046120 | 6/2004 |
| WO | WO 2004052862 | 6/2004 |
| WO | WO 2004056786 | 7/2004 |
| WO | WO 2004065378 | 8/2004 |
| WO | WO 2004080980 | 9/2004 |
| WO | WO 2004085425 | 10/2004 |
| WO | WO 2004089913 | 10/2004 |
| WO | WO 2004110350 | 12/2004 |
| WO | WO 2005009443 | 2/2005 |
| WO | WO 2005009978 | 2/2005 |
| WO | WO 2005013996 | 2/2005 |
| WO | WO 2005016894 | 2/2005 |
| WO | WO 2005028444 | 3/2005 |
| WO | WO 2005042497 | 5/2005 |
| WO | WO 2005042518 | 5/2005 |
| WO | WO 2005042525 | 5/2005 |
| WO | WO 2005060970 | 7/2005 |
| WO | WO 2005076854 | 8/2005 |
| WO | WO 2005080346 | 9/2005 |
| WO | WO 2005080393 | 9/2005 |
| WO | WO 2005105790 | 11/2005 |
| WO | WO 2005107760 | 11/2005 |
| WO | WO 2005118544 | 12/2005 |
| WO | WO 2005121121 | 12/2005 |
| WO | WO 2006004702 | 1/2006 |
| WO | WO 2006034341 | 3/2006 |
| WO | WO 2006037117 | 4/2006 |
| WO | WO 2006038001 | 4/2006 |
| WO | WO 2006044869 | 4/2006 |
| WO | WO 2006050076 | 5/2006 |
| WO | WO 2006056399 | 6/2006 |
| WO | WO 2006067614 | 6/2006 |
| WO | WO 2006069258 | 6/2006 |
| WO | WO 2006074057 | 7/2006 |
| WO | WO 2006076595 | 7/2006 |
| WO | WO 2006082371 | 8/2006 |
| WO | WO 2006082373 | 8/2006 |
| WO | WO 2006091737 | 8/2006 |
| WO | WO 2006097260 | 9/2006 |
| WO | WO 2006099941 | 9/2006 |
| WO | WO 2006099943 | 9/2006 |
| WO | WO 2006101977 | 9/2006 |
| WO | WO 2006103449 | 10/2006 |
| WO | WO 2006105222 | 10/2006 |
| WO | WO 2006128129 | 11/2006 |
| WO | WO 2006128172 | 11/2006 |
| WO | WO 2006138304 | 12/2006 |
| WO | WO 2007003934 | 1/2007 |
| WO | WO 2007024680 | 3/2007 |
| WO | WO 2007030438 | 3/2007 |
| WO | WO 2007039285 | 4/2007 |
| WO | WO 2007042784 | 4/2007 |
| WO | WO 2007056221 | 5/2007 |
| WO | WO 2007059299 | 5/2007 |
| WO | WO 2007095124 | 8/2007 |
| WO | WO 2007104053 | 9/2007 |
| WO | WO 2007109045 | 9/2007 |
| WO | WO 2007110344 | 10/2007 |
| WO | WO 2007114827 | 10/2007 |
| WO | WO 2007121918 | 11/2007 |
| WO | WO 2007123892 | 11/2007 |
| WO | WO 2007129044 | 11/2007 |
| WO | WO 2007138277 | 12/2007 |
| WO | WO 2008002245 | 1/2008 |
| WO | WO 2008003766 | 1/2008 |
| WO | WO 2008036967 | 3/2008 |
| WO | WO 2008040778 | 4/2008 |
| WO | WO 2008057280 | 5/2008 |
| WO | WO 2008068171 | 6/2008 |
| WO | WO 2008071587 | 6/2008 |
| WO | WO 2008077057 | 6/2008 |
| WO | WO 2008079346 | 7/2008 |
| WO | WO 2008092199 | 8/2008 |
| WO | WO 2008094575 | 8/2008 |
| WO | WO 2008094602 | 8/2008 |
| WO | WO 2008113469 | 9/2008 |
| WO | WO 2008126898 | 10/2008 |
| WO | WO 2008129380 | 10/2008 |
| WO | WO 2008135232 | 11/2008 |
| WO | WO 2008156712 | 12/2008 |
| WO | WO 2009017838 | 2/2009 |
| WO | WO 2009022171 | 2/2009 |
| WO | WO 2009028629 | 3/2009 |
| WO | WO 2009029622 | 3/2009 |
| WO | WO 2009032861 | 3/2009 |
| WO | WO 2009054332 | 4/2009 |
| WO | WO 2009062059 | 5/2009 |
| WO | WO 2009071701 | 6/2009 |
| WO | WO 2009085185 | 7/2009 |
| WO | WO 2009127321 | 10/2009 |
| WO | WO 2009127822 | 10/2009 |
| WO | WO 2009131687 | 10/2009 |
| WO | WO 2009158571 | 12/2009 |
| WO | WO 2009158587 | 12/2009 |
| WO | WO 2010011756 | 1/2010 |
| WO | WO 2010020432 | 2/2010 |
| WO | WO 2010027005 | 3/2010 |
| WO | WO 2010036959 | 4/2010 |
| WO | WO 2010048012 | 4/2010 |
| WO | WO 2010058032 | 5/2010 |
| WO | WO 2010075074 | 7/2010 |
| WO | WO 2010088050 | 8/2010 |
| WO | WO 2010089411 | 8/2010 |
| WO | WO 2010100431 | 9/2010 |
| WO | WO 2010129053 | 11/2010 |
| WO | WO 2010138575 | 12/2010 |
| WO | WO 2010138576 | 12/2010 |
| WO | WO 2011016472 | 2/2011 |
| WO | WO 2011029915 | 3/2011 |
| WO | WO 2011032050 | 3/2011 |
| WO | WO 2011034907 | 3/2011 |
| WO | WO 2011039344 | 4/2011 |
| WO | WO 2011066342 | 6/2011 |
| WO | WO 2011082400 | 7/2011 |
| WO | WO 2011101409 | 8/2011 |
| WO | WO 2011106168 | 9/2011 |
| WO | WO 2011119465 | 9/2011 |
| WO | WO 2011133750 | 10/2011 |
| WO | WO 2011133888 | 10/2011 |

(56) References Cited

FOREIGN PATENT DOCUMENTS

| | | |
|---|---|---|
| WO | WO 2011134831 | 11/2011 |
| WO | WO 2011143495 | 11/2011 |
| WO | WO 2011156698 | 12/2011 |
| WO | WO 2011159877 | 12/2011 |
| WO | WO 2011161699 | 12/2011 |
| WO | WO 2012009649 | 1/2012 |
| WO | WO 2012016217 | 2/2012 |
| WO | WO 2012022045 | 2/2012 |
| WO | WO 2012022265 | 2/2012 |
| WO | WO 2012061057 | 5/2012 |
| WO | WO 2012061156 | 5/2012 |
| WO | WO 2012062704 | 5/2012 |
| WO | WO 2012066070 | 5/2012 |
| WO | WO 2012083121 | 6/2012 |
| WO | WO 2012083122 | 6/2012 |
| WO | WO 2012086735 | 6/2012 |
| WO | WO 2012101065 | 8/2012 |
| WO | WO 2012101066 | 8/2012 |
| WO | WO 2012104388 | 8/2012 |
| WO | WO 2012129344 | 9/2012 |
| WO | WO 2012142498 | 10/2012 |
| WO | WO 2012151561 | 11/2012 |
| WO | WO 2013017480 | 2/2013 |
| WO | WO 2013041605 | 3/2013 |
| WO | WO 2013130890 | 9/2013 |
| WO | WO 2013151938 | 10/2013 |
| WO | WO 2013155262 | 10/2013 |
| WO | WO 2014048865 | 4/2014 |
| WO | WO 2014109858 | 7/2014 |
| WO | WO 2014113303 | 7/2014 |
| WO | WO 2014124230 | 8/2014 |
| WO | WO 2014128486 | 8/2014 |
| WO | WO 2014130856 | 8/2014 |
| WO | WO 2014135244 | 9/2014 |
| WO | WO 2014135245 | 9/2014 |
| WO | WO 2014152716 | 9/2014 |
| WO | WO 2014159690 | 10/2014 |
| WO | WO 2014196793 | 12/2014 |
| WO | WO 2014202827 | 12/2014 |
| WO | WO 2014207260 | 12/2014 |
| WO | WO 2015004024 | 1/2015 |
| WO | WO 2015006875 | 1/2015 |
| WO | WO 2015030847 | 3/2015 |
| WO | WO 2015048662 | 4/2015 |
| WO | WO 2015054572 | 4/2015 |
| WO | WO 2015056782 | 4/2015 |
| WO | WO 2015058126 | 4/2015 |
| WO | WO 2015058140 | 4/2015 |
| WO | WO 2015058163 | 4/2015 |
| WO | WO 2015104677 | 7/2015 |
| WO | WO 2015115673 | 8/2015 |
| WO | WO 2015144605 | 10/2015 |
| WO | WO 2015154022 | 10/2015 |
| WO | WO 2015154039 | 10/2015 |
| WO | WO 2015158310 | 10/2015 |
| WO | WO 2015164614 | 10/2015 |
| WO | WO 2015180642 | 12/2015 |
| WO | WO 2015196072 | 12/2015 |
| WO | WO 2016016421 | 2/2016 |
| WO | WO 2016058544 | 4/2016 |
| WO | WO 2016065461 | 5/2016 |
| WO | WO 2016084816 | 6/2016 |
| WO | WO 2016113273 | 7/2016 |
| WO | WO 2016142855 | 9/2016 |
| WO | WO 2016160617 | 10/2016 |
| WO | WO 2016169504 | 10/2016 |
| WO | WO 2016173557 | 11/2016 |
| WO | WO 2016193939 | 12/2016 |
| WO | WO 2016195776 | 12/2016 |
| WO | WO 2016201370 | 12/2016 |
| WO | WO 2016210291 | 12/2016 |
| WO | WO 2016210296 | 12/2016 |
| WO | WO 2017044858 | 3/2017 |
| WO | WO 2017049068 | 3/2017 |
| WO | WO 2017163076 | 9/2017 |
| WO | WO 2017181177 | 10/2017 |
| WO | WO 2017184662 | 10/2017 |
| WO | WO 2017185023 | 10/2017 |
| WO | WO 2017220431 | 12/2017 |
| WO | WO 2018005533 | 1/2018 |
| WO | WO 2018013867 | 1/2018 |
| WO | WO 2018040885 | 3/2018 |
| WO | WO 2018081167 | 5/2018 |
| WO | WO 2018086593 | 5/2018 |
| WO | WO 2018089499 | 5/2018 |
| WO | WO 2018098361 | 5/2018 |
| WO | WO 2018098561 | 6/2018 |
| WO | WO 2018106818 | 6/2018 |
| WO | WO 2018141002 | 8/2018 |
| WO | WO 2018154133 | 8/2018 |
| WO | WO 2018183923 | 10/2018 |
| WO | WO 2018195450 | 10/2018 |
| WO | WO 2018203691 | 11/2018 |
| WO | WO 2018208132 | 11/2018 |
| WO | WO 2018232094 | 12/2018 |
| WO | WO 2019001572 | 1/2019 |
| WO | WO 2019037678 | 2/2019 |
| WO | WO 2019037860 | 2/2019 |
| WO | WO 2019057825 | 3/2019 |
| WO | WO 2019058132 | 3/2019 |
| WO | WO 2019060365 | 3/2019 |
| WO | WO 2019079596 | 4/2019 |
| WO | WO 2019079607 | 4/2019 |
| WO | WO 2019090076 | 5/2019 |
| WO | WO 2019096322 | 5/2019 |
| WO | WO 2019133445 | 7/2019 |
| WO | WO 2019143730 | 7/2019 |
| WO | WO 2019162323 | 8/2019 |
| WO | WO 2019165315 | 8/2019 |
| WO | WO 2019169065 | 9/2019 |
| WO | WO 2019193509 | 10/2019 |
| WO | WO 2019212256 | 11/2019 |
| WO | WO 2019213403 | 11/2019 |
| WO | WO 2019236631 | 12/2019 |
| WO | WO 2020006497 | 1/2020 |
| WO | WO 2020007273 | 1/2020 |
| WO | WO 2020022787 | 1/2020 |
| WO | WO 2020023782 | 1/2020 |
| WO | WO 2020033413 | 2/2020 |
| WO | WO 2020123925 | 6/2020 |
| WO | WO 2020140052 | 7/2020 |
| WO | WO 2020140054 | 7/2020 |
| WO | WO 2020140098 | 7/2020 |
| WO | WO 2020150474 | 7/2020 |
| WO | WO 2020180959 | 9/2020 |
| WO | WO 2020202001 | 10/2020 |
| WO | WO 2020206034 | 10/2020 |
| WO | WO 2020210320 | 10/2020 |
| WO | WO 2020210381 | 10/2020 |
| WO | WO 2020219650 | 10/2020 |
| WO | WO 2020219926 | 10/2020 |
| WO | WO 2020224568 | 11/2020 |
| WO | WO 2020227563 | 11/2020 |
| WO | WO 2020233669 | 11/2020 |
| WO | WO 2020238900 | 12/2020 |
| WO | WO 2020254494 | 12/2020 |
| WO | WO 2020254552 | 12/2020 |
| WO | WO 2021003314 | 1/2021 |
| WO | WO 2021011796 | 1/2021 |
| WO | WO 2021016388 | 1/2021 |
| WO | WO 2021028362 | 2/2021 |
| WO | WO 2021057696 | 4/2021 |
| WO | WO 2021062036 | 4/2021 |
| WO | WO 2021073593 | 4/2021 |
| WO | WO 2021092240 | 5/2021 |
| WO | WO 2021104305 | 6/2021 |
| WO | WO 2021116178 | 6/2021 |
| WO | WO 2021122745 | 6/2021 |
| WO | WO 2021127045 | 6/2021 |
| WO | WO 2021133915 | 7/2021 |
| WO | WO 2021138215 | 7/2021 |
| WO | WO 2021176045 | 9/2021 |
| WO | WO 2021176049 | 9/2021 |
| WO | WO 2022093742 | 5/2022 |

(56) References Cited

FOREIGN PATENT DOCUMENTS

| WO | WO 2022130304 | 6/2022 |
|---|---|---|
| WO | WO 2022243346 | 11/2022 |
| WO | WO 2022263604 | 12/2022 |
| WO | WO 2021072232 | 4/2023 |
| WO | WO 2023091726 | 5/2023 |
| WO | WO 2023102184 | 6/2023 |
| WO | WO 2023107705 | 6/2023 |
| WO | WO 2023250430 | 12/2023 |
| WO | WO 2024032561 | 2/2024 |

OTHER PUBLICATIONS

Blom et al., "Preparative LC-MS Purification: Improved Compound Specific Method Optimization," J. Combi. Chem., 2004, 6:874-883.

Blom, "Two-Pump at-Column Dilution Configuration for Preparative LC-MS," J. Combi. Chem., 2002, 4:295-301.

Choi et al., "Gene expression regulation by CDK12: a versatile kinase in cancer with functions beyond CTD phosphorylation," Exp. & Mol. Med., 2020, 52(5):762-771.

Dias et al., "Understanding and overcoming resistance to PARP inhibitors in cancer therapy," Nat. Rev. Clin. Oncol., 2021, 18(12):773-791.

Dieter et al., "Degradation of CCNK/CDK12 is a druggable vulnerability of colorectal cancer," Cell Rep., 2021, 36(109394):1-15.

Dubbury et al., "Cdk12 regulates DNA repair genes by suppressing intronic polyadenylation," Nature, 2018, 564(7734):141-145.

Ekumi et al., "Ovarian carcinoma CDK12 mutations misregulate expression of DNA repair genes via deficient formation and function of the Cdk12/CycK complex," Nucleic Acids Res., 2015, 43(5):2575-2589.

Farmer et al., "Targeting the DNA repair defect in BRCA mutant cells as a therapeutic strategy," Nature, 2005, 434(7035): 917-921.

Iniguez et al., "EWS/FLI Confers Tumor Cell Synthetic Lethality to CDK12 Inhibition in Ewing Sarcoma," Cancer Cell, 2018, 33(2):202-216.

International Search Report and Written Opinion in International Application No. PCT/US2022/051658, dated Feb. 28, 2023, 17 pages.

International Search Report and Written Opinion in International Application No. PCT/US2022/052426, dated Mar. 15, 2023, 13 pages.

International Search Report and Written Opinion in International Application No. PCT/US2023/068895, dated Nov. 27, 2023, 21 pages.

Jiang et al., "Discovery and Resistance Mechanism of a Selective CDK12 Degrader," Nat. Chem. Biol., 2021, 17(6):675-683.

Jiang et al., "Structure-activity relationship study of THZ531 derivatives enables the discovery of BSJ-01-175 as a dual CDK12/13 covalent inhibitor with efficacy in Ewing sarcoma," European Journal of Medicinal Chemistry, 2021, 221(11348):1-16.

Johnson et al., "CDK12 Inhibition Reverses De Novo and Acquired PARP Inhibitor Resistance in BRCA Wild-Type and Mutated Models of Triple-Negative Breast Cancer," Cell Rep., 2016, 17(9):2367-2381.

Kerekes et al., "Aurora kinase inhibitors based on the imidazo[1,2-a]pyrazine core: fluorine and deuterium incorporation improve oral absorption and exposure," J. Med. Chem., 2011, 54:201-210.

Knijnenburg et al., "Genomic and Molecular Landscape of DNA Damage Repair Deficiency across the Cancer Genome Atlas," Cell Rep., 2018, 23(1):239-254.

Kohoutek et al., "Cyclin K goes with Cdk12 and Cdk13," Cell Div., 2012, 7(12):1-10.

Liu et al., "Discovery of MFH290: A Potent and Highly Selective Covalent Inhibitor for Cyclin-Dependent Kinase 12/13," Journal of Medicinal Chemistry, 2020, 63(13):6708-6726.

Malumbres et al., "Cell cycle, CDKs and cancer: a changing paradigm," Nat. Rev. Cancer., 2009, 9(3):153-166.

Noordermeer et al., "PARP Inhibitor Resistance: A Tug-of-War in BRCA-Mutated Cells," Trends Cell Biol., 2019, 29(10):820-834.

Peturssion et al., "Protecting Groups in Carbohydrate Chemistry," J. Chem. Educ., 1997, 74(11):1297-1303.

Remington's Pharmaceutical Sciences, 17th ed., Gennaro (ed)., 1985, p. 1418.

Wang et al., "CDK12 inhibition mediates DNA damage and is synergistic with sorafenib treatment in hepatocellular carcinoma," Gut, 2020, 69(4):727-736.

Wu et al., "Inactiviation of CDK12 delineates a distinct immunogenic class of advanced prostate cancer," Cell, 2018, 173(7):1770-1782.

Xu et al., "Design, synthesis and biological evaluation of deuterated nintedanib for improving pharmacokinetic properties," J. Label Compd. Radiopharm., 2015, 58:308-312.

Ajakane et al., "Identification of 6-amino-1 H-pyrazolo [3, 4-d] pyrimidines with in vivo efficacy against visceral leishmaniasis," RSC medicinal chemistry, Aug. 2020, 11(10):1168-77.

Amato et al., "Functionalized 6-(piperidin-1-yl)-8, 9-diphenyl purines as inverse agonists of the CB1 receptor-SAR efforts towards selectivity and peripheralization," Bioorganic & medicinal chemistry, Aug. 2019, 27(16):3632-49.

Cindric et al., "Novel amidino substituted benzimidazole and benzothiazole benzo [b] thieno-2-carboxamides exert strong antiproliferative and DNA binding properties," European journal of medicinal chemistry, Aug. 2017, 136:468-79.

Grädler et al., "Biochemical, cellular and structural characterization of novel and selective ERK3 inhibitors," Bioorganic & Medicinal Chemistry Letters, Nov. 2020, 30(22):127551.

Perales et al., "SAR of 2-amino and 2, 4-diamino pyrimidines with in vivo efficacy against Trypanosoma brucei," Bioorganic & medicinal chemistry letters, May 2011, 21(10):2816-9.

Sović et al., "Synthesis, antitumor activity and DNA binding features of benzothiazolyl and benzimidazolyl substituted isoindolines," Bioorganic & Medicinal Chemistry, May 2018, 26(8): 1950-60.

* cited by examiner

BICYCLIC AMINES AS CDK12 INHIBITORS

CROSS-REFERENCE TO RELATED APPLICATIONS

This application claims the benefit of U.S. Provisional Application Ser. No. 63/288,247, filed Dec. 10, 2021, the disclosure of which is incorporated herein by reference in its entirety.

SEQUENCE LISTING

This application contains a Sequence Listing that has been submitted electronically as an XML file named 20443-0752001_SL_ST26.xml. The XML file, created on Nov. 30, 2022, is 2,780 bytes in size. The material in the XML file is hereby incorporated by reference in its entirety.

TECHNICAL FIELD

This application is directed to bicyclic amines which inhibit cyclin-dependent kinase 12 (CDK12) and are useful for treating cancer.

BACKGROUND

CDK12 belongs to a family of serine/threonine kinases collectively known as cyclin-dependent kinases (Seung, H. C., et al., *Exp. Mol. Med.*, 2020, 52(5): 762-771). Collectively, CDK's are unique in that they require the binding of specific cyclin proteins for proper functionality (Malumbres, M., et al., *Nat. Rev. Cancer.*, 2009, 9(3): 153-66). Specifically, CDK12 (as well as CDK13) requires the binding of cyclin K in the cyclin binding domain for activation (Kohoutek, J., et al., *Cell Div.*, 2012, 7(12)). Mechanistically, CDK12 and CDK13 phosphorylate serine 2 (pser2) on the C-terminal tail of RNA polymerase II (RNA Pol II), which is required for transcriptional elongation (Bartkowiak, B., et al., *Genes Dev*, 2010, 24(20): 2303-2316). Therefore, inhibition of CDK12/13 can impact the expression of multiple genes.

Interestingly, CDK12 appears unique among the CDK's in that its inhibition can lead to a selective loss of expression of multiple genes involved in DNA damage repair (Blazek, D., et al., *Genes Dev*, 2011, 25(20): 2158-2172). Mechanistically, this is attributed to a role of CDK12 in maintaining proper mRNA splicing. Indeed, inhibition or genetic depletion of CDK12 leads to a decrease in proper exon splicing, which in turn increases intronic polyadenylation (IPA) and a subsequent loss of full length mRNA and translated protein (Dubbury, S. J., et al., *Nature*, 2018, 564(7734): 141-145). Many DNA repair genes are large genes with multiple IPA sites, which explains the selective loss of expression of these repair genes following CDK12 inhibition. Of note, multiple genes involved in the homologous recombination (HR) DNA repair pathway, such as BRCA1 and BRCA2, are especially sensitive to CDK12 inhibition, and indeed inactivating mutations in CDK12 are known to cause a "BRCAness" phenotype in certain cancers (Ekumi, K. M., et al., *Nucleic Acids Res*, 2015, 43(5): 2575-2589; Wu, Y. M., et al., *Cell*, 2018, 173(7): 1770-1782).

It is well known that many cancers exhibit defects in various DNA repair pathways; which can confer a selective advantage due to an increased mutation rate (Knijnenburg, T. A., et al., *Cell Rep*, 2018, 23(1): 239-254). However, these alterations can render cancer cells more susceptible to DNA-damage inducing chemotherapies, or targeted therapies that inhibit additional DNA repair pathways. A well-known example of this paradigm is the increased dependence on the DNA repair enzyme PARP in cancers with defects in HR signaling (i.e. cancers with a "BRCAness" phenotype) (Farmer, H., et al., *Nature*, 2005, 434(7035): 917-921). Indeed, preliminary studies have demonstrated that cancers with defective HR exhibit increased sensitivity to pharmacologic or genetic inhibition of CDK12 (Johnson, S. F., et al., *Cell Rep.*, 2016, 17(9): 2367-2381). This therapeutic effect is a consequence of the loss of expression of CDK12-dependent DNA repair genes; which leads to a lethal increase in DNA damage and loss of cell viability (Blazek, D., et al., *Genes Dev.*, 2011, 25(20): 2158-2172).

Despite the clinical emergence of PARP inhibitors as a therapy for patients with HR deficient cancers, de novo resistance or rapid relapse remain an unmet clinical need (Dias, M. P., et al., *Nat. Rev. Clin. Oncol.*, 2021). In the clinic, resistance to PARP inhibitors is most commonly attributed to a reversion to an HR restored tumor, or reliance on additional compensatory DNA repair pathways (Noordermeer, S. M., et al., *Trends Cell Biol.*, 2019, 29(10): 820-834). Similar to a PARP inhibitor, a CDK12 inhibitor is expected to yield the same synthetic lethal interaction in HR deficient tumors. However, given that CDK12 inhibition prevents the expression of HR genes (e.g., BRCA1, BRCA2) it is likely that a CDK12 inhibitor could avoid or overcome the HR-restoration mediate mechanism of resistance observed for PARP inhibitors. Therefore, a CDK12 inhibitor may help fill this unmet clinical need by preventing or overcoming HR restoration during or after PARP inhibitor therapy.

SUMMARY

The present invention relates to, inter alia, compounds of Formula (I):

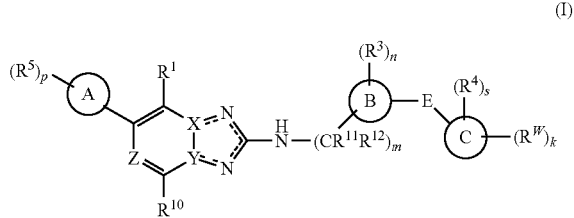

or pharmaceutically acceptable salts thereof, wherein the constituent members are defined herein.

The present invention further provides pharmaceutical compositions comprising a compound described herein, or a pharmaceutically acceptable salt thereof, and a pharmaceutically acceptable carrier.

The present invention further provides methods of inhibiting CDK12, comprising contacting the CDK12 with a compound described herein, or a pharmaceutically acceptable salt thereof.

The present invention further provides methods of inhibiting CDK12 in a patient, comprising administering to the patient a compound described herein, or a pharmaceutically acceptable salt thereof.

The present invention further provides methods of treating a disease or disorder associated with CDK12 in a patient, comprising administering to the patient a compound described herein, or a pharmaceutically acceptable salt thereof.

The present invention further provides compounds described herein, or a pharmaceutically acceptable salt thereof, for use in any of the methods described herein.

The present invention further provides uses of a compound described herein, or a pharmaceutically acceptable salt thereof, for the preparation of a medicament for use in any of the methods described herein.

DETAILED DESCRIPTION

The present application provides, inter alia, a compound of Formula (I):

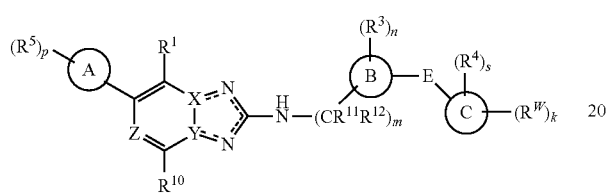
(I)

or a pharmaceutically acceptable salt thereof, wherein:

k is 1 or 2;
m is 0 or 1;
n is 0, 1, 2, 3, 4, 5, or 6;
p is 0, 1, 2, 3, 4, 5, or 6;
s is 0, 1, 2, 3, 4, 5, or 6;
each ═ is independently a single or a double bond;
X is N, Y is C, and Ring

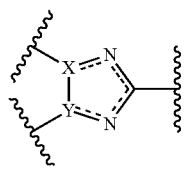

is

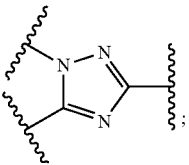 [SMILES: *c1nc(*)n(*)n1]

or

X is C, Y is N, and Ring

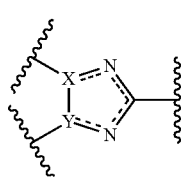

is;

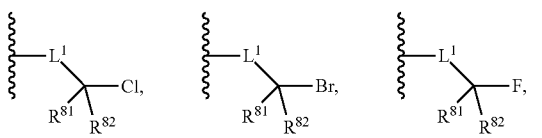

Z is $CR^2$ or N;

Ring moiety A is a 5-10 membered heteroaryl;

Ring moiety B is $C_{3-10}$ membered cycloalkyl or 4-10 membered heterocycloalkyl;

Ring moiety C is $C_{6-10}$ aryl, 5-10 membered heteroaryl, $C_{5-12}$ partially unsaturated cycloalkyl, or 5-12 membered partially unsaturated heterocycloalkyl;

E is a bond, —C(O)—, —CH$_2$—, —CHR$^6$—, —CR$^6$R$^7$—, or —O—, wherein $R^6$ and $R^7$ are each independently selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^W$, attached to the C ring, is independently:

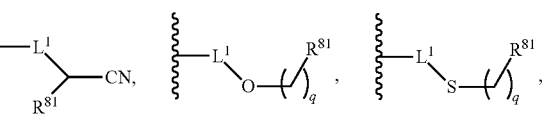

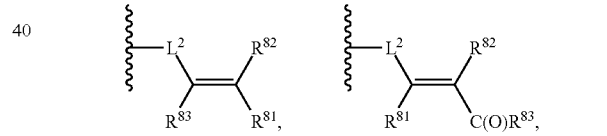

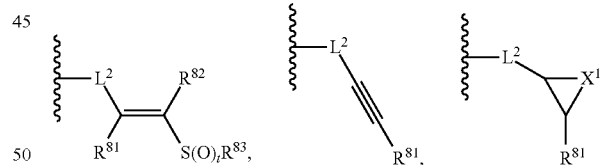

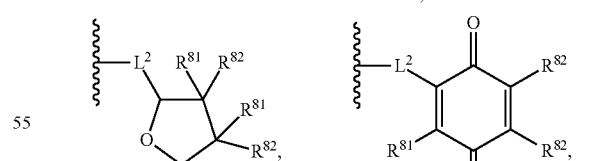

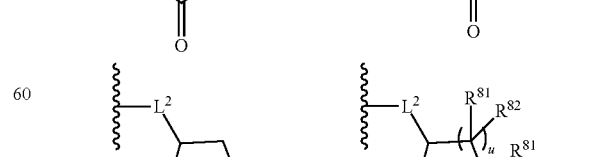

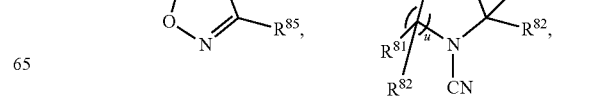

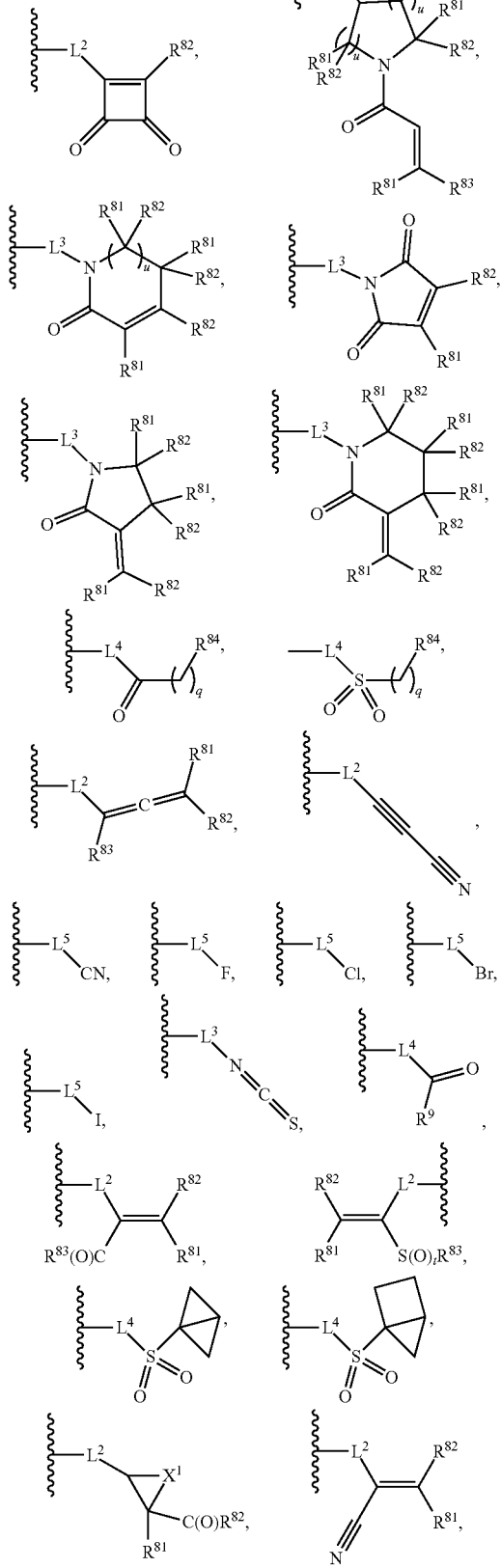

or $L^1$-Ar;
  each $L^1$ is independently -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$— or -L-OS(O)$_2$—, wherein $L^1$ is attached to Ring moiety C through the L linking group;
  each $L^2$ is independently -L-, -L-O—, -L-NR$^9$—, -L-S—, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)NR$^9$—, -L-NR$^9$S(O)O—, -L-OS(O)NR$^9$—, -L-NR$^9$S(O)$_2$—, -L-OS(O)$_2$—, -L-NR$^9$S(O)$_2$NR$^9$—, -L-NR$^9$S(O)$_2$O—, -L-S(O)(NR$^9$)—, -L-S(O)$_2$(NR$^9$)—, or -L-OS(O)$_2$NR$^9$—, wherein $L^2$ is attached to Ring moiety C through the L linking group;
  each $L^3$ is independently -L-, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$—, or -L-OS(O)$_2$—, wherein $L^3$ is attached to Ring moiety C through the L linking group;
  each $L^4$ is independently -L-, -L-O—, L-S—, -L-NR$^9$—, wherein $L^4$ is attached to Ring moiety C through the L linking group;
  each $L^5$ is independently -L-O-L$^x$-, -L-NR$^9$-L$^x$-, -L-S-L$^x$-, -L-C(O)-L$^x$-, -L-NR$^9$C(O)-L$^x$-, -L-OC(O)-L$^x$-, -L-S(O)-L$^x$-, -L-S(O)$_2$-L$^x$-, -L-NR$^9$S(O)-L$^x$-, -L-OS(O)-L$^x$-, -L-NR$^9$S(O)NR$^9$-L$^x$-, -L-NR$^9$S(O)O-L$^x$-, -L-OS(O)NR$^9$-L$^x$-, -L-NR$^9$S(O)$_2$-L$^x$-, -L-OS(O)$_2$-L$^x$-, -L-NR$^9$S(O)$_2$NR$^9$-L$^x$-, -L-NR$^9$S(O)$_2$O-L$^x$-, -L-S(O)(NR$^9$)-L$^x$-, -L-S(O)$_2$(NR$^9$)-L$^x$-, or -L-OS(O)$_2$NR$^9$-L$^x$-, wherein $L^5$ is attached to Ring moiety C through the L linking group;
  each L independently is a bond or $C_{1-6}$ alkylene, wherein said $C_{1-6}$ alkylene is optionally substituted by 1, 2, 3 or 4 independently selected $R^G$ substituents;
  each $L^x$ is independently is a $C_{1-6}$ alkylene, wherein said $C_{1-6}$ alkylene is optionally substituted by 1, 2, 3 or 4 independently selected $R^G$ substituents;
  each $X^1$ independently is O or NR$^9$;
  each q is independently 0, 1, 2, or 3;
  each t is independently 0, 1, 2, or 3;
  each u is independently 0, 1, 2, or 3;
  each Ar is independently $C_{6-10}$ aryl or 5-10 membered heteroaryl, which are each optionally substituted with 1, 2, 3, or 4 independently selected $R^{gA}$ substituents;
  each $R^{81}$, $R^{82}$, and $R^{83}$ is independently selected from D, halo, NO$_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-membered heterocycloalkyl, 5-10 membered heteroaryl, $C_{3-10}$ cycloalkyl-$C_{1-4}$ alkyl, 6-membered aryl-$C_{1-4}$ alkyl, 4-10 membered heterocycloalkyl-$C_{1-4}$ alkyl, 5-10 membered heteroaryl-$C_{1-4}$ alkyl, OR$^{a8}$, SR$^{a8}$, NHOR$^{a8}$, C(O)R$^{a8}$, C(O)NR$^{c8}$R$^{d8}$, C(O)NR$^{c8}$(OR$^{a8}$), C(O)OR$^{a8}$, OC(O)R$^{a8}$, OC(O)NR$^{c8}$R$^{d8}$, NR$^{c8}$R$^{d8}$, NR$^{c8}$NR$^{c8}$R$^{d8}$, NR$^{c8}$C(O)R$^{a8}$, NR$^{c8}$C(O)OR$^{a8}$, NR$^{c8}$C(O)NR$^{c8}$R$^{d8}$, C(=NR$^{e8}$)R$^{b8}$, C(=NR$^{e8}$)NR$^{c8}$R$^{d8}$, NR$^{c8}$C(=NR$^{e8}$)NR$^{c8}$R$^{d1}$, NR$^{c8}$C(=NR$^{e8}$)R$^{b8}$, NR$^{c8}$S(O)NR$^{c8}$R$^{d8}$, NR$^{c8}$S(O)R$^{a8}$, NR$^{c8}$S(O)$_2$R$^{b8}$, NR$^{c8}$S(O)(=NR$^{e8}$)R$^{b8}$, NR$^{c8}$S(O)$_2$NR$^{c8}$R$^{d8}$, S(O)R$^{a8}$, S(O)NR$^{c8}$R$^{d8}$, S(O)$_2$R$^{a8}$, S(O)$_2$NR$^{c8}$R$^{d8}$, OS(O)(=NR$^{e8}$)R$^{b8}$, OS(O)$_2$R$^{a8}$, S(O)(=NR$^{e8}$)R$^{b8}$, SF$_5$, P(O)R$^{f8}$R$^{g8}$, OP(O)(OR$^{h8}$)(OR$^{i8}$), P(O)(OR$^{h8}$)(OR$^{i8}$), and BR$^{j8}$R$^{k8}$;
  wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ substituents;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^G$ substituents;

or, any $R^{c8}$ and $R^{d8}$ attached to the same N atom, together with the N atom to which they are attached, form a 4-10 membered heterocycloalkyl group, which is optionally substituted with 1, 2, 3, or 4 independently selected $R^G$ substituents;

each $R^{b8}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^G$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f8}$ and $R^{g8}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h8}$ and $R^{i8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j8}$ and $R^{kg}$ is independently selected from OH, $C_{1-6}$ alkoxy, and $C_{1-6}$ haloalkoxy;

or any $R^{j8}$ and $R^{kg}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

or any two $R^{81}$ and $R^{82}$ together with the atoms to which they are attached, form $C_{3-7}$ cycloalkyl, 4-7 membered heterocycloalkyl, phenyl, or 5-6-membered heteroaryl ring, each of which is optionally substituted with 1, 2, 3, or 4 independently selected $R^G$ substituents;

each $R^{84}$ is independently selected from H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ substituents;

each $R^{85}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl, wherein said $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl are each optionally substituted by 1, 2, 3, or 4 independently selected $R^G$ substituents;

each $R^9$ is independently selected from H, halo, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{a9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $C(=NR^{e9})R^{b9}$, $C(=NR^{e9})NR^{c9}R^{d9}$, $NR^{c9}C(=NR^{e9})NR^{c9}R^{d9}$, $NR^{c9}C(=NR^{e9})R^{b9}$, $NR^{c9}S(O)NR^{c9}R^{d9}$, $NR^{c9}S(O)R^{a9}$, $NR^{c9}S(O)_2R^{a9}$, $NR^{c9}S(O)(=NR^{e9})R^{b9}$, $NR^{c9}S(O)_2NR^{c9}R^{d9}$, $S(O)R^{a9}$, $S(O)NR^{c9}R^{d9}$, $S(O)_2R^{a9}$, $S(O)_2NR^{c9}R^{d9}$, $OS(O)(=NR^{e9})R^{b9}$, $OS(O)_2R^{b9}$, and $S(O)(=NR^{e9})R^{b9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

or, any $R^{c9}$ and $R^{d9}$ attached to the same N atom, together with the N atom to which they are attached, form a 4-10 membered heterocycloalkyl group, which is optionally substituted with 1, 2, 3, or 4 independently selected $R^{9A}$ substituents;

each $R^{b9}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{9A}$ substituents;

each $R^{e9}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)NR^{c91}(OR^{a91})$, $C(O)OR^{a91}$, $OC(O)R^{b91}$, $OC(O)NR^{c91}R^{d91}$, $NR^{c91}R^{d91}$, $NR^{c91}NR^{c91}R^{d91}$, $NR^{c91}C(O)R^{b91}$, $NR^{c91}C(O)OR^{a91}$, $NR^{c91}C(O)NR^{c91}R^{d91}$, $C(=NR^{e91})R^{b91}$, $C(=NR^{e91})NR^{c91}R^{d91}$, $NR^{c91}C(=NR^{e91})NR^{c91}R^{d91}$, $NR^{c91}C(=NR^{e91})R^{b91}$, $NR^{c91}S(O)NR^{c91}R^{d91}$, $NR^{c91}S(O)R^{a91}$, $NR^{c91}S(O)_2R^{a91}$, $NR^{c91}S(O)(=NR^{e91})R^{b91}$, $NR^{c91}S(O)_2NR^{c91}R^{d91}$, $S(O)R^{b91}$, $S(O)NR^{c91}R^{d91}$, $S(O)_2R^{b91}$, $S(O)_2NR^{c91}R^{d91}$, $OS(O)(=NR^{e91})R^{b91}$, $OS(O)_2R^{b91}$, $S(O)(=NR^{e91})R^{91}$, $SF_5$, $P(O)R^{f91}R^{g91}$, $OP(O)(OR^{h91})(OR^{i91})$, $P(O)(OR^{h91})(OR^{i91})$, and $BR^{j91}R^{k91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

or, any $R^{c91}$ and $R^{d91}$ attached to the same N atom, together with the N atom to which they are attached, form a 4-7 membered heterocycloalkyl group, which is optionally substituted with 1, 2, 3, or 4 independently selected $R^{9B}$ substituents;

each $R^{b91}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9B}$ substituents;

each $R^{e91}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f91}$ and $R^{g91}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h91}$ and $R^{i91}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j91}$ and $R^{k91}$ is independently selected from OH, $C_{1-6}$ alkoxy, and $C_{1-6}$ haloalkoxy;

or any $R^{j91}$ and $R^{k91}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a92}$, $SR^{a92}$, $NHOR^{a92}$, $C(O)R^{b92}$, $C(O)NR^{c92}R^{d92}$, $C(O)NR^{c92}(OR^{a92})$, $C(O)OR^{a92}$, $OC(O)R^{b92}$, $OC(O)NR^{c92}R^{d92}$, $NR^{c92}R^{d92}$, $NR^{c92}NR^{c92}R^{d92}$, $NR^{c92}C(O)R^{b92}$, $NR^{c92}C(O)OR^{a92}$, $NR^{c92}C(O)NR^{c92}R^{d92}$, $C(=NR^{e92})R^{b92}$, $C(=NR^{e92})NR^{c92}R^{d92}$, $NR^{c92}C(=NR^{e92})NR^{c92}R^{d92}$, $NR^{c92}C(=NR^{e92})R^{b92}$, $NR^{c92}S(O)NR^{c92}R^{d92}$, $NR^{c92}S(O)R^{b92}$, $NR^{c92}S(O)_2R^{b92}$, $NR^{c92}S(O)(=NR^{e92})R^{b92}$, $NR^{c92}S(O)_2NR^{c92}R^{d92}$, $S(O)R^{b92}$, $S(O)NR^{c92}R^{d92}$, $S(O)_2R^{b92}$, $S(O)_2NR^{c92}R^{d92}$, $OS(O)(=NR^{e92})R^{b92}$, $OS(O)_2R^{b92}$, $S(O)(=NR^{e92})R^{b92}$, $SF_5$, $P(O)R^{f92}R^{g92}$, $OP(O)(OR^{h92})(OR^{i92})$, $P(O)(OR^{h92})(OR^{i92})$, and $BR^{j92}R^{k92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c92}$ and $R^{d92}$ attached to the same N atom, together with the N atom to which they are attached, form a 4-7 membered heterocycloalkyl group, which is optionally substituted with 1, 2, 3, or 4 independently selected $R^G$ substituents;

each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e92}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{e2}$ and $R^{g92}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h92}$ and $R^{i92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j92}$ and $R^{k92}$ is independently selected from OH, $C_{1-6}$ alkoxy, and $C_{1-6}$ haloalkoxy;

or any $R^{j92}$ and $R^{k92}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $R^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents;

or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{14}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{14}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f1}$ and $R^{g1}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{14}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)NR^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, $OS(O)_2R^{b11}$, $S(O)(=NR^{e11})R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

or, any $R^{c11}$ and $R^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f11}$ and $R^{g11}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$ $SR^{a12}$, $NHOR^{a12}$, $C(O)R^{b12}$, $C(O)NR^{c12}R^{a12}$, $C(O)NR^{c12}(OR^{a12})$, $C(O)OR^{a12}$, $OC(O)R^{b12}$ $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)NR^{c12}R^{d12}$, $NR^{c12}S(O)R^{b12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, $OS(O)_2R^{b12}$, $S(O)(=NR^{e12})R^{b12}$, $SF_5$, $P(O)R^{f12}R^{g12}$, $OP(O)(OR^{h12})(OR^{i12})$, $P(O)(OR^{h12})(OR^{i12})$, and $BR^{j12}R^{k12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f12}$ and $R^{g12}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h12}$ and $R^{i12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j12}$ and $R^{k12}$ is independently selected from OH, $C_{1-6}$ alkoxy, and $C_{1-6}$ haloalkoxy;

or any $R^{j12}$ and $R^{k12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^2$ is selected from H, D, halo, CN, OH, $NO_2$, $C_{1-4}$ alkyl, $C_{1-4}$ haloalkyl, $C_{2-4}$ alkenyl, $C_{2-4}$ alkynyl, $C_{1-4}$ alkoxy, $C_{1-4}$ haloalkoxy, amino, $C_{1-4}$ alkylamino, di($C_{1-4}$ alkyl)amino, cyano-$C_{1-4}$ alkyl, HO—$C_{1-4}$ alkyl, $C_{1-4}$ alkoxy-$C_{1-4}$ alkyl, $C_{3-4}$ cycloalkyl, thio, $C_{1-4}$ alkylthio, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkoxycarbonylamino, $C_{1-4}$ alkylaminocarbonyloxy, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino;

each $R^3$ is independently selected from D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^4$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)NR^{c4}R^{d4}$, $NR^{c4}S(O)R^{b4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $S(O)(=NR^{e4})R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{a4}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{44}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{44}$ substituents;

or, any $R^{c4}$ and $R^{d4}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{44}$ substituents;

each $R^{b4}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{44}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f4}$ and $R^{g4}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j4}$ and $R^{k4}$ is independently selected from OH, $C_{1-6}$ alkoxy, and $C_{1-6}$ haloalkoxy;

or any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{44}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c4}R^{d41}$, $NR^{c41}C(O)R^{b41}$, $NR^{c41}C(O)OR^{a41}$, $NR^{c41}C(O)NR^{c4}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}C(=NR^{e41})R^{b41}$, $NR^{c41}S(O)NR^{c41}R^{d41}$, $NR^{c41}S(O)R^{b41}$, $NR^{c41}S(O)_2R^{b41}$, $NR^{c41}S(O)(=NR^{e41})R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, $OS(O)(=NR^{e41})R^{b41}$, $OS(O)_2R^{b41}$, $S(O)(=NR^{e41})R^{b41}$, $SF_5$, $P(O)R^{f41}R^{g41}$, $OP(O)(OR^{h41})(OR^{i41})$, $P(O)(OR^{h41})(OR^{i41})$, and $BR^{j41}R^{k41}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

or, any $R^{c41}$ and $R^{d41}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{4B}$ substituents;

each $R^{b41}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f41}$ and $R^{g41}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h41}$ and $R^{i41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j41}$ and $R^{k41}$ is independently selected from OH, $C_{1-6}$ alkoxy, and $C_{1-6}$ haloalkoxy;

or any $R^{j41}$ and $R^{k41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a42}$, $SR^{a42}$, $NHOR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}NR^{c42}R^{d42}$, $NR^{c42}C(O)R^{b42}$, $NR^{c42}C(O)OR^{a42}$, $NR^{c42}C(O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}C(=NR^{e42})R^{42}$, $NR^{c42}S(O)NR^{c42}R^{d42}$, $NR^{c42}S(O)R^{b42}$, $NR^{c42}S(O)_2R^{b42}$, $NR^{c42}S(O)(=NR^{e42})R^{b42}$, $NR^{42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, $OS(O)(=NR^{e42})R^{b42}$, $OS(O)_2R^{b42}$, $S(O)(=NR^{e42})R^{b42}$, $SF_5$, $P(O)R^{f42}R^{g42}$, $OP(O)(OR^{h42})(OR^{i42})$, $P(O)(OR^{h42})(OR^{i42})$, and $BR^{j42}R^{k42}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c42}$ and $R^{d42}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b42}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e42}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f42}$ and $R^{g42}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h42}$ and $R^{i42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j42}$ and $R^{k42}$ is independently selected from OH, $C_{1-6}$ alkoxy, and $C_{1-6}$ haloalkoxy;

or any $R^{j42}$ and $R^{k42}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^5$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^5C(=NR^{e5})NR^{c5}R^{d5}$, $NR^{c5}C(=NR^{a5})R^{b5}$, $NR^{c5}S(O)NR^{c5}R^{d5}$, $NR^{c5}S(O)R^{b5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $S(O)(=NR^{e5})R^{b5}$, $SF_5$, $P(O)R^{j5}R^{g5}$, $OP(O)(OR^{h5})(OR^{i5})$, $P(O)(OR^{h5})(OR^{i5})$, and $BR^{j5}R^{k5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a8}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f5}$ and $R^{g5}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}C(=NR^{e51})R^{b51}$, $NR^{c51}S(O)NR^{c51}R^{d51}$, $NR^{c51}S(O)R^{b51}$, $NR^{c51}S(O)_2R^{b51}$, $NR^{c51}S(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$ $OS(O)(=NR^{e51})R^{b51}$, $OS(O)_2R^{b51}$, $S(O)(=NR^{e51})R^{b51}$, $SF_5$, $P(O)R^{f51}R^{b51}$, $OP(O)(OR^{h51})(OR^{i51})$, $P(O)(OR^{h51})(OR^{i51})$, and $BR^{j51}R^{k51}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

or, any $R^{c51}$ and $R^{d51}$ attached to the same N atom, together with the N atom to which they are attached, form a 4-7 membered heterocycloalkyl group, which is optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f51}$ and $R^{g51}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h51}$ and $R^{i51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j51}$ and $R^{k51}$ is independently selected from OH, $C_{1-6}$ alkoxy, and $C_{1-6}$ haloalkoxy;

or any $R^{j51}$ and $R^{k51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{e52}R^{d52}$, $NR^{c52}R^{d52}$, $NR^{c52}N_{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{52}C(=NR^{e52})NR^{c52}R^{d52}$, $NR^{c52}C(=NR^{e52})R^{b52}$, $NR^{c52}S(O)NR^{c52}R^{d52}$, $NR^{c52}S(O)R^{b52}$, $NR^{c52}S(O)_2R^{b52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, $OS(O)_2R^{b52}$, $S(O)(=NR^{e52})R^{b52}$, $SF_5$, $P(O)R^{f52}R^{g52}$, $OP(O)(OR^{h52})(OR^{i52})$, $P(O)(OR^{h52})(OR^{i52})$, and $BR^{j52}R^{k52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

or, any $R^{c52}$ and $R^{d52}$ attached to the same N atom, together with the N atom to which they are attached, form a 4-7 membered heterocycloalkyl group, which is optionally substituted with 1, 2, 3, or 4 independently selected $R^{5C}$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5C}$ substituents;

each $R^{e52}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f52}$ and $R^{g52}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h52}$ and $R^{i52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j52}$ and $R^{k52}$ is independently selected from OH, $C_{1-6}$ alkoxy, and $C_{1-6}$ haloalkoxy;

or any $R^{j52}$ and $R^{k52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5C}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a53}$, $SR^{a53}$, $NHOR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}NR^{c53}R^{d53}$, $NR^{c53}C(O)R^{b53}$, $NR^{c53}C(O)OR^{a53}$, $NR^{c53}C(O)NR^{c53}R^{d53}$, $C(=NR^{e53})R^{b53}$, $C(=NR^{e53})NR^{c53}R^{d53}$, $NR^{c53}C(=NR^{e53})NR^{c53}R^{d53}$, $NR^{c53}C(=NR^{e53})R^{b53}$, $NR^{c53}S(O)NR^{c53}R^{d53}$, $NR^{c53}S(O)R^{b53}$, $NR^{c53}S(O)_2$ $R^{b53}$, $NR^{c53}S(O)(=NR^{e53})R^{b53}$, $NR^{c53}S(O)_2$ $NR^{c53}R^{d53}$, $S(O)R^{b53}$, $S(O)NR^{c53}R^{d53}$, $S(O)_2R^{b53}$, $S(O)_2NR^{c53}R^{d53}$, $OS(O)(=NR^{e53})R^{b53}$, $OS(O)_2R^{b53}$, $S(O)(=NR^{e53})R^{b53}$, $SF_5$, $P(O)R^{f53}R^{g53}$, $OP(O)(OR^{h53})(OR^{i53})$, $P(O)(OR^{h53})(OR^{i53})$, and $BR^{j53}R^{k53}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a53}$, $R^{c53}$ and $R^{d53}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c53}$ and $R^{d53}$ attached to the same N atom, together with the N atom to which they are attached, form a 4-7 membered heterocycloalkyl group, which is optionally substituted with 1, 2, 3, or 4 independently selected $R^G$ substituents;

each $R^{b53}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e53}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f53}$ and $R^{g53}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h53}$ and $R^{i53}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j53}$ and $R^{k53}$ is independently selected from OH, $C_{1-6}$ alkoxy, and $C_{1-6}$ haloalkoxy;

or any $R^{j53}$ and $R^{k53}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^{10}$, $R^{11}$, and $R^{12}$ are each independently selected from H, D, halo, CN, $C_{1-4}$ alkyl, $C_{1-4}$ haloalkyl, $C_{1-3}$ alkoxy, $C_{1-3}$ haloalkoxy, cyano-$C_{1-4}$ alkyl, HO—$C_{1-4}$ alkyl, $C_{1-3}$ alkoxy-$C_{1-4}$ alkyl, and $C_{3-4}$ cycloalkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, X is N, Y is C, and Ring

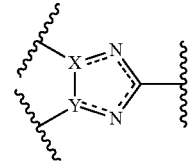

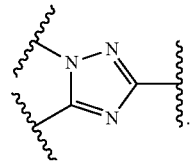 [SMILES: *c1nc(*)n(*)n1]

In some embodiments, X is N, Y is C, and Ring

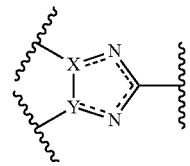

is

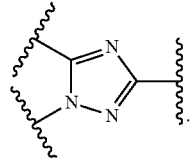 [SMILES: *c1nc(*)n(*)n1]

In some embodiments, $R^1$ is selected from H, D, halo, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a1}$, $SR^{a1}$, $NHOR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents;

- each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents;
- or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{14}$ substituents; and
- each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{14}$ substituents.

In some embodiments, $R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $NR^{c1}R^{d1}$, and $OR^{a1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents; and

- each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, and 5-10 membered heteroaryl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, and 5-10 membered heteroaryl are each optionally substituted with 1, 2, 3, or 4 independently selected $R^{14}$ substituents.

In some embodiments, $R^1$ is independently selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $NHOR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{14}$ substituents;

- each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{14}$ substituents;
- or, any $R^{c1}$ and $R^{d1}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{14}$ substituents; and
- each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{14}$ substituents In some embodiments, $R^1$ is selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $NR^{c1}R^{d1}$, and $OR^{a1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{14}$ substituents; and

- each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, and 5-6 membered heteroaryl are each optionally substituted with 1, 2, 3, or 4 independently selected $R^{14}$ substituents.

In some embodiments, $R^1$ is selected from H, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, and $OR^{a1}$, wherein said $C_{1-6}$ alkyl, $C_{3-7}$ cycloalkyl, phenyl, 4-7 membered heterocycloalkyl, and 5-6 membered heteroaryl are each optionally substituted with 1, 2, 3, or 4 independently selected $R^{1A}$ substituents; and each $R^{a1}$ is independently selected from H, $C_{1-6}$ alkyl, $C_{3-7}$ cycloalkyl, phenyl, 4-7 membered heterocycloalkyl, and 5-6 membered heteroaryl, wherein said $C_{1-6}$ alkyl, $C_{3-7}$ cycloalkyl, phenyl, 4-7 membered heterocycloalkyl, and 5-6 membered heteroaryl are each optionally substituted with 1, 2, 3, or 4 independently selected $R^{1A}$ substituents.

In some embodiments, $R^1$ is selected from H, CN, $C_{1-6}$ alkyl, $C_{1-6}$ haloalkyl, 4-7 membered heterocycloalkyl, and $OR^{a1}$, wherein said $C_{1-6}$ alkyl and 4-7 membered heterocycloalkyl are each optionally substituted with 1, 2, 3, or 4 independently selected $R^{1A}$ substituents;

each $R^{a1}$ is independently selected from H, $C_{1-6}$ alkyl, $C_{3-7}$ cycloalkyl, and 4-7 membered heterocycloalkyl, wherein said $C_{1-6}$ alkyl, $C_{3-7}$ cycloalkyl, and 4-7 membered heterocycloalkyl are each optionally substituted with 1, 2, 3, or 4 independently selected $R^{1A}$ substituents.

In some embodiments, $R^1$ is selected from H, CN, $C_{1-6}$ alkyl, $C_{1-6}$ haloalkyl, 4-7 membered heterocycloalkyl, and $OR^{a1}$, wherein said $C_{1-6}$ alkyl and 4-7 membered heterocycloalkyl are each optionally substituted with 1, 2, 3, or 4 independently selected $R^{1A}$ substituents; and each $R^{a1}$ is independently selected from H, methyl, isopropyl, cyclobutyl, and tetrahydrofuranyl, wherein said methyl, isopropyl, cyclobutyl, and tetrahydrofuranyl are each optionally substituted with 1, 2, 3, or 4 independently selected $R^{1A}$ substituents.

In some embodiments, $R^1$ is H, methyl, isopropyl, trifluoromethyl, cyano, pyrrolidinyl, piperidinyl, N-morpholinyl, methoxy, isopropoxy, cyclobutoxy, tetrahydrofuranyloxy, or tetrahydropyranyloxy, wherein the methyl, isopropyl, pyrrolidinyl, piperidinyl, N-morpholinyl, methoxy, isopropoxy, cyclobutoxy, tetrahydrofuranyloxy, and tetrahydropyranyloxy are each optionally substituted with 1, 2, 3, or 4 independently selected $R^{1A}$ substituents.

In some embodiments, $R^1$ is H, methyl, isopropyl, cyano, pyrrolidinyl, piperidinyl, N-morpholinyl, methoxy, isopropoxy, cyclobutoxy, tetrahydrofuranyloxy, or tetrahydropyranyloxy, wherein the methyl, isopropyl, pyrrolidinyl, piperidinyl, N-morpholinyl, methoxy, isopropoxy, cyclobutoxy, tetrahydrofuranyloxy, and tetrahydropyranyloxy are each optionally substituted with 1, 2, 3, or 4 independently selected $R^{1A}$ substituents.

In some embodiments, each $R^{1A}$ is independently selected from H, D, halo, CN, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1}$ substituents; and each $R^{1B}$ is independently selected from H, D, halo, CN, $C_{1-6}$ alkyl, $C_{2-6}$ alkenyl, $C_{2-6}$ alkynyl, and $C_{1-6}$ haloalkyl.

In some embodiments, each $R^{1A}$ is independently selected from H, D, halo, CN, $C_{1-6}$ alkyl, and $C_{1-6}$ haloalkyl.

In some embodiments, each $R^{1A}$ is independently selected from halo, $C_{1-6}$ alkyl, and $C_{1-6}$ haloalkyl.

In some embodiments, each $R^{1A}$ is an independently selected halo.

In some embodiments, each $R^{1A}$ is fluoro.

In some embodiments, Z is $CR^2$.

In some embodiments, Z is N.

In some embodiments, $R^2$ is selected from H, D, halo, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-4}$ cycloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^2$ is selected from H, D, $C_{1-3}$ alkyl, $C_{1-3}$ haloalkyl, $C_{2-3}$ alkenyl, and $C_{2-3}$ alkynyl.

In some embodiments, $R^2$ is selected from H and $C_{1-3}$ alkyl.

In some embodiments, $R^2$ is H or methyl.

In some embodiments, Ring moiety A is a monocyclic 5-6 membered heteroaryl.

In some embodiments, Ring moiety A is a monocyclic 5-membered heteroaryl.

In some embodiments, Ring moiety A is a monocyclic 6-membered heteroaryl.

In some embodiments, Ring moiety A is selected from pyrazolyl and oxazolyl.

In some embodiments, Ring moiety B is monocyclic $C_{3-7}$ cycloalkyl or monocyclic 4-7 membered heterocycloalkyl.

In some embodiments, Ring moiety B is cyclohexyl, azetidinyl, pyrrolidinyl, or piperidinyl.

In some embodiments, Ring moiety B is cyclohexan-1,3-diyl, azetidin-1,3-diyl, pyrrolidin-1,3-diyl, piperidin-1,3-diyl, or piperidin-1,4-diyl.

In some embodiments, Ring moiety C is $C_{6-10}$ aryl, 5-10 membered heteroaryl, or 5-12 membered partially unsaturated heterocycloalkyl.

In some embodiments, Ring moiety C is phenyl, monocyclic 5-6 membered heteroaryl, bicyclic 8-10 membered heteroaryl, or bicyclic 8-10 membered partially unsaturated heterocycloalkyl.

In some embodiments, Ring moiety C is phenyl, bicyclic 8-10 membered heteroaryl, or bicyclic 8-10 membered partially unsaturated heterocycloalkyl.

In some embodiments, Ring moiety C is phenyl, pyridinyl, benzothiazolyl, isoindolinonyl, or benzoimidazolyl.

In some embodiments, Ring moiety C is phenyl, benzothiazolyl, isoindolinonyl, or benzoimidazolyl.

In some embodiments, n is 0, 1, 2, 3, or 4.
In some embodiments, n is 0, 1, 2, or 3.
In some embodiments, n is 0, 1, or 2.
In some embodiments, n is 0 or 1.
In some embodiments, n is 1.
In some embodiments, n is 0.

In some embodiments, each $R^3$ is independently selected from D, halo, and $C_{1-4}$ alkyl.

In some embodiments, s is 0, 1, 2, 3, or 4.
In some embodiments, s is 0, 1, 2, or 3.
In some embodiments, s is 0, 1, or 2.
In some embodiments, s is 0 or 1.
In some embodiments, s is 1.
In some embodiments, s is 0.

In some embodiments, each $R^4$ is independently selected from H, D, halo, CN, $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, 5-6 membered heteroaryl-$C_{1-3}$ alkyl, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl are each optionally substituted by 1, 2, 3, or 4 independently selected $R^{4A}$ substituents;

each $R^{a4}$, $R^{c4}$, and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl are each optionally substituted with 1, 2, 3, or 4 independently selected $R^{4A}$ substituents;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl, which are each optionally substituted with 1, 2, 3, or 4 independently selected $R^{4A}$ substituents;

each $R^{4A}$ is independently selected from H, D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^4$, $NR^{c41}C(O)OR^{a41}$, $NR^{c41}C(O)NR^{c41}R^{d41}$, $NR^{c41}S(O)NR^{c41}R^{d41}$, $NR^{c41}S(O)R^{b41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{41}$, and $S(O)_2NR^{c41}R^{d41}$, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl are each optionally substituted with 1, 2, 3, or 4 independently selected $R^G$ substituents;

each $R^{a41}$, $R^{c41}$, and $R^{d41}$ is independently selected from H, $C_{1-6}$ alkyl, $C_{2-6}$ alkenyl, $C_{2-6}$ alkynyl, $C_{1-6}$ haloalkyl, and $C_{3-4}$ cycloalkyl, wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted with 1, 2, 3, or 4 independently selected $R^G$ substituents; and each $R^{b41}$ is independently selected from $C_{1-6}$ alkyl, $C_{2-6}$ alkenyl, $C_{2-6}$ alkynyl, $C_{1-6}$ haloalkyl, and $C_{3-4}$ cycloalkyl, which are each optionally substituted with 1, 2, 3, or 4 independently selected $R^G$ substituents.

In some embodiments, each $R^4$ is independently selected from H, D, halo, CN, $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, 5-6 membered heteroaryl-$C_{1-3}$ alkyl, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^4C(O)OR^{a4}$, $NR^{c4}C(O)NR^{c4}R^{d4}$, $NR^{c4}S(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl are each optionally substituted by 1, 2, 3, or 4 independently selected $R^{4A}$ substituents;

each $R^{a4}$, $R^{c4}$, and $R^{d4}$ is independently selected from H, $C_{1-6}$ alkyl and $C_{1-6}$ haloalkyl, wherein said $C_{1-6}$ alkyl and $C_{1-6}$ haloalkyl; and each $R^{b4}$ is independently selected from $C_{1-6}$ alkyl and $C_{1-6}$ haloalkyl.

In some embodiments, each $R^4$ is independently selected from H, D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^{44}$ substituents;

each $R^{a4}$, $R^{c4}$, and $R^{d4}$ is independently selected from H, $C_{1-6}$ alkyl and $C_{1-6}$ haloalkyl, wherein said $C_{1-6}$ alkyl and $C_{1-6}$ haloalkyl; and each $R^{b4}$ is independently selected from $C_{1-6}$ alkyl and $C_{1-6}$ haloalkyl.

In some embodiments, each $R^4$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^4$ is independently selected from D, halo, $C_{1-3}$ alkyl, and $C_{1-3}$ haloalkyl.

In some embodiments, each $R^4$ is independently selected from halo and $C_{1-3}$ alkyl.

In some embodiments, each $R^4$ is independently selected from fluoro and methyl.

In some embodiments, p is 0, 1, 2, 3, or 4.

In some embodiments, p is 0, 1, 2, or 3.

In some embodiments, p is 0, 1, or 2.

In some embodiments, p is 0 or 1.

In some embodiments, p is 1.

In some embodiments, p is 0.

In some embodiments, each $R^5$ is independently selected from H, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{e5}S(O)R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents; and each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents.

In some embodiments, each $R^5$ is independently selected from H, D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents; and each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5A}$ substituents.

In some embodiments, each $R^5$ is independently selected from H, D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, and $NR^{c5}R^{d5}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5A}$ substituents; and each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents.

In some embodiments, each $R^{5A}$ is independently selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{b51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5B}$ substituents;

each $R^{5B}$ is independently selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^2C(O)OR^{a52}$, $NR^{c52}C(O)NR^{c52}R^{d52}$, $NR^{c52}S(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, and $S(O)_2NR^{c52}R^{d52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5C}$ substituents;

each $R^{5C}$ is independently selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a53}$, $SR^{a53}$, $NHOR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}C(O)R^{b53}$, $NR^{c53}C(O)OR^{a53}$, $NR^{c53}C(O)NR^{c53}R^{d53}$, $NR^{c53}S(O)NR^{c53}R^{d53}$, $NR^{c53}S(O)R^{b53}$, $NR^{c53}S(O)_2R^{b53}$, $NR^{c53}S(O)_2NR^{c53}R^{d53}$, $S(O)R^{b53}$, $S(O)NR^{c53}R^{d53}$, $S(O)_2R^{b53}$, and $S(O)_2NR^{c53}R^{d53}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a53}$, $R^{c53}$ and $R^{d53}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b53}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

In some embodiments, each $R^{5A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, and 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ substituents;

each $R^{5B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)NR^{c52}R^{d52}$, $NR^{b52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, and $S(O)_2NR^{c52}R^{d52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5C}$ substituents; and each $R^{5C}$ is independently selected from H, D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl) aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^{5A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, and 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{51}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{51}$ substituents; and each $R^{5B}$ is independently selected from H, D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^{5A}$ is independently selected from H, D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^5$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^5$ is independently selected from halo, CN, $C_{1-3}$ alkyl, and $C_{1-3}$ haloalkyl.

In some embodiments, each $R^5$ is independently selected from halo, $C_{1-3}$ alkyl, and $C_{1-3}$ haloalkyl.

In some embodiments, each $R^5$ is methyl.

In some embodiments, E is a bond, —C(O)—, —$CH_2$— or —O—.

In some embodiments, E is a bond, —C(O)—, or —O—.

In some embodiments, E is a bond or —C(O)—.

In some embodiments, E is a bond.

In some embodiments, E is —C(O)—.

In some embodiments, E is —O—.

In some embodiments, m is 0.

In some embodiments, m is 1.

In some embodiments, $R^{11}$ and $R^{12}$ are each independently selected from H, D, halo, CN, $C_{1-4}$ alkyl, and $C_{1-4}$ haloalkyl.

In some embodiments, m is 1, and $R^{11}$ and $R^{12}$ are each H.

In some embodiments, k is 1.

In some embodiments, k is 2.

In some embodiments, each $R^W$ is independently:

In some embodiments, each $L^1$ is independently -L-C(O)— or -L-$NR^9$C(O)—, wherein $L^2$ is attached to Ring moiety C through the L linking group.

In some embodiments, each $L^2$ is independently -L-C(O)— or -L-$NR^9$C(O)—, wherein $L^2$ is attached to Ring moiety C through the L linking group.

In some embodiments, each $L^3$ is independently -L-C(O)— or -L-$NR^9$C(O)—, wherein each $L^3$ is attached to Ring moiety C through the L linking group.

In some embodiments, each $L^4$ is -L-$NR^9$—, wherein $L^4$ is attached to Ring moiety C through the L linking group.

In some embodiments, each $L^5$ is independently -L-O-$L^x$-, -L-$NR^9$-$L^x$-, -L-S-$L^x$-, -L-C(O)-$L^x$-, —$NR^9$C(O)-$L^x$-, -L-OC(O)-$L^x$-, -L-S(O)-$L^x$-, -L-S(O)$_2$-$L^x$-, —$NR^9$S(O)-$L^x$-, -L-OS(O)-$L^x$-, -L-$NR^9$S(O)$NR^9$-$L^x$-, -L-$NR^9$S(O)O-$L^x$-, -L-OS(O)$NR^9$-$L^x$-, —$NR^9$S(O)$_2$-$L^x$-, -L-OS(O)$_2$-$L^x$-, -L-$NR^9$S(O)$_2$ $NR^9$-$L^x$-, -L-$NR^9$S(O)$_2$O-$L^x$-, -L-S(O)($NR^9$)-$L^x$-, -L-S(O)$_2$($NR^9$)-$L^x$-, or -L-OS(O)$_2$$NR^9$-$L^x$-, wherein $L^5$ is attached to Ring C through the L linking group.

In some embodiments, $L^1$ is NHC(O) or N(CH$_3$)C(O).

In some embodiments, $L^1$ is NHC(O).

In some embodiments, $L^2$ is NHC(O) or N(CH$_3$)C(O).

In some embodiments, $L^2$ is NHC(O).

In some embodiments, $L^2$ is N(CH$_3$)C(O).

In some embodiments, $L^3$ is NHC(O) or N(CH$_3$)C(O).

In some embodiments, $L^3$ is NHC(O).

In some embodiments, $L^3$ is N(CH$_3$)C(O).

In some embodiments, $L^4$ is NHC(O) or N(CH$_3$)C(O).

In some embodiments, $L^4$ is NHC(O).

In some embodiments, $L^5$ is NHC(O) or N(CH$_3$)C(O).

In some embodiments, $L^5$ is NHC(O).

In some embodiments, each $R^W$ is independently:

and each L² is independently -L-NR⁹C(O)—, wherein L² is attached to Ring moiety C through the L linking group.

In some embodiments, each $R^W$ is independently:

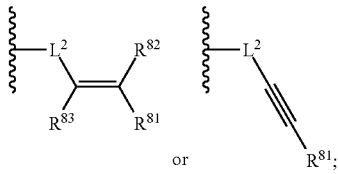

and
each L² is independently NHC(O) or N(CH₃)C(O).

In some embodiments, each L is a bond or $C_{1-3}$ alkylene, wherein said $C_{1-3}$ alkylene is optionally substituted by 1, 2, 3 or 4 independently selected $R^G$ substituents.

In some embodiments, each L is a bond or methylene, wherein said methylene is optionally substituted by 1, 2, or 3 independently selected $R^G$ substituents.

In some embodiments, each L is a bond.

In some embodiments, each $R^9$ is independently selected from H, halo, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents; and each $R^{a9}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{9A}$ substituents.

In some embodiments, each $R^9$ is independently selected from H, halo, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(O)R^{a9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{a9}$, $NR^{c9}C(O)OR^{a9}$, $NR^{c9}C(O)NR^{c9}R^{d9}$, $NR^{c9}S(O)NR^{c9}R^{d9}$, $NR^{c9}S(O)R^{b9}$, $NR^{c9}S(O)_2R^{a9}$, $NR^{c9}S(O)_2NR^{c9}R^{d9}$, $S(O)R^{a9}$, $S(O)NR^{c9}R^{d9}$, $S(O)_2R^{a9}$, and $S(O)_2NR^{c9}R^{d9}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{9A}$ substituents;

each $R^{a9}$, $R^{c9}$, and $R^{d9}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents; and each $R^{a9}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{9A}$ substituents.

In some embodiments, each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{a91}$, $NR^{c91}S(O)_2R^{a91}$, $NR^{c91}S(O)_2NR^{c91}R^{d91}$, $S(O)R^{a91}$, $S(O)NR^{c91}R^{d91}$, $S(O)_2R^{a91}$, and $S(O)_2NR^{c91}R^{d91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^9$ substituents;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$ $SR^{a92}$, $NHOR^{a92}$, $C(O)R^{b92}$, $C(O)NR^{c92}R^{d92}$, $C(O)OR^{a92}$, $OC(O)R^{b92}$, $OC(O)NR^{c92}R^{d92}$, $NR^{c92}R^{d92}$, $NR^{c92}C(O)R^{92}$, $NR^{c92}C(O)OR^{a92}$, $NR^{c92}C(O)NR^{c92}R^{d92}$, $NR^{c92}S(O)NR^{c92}R^{d92}$, $NR^{c92}S(O)R^{b92}$, $NR^{c92}S(O)_2R^{b92}$, $NR^{c92}S(O)_2NR^{c92}R^{d92}$, $S(O)R^{b92}$, $S(O)NR^{c92}R^{d92}$, $S(O)_2R^{b92}$, and $S(O)_2NR^{c92}R^{d92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

In some embodiments, each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{a91}$, and $S(O)_2NR^{c91}R^{d91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^9$ substituents;

each $R^{9B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$ $SR^{a92}$, $NHOR^{a92}$, $C(O)R^{b92}$, $C(O)NR^{c92}R^{d92}$, $C(O)OR^{a92}$, $OC(O)R^{b92}$, $OC(O)NR^{c92}R^{d92}$, $NR^{c92}R^{d92}$, $NR^{c92}C(O)R^{b92}$, $NR^{c92}C(O)OR^{a92}$, $NR^{c92}C(O)NR^{c92}R^{d92}$, $NR^{c92}S(O)NR^{c92}R^{d92}$, $NR^{e92}S(O)R^{b92}$, $NR^{c92}S(O)_2R^{b92}$, $NR^{c92}S(O)_2NR^{c92}R^{d92}$, $S(O)R^{b92}$, $S(O)NR^{e92}R^{d92}$, $S(O)_2R^{b92}$, and $S(O)_2NR^{c92}R^{d92}$;

each $R^{a92}$, $R^{c92}$, and $R^{d92}$ is independently selected from H, $C_{1-6}$ alkyl, $C_{1-6}$ haloalkyl, $C_{2-6}$ alkenyl, and $C_{2-6}$ alkynyl; and each $R^{b92}$ is independently selected from $C_{1-6}$ alkyl, $C_{1-6}$ haloalkyl, $C_{2-6}$ alkenyl, and $C_{2-6}$ alkynyl.

In some embodiments, each $R^{9A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{b91}$, $NR^{c91}S(O)_2NR^{c91}R^{d91}$, $S(O)R^{b91}$, $S(O)NR^{c91}R^{d91}$, $S(O)_2R^{a91}$, and $S(O)_2NR^{c91}R^{d91}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a91}$, $R^{c91}$, and $R^{d91}$ is independently selected from H, $C_{1-6}$ alkyl, $C_{1-6}$ haloalkyl, $C_{2-6}$ alkenyl, $C_{2-6}$ alkynyl$C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{a1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^9$ substituents;

each $R^{9B}$ is independently selected from D, halo, CN, $C_{1-6}$ alkyl, $C_{2-6}$ alkenyl, $C_{2-6}$ alkynyl, $C_{1-6}$ haloalkyl, $OR^{a92}$, $SR^{a92}$, $NHOR^{a92}$, $C(O)R^{b92}$, $C(O)NR^{c92}R^{d92}$, $C(O)OR^{a92}$, $OC(O)R^{b92}$, $OC(O)NR^{e92}R^{d92}$, $NR^{c92}R^{d92}$, $NR^{c92}C(O)R^{b92}$, $NR^{c92}C(O)OR^{a92}$, $NR^{c92}C(O)NR^{c92}R^{d92}$, $NR^{c92}S(O)NR^{c92}R^{d92}$, $NR^{c92}S(O)R^{b92}$, $NR^{c92}S(O)_2R^{b92}$, $NR^{c92}S(O)_2NR^{c92}R^{d92}$, $S(O)R^{b92}$, $S(O)NR^{c92}R^{d92}$, $S(O)_2R^{b92}$, and $S(O)_2NR^{c92}R^{d92}$;

each $R^{a92}$, $R^{c92}$, and $R^{d92}$ is independently selected from H, $C_{1-6}$ alkyl, $C_{1-6}$ haloalkyl, $C_{2-6}$ alkenyl, and $C_{2-6}$ alkynyl; and each $R^{b92}$ is independently selected from $C_{1-6}$ alkyl, $C_{1-6}$ haloalkyl, $C_{2-6}$ alkenyl, and $C_{2-6}$ alkynyl.

In some embodiments, each $R^{9A}$ is independently selected from D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{b91}$, $OC(O)NR^{c91}R^{d91}$, $NR^{c91}R^{d91}$, $NR^{c91}C(O)R^{a9}$, $NR^{c91}C(O)OR^{a91}$, $NR^{c91}C(O)NR^{c91}R^{d91}$, $N^{c91}S(O)NR^{c91}R^{d91}$, $NR^{c91}S(O)R^{a91}$, $NR^{c91}S(O)_2R^{a91}$, $NR^{c91}S(O)_2NR^{c91}R^{d91}$, $S(O)R^{a91}$, $S(O)NR^{c91}R^{d91}$, $S(O)_2R^{a91}$, and $S(O)_2 NR^{c91}R^{d91}$;

each $R^{a91}$, $R^{c91}$, and $R^{d91}$ is independently selected from H, $C_{1-6}$ alkyl, and $C_{1-6}$ haloalkyl; and each $R^{b91}$ is independently selected from $C_{1-6}$ alkyl and $C_{1-6}$ haloalkyl.

In some embodiments, each $R^{9A}$ is independently selected from D, halo, CN, $C_{1-6}$ alkyl, $C_{2-6}$ alkenyl, $C_{2-6}$ alkynyl, $C_{1-6}$ haloalkyl, $OR^{a91}$, $SR^{a91}$, $NHOR^{a91}$, $C(O)R^{b91}$, $C(O)NR^{c91}R^{d91}$, $C(O)OR^{a91}$, $OC(O)R^{a91}$, $OC(O)NR^{c91}R^{d91}$, $NR^{c91}R^{d91}$, $NR^{c91}C(O)R^{b91}$, $NR^{c91}C(O)OR^{a91}$, $NR^{c91}C(O)NR^{c91}R^{d91}$, $NR^{c91}S(O)NR^{c91}R^{d91}$, $NR^{c91}S(O)R^{b91}$, $NR^{c91}S(O)_2R^{a91}$, $NR^{c91}S(O)_2NR^{c91}R^{d9}$, $S(O)R^{a91}$, $S(O)NR^{c91}R^{d91}$, $S(O)_2R^{a91}$, and $S(O)_2NR^{c91}R^{d91}$;

each $R^{a91}$, $R^{c91}$, and $R^{d91}$ is independently selected from H, $C_{1-6}$ alkyl, and $C_{1-6}$ haloalkyl; and each $R^{b91}$ is independently selected from $C_{1-6}$ alkyl and $C_{1-6}$ haloalkyl.

In some embodiments, each $R^9$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^9$ is independently selected from H, D, halo, $C_{1-3}$ alkyl, and $C_{1-3}$ haloalkyl.

In some embodiments, each $R^9$ is independently H or $C_{1-4}$ alkyl.

In some embodiments, each $R^9$ is independently H or methyl.

In some embodiments, each Ar is independently phenyl or 5-6 membered heteroaryl, which are each optionally substituted with 1, 2, 3, or 4 independently selected $R^{9A}$ substituents.

In some embodiments, each Ar is independently 5-6 membered heteroaryl, which are each optionally substituted with 1, 2, 3, or 4 independently selected $R^{9A}$ substituents.

In some embodiments, each Ar is independently $C_{6-10}$ aryl or 5-10 membered heteroaryl, wherein said $C_{6-10}$ aryl or 5-10 membered heteroaryl are each substituted with 1, 2, 3, or 4 substituents independently selected from CN and halo; and wherein said $C_{6-10}$ aryl or 5-10 membered heteroaryl are each optionally substituted with 1, 2, 3, or 4 independently selected $R^{9A}$ substituents.

In some embodiments, each Ar is independently phenyl or 5-6 membered heteroaryl, wherein said phenyl or 5-6 membered heteroaryl are each substituted with 1, 2, 3, or 4 substituents independently selected from CN and halo; and wherein said phenyl or 5-6 membered heteroaryl are each optionally substituted with 1, 2, 3, or 4 independently selected $R^{9A}$ substituents.

In some embodiments, each $R^{81}$, $R^{82}$, and $R^{83}$ is independently selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, $C(O)R^{a8}$, $C(O)NR^{c8}R^{d8}$, $C(O)OR^{a8}$, $OC(O)R^{a8}$, $OC(O)NR^{c8}R^{d8}$, $NR^{c8}R^{d8}$, $NR^{c8}C(O)R^{a8}$, $NR^{c8}C(O)OR^{a8}$, $NR^{c8}C(O)NR^{c8}R^{d8}$, $NR^{c8}S(O)NR^{c8}R^{d8}$, $NR^{c8}VS(O)R^{b8}$, $NR^{c8}S(O)_2R^{b8}$, $NR^{c8}S(O)_2NR^{c8}R^{d8}$, $S(O)R^{a8}$, $S(O)NR^{c8}R^{d8}$, $S(O)_2R^{a8}$, and $S(O)_2 NR^{c8}R^{d8}$; wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^G$ substituents;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents; and each $R^{b8}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents.

In some embodiments, each $R^{81}$, $R^{82}$, and $R^{83}$ is independently selected from H, D, halo, CN, C(O)H, $OR^{a8}$, $C(O)OR^{a8}$, $C_{1-6}$ alkyl, $C_{2-6}$ alkenyl, $C_{2-6}$ alkynyl, $C_{1-6}$ haloalkyl, and $C_{3-4}$ cycloalkyl; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^G$ substituents; and each $R^{a8}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^G$ substituents.

In some embodiments, each $R^{84}$ is independently selected from H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-6 membered heterocycloalkyl, 5-6 membered heteroaryl, $C_{3-7}$ cycloalkyl-$C_{1-4}$ alkyl, phenyl-$C_{1-4}$ alkyl, 4-6 membered heterocycloalkyl-$C_{1-4}$ alkyl, and 5-6 membered heteroaryl-$C_{1-4}$ alkyl, wherein said $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-6 membered heterocycloalkyl, 5-6 membered heteroaryl, $C_{3-7}$ cycloalkyl-$C_{1-4}$ alkyl, phenyl-$C_{1-4}$ alkyl, 4-6 membered heterocycloalkyl-$C_{1-4}$ alkyl, and 5-6 membered heteroaryl-$C_{1-4}$ alkyl are each optionally substituted by 1, 2, 3, or 4 independently selected $R^G$ substituents.

In some embodiments, each $R^{84}$ is independently selected from H, D, halo, CN, $C_{1-3}$ alkoxy, $C_{1-3}$ haloalkoxy, $C_{1-6}$ alkyl, $C_{2-6}$ alkenyl, $C_{2-6}$ alkynyl, and $C_{1-6}$ haloalkyl, wherein said $C_{1-3}$ alkoxy, $C_{1-3}$ haloalkoxy, $C_{1-6}$ alkyl, $C_{2-6}$ alkenyl, $C_{2-6}$ alkynyl, and $C_{1-6}$ haloalkyl are each optionally substituted by 1, 2, 3, or 4 independently selected $R^G$ substituents.

In some embodiments, each $R^{84}$ is independently selected from H, D, halo, CN, $C_{1-3}$ alkoxy, $C_{1-3}$ haloalkoxy, $C_{1-6}$ alkyl, $C_{2-6}$ alkenyl, $C_{2-6}$ alkynyl, and $C_{1-6}$ haloalkyl.

In some embodiments, each $R^{85}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-7}$ cycloalkyl, 4-6 membered heterocycloalkyl, and $C_{3-7}$ cycloalkyl-$C_{1-4}$ alkyl, wherein said $C_{1-6}$ alkyl, $C_{1-6}$ haloalkyl, $C_{3-10}$ cycloalkyl, 4-6 membered heterocycloalkyl, and $C_{3-7}$ cycloalkyl-$C_{1-4}$ alkyl are each optionally substituted by 1, 2, 3, or 4 independently selected $R^G$ substituents.

In some embodiments, each $R^{85}$ is independently selected from H, D, halo, CN, C(O)H, OH, $C_{1-3}$ alkoxy, $C_{1-3}$ haloalkoxy, amino, $C_{1-6}$ alkyl, and $C_{1-6}$ haloalkyl, wherein said $C_{1-6}$ alkyl and $C_{1-6}$ haloalkyl are each optionally substituted by 1, 2, 3, or 4 independently selected $R^G$ substituents.

In some embodiments, each $R^{85}$ is independently selected from H, D, halo, CN, C(O)H, OH, $C_{1-3}$ alkoxy, $C_{1-3}$ haloalkoxy, amino, $C_{1-6}$ alkyl, and $C_{1-6}$ haloalkyl.

In some embodiments, each $R^{81}$, $R^{82}$, and $R^{83}$ is independently selected from H, D, halo, CN, C(O)H, OH, $C_{1-3}$ alkoxy, $C_{1-3}$ haloalkoxy, amino, $C_{1-6}$ alkyl, and $C_{1-6}$ haloalkyl;

each $R^{84}$ is independently selected from H, D, halo, CN, OH, $C_{1-3}$ alkoxy, $C_{1-3}$ haloalkoxy, $C_{1-6}$ alkyl, and $C_{1-6}$ haloalkyl; and each $R^{85}$ is independently selected from H, D, halo, CN, C(O)H, OH, $C_{1-3}$ alkoxy, $C_{1-3}$ haloalkoxy, amino, $C_{1-6}$ alkyl, and $C_{1-6}$ haloalkyl.

In some embodiments, each $R^{81}$, $R^{82}$, $R^{83}$, $R^{84}$, and $R^{85}$ is independently selected from H, D, halo, and $C_{1-3}$ alkyl;

In some embodiments, each $R^{81}$, $R^{82}$, $R^{83}$, $R^{84}$, and $R^{85}$ is independently selected from H, halo, and $C_{1-3}$ alkyl.

In some embodiments, each $R^{81}$, $R^{82}$, and $R^{83}$ is independently selected from H, D, halo, CN, C(O)H, OH, $C_{1-3}$ alkoxy, $C_{1-3}$ haloalkoxy, amino, $C_{1-6}$ alkyl, and $C_{1-6}$ haloalkyl.

In some embodiments, each $R^{81}$, $R^{82}$, and $R^{83}$ is independently selected from H, D, halo, and $C_{1-3}$ alkyl.

In some embodiments, each $R^{81}$, $R^{82}$, and $R^{83}$ is independently selected from H, halo, and $C_{1-3}$ alkyl.

In some embodiments, each $R^{81}$, $R^{82}$, and $R^{83}$ is independently selected from H, fluoro, and methyl.

In some embodiments, each $R^{81}$ and $R^{82}$ is independently selected from H and $C_{1-6}$ alkyl; and each $R^{83}$ is independently selected from H and halo.

In some embodiments, each $R^{81}$ and $R^{82}$ is independently selected from H and methyl; and each $R^{83}$ is independently selected from H and fluoro.

In some embodiments:

each $R^{81}$ is independently selected from H and $C_{1-6}$ alkyl;

each $R^{82}$ is H;

and each $R^{83}$ is independently selected from H and halo.

In some embodiments:

each $R^{81}$ is independently selected from H and methyl;

each $R^{82}$ is H;

and each $R^{83}$ is independently selected from H and fluoro.

In some embodiments, $R^{10}$ is H, D, halo, or $C_{1-4}$ alkyl.

In some embodiments, $R^{10}$ is H.

In some embodiments:

k is 1 or 2;

m is 0 or 1;

n is 0, 1, 2, 3, or 4;

p is 0, 1, 2, 3, or 4;

s is 0, 1, 2, 3, or 4;

each ═ is independently a single or a double bond;

X is N, Y is C, and Ring

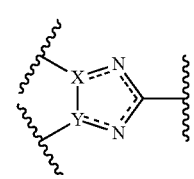

is

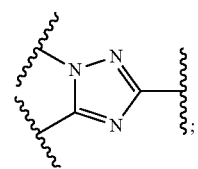 [SMILES: *c1nc(*)n(*)n1]

or

X is C, Y is N, and Ring

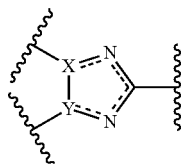

is

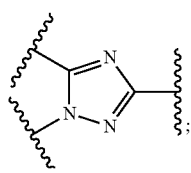 [SMILES: *c1nc(*)n(*)n1]

Z is $CR^2$ or N;

Ring moiety A is a 5-10 membered heteroaryl;

Ring moiety B is $C_{3-10}$ membered cycloalkyl or 4-10 membered heterocycloalkyl;

Ring moiety C is $C_{6-10}$ aryl, 5-10 membered heteroaryl, $C_{5-12}$ partially unsaturated cycloalkyl, or 5-12 membered partially unsaturated heterocycloalkyl;

E is a bond, —C(O)—, —CH$_2$—, —CHR$^6$—, —CR$^6$R$^7$—, or —O—, wherein R$^6$ and R$^7$ are each independently selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^W$, attached to the C ring, is independently:

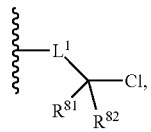 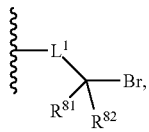 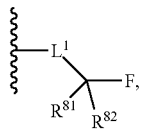

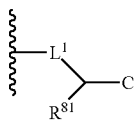 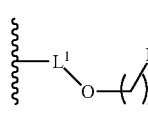 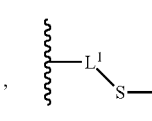

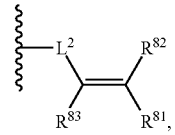 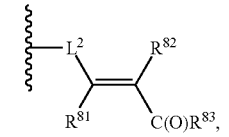

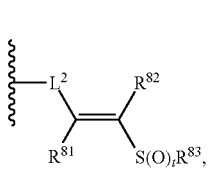 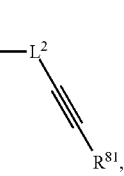 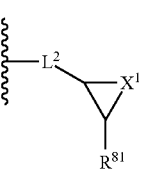

-continued

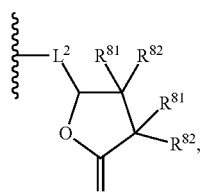 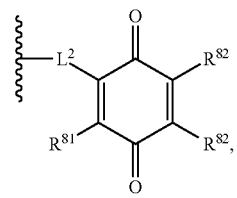

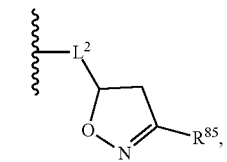 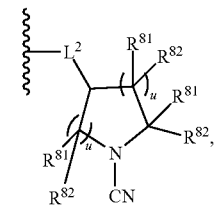

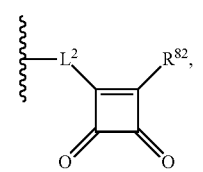 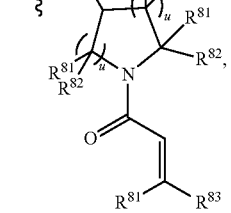

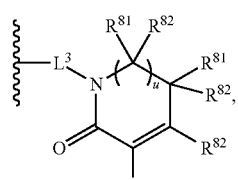 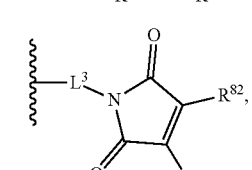

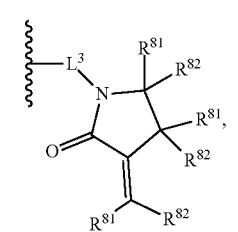 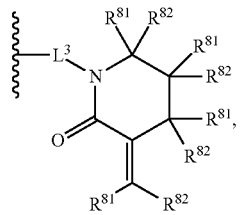

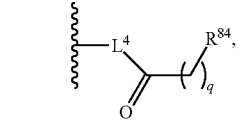 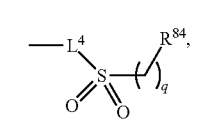

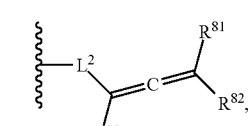 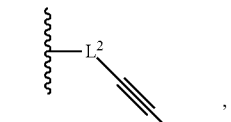

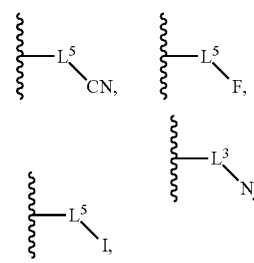 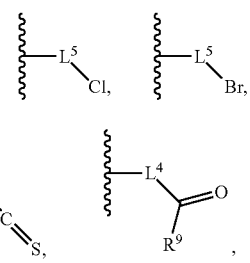

-continued

[chemical structures showing: L²-C(=CR⁸¹)-C(O)R⁸³ with R⁸², L²-C(=CR⁸¹)-S(O)ₜR⁸³ with R⁸², L⁴-cyclopropyl-S(O)₂ group, L⁴-cyclobutyl-S(O)₂ group, L²-cyclopropyl with X¹, C(O)R⁸², R⁸¹, and L²-C(=CR⁸¹)-CN with R⁸²]

or $L^1$-Ar;

- each $L^1$ is independently -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$— or -L-OS(O)$_2$—, wherein $L^1$ is attached to Ring moiety C through the L linking group;

- each $L^2$ is independently -L-, -L-O—, -L-NR$^9$—, -L-S—, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)NR$^9$—, -L-NR$^9$S(O)O—, -L-OS(O)NR$^9$—, -L-NR$^9$S(O)$_2$—, -L-OS(O)$_2$—, -L-NR$^9$S(O)$_2$NR$^9$—, -L-NR$^9$S(O)$_2$O—, -L-S(O)(NR$^9$)—, -L-S(O)$_2$(NR$^9$)—, or -L-OS(O)$_2$NR$^9$—, wherein $L^2$ is attached to Ring moiety C through the L linking group;

- each $L^3$ is independently -L-, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$—, or -L-OS(O)$_2$—, wherein $L^3$ is attached to Ring moiety C through the L linking group;

- each $L^4$ is independently -L-, -L-O—, L-S—, -L-NR$^9$—, wherein $L^4$ is attached to Ring moiety C through the L linking group;

- each $L^5$ is independently -L-O-L$^x$-, -L-NR$^9$-L$^x$-, -L-S-L$^x$-, -L-C(O)-L$^x$-, -L-NR$^9$C(O)-L$^x$-, -L-OC(O)-L$^x$-, -L-S(O)-L$^x$-, -L-S(O)$_2$-L$^x$-, -L-NR$^9$S(O)-L$^x$-, -L-OS(O)-L$^x$-, -L-NR$^9$S(O)NR$^9$-L$^x$-, -L-NR$^9$S(O)O-L$^x$-, -L-OS(O)NR$^9$-L$^x$-, -L-NR$^9$S(O)$_2$-L$^x$-, -L-OS(O)$_2$-L$^x$-, -L-NR$^9$S(O)$_2$NR$^9$-L$^x$-, -L-NR$^9$S(O)$_2$O-L$^x$-, -L-S(O)(NR$^9$)-L$^x$-, -L-S(O)$_2$(NR$^9$)-L$^x$-, or -L-OS(O)$_2$NR$^9$-L$^x$-, wherein $L^5$ is attached to Ring moiety C through the L linking group;

- each L is independently is a bond or $C_{1-6}$ alkylene, wherein said $C_{1-6}$ alkylene is optionally substituted by 1, 2, 3 or 4 independently selected $R^G$ substituents;

- each $L^x$ is independently is a $C_{1-6}$ alkylene, wherein said $C_{1-6}$ alkylene is optionally substituted by 1, 2, 3 or 4 independently selected $R^G$ substituents;

- each $X^1$ is independently O or NR$^9$;
- each q is independently 0, 1, or 2;
- each t is independently 0, 1, or 2;
- each u is independently 0, 1, or 2;
- each Ar is independently $C_{6-10}$ aryl or 5-10 membered heteroaryl, which are each optionally substituted with 1, 2, 3, or 4 independently selected $R^{9A}$ substituents;
- each $R^{81}$, $R^{82}$, and $R^{83}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, $C_{3-10}$ cycloalkyl-$C_{1-4}$ alkyl, 6-10 membered aryl-$C_{1-4}$ alkyl, 4-membered heterocycloalkyl-$C_{1-4}$ alkyl, and 5-10 membered heteroaryl-$C_{1-4}$ alkyl, wherein said $C_{1-6}$ alkyl, $C_{1-6}$ haloalkyl, $C_{3-10}$ cycloalkyl, 4-10 membered heterocycloalkyl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ substituents;

- each $R^{84}$ is independently selected from H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, each of which is optionally substituted by 1, 2, 3, or 4 independently selected $R^G$ substituents;

- each $R^{85}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, $C_{3-10}$ cycloalkyl-$C_{1-4}$ alkyl, wherein said $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl are each optionally substituted by 1, 2, 3, or 4 independently selected $R^G$ substituents;

- each $R^9$ is independently H, $C_{1-4}$ alkyl, or $C_{1-4}$ haloalkyl;

- $R^1$ is selected from H, D, halo, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, OR$^{a1}$, SR$^{a1}$, NHOR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents;

- each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{14}$ substituents;

- or, any $R^{c1}$ and $R^{d1}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1A}$ substituents;

each $R^{1A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{a11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

or, any $R^{c11}$ and $R^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^2$ is selected from H, D, halo, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-4}$ cycloalkyl, $C_{1-3}$ alkoxy, $C_{1-3}$ haloalkoxy, amino, $C_{1-3}$ alkylamino, and di($C_{1-3}$ alkyl)amino;

each $R^3$ is independently selected from D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^4$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)NR^{c4}R^{d4}$, $NR^{c4}S(O)R^{b4}$, $NR^{c4}S(O)_2R^{b4}$, $NR^4S(O)_2NR^{c4}R^{d4}$ $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4A}$ substituents;

each $R^{a4}$, $R^{c4}$ and $R^{d4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4A}$ substituents;

or, any $R^{c4}$ and $R^{d4}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{4A}$ substituents;

each $R^{b4}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4A}$ substituents;

each $R^{4A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^4$, $NR^{c41}C(O)OR^{a41}$, $NR^{c41}C(O)NR^{c41}R^{d41}$, $NR^{c41}S(O)NR^{c41}R^{d41}$, $NR^{c41}S(O)R^{b41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{41}$, and $S(O)_2NR^{c41}R^{d41}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

or, any $R^{c41}$ and $R^{d41}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{4B}$ substituents;

each $R^{b41}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4B}$ substituents;

each $R^{4B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a42}$ $SR^{a42}$, $NHOR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)OR^{a42}$, $NR^{c42}C(O)NR^{c42}R^{d42}$, $NR^{c42}S(O)NR^{c42}R^{d42}$, $NR^{c42}S(O)R^{b42}$, $NR^{c42}S(O)_2R^{b42}$, $NR^{c42}S(O)_2NR^{c42}R^{d42}$, $S(O)R^{b42}$, $S(O)NR^{c42}R^{d42}$, $S(O)_2R^{b42}$, and $S(O)_2NR^{c42}R^{d42}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c42}$ and $R^{d42}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b42}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^5$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, NHOR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$; wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^{5A}$ substituents;

each R$^{a5}$, R$^{c5}$, and R$^{d5}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{5A}$ substituents;

or, any R$^{c5}$ and R$^{d5}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected R$^{5A}$ substituents;

each R$^{b5}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^{5A}$ substituents;

each R$^{5A}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, 5-10 membered heteroaryl-C$_{1-4}$ alkyl, OR$^{a51}$, SR$^{a51}$, NHOR$^{a51}$, C(O)R$^{b51}$, C(O)NR$^{c51}$R$^{d51}$, C(O)OR$^{a51}$ OC(O)R$^{b51}$, OC(O)NR$^{c51}$R$^{d51}$, NR$^{c51}$R$^{d51}$, NR$^{c51}$C(O)R$^{b51}$, NR$^{c51}$C(O)OR$^{a51}$, NR$^{c51}$C(O)NR$^{c51}$R$^{d51}$, NR$^{c51}$S(O)NR$^{c51}$R$^{d51}$, NR$^{c51}$S(O)R$^{b51}$, NR$^{c51}$S(O)$_2$R$^{b51}$ NR$^{c51}$S(O)$_2$NR$^{c51}$R$^{d51}$ S(O)R$^{b51}$, S(O)NR$^{c51}$R$^{d51}$, S(O)$_2$R$^{b51}$, and S(O)$_2$NR$^{c51}$R$^{d51}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-membered heteroaryl-C$_{1-4}$ alkyl are each optionally substituted with 1, 2, 3, or 4 independently selected R$^{5B}$ substituents;

each R$^{a51}$, R$^{c51}$, and R$^{d51}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{5B}$ substituents;

or, any R$^{c51}$ and R$^{d51}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected R$^{51}$ substituents;

each R$^{b51}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^{51}$ substituents;

each R$^{5B}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a52}$ SR$^{a52}$, NHOR$^{a52}$, C(O)R$^{b52}$, C(O)NR$^{c52}$R$^{d52}$, C(O)OR$^{a52}$, OC(O)R$^{b52}$, OC(O)NR$^{c52}$R$^{d52}$, NR$^{c52}$R$^{d52}$, NR$^{c52}$C(O)R$^{b52}$, NR$^{c52}$C(O)OR$^{a52}$, NR$^{c52}$C(O)NR$^{c52}$R$^{d52}$, NR$^{c52}$S(O)NR$^{c52}$R$^{d52}$, NR$^{c52}$S(O)R$^{b52}$, R$^{c52}$S(O)$_2$R$^{b52}$, NR$^{c52}$S(O)$_2$NR$^{c52}$R$^{d52}$, S(O)R$^{b52}$, S(O)NR$^{c52}$R$^{d52}$, S(O)$_2$R$^{b52}$, and S(O)$_2$NR$^{c52}$R$^{d52}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{5C}$ substituents;

each R$^{a52}$, R$^{c52}$, and R$^{d52}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{5C}$ substituents;

or, any R$^{c52}$ and R$^{d52}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected R$^{5C}$ substituents;

each R$^{b52}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5C}$ substituents;

each $R^{5C}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a53}$, $SR^{a53}$, $NHOR^{a53}$, $C(O)R^{b53}$, $C(O)NR^{c53}R^{d53}$, $C(O)OR^{a53}$, $OC(O)R^{b53}$, $OC(O)NR^{c53}R^{d53}$, $NR^{c53}R^{d53}$, $NR^{c53}C(O)R^{b53}$, $NR^{c53}C(O)OR^{a53}$, $NR^{c53}C(O)NR^{c53}R^{d53}$, $NR^{c53}S(O)NR^{c53}R^{d53}$, $NR^{c53}S(O)R^{b53}$, $NR^{c53}S(O)_2R^{b53}$, $NR^{c53}S(O)_2NR^{c53}R^{d53}$, $S(O)R^{b53}$, $S(O)NR^{c53}R^{d53}$, $S(O)_2R^{b53}$, and $S(O)_2NR^{c53}R^{d53}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a53}$, $R^{c53}$ and $R^{d53}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c53}$ and $R^{d53}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b53}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^{10}$, $R^{11}$, and $R^{12}$ are each independently selected from H, D, halo, CN, $C_{1-4}$ alkyl, $C_{1-4}$ haloalkyl, $C_{1-3}$ alkoxy, $C_{1-3}$ haloalkoxy, cyano-$C_{1-4}$ alkyl, HO—$C_{1-4}$ alkyl, $C_{1-3}$ alkoxy-$C_{1-4}$ alkyl, and $C_{3-4}$ cycloalkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments:
k is 1 or 2;
m is 0 or 1;
n is 0, 1, or 2;
p is 0, 1, or 2;
s is 0, 1, or 2;
each $\rule{1em}{0.4pt}\rule{0.5em}{0pt}\rule{1em}{0.4pt}$ is independently a single or a double bond;
X is N, Y is C, and Ring

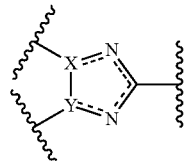

is

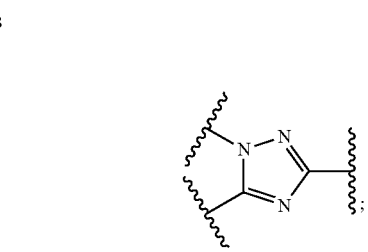

X is C, Y is N, and Ring

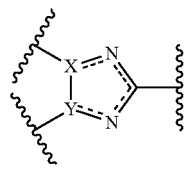

is

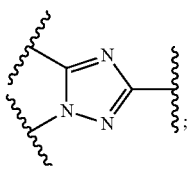 [SMILES: *c1nc(*)n(*)n1]

Z is $CR^2$ or N;
Ring moiety A is a 5-10 membered heteroaryl;
Ring moiety B is $C_{3-10}$ membered cycloalkyl or 4-10 membered heterocycloalkyl;
Ring moiety C is $C_{6-10}$ aryl, 5-10 membered heteroaryl, $C_{5-12}$ partially unsaturated cycloalkyl, or 5-12 membered partially unsaturated heterocycloalkyl;
E is a bond, —C(O)—, —$CH_2$—, —$CHR^6$—, —$CR^6R^7$—, or —O—, wherein $R^6$ and $R^7$ are each independently selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^W$, attached to the C ring, is independently:

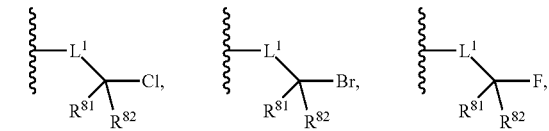

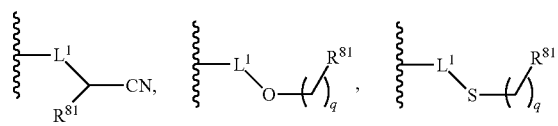

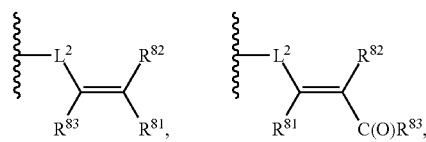

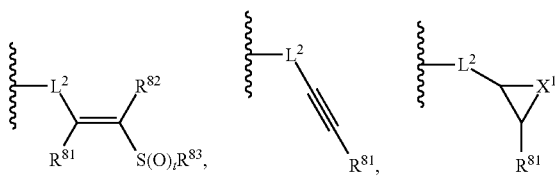

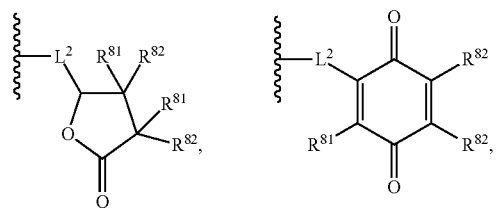

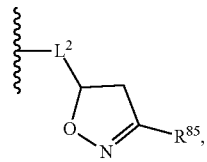

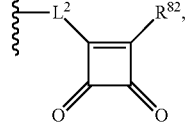

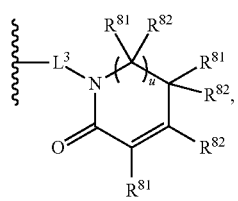

-continued

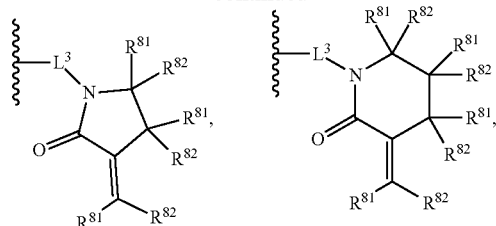

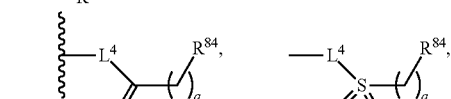

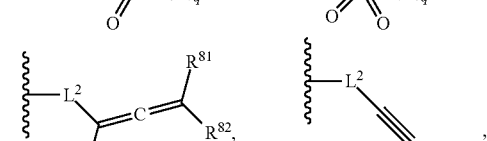

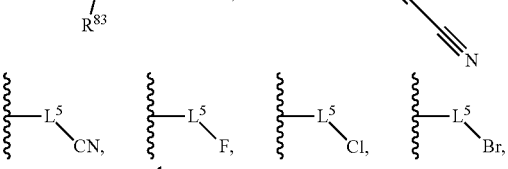

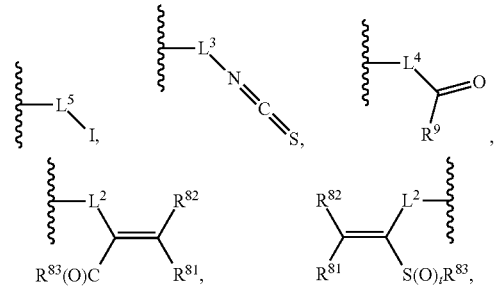

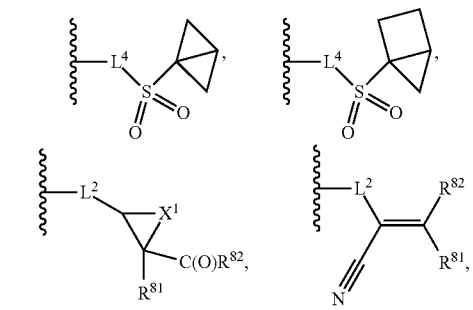

or $L^1$-Ar each $L^1$ is independently -L-C(O)—, -L-NR$^9$C(O)—, -L-OC(O)—, -L-S(O)—, -L-S(O)$_2$, -L-NR$^9$S(O)—, -L-OS(O)—, -L-NR$^9$S(O)$_2$— or -L-OS(O)$_2$—, wherein $L^2$ is attached to Ring moiety C through the L linking group;

each $L^2$ is independently -L-, -L-O—, -L-NR$^9$—, -L-S—, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)NR$^9$—, -L-NR$^9$S(O)O—, -L-OS(O)NR$^9$—, -L-NR$^9$S(O)$_2$—, -L-OS(O)$_2$—, -L-NR$^9$S(O)$_2$NR$^9$—, -L-NR$^9$S(O)$_2$O—, -L-S(O)(NR$^9$)—, -L-S(O)$_2$(NR$^9$)—, or -L-OS(O)$_2$NR$^9$—, wherein $L^2$ is attached to Ring moiety C through the L linking group;

each $L^3$ is independently -L-, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$—, or -L-OS(O)$_2$—, wherein $L^3$ is attached to Ring moiety C through the L linking group;

each $L^4$ is independently -L-, -L-O—, L-S—, -L-NR$^9$—, wherein $L^4$ is attached to Ring moiety C through the L linking group;

each $L^5$ is independently -L-O-$L^x$-, -L-NR$^9$-$L^x$-, -L-S-$L^x$-, -L-C(O)-$L^x$-, -L-NR$^9$C(O)-$L^x$-, -L-OC(O)-$L^x$-, -L-S(O)-$L^x$-, -L-S(O)$_2$-$L^x$-, -L-NR$^9$S(O)-$L^x$-, -L-OS(O)-$L^x$-, -L-NR$^9$S(O)NR$^9$-$L^x$-, -L-NR$^9$S(O)O-$L^x$-, -L-OS(O)NR$^9$-$L^x$-, -L-NR$^9$S(O)$_2$-$L^x$-, -L-OS(O)$_2$-$L^x$-, -L-NR$^9$S(O)$_2$NR$^9$-$L^x$-, -L-NR$^9$S(O)$_2$O-$L^x$-, -L-S(O)(NR$^9$)-$L^x$-, -L-S(O)$_2$(NR$^9$)-$L^x$-, or -L-OS(O)$_2$NR$^9$-$L^x$-, wherein $L^5$ is attached to Ring moiety C through the L linking group;

each L is independently is a bond or $C_{1-6}$ alkylene, wherein said $C_{1-6}$ alkylene is optionally substituted by 1, 2, 3 or 4 independently selected $R^G$ substituents;

each $L^x$ is independently is a $C_{1-6}$ alkylene, wherein said $C_{1-6}$ alkylene is optionally substituted by 1, 2, 3 or 4 independently selected $R^G$ substituents;

each $X^1$ is independently O or NR$^9$;

each q is independently 0, 1, or 2;

each t is independently 0, 1, or 2;

each u is independently 0, 1, or 2;

each Ar is independently $C_{6-10}$ aryl or 5-10 membered heteroaryl, which are each optionally substituted with 1, 2, 3, or 4 independently selected $R^{9A}$ substituents;

each $R^{81}$, $R^{82}$, and $R^{83}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, $C_{3-10}$ cycloalkyl-$C_{1-4}$ alkyl, 6-10 membered aryl-$C_{1-4}$ alkyl, 4-membered heterocycloalkyl-$C_{1-4}$ alkyl, and 5-10 membered heteroaryl-$C_{1-4}$ alkyl, wherein said $C_{1-6}$ alkyl, $C_{1-6}$ haloalkyl, $C_{3-10}$ cycloalkyl, 4-10 membered heterocycloalkyl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ substituents;

each $R^{84}$ is independently selected from H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, each of which is optionally substituted by 1, 2, 3, or 4 independently selected $R^G$ substituents;

each $R^{85}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl, wherein said $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl are each optionally substituted by 1, 2, 3, or 4 independently selected $R^G$ substituents;

each $R^9$ is independently H, $C_{1-4}$ alkyl, or $C_{1-4}$ haloalkyl;

$R^1$ is selected from H, D, halo, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, OR$^{a1}$, SR$^{a1}$, NHOR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{14}$ substituents;

or, any $R^{c1}$ and $R^{d1}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{14}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{14}$ substituents;

each $R^{14}$ is independently selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, OR$^{a11}$, SR$^{a11}$, NHOR$^{a11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O)R$^{b11}$, NR$^{c11}$C(O)OR$^{a11}$, NR$^{c11}$C(O)NR$^{c11}$R$^{d11}$, NR$^{c11}$S(O)NR$^{c11}$R$^{d11}$, NR$^{c11}$S(O)R$^{b11}$, NR$^{c11}$S(O)$_2$R$^{b11}$, NR$^{c11}$S(O)$_2$NR$^{c11}$R$^{d11}$, S(O)R$^{b11}$, S(O)NR$^{c11}$R$^{d11}$, S(O)$_2$R$^{b11}$, and S(O)$_2$NR$^{c11}$R$^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

or, any $R^{d1}$ and $R^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^2$ is selected from H, D, halo, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-4}$ cycloalkyl, $C_{1-3}$ alkoxy, $C_{1-3}$ haloalkoxy, amino, $C_{1-3}$ alkylamino, and di($C_{1-3}$ alkyl)amino;

each $R^3$ is independently selected from D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^4$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_3$-7 cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^5$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^{10}$ is H, D, halo, or $C_{1-4}$ alkyl;

$R^{11}$ and $R^{12}$ are each independently selected from H, D, halo, CN, $C_{1-4}$ alkyl, $C_{1-4}$ haloalkyl, $C_{1-3}$ alkoxy, $C_{1-3}$ haloalkoxy, cyano-$C_{1-4}$ alkyl, HO—$C_{1-4}$ alkyl, $C_{1-3}$ alkoxy-$C_{1-4}$ alkyl, and $C_{3-4}$ cycloalkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments:

k is 1 or 2;

m is 0 or 1;

n is 0, 1, or 2;

p is 0, 1, or 2;
s is 0, 1, or 2;
each ≡ is independently a single or a double bond;
X is N, Y is C, and Ring

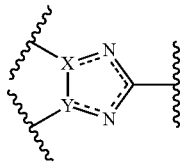

is

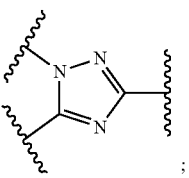 [SMILES: *c1nc(*)n(*)n1]

or

X is C, Y is N, and Ring

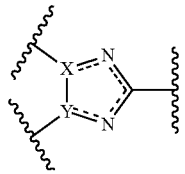

is

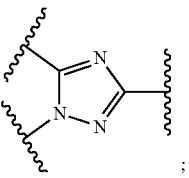 [SMILES: *c1nc(*)n(*)n1]

Z is CR² or N;
Ring moiety A is a monocyclic 5-6 membered heteroaryl;
Ring moiety B is monocyclic $C_{3-7}$ cycloalkyl or monocyclic 4-7 membered heterocycloalkyl;
Ring moiety C is $C_{6-10}$ aryl, 5-10 membered heteroaryl, or 5-12 membered partially unsaturated heterocycloalkyl;
E is a bond, —C(O)—, or —O—;
each $R^W$, attached to the C ring, is independently:

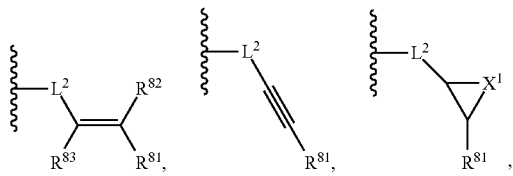

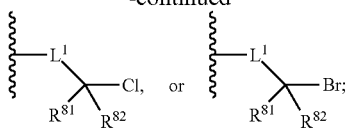

each $L^1$ is independently -L-C(O)— or -L-NR⁹C(O)—, wherein each $L^1$ is attached to Ring moiety C through the L linking group;
each $L^2$ is independently -L-C(O)— or -L-NR⁹C(O)—, wherein $L^2$ is attached to Ring moiety C through the L linking group.
each L is independently a bond or $C_{1-6}$ alkylene;
each $X^1$ is independently O or NR⁹;
each $R^{81}$, $R^{82}$, and $R^{83}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl;
each R⁹ is independently H, $C_{1-4}$ alkyl, or $C_{1-4}$ haloalkyl;
R¹ is selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, and $OR^{a1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents;
each $R^{a1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, and 5-6 membered heteroaryl are each optionally substituted with 1, 2, 3, or 4 independently selected $R^{1A}$ substituents;
each $R^{1A}$ is independently selected from H, D, halo, CN, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1B}$ substituents;
each $R^{1B}$ is independently selected from H, D, halo, CN, $C_{1-6}$ alkyl, $C_{2-6}$ alkenyl, $C_{2-6}$ alkynyl, and $C_{1-6}$ haloalkyl;
R² is selected from H, D, halo, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-4}$ cycloalkyl, $C_{1-3}$ alkoxy, $C_{1-3}$ haloalkoxy, amino, $C_{1-3}$ alkylamino, and di($C_{1-3}$ alkyl)amino;
each R³ is independently selected from D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;
each R⁴ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, C$_{1-3}$ alkylcarbonylamino, C$_{1-3}$ alkoxycarbonylamino, C$_{1-3}$ alkylaminocarbonyloxy, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino;

each R$^5$ is independently selected from D, halo, CN, NO$_2$, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-3}$ alkoxycarbonyl, C$_{1-3}$ alkylcarbonyloxy, C$_{1-3}$ alkylcarbonylamino, C$_{1-3}$ alkoxycarbonylamino, C$_{1-3}$ alkylaminocarbonyloxy, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino;

R$^{10}$ is H, D, halo, or C$_{1-4}$ alkyl; and

R$^{11}$ and R$^{12}$ are each independently selected from H, D, halo, CN, C$_{1-4}$ alkyl, C$_{1-4}$ haloalkyl, C$_{1-3}$ alkoxy, C$_{1-3}$ haloalkoxy, cyano-C$_{1-4}$ alkyl, HO—C$_{1-4}$ alkyl, C$_{1-3}$ alkoxy-C$_{1-4}$ alkyl, and C$_{3-4}$ cycloalkyl.

In some embodiments:

k is 1;

m is 0;

n is 0 or 1;

p is 0 or 1;

s is 0 or 1;

each ≡ is independently a single or a double bond;

X is N, Y is C, and Ring

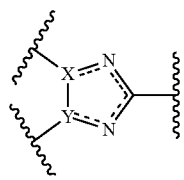

is

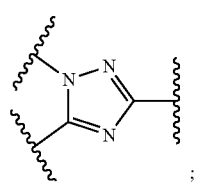 [SMILES: *c1nc(*)n(*)n1]

or

X is C, Y is N, and Ring

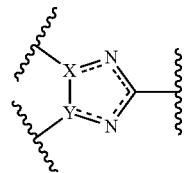

is

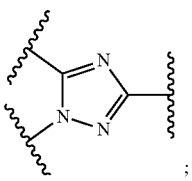 [SMILES: *c1nc(*)n(*)n1]

;

Z is CR$^2$ or N;

Ring moiety A is a monocyclic 5-membered heteroaryl;

Ring moiety B is monocyclic C$_{4-6}$ cycloalkyl or monocyclic 4-6 membered heterocycloalkyl;

Ring moiety C is phenyl, 5-10 membered heteroaryl, or 5-10 membered partially unsaturated heterocycloalkyl;

E is a bond, —C(O)—, or —O—;

R$^W$, attached to the C ring, is:

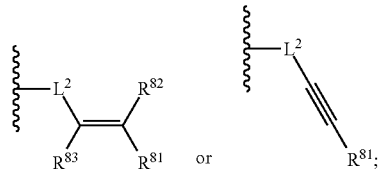

L$^2$ is -L-NR$^9$C(O)—, wherein L$^2$ is attached to Ring moiety C through the L linking group;

L is a bond;

R$^{81}$, R$^{82}$, and R$^{83}$ are each independently selected from H, halo, and C$_{1-6}$ alkyl;

R$^9$ is H or C$_{1-4}$ alkyl;

R$^1$ is selected from H, CN, C$_{1-6}$ alkyl, C$_{1-6}$ haloalkyl, and OR$^{a1}$, wherein said C$_{1-6}$ alkyl and C$_{1-6}$ haloalkyl are each optionally substituted with 1 or 2 independently selected R$^{1A}$ substituents;

each R$^{a1}$ is independently selected from C$_{1-6}$ alkyl, C$_{3-7}$ cycloalkyl, and 4-7 membered heterocycloalkyl, wherein each of which is optionally substituted with 1 or 2 independently selected R$^{1A}$ substituents;

each R$^{1A}$ is independently selected from halo and C$_{1-6}$ alkyl;

R$^2$ is selected from H and C$_{1-3}$ alkyl;

each R$^3$ is independently selected from halo and C$_{1-4}$ alkyl;

each R$^4$ is independently selected from halo and C$_{1-4}$ alkyl;

each R$^5$ is independently selected from halo and C$_{1-4}$ alkyl; and

R$^{10}$ is H.

In some embodiments, the compound of Formula (I) is a compound of Formula (Ia):

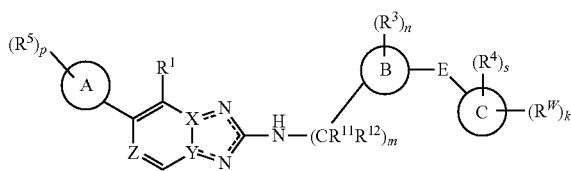

or a pharmaceutically acceptable salt thereof.

In some embodiments, the compound of Formula (I) is a compound of Formula (II):

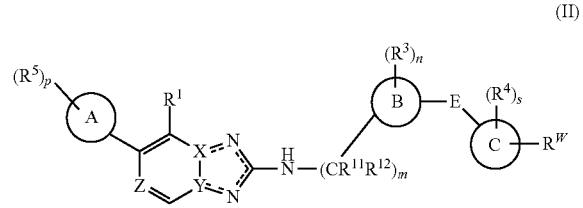

or a pharmaceutically acceptable salt thereof.

In some embodiments, the compound of Formula (I) is a compound of Formula (III):

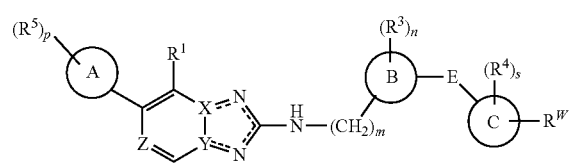

or a pharmaceutically acceptable salt thereof.

In some embodiments, the compound of Formula (I) is a compound of Formula (IV):

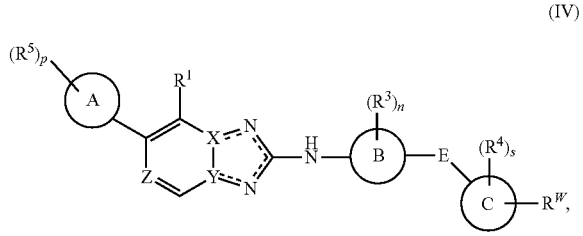

or a pharmaceutically acceptable salt thereof.

In some embodiments, the compound of Formula (I) is a compound of Formula (V):

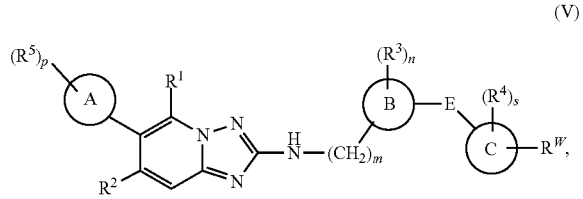

or a pharmaceutically acceptable salt thereof.

In some embodiments, the compound of Formula (I) is a compound of Formula (VI):

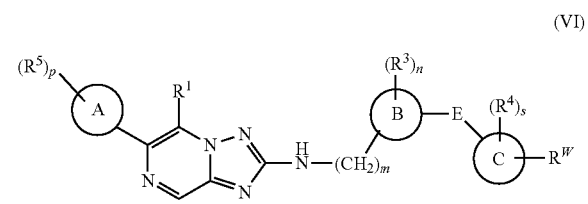

or a pharmaceutically acceptable salt thereof.

In some embodiments, the compound of Formula (I) is a compound of Formula

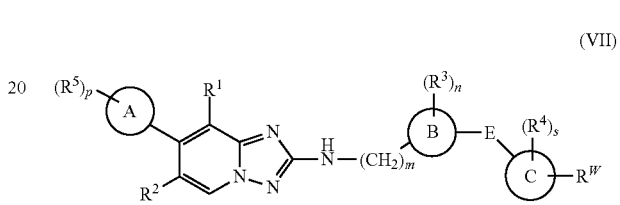

or a pharmaceutically acceptable salt thereof.

In some embodiments, the compound of Formula (I) is a compound of Formula (VIII):

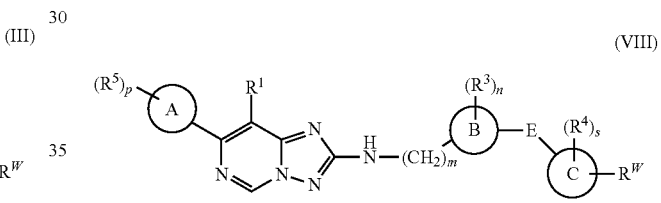

or a pharmaceutically acceptable salt thereof.

In some embodiments, the compound of Formula (I) is a compound of Formula (IX):

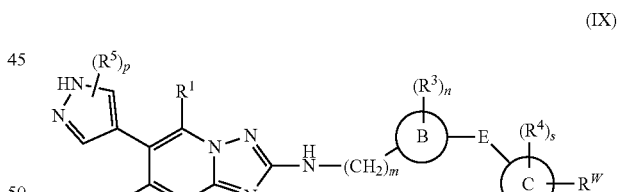

or a pharmaceutically acceptable salt thereof.

In some embodiments, the compound of Formula (I) is a compound of Formula

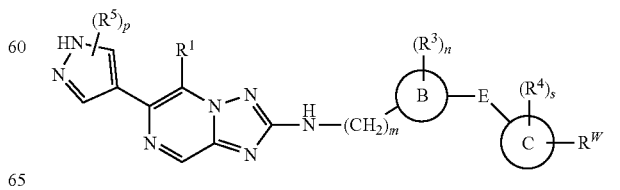

or a pharmaceutically acceptable salt thereof.

In some embodiments, the compound of Formula (I) is a compound of Formula (XI):

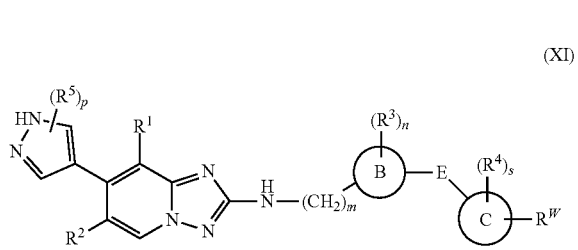

(XI)

or a pharmaceutically acceptable salt thereof.

In some embodiments, the compound of Formula (I) is a compound of Formula (XII):

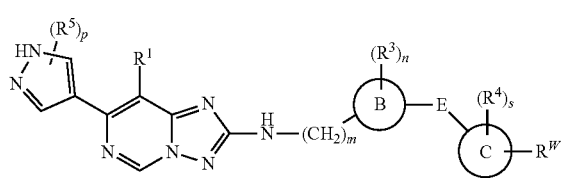

(XII)

or a pharmaceutically acceptable salt thereof.

In some embodiments, the compound of Formula (I) is a compound of Formula (XIII):

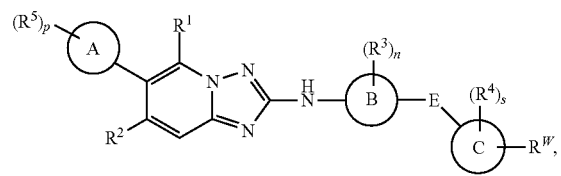

(XIII)

or a pharmaceutically acceptable salt thereof.

In some embodiments, the compound of Formula (I) is a compound of Formula (XIV):

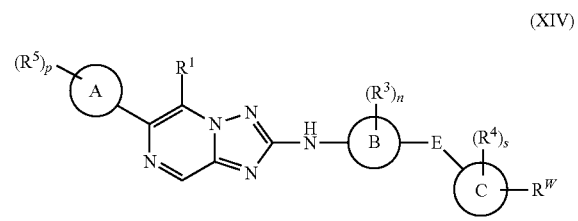

(XIV)

or a pharmaceutically acceptable salt thereof.

In some embodiments, the compound of Formula (I) is a compound of Formula (XV):

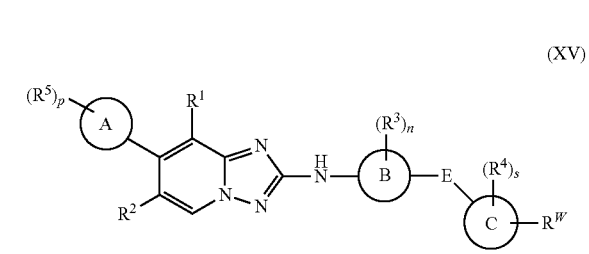

(XV)

or a pharmaceutically acceptable salt thereof.

In some embodiments, the compound of Formula (I) is a compound of Formula (XVI):

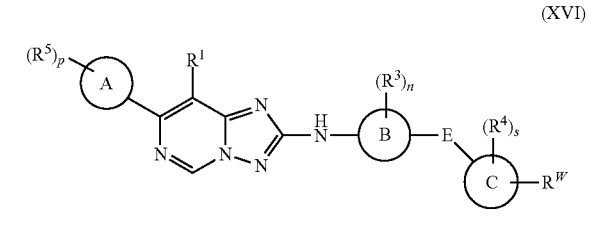

(XVI)

or a pharmaceutically acceptable salt thereof.

In some embodiments, the compound of Formula (I) is a compound of Formula (XVII):

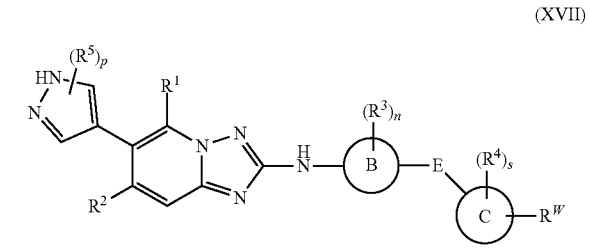

(XVII)

or a pharmaceutically acceptable salt thereof.

In some embodiments, the compound of Formula (I) is a compound of Formula (XVIII):

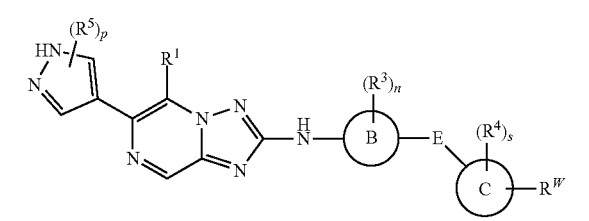

(XVIII)

or a pharmaceutically acceptable salt thereof.

In some embodiments, the compound of Formula (I) is a compound of Formula (XIX):

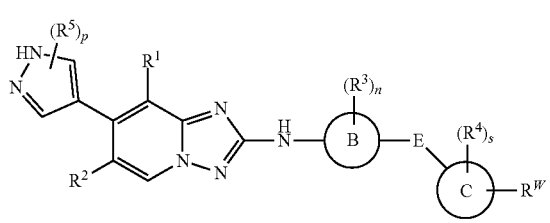

(XIX)

or a pharmaceutically acceptable salt thereof.

In some embodiments, the compound of Formula (I) is a compound of Formula (XX):

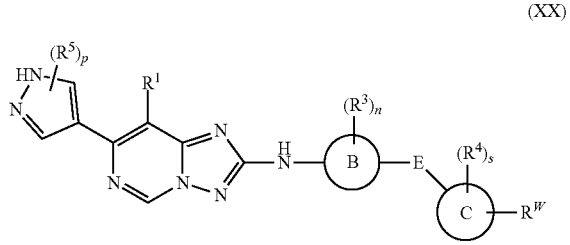

(XX)

or a pharmaceutically acceptable salt thereof.

In some embodiments, 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-4}$ alkyl-" and "alkylene" linking groups, as described herein, are optionally replaced by deuterium atoms.

It is further appreciated that certain features of the invention, which are, for clarity, described in the context of separate embodiments, can also be provided in combination in a single embodiment (as if the embodiments were written in multiply dependent form). Conversely, various features of the invention which are, for brevity, described in the context of a single embodiment, can also be provided separately or in any suitable subcombination.

At various places in the present specification, divalent linking substituents are described. Unless otherwise specified, it is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency, that the designated atom's normal valency is not exceeded, and that the substitution results in a stable compound.

As used herein, the term "independently selected from" means that each occurrence of a variable or substituent are independently selected at each occurrence from the applicable list.

As used herein, the phrase "each 'variable' is independently selected from" means substantially the same as wherein "at each occurrence 'variable' is selected from."

When any variable (e.g., $R^G$) occurs more than one time in any constituent or formula for a compound, its definition at each occurrence is independent of its definition at every other occurrence. Thus, for example, if a group is shown to be substituted with 1, 2, 3, or 4 independently selected $R^G$ substituents, then said group may optionally be substituted with up to four $R^G$ groups and $R^G$ at each occurrence is selected independently from the definition of $R^G$.

In some embodiments, when an optionally multiple substituent is designated in the form:

$$Q\underset{(CH_2)_n}{\overset{(R)_p}{\diagup}}$$

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (i-Pr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms. As used herein, the term "$C_{n-m}$ alkoxy", employed alone or in combination with other terms, refers to a group of formula-O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. In some embodiments, the aryl group has 6 to 10 carbon atoms. In some embodiments, the aryl group is phenyl or naphthyl. In some embodiments, the aryl is phenyl.

As used herein, "halo" refers to F, Cl, Br, or I. In some embodiments, halo is F, Cl, or Br. In some embodiments, halo is F or Cl. In some embodiments, halo is F. In some embodiments, halo is Cl.

As used herein, "$C_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group of the haloalkyl has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, the term "$C_{n-m}$ fluoroalkyl" refers to an alkyl group having from one fluoro atom to 2s+1 fluoro atoms, where "s" is the number of carbon atoms in the alkyl group, wherein the alkyl group has n to m carbon atoms. In some embodiments, the alkyl group of the fluoroalkyl has 1 to 6, 1 to 4, or 1 to 3 carbon atoms. Example fluoroalkyl groups include CF$_3$, C$_2$F$_5$, CHF$_2$, CH$_2$F, and the like.

As used herein, the term "thio" refers to a group of formula —SH.

As used herein, the term "$C_{n-m}$ alkylamino" refers to a group of formula —NH(alkyl), wherein the alkyl group has n to m carbon atoms. In some embodiments, the alkyl group of the alkylamino has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group of the alkoxycarbonyl has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group of the alkylcarbonyl has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group of the alkylcarbonylamino has 1 to 6, 1 to 4, or 1 to 3 carbon atoms.

As used herein, the term "$C_{n-m}$ alkoxycarbonylamino" refers to a group of formula —NHC(O)O($C_{n-m}$ alkyl), wherein the alkyl group has n to m carbon atoms. In some embodiments, the alkyl group of the alkoxycarbonylamino has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group of the alkylsulfonylamino has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group of the alkylaminosulfonyl has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group of the dialkylaminosulfonyl has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group of the alkylaminosulfonylamino has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group of the dialkylaminosulfonylamino has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group of the alkylaminocarbonylamino has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group of the dialkylaminocarbonylamino has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group of the alkylcarbamyl has 1 to 6, 1 to 4, or 1 to 3 carbon atoms.

As used herein, the term "$C_{n-m}$ alkylthio" refers to a group of formula —S-alkyl, wherein the alkyl group has n to m carbon atoms. In some embodiments, the alkyl group of the alkylthio has 1 to 6, 1 to 4, or 1 to 3 carbon atoms.

As used herein, the term "$C_{n-m}$ alkylsulfinyl" refers to a group of formula —S(O)— alkyl, wherein the alkyl group has n to m carbon atoms. In some embodiments, the alkyl group of the alkylsulfinyl has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group of the alkylsulfonyl has 1 to 6, 1 to 4, or 1 to 3 carbon atoms.

As used herein, the term "cyano-$C_{n-m}$ alkyl" refers to a group of formula —($C_{n-m}$ alkylene)-CN, wherein the alkylene group has n to m carbon atoms. As used herein, the term "cyano-$C_{1-6}$ alkyl" refers to a group of formula —($C_{1-6}$ alkylene)-CN. As used herein, the term "cyano-$C_{1-3}$ alkyl" refers to a group of formula —($C_{1-3}$ alkylene)-CN.

As used herein, the term "HO—$C_{n-m}$ alkyl" refers to a group of formula —($C_{n-m}$ alkylene)-OH, wherein the alkylene group has n to m carbon atoms. As used herein, the term "HO—$C_{1-3}$ alkyl" refers to a group of formula —($C_{1-3}$ alkylene)-OH.

As used herein, the term "$C_{n-m}$ alkoxy-$C_{o-p}$ alkyl" refers to a group of formula —($C_{n-m}$ alkylene)-O(Cop alkyl), wherein the alkylene group has n to m carbon atoms and the alkyl group has o to p carbon atoms. As used herein, the term "$C_{1-6}$ alkoxy-$C_{1-6}$ alkyl" refers to a group of formula —($C_{1-6}$ alkylene)-O($C_{1-6}$ alkyl). As used herein, the term "$C_{1-3}$ alkoxy-$C_{1-3}$ alkyl" refers to a group of formula —($C_{1-3}$ alkylene)-O($C_{1-3}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group of the dialkylamino independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group of the dialkylcarbamyl independently has 1 to 6, 1 to 4, or 1 to 3 carbon atoms.

As used herein, the term "$C_{n-m}$ alkylcarbonyloxy" is a group of formula —OC(O)— alkyl, wherein the alkyl group has n to m carbon atoms. In some embodiments, the alkyl group of the alkylcarbonyloxy has 1 to 6, 1 to 4, or 1 to 3 carbon atoms.

As used herein, "aminocarbonyloxy" is a group of formula —OC(O)—NH$_2$.

As used herein, "$C_{n-m}$ alkylaminocarbonyloxy" is a group of formula —OC(O)—NH— alkyl, wherein the alkyl group has n to m carbon atoms. In some embodiments, the alkyl group of the alkylaminocarbonyloxy has 1 to 6, 1 to 4, or 1 to 3 carbon atoms.

As used herein, "di($C_{n-m}$alkyl)aminocarbonyloxy" is a group of formula —OC(O)—N(alkyl)$_2$, wherein each alkyl group has, independently, n to m carbon atoms. In some embodiments, each alkyl group of the dialkylaminocarbonyloxy independently has 1 to 6, 1 to 4, or 1 to 3 carbon atoms.

As used herein "$C_{n-m}$ alkoxycarbonylamino" refers to a group of formula —NHC(O)—O-alkyl, wherein the alkyl group has n to m carbon atoms.

As used herein, the term "carbamyl" to a group of formula —C(O)NH$_2$.

As used herein, the term "carbonyl", employed alone or in combination with other terms, refers to a —C(O)— group.

As used herein, "cycloalkyl" refers to non-aromatic cyclic hydrocarbons including cyclized alkyl and alkenyl groups. For example, a "partially unsaturated" cycloalkyl refers to a cycloalkyl moiety, wherein at least one ring of the cycloalkyl is non-aromatic, but has at least one point of unsaturation. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2, 3, or 4 fused rings) aromatic heterocycle having at least one heteroatom ring member selected from N, O, or S. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, and S. In some embodiments, the heteroaryl group contains 5 to 10 or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridyl, pyrimidinyl, pyrazinyl, pyridazinyl, pyrrolyl, pyrazolyl, azolyl, oxazolyl, isoxazolyl, thiazolyl, isothiazolyl, imidazolyl, furyl, thienyl, triazolyl (e.g., 1,2,3-triazolyl, 1,2,4-triazolyl, 1,3,4-triazolyl), tetrazolyl, thiadiazolyl (e.g., 1,2,3-thiadiazolyl, 1,2,4-thiadiazolyl, 1,3,4-thiadiazolyl), quinolinyl, isoquinolinyl, indolyl, benzothienyl, benzofuranyl, benzisoxazolyl, benzoimidazolyl, benzothiazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, oxadiazolyl (e.g., 1,2,3-oxadiazolyl, 1,2,4-oxadiazolyl, 1,3,4-oxadiazolyl), 1,2-dihydro-1,2-azoborinyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, or S, and wherein the ring-forming carbon atoms and heteroatoms of the heterocycloalkyl group can be optionally substituted by one or more oxo or sulfido (e.g., C(O), S(O), C(S), or S(O)$_2$, etc.). As used herein, the term "partially unsaturated heteroacycloalkyl" refers to a heterocycloalkyl, wherein at least one ring of the heterocycloalkyl is non-aromatic, but has at least one point of unsaturation. Heterocycloalkyl groups include monocyclic and polycyclic (e.g., having 2 fused rings) systems. Included in heterocycloalkyl are monocyclic and polycyclic 4-10-, 4-7-, and 5-6-membered heterocycloalkyl groups. Heterocycloalkyl groups can also include spirocycles and bridged rings. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. A partially unsaturated heterocycloalkyl group which is bicyclic or polycyclic can also include a fused aromatic ring attached through any ring-forming atom including a ring-forming atom of the fused aromatic ring, as long as at least one ring of the partially saturated heterocycloalkyl is non-aromatic. In some embodiments, the heterocycloalkyl group contains 4 to 10 ring-forming atoms, 4 to 7 ring-forming atoms, 4 to 6 ring-forming atoms or 5 to 6 ring-forming atoms. In some embodiments, the heterocycloalkyl group has 1 to 4 heteroatoms, 1 to 3 heteroatoms, 1 to 2 heteroatoms or 1 heteroatom.

In some embodiments, the heterocycloalkyl is a 4-10 membered monocyclic, bicyclic, or tricyclic heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido. In some embodiments, the heterocycloalkyl is a 4-10 membered bicyclic heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido. In some embodiments, the heterocycloalkyl is a 4-7 membered monocyclic heterocycloalkyl having 1 or 2 ring-forming heteroatoms independently selected from N, O, and S, and wherein 1, 2 or 3 ring-forming carbon or heteroatoms can be optionally substituted by one or more oxo or sulfido. In some embodiments, the heterocycloalkyl is a monocyclic 4-6 membered heterocycloalkyl having 1 or 2 heteroatoms independently selected from N, O, S, and B and having one or more oxidized ring members.

Examples of heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, isoindolinonyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, azabicyclo[2.2.1]heptan-7-yl, azabicyclo[2.2.1]heptan-2-yl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxaadamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl, and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon ring members and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, the term "alkylene" refers a divalent straight chain or branched alkyl linking group. Examples of "alkylene groups" include methylene, ethan-1,1-diyl, ethan-1,2-diyl, propan-1,3-diyl, propan-1,2-diyl, propan-1,1-diyl and the like.

As used herein, the term "alkenylene" refers a divalent straight chain or branched alkenyl linking group. Examples of "alkenylene groups" include ethen-1,1-diyl, ethen-1,2-diyl, propen-1,3-diyl, 2-buten-1,4-diyl, 3-penten-1,5-diyl, 3-hexen-1,6-diyl, 3-hexen-1,5-diyl, and the like.

As used herein, the term "alkynylene" refers a divalent straight chain or branched alkynyl linking group. Examples of "alkynylene groups" include propyn-1,3-diyl, 2-butyn-1,4-diyl, 3-pentyn-1,5-diyl, 3-hexyn-1,6-diyl, 3-hexyn-1,5-diyl, and the like.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-diyl, propan-1,2-diyl, propan-1,1-diyl and the like.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent are independently selected at each occurrence from the applicable list.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g., hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of PharmaceuticalScience*, 66, 2 (1977), each of which is incorporated herein by reference in its entirety Synthesis As will be appreciated by those skilled in the art, the compounds provided herein, including salts and stereoisomers thereof, can be prepared using known organic synthesis techniques and can be synthesized according to any of numerous possible synthetic routes, such as those provided in the Schemes below.

The reactions for preparing compounds described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

The expressions, "ambient temperature" or "room temperature", or "r.t." as used herein, are understood in the art, and refer generally to a temperature, e.g., a reaction temperature, that is about the temperature of the room in which the reaction is carried out, for example, a temperature from about 20° C. to about 30° C.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry*: Reactions, *Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in the schemes below. Compounds of Formula (Ia) (i.e., compounds of Formula (I) wherein R$^{10}$ is H) can be prepared using a process as illustrated in Scheme 1 and Scheme 2.

Compounds of Formula 1-5 can be prepared, using processes as illustrated in Scheme 1. Compounds of formula 1-1a or 1-1b are subjected to reaction with ethoxycarbonyl isothiocyanate, followed by reaction with hydroxylammonium chloride in the presence of N,N-diisopropylethylamine to generate compounds of formula 1-2. Compounds 1-2 can undergo Pd-catalyzed cross-coupling reaction with compounds 1-3 to afford compounds of formula 1-4. Compounds 1-4 can be subjected to a nucleophilic aromatic substitution (e.g., S$_N$Ar) or a number of cross-coupling reactions, including Buchwald-Hartwig amination, Suzuki, Stille, Negishi, and others, to give compounds of formula 1-5. Alternatively, compounds of formula 1-1a or 1-1b can undergo Pd-catalyzed cross-coupling reactions with 1-3 to generate compounds of formula 1-6a or 1-6b. Reaction with ethoxycarbonyl isothiocyanate, followed by reaction with hydroxylammonium chloride in the presence of N,N-diisopropylethylamine then forms compounds of formula 1-4. Compounds of formula 1-7a or 1-7b can be subjected to a Pd-catalyzed cross-coupling reactions with 1-3 to generate compounds of formula 1-8a or 1-8b. Reaction with ethoxycarbonyl isothiocyanate, followed by reaction with hydroxylammonium chloride in the presence of N,N-diisopropylethylamine then forms compounds of formula 1-5. Alternatively, compounds of formula 1-7a or 1-7b can react with ethoxycarbonyl isothiocyanate, followed by reaction with hydroxylammonium chloride in the presence of N,N-diisopropylethylamine to generate compounds of formula 1-9. Pd-catalyzed cross-coupling reaction between 1-9 and 1-3 then forms compounds 1-5.

Scheme 1.

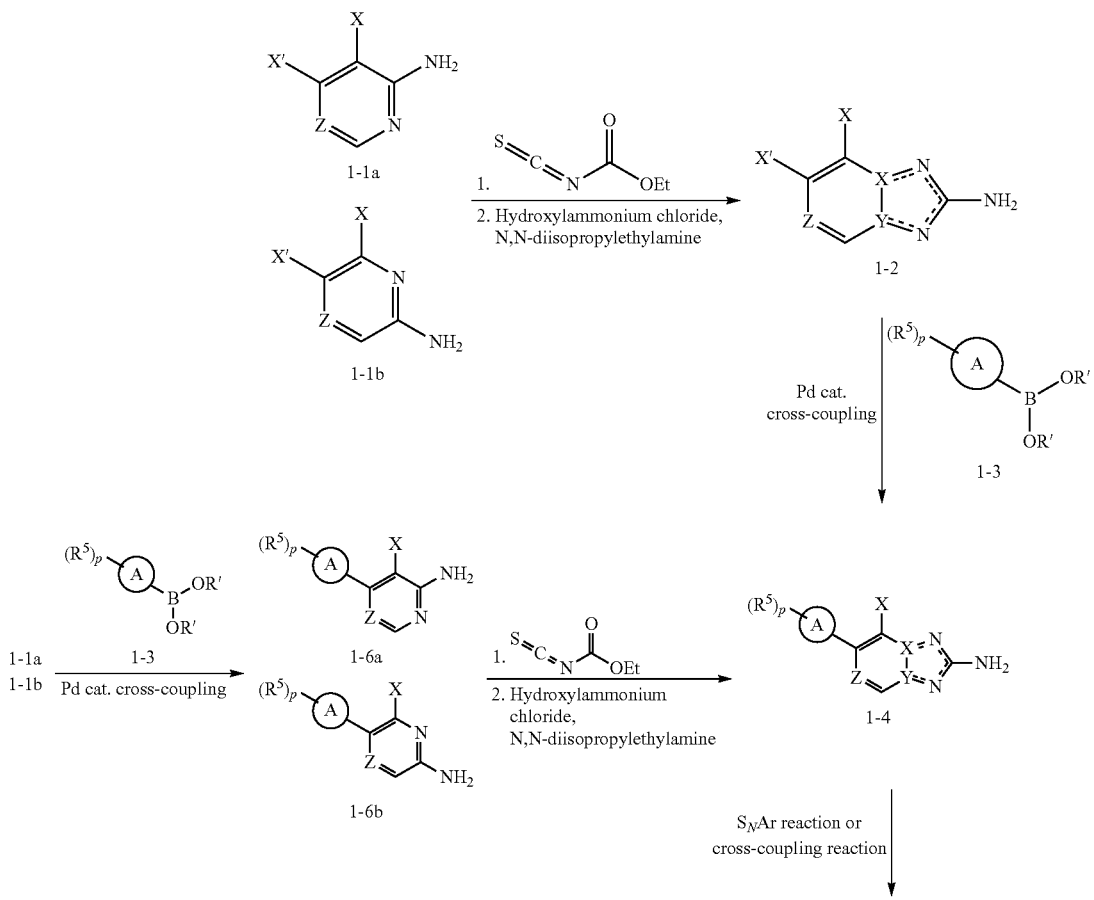

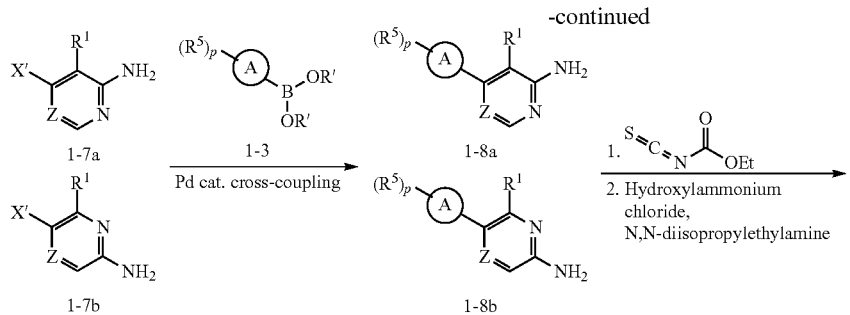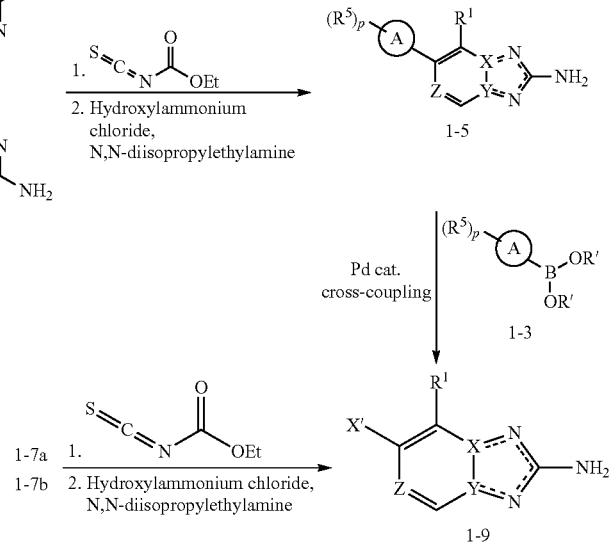

Compounds of Formula (Ia) can be prepared from compounds of formula 1-5 or compounds of formula 1-4, using processes as illustrated in Scheme 2. Sandmeyer reaction of compounds 1-5 generate compounds of formula 1-10. Alternatively, compound of formula 1-4 can undergo Sandmeyer reaction to generate compounds of formula 1-11, which can be subjected to a nucleophilic aromatic substitution (e.g., $S_NAr$) or a number of cross-coupling reactions, including Buchwald-Hartwig amination, Suzuki, Stille, Negishi, and others, to give compounds of formula 1-10. Compounds 1-10 can react with compounds of formula 1-12 under a nucleophilic aromatic substitution (e.g., $S_NAr$) or a number of cross-coupling reactions, including Pd-catalyzed Buchwald-Hartwig amination or Cu-catalyzed amination to give compounds of formula Ia. Alternatively, compounds 1-10 can react with compounds of formula 1-13 under a nucleophilic aromatic substitution (e.g., $S_NAr$) or a number of cross-coupling reactions, including Pd-catalyzed Buchwald-Hartwig amination or Cu-catalyzed amination to give compounds of formula 1-14. Compounds 1-14 can react with compounds of formula 1-15 to generate compounds of Formula (Ia).

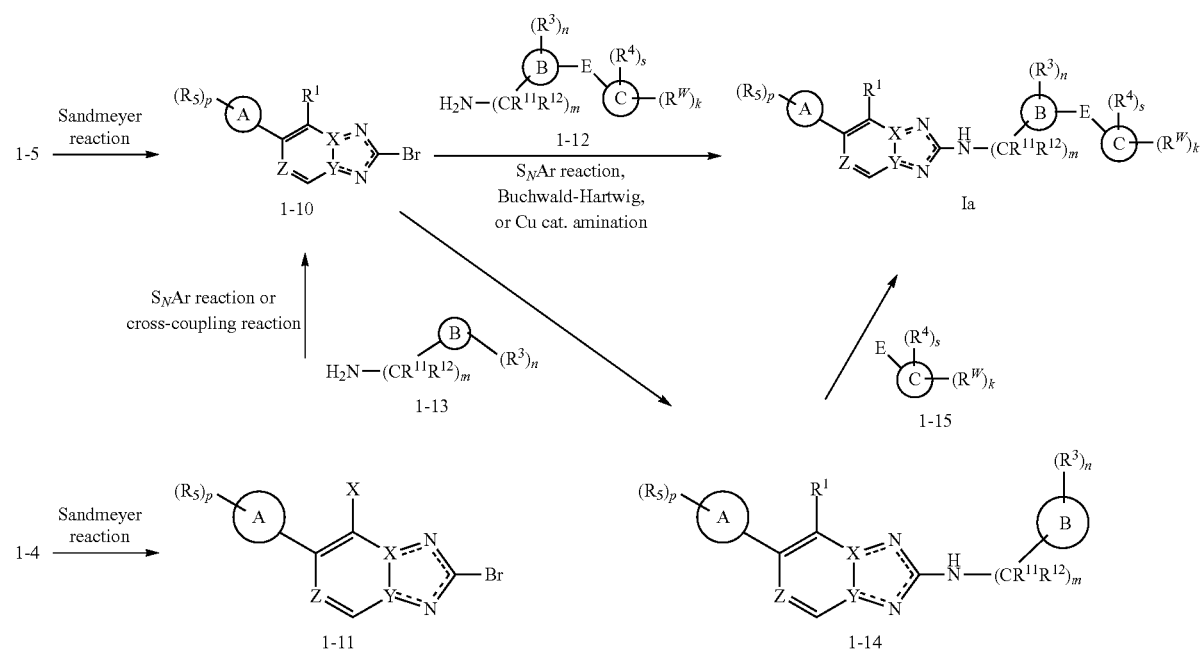

For the synthesis of particular compounds, the general schemes described above can be modified. For example, the products or intermediates can be modified to introduce particular functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: Advances in Heterocyclic Chemistry, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry*: Reactions, *Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

Methods of Use

Compounds of the present disclosure can inhibit CDK12 and therefore are useful for treating diseases wherein the underlying pathology is wholly or partially mediated by CDK12. Such diseases include cancer and other diseases with proliferation disorder. In some embodiments, the present disclosure provides treatment of an individual or a patient in vivo using a compound of Formula (I) or a salt thereof such that growth of cancerous tumors is inhibited. A compound of Formula (I) or of any of the formulas as described herein, or a compound as recited in any of the claims and described herein, or a salt thereof, can be used to inhibit the growth of cancerous tumors with aberrations that activate the CDK12 kinase activity.

Alternatively, a compound of Formula (I) or of any of the formulas as described herein, or a compound as recited in any of the claims and described herein, or a salt thereof, can be used in conjunction with other agents or standard cancer treatments, as described below.

In some embodiments, the present disclosure provides a method for inhibiting growth of tumor cells in vitro. The method includes contacting the tumor cells in vitro with a compound of Formula (I), or any of the formulas as described herein, or a compound as recited in any of the claims and described herein, or a salt thereof.

In some embodiments, provided herein is a method of inhibiting CDK12, comprising contacting the CDK12 with a compound of Formula (I), or any of the formulas as described herein, a compound as recited in any of the claims and described herein, or a salt thereof. In some embodiments, provided herein is a method of inhibiting CDK12 in a patient, comprising administering to the patient a compound of Formula (I), or any of the formulas as described herein, a compound as recited in any of the claims and described herein, or a salt thereof.

In some embodiments, the compounds of the present disclosure are selective inhibitors of CDK12 over one or more other CDKs. For example, some of the compounds described herein, or a pharmaceutically acceptable salts thereof, preferentially inhibit CDK12 over one or more of CDK1, CDK2, CDK4, CDK5, CDK6, CDK7, CDK9, and CDK13 as determined by one or more assays disclosed herein.

In some embodiments, the compounds of the present disclosure are selective inhibitors of CDK12 over one or more of CDK1, CDK2, CDK7, and CDK9.

In some embodiments, the compounds of the present disclosure are selective inhibitors of CDK12 over one or more of CDK1, CDK2, and CDK7.

In some embodiments, provided herein is a method for treating cancer. The method includes administering to a patient (in need thereof), a therapeutically effective amount of a compound of Formula (I), or any of the formulas as described herein, a compound as recited in any of the claims and described herein, or a salt thereof.

In some embodiments, provided herein is a method of treating a disease or disorder associated with CDK12 in a patient, comprising administering to the patient a therapeutically effective amount of a compound of Formula (I), or any of the formulas as described herein, a compound as recited in any of the claims and described herein, or a salt thereof.

In some embodiments, the disease or disorder associated with CDK12 is a cancer.

In some embodiments, the disease or disorder associated with CDK12 is a cancer which has been previously identified as homologous recombination deficiency (HRD) high. In some embodiments, the patient has been identified as a patient having homologous recombination deficiency (HRD). In some embodiments, the patient has been identified as having a positive test result for deleterious or suspected deleterious mutations in BRCA1 or BRCA2 genes. In some embodiments, the patient has been identified as having a positive Genomic Instability Score (see e.g., myChoice® CDx, Myriad Genetics, 2019, https://myriad.com/products-services/precision-medicine/mychoice-cdx/).

In some embodiments, the cancer is ovarian cancer, breast cancer, Ewing's sarcoma, osteosarcoma, liver cancer, hepatocellular carcinoma, or colorectal cancer.

In some embodiments, the cancer is ovarian cancer.

In some embodiments, the cancer is serous ovarian carcinoma.

In some embodiments, the cancer is HRD high grade serous ovarian carcinoma (see Bajrami, I., et al., *Cancer Res*, 2014. 74(1): 287-297).

In some embodiments, the cancer is breast cancer.

In some embodiments, the cancer is homologous recombination deficient breast cancer (see Johnson, S. F., et al., *Cell Rep*, 2016. 17(9): 2367-2381).

In some embodiments, the cancer is Ewing's sarcoma (see Iniguez, A. B., et al., *Cancer Cell*, 2018. 33(2): 202-216).

In some embodiments, the cancer is osteosarcoma (see Bayles, I., et al., *JCI*, 2019. 129(10): 4377-4392).

In some embodiments, the cancer is liver cancer.

In some embodiments, the cancer is hepatocellular carcinoma (see Wang, C., et al., *Gut*, 2020. 69(4): 727-736).

In some embodiments, the cancer is colorectal cancer (see Jiang, B., et al., *Nat. Chem. Biol.*, 2021. 17: 675-683; and Dieter, S. M., et al., *Cell Rep.*, 2021, 36, 109394).

In some embodiments, the cancer is uterine carcinosarcoma.

In some embodiments, the cancer is melanoma.

In some embodiments, the cancer is lung squamous cell carcinoma, lung adenocarcinoma, pancreatic adenocarcinoma, breast invasive carcinoma, uterine carcinosarcoma, ovarian serous cystadenocarcinoma, stomach adenocarcinoma, esophageal carcinoma, bladder urothelial carcinoma, mesothelioma, or sarcoma.

In some embodiments, the cancer is lung adenocarcinoma, breast invasive carcinoma, uterine carcinosarcoma, ovarian serous cystadenocarcinoma, or stomach adenocarcinoma.

In some embodiments, the cancer is an adenocarcinoma, carcinoma, or cystadenocarcinoma.

In some embodiments, the cancer is uterine cancer, ovarian cancer, stomach cancer, esophageal cancer, lung cancer, bladder cancer, pancreatic cancer, or breast cancer.

In some embodiments, the breast cancer is chemotherapy or radiotherapy resistant breast cancer, endocrine resistant breast cancer, trastuzumab resistant breast cancer, or breast cancer demonstrating primary or acquired resistance to CDK4/6 inhibition. In some embodiments, the breast cancer is advanced or metastatic breast cancer.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include melanoma (e.g., metastatic malignant melanoma, BRAF and HSP90 inhibition-resistant melanoma), renal cancer (e.g., clear cell carcinoma), prostate cancer (e.g., hormone refractory prostate adenocarcinoma), breast cancer, colon cancer, lung cancer (e.g., non-small cell lung cancer and small cell lung cancer), squamous cell head and neck cancer, urothelial cancer (e.g., bladder) and cancers with high microsatellite instability ($MSI^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including follicular lymphoma, including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer (SCLC), bronchogenic carcinoma, squamous cell, undifferentiated small cell, undifferentiated large cell, adenocarcinoma, alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, Merkel cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual", "patient," and "subject" used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The present disclosure further provides a compound described herein (i.e., a compound of Formula (I), or any of the formulas as described herein, a compound as recited in any of the claims and described herein, or a salt thereof), for use in any of the methods described herein.

The present disclosure further provides uses of a compound described herein (i.e., a compound of Formula (I), or any of the formulas as described herein, a compound as recited in any of the claims and described herein, or a salt thereof), for the preparation of a medicament for use in any of the methods described herein.

Combination Therapies

I. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions.

Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, and CDK4/6 kinase inhibitors such as, for example, those described in WO 2006/056399 can be used in combination with the compounds of the present disclosure for treatment of CDK12-associated diseases, disorders or conditions. Other agents such as therapeutic antibodies can be used in combination with the compounds of the present disclosure for treatment of CDK12-associated diseases, disorders or conditions. The one or more additional pharmaceutical agents can be administered to a patient simultaneously or sequentially.

In some embodiments, the CDK12 inhibitor is administered or used in combination with a BCL2 inhibitor or a CDK4/6 inhibitor.

The compounds as disclosed herein can be used in combination with one or more other enzyme/protein/receptor inhibitors therapies for the treatment of diseases, such as cancer and other diseases or disorders described herein. Examples of diseases and indications treatable with combination therapies include those as described herein. Examples of cancers include solid tumors and non-solid tumors, such as liquid tumors, and blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK4/6, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, fit-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCB54828), INCB62079), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2, e.g., ruxolitinib or baricitinib; JAK1, e.g., itacitinib (INCB39110), INCB052793, or INCB054707), an IDO inhibitor (e.g., epacadostat, NLG919, or BMS-986205, MK7162), an LSD1 inhibitor (e.g., GSK2979552, INCB59872 and INCB60003), a TDO inhibitor, a PI3K-delta inhibitor (e.g., parsaclisib (INCB50465) or INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer; e.g., INCB081776), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptosar, topotecan, paclitaxel, docetaxel, epothilones, tamoxifen, 5-fluorouracil, methotrexate, temozolomide, cyclophosphamide, SCH 66336, R115777, L778,123, BMS 214662, IRESSA™(gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR® (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteasome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a CDK12 inhibitor of the present disclosure with an additional agent.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa*.

Viruses causing infections treatable by methods of the present disclosure include, but are not limited to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis*.

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "*Physicians' Desk Reference*" (PDR, e.g., 1996 edition, Medical Economics Company, Montvale, NJ), the disclosure of which is incorporated herein by reference as if set forth in its entirety.

II. Immune-Checkpoint Therapies

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (IB1I308), AB122 (GLS-010), AMP-224, AMP-514/MEDI-0680, BMS936559, JTX-4014, BGB-108, SHR-1210, MEDI4736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217, 149, WO 03042402, WO 2008156712, WO 2010089411, WO 2010036959, WO 2011066342, WO 2011159877, WO 2011082400, or WO 2011161699, which are each incorporated herein by reference in its entirety.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L$^1$ antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MEDI1873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, R07009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), or more, such as about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating CDK12 in tissue samples, including human, and for identifying CDK12 activators by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes CDK12 assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups of the disclosed Formulas (e.g., Formula (I)) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene and alkynylene linking groups, as described herein, are optionally replaced by deuterium atoms.

Synthetic methods for including isotopes into organic compounds are known in the art (Deuterium Labeling in Organic Chemistry by Alan F. Thomas, New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et al. *J. Med. Chem.* 2011, 54, 201-210; R. Xu et al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro CDK12 labeling and competition assays, compounds that incorporate $^3$H, $^{14}$C, $^{82}$Br, $^{125}$I, $^{131}$I, or $^{35}$S can be useful. For radio-imaging applications $^{11}$C, $^{18}$F, $^{125}$I, $^{123}$I, $^{124}$I, $^{131}$I, $^{75}$Br, $^{76}$Br, or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S, and $^{82}$Br.

The present disclosure can further include synthetic methods for incorporating radio-isotopes into compounds of the disclosure. Synthetic methods for incorporating radio-isotopes into organic compounds are well known in the art, and one of ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind and activate CDK12 by monitoring its concentration variation when contacting with CDK12, through tracking of the labeling. For example, a test compound (labeled) can be evaluated for its ability to reduce binding of another compound which is known to inhibit CDK12 (i.e., standard compound). Accordingly, the ability of a test compound to compete with the standard compound for binding to CDK12 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of CDK12-associated diseases or disorders (such as, e.g., cancer) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g., "Two-Pump at-Column Dilution Configuration for Preparative LC-MS," K. Blom, J. Combi. Chem., 4, 295 (2002); "Optimizing Preparative LC-MS Configurations and Methods for Parallel Synthesis Purification," K. Blom, R. Sparks, J. Doughty, G. Everlof, T. Haque, A. Combs, J. Combi. Chem., 5, 670 (2003); and "Preparative LC-MS Purification: Improved Compound Specific Method Optimization," K. Blom, B. Glass, R. Sparks, A. Combs, J. Combi. Chem., 6, 874-883 (2004). The separated compounds were typically subjected to analytical liquid chromatography mass spectrometry (LCMS) for purity check under the following conditions: Instrument: Agilent 1100 series, LC/MSD; Column: Waters Sunfire™ $C_{18}$ 5 μm particle size, 2.1×5.0 mm; Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see "Preparative LCMS Purification: Improved Compound Specific Method Optimization," K. Blom, B. Glass, R. Sparks, A. Combs, J. Comb. Chem., 6, 874-883 (2004)). Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature (See "Preparative LCMS Purification: Improved Compound Specific Method Optimization," K. Blom, B. Glass, R. Sparks, A. Combs, J. Comb. Chem., 6, 874-883 (2004)). Typically, the flow rate used with 30×100 mm column was 60 mL/minute.

Example 1. N-(4-(3-((5-Isopropoxy-6-(1H-pyrazol-4-yl)-[1,2,4]triazolo[1,5-a]pyrazin-2-yl)amino)azetidine-1-carbonyl)phenyl)acrylamide

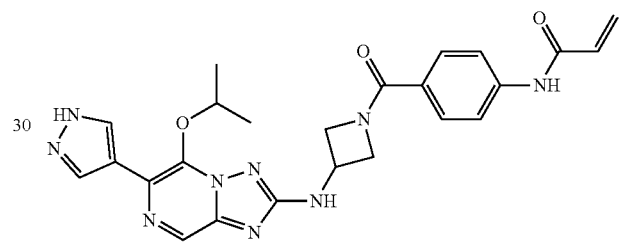

Step 1. 6-Chloro-5-(1-(1-ethoxyethyl)-1H-pyrazol-4-yl)pyrazin-2-amine

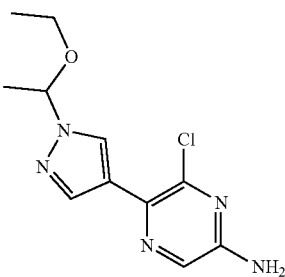 [SMILES: CCOC(C)n1cc(-c2ncc(N)nc2Cl)cn1]

A mixture of 5-bromo-6-chloropyrazin-2-amine (13 g, 62.4 mmol), 1-(1-ethoxyethyl)-4-(4,4,5,5-tetramethyl-1,3,2-dioxaborolan-2-yl)-1H-pyrazole (16.60 g, 62.4 mmol), 1,1'-bis(diphenylphosphino)ferrocene-palladium(II)dichloride dichloromethane complex (5.1 g, 6.24 mmol), and potassium phosphate, tribasic (26.5 g, 125 mmol) in 1,4-dioxane (100 mL) and water (20 mL) was purged with nitrogen and stirred at 90° C. overnight. After cooling to r.t., the reaction mixture was diluted with water and extracted with $CH_2Cl_2$. The organic phases were dried over $MgSO_4$, filtered, and concentrated. The crude material was purified by Biotage Isolera. The purification gave 15.2 g (91%) of the desired product. LC-MS calculated for $C_{11}H_{15}ClN_5O(M+H)^+$: m/z=268.1; found 268.0.

Step 2. 5-Chloro-6-(1-(1-ethoxyethyl)-1H-pyrazol-4-yl)-[1,2,4]triazolo[1,5-a]pyrazin-2-amine

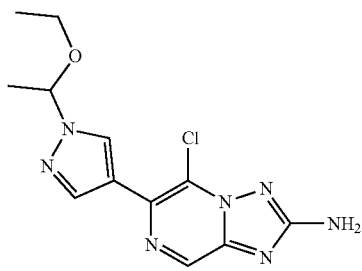 [SMILES: CCOC(C)n1cc(-c2ncc3nc(N)nn3c2Cl)cn1]

To a mixture of 6-chloro-5-(1-(1-ethoxyethyl)-1H-pyrazol-4-yl)pyrazin-2-amine (15.2 g, 56.8 mmol) in acetonitrile (160 mL) was added O-ethyl carbonisothiocyanatidate (10 mL, 85 mmol) and the reaction mixture was purged with nitrogen and stirred at 90° C. for 2 hours. The reaction mixture was concentrated in vacuo, and to the residue was added a mixture of hydroxylamine hydrochloride (11.84 g, 170 mmol) and DIPEA (29.7 mL, 170 mmol) in methanol (80 mL) and ethanol (80 mL) and the reaction mixture was stirred under nitrogen at 90° C. for 2 hours. After cooling to r.t., the reaction mixture was diluted with saturated aqueous NH$_4$Cl and extracted with CH$_2$Cl$_2$. The combined organic phases were dried over MgSO$_4$, filtered, and concentrated to ⅕ volume. The solid formed was filtered, rinsed with EtOAC/Hexane (⅕, v/v), and dried to give 8.20 g (47%) of desired product. LC-MS calculated for C$_{12}$H$_{15}$ClN$_7$O(M+H)$^+$: m/z=308.1; found 308.0.

Step 3. 2-Bromo-5-chloro-6-(1-(1-ethoxyethyl)-1H-pyrazol-4-yl)-[1,2,4]triazolo[1,5-a]pyrazine

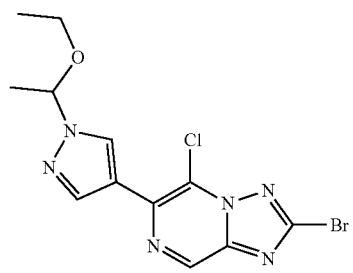 [SMILES: CCOC(C)n1cc(-c2ncc3nc(Br)nn3c2Cl)cn1]

A mixture of copper(II) bromide (8.9 g, 40.0 mmol) and tert-butyl nitrite (8.45 mL, 63.9 mmol) in acetonitrile (80 mL) was stirred at 60° C. for 30 minutes. After cooling to r.t., the mixture was added to a solution of 5-chloro-6-(1-(1-ethoxyethyl)-1H-pyrazol-4-yl)-[1,2,4]triazolo[1,5-a]pyrazin-2-amine (8.20 g, 26.6 mmol) in acetonitrile (80 mL), and the reaction mixture was stirred at ambient temperature for 1 h. The reaction mixture was then diluted with sat. aq. NaHCO$_3$ and extracted with CH$_2$Cl$_2$. The combined organic phases were dried over MgSO$_4$ and filtered. The filtrate was concentrated. The crude material was purified by Biotage Isolera. The purification gave 3.4 g (34%) of desired product. LC-MS calculated for C$_{12}$H$_{13}$BrClN$_6$O (M+H)$^+$: m/z=371.0; found 371.0.

Step 4. 2-Bromo-6-(1-(1-ethoxyethyl)-1H-pyrazol-4-yl)-5-isopropoxy-[1,2,4]triazolo[1,5-a]pyrazine

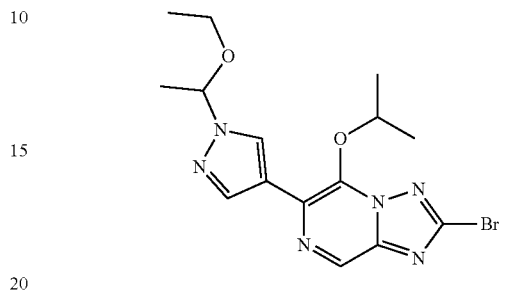

To a solution of propan-2-ol (1.85 mL, 24.22 mmol) in dioxane (50 mL) was added NaH (60%, 0.775 g, 19.37 mmol) portionwise, and the reaction mixture was stirred under nitrogen at r.t. After 15 min, 2-bromo-5-chloro-6-(1-(1-ethoxyethyl)-1H-pyrazol-4-yl)-[1,2,4]triazolo[1,5-a]pyrazine (6 g, 16.15 mmol) was added and the reaction mixture was stirred at r.t. for 15 minutes before heating to 130° C. for 2 hours. After cooling to r.t., the mixture was diluted with saturated aqueous NaHCO$_3$ and extracted with CH$_2$Cl$_2$. The combined organic layer was dried over MgSO$_4$, concentrated, and the crude residue was purified by Biotage Isolera. LC-MS calculated for C$_{15}$H$_{20}$BrN$_6$O$_2$(M+H)$^+$: m/z=395.1; found 395.1.

Step 5. N-(Azetidin-3-yl)-5-isopropoxy-6-(1H-pyrazol-4-yl)-[1,2,4]triazolo[1,5-a]pyrazin-2-amine

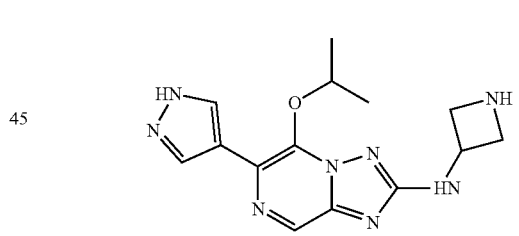

A mixture of tert-butyl 3-aminoazetidine-1-carboxylate (35 mg, 0.202 mmol), 2-bromo-6-(1-(1-ethoxyethyl)-1H-pyrazol-4-yl)-5-isopropoxy-[1,2,4]triazolo[1,5-α]pyrazine (80 mg, 0.202 mmol), AdBrettPhos Pd G3 (20 mg, 0.020 mmol), and sodium tert-butoxide (39 mg, 0.4 mmol) in 1,4-dioxane (2 mL) was sparged with nitrogen and heated to 110° C. for 2 hours. After cooling to r.t., the solution was diluted with sat. aq. NaHCO$_3$ and extracted with CH$_2$Cl$_2$. The organic phases were dried over MgSO$_4$ and concentrated, the crude material was purified by Biotage Isolera. The obtained intermediate was treated with DCM (0.5 mL) and TFA (0.5 mL) at r.t. for 2 h, and then concentrated to give desired product. LC-MS calculated for C$_{14}$H$_{19}$N$_8$O(M+H)$^+$: m/z=315.2; found 315.1.

Step 6. 4-Acrylamidobenzoic Acid

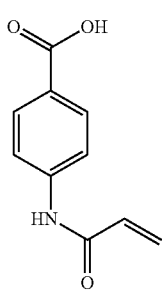

To a solution of tert-butyl 4-aminobenzoate (3.0 g, 15.52 mmol) and DIPEA (5.4 mL, 31.0 mmol) in 1,4-dioxane (30 mL) at 0° C. was added acryloyl chloride (1.4 mL, 17.1 mmol) slowly. The mixture was stirred at r.t. for 0.5 h. The mixture was then diluted with EtOAc. The organic layer was then washed with water and brine, dried and concentrated. The crude material was purified by Biotage Isolera. To the obtained intermediate in DCM (20 mL) at 0° C. was added TFA (20 mL, 260 mmol) slowly. The mixture was stirred at r.t. for 1 hour. The reaction mixture was concentrated, and the residue was stirred in diethyl ether (30 mL) for 30 min. The solid formed was filtered, washed with diethyl ether, and dried to give desired product as white solid. LC-MS calculated for $C_{10}H_{10}NO_3$ (M+H)$^+$: m/z=192.1; found 192.0.

Step 7. N-(4-(3-((5-Isopropoxy-6-(1H-pyrazol-4-yl)-[1,2,4]triazolo[1,5-a]pyrazin-2-yl)amino)azetidine-1-carbonyl)phenyl)acrylamide To a mixture of N-(azetidin-3-yl)-5-isopropoxy-6-(1H-pyrazol-4-yl)-[1,2,4]triazolo[1,5-a]pyrazin-2-amine (8 mg, 0.025 mmol) and 4-acrylamidobenzoic acid (5 mg, 0.025 mmol) in DMF (0.4 mL) at r.t. was added BOP (11 mg, 0.025 mmol), followed by DIPEA (4 μl, 0.025 mmol). The mixture was stirred at r.t. for 1 h. The mixture was diluted with CH$_3$CN and water, purified with prep-LCMS (XBridge C18 column, eluting with a gradient of acetonitrile/water containing 0.1% TFA, at flow rate of 60 mL/min) to obtain the desired product. LC-MS calculated for $C_{24}H_{26}N_9O_3$ (M+H)$^+$: m/z=488.2; found 488.1.

Example 2. N-(4-(4-((8-Methoxy-7-(1H-pyrazol-4-yl)-[1,2,4]triazolo[1,5-c]pyrimidin-2-yl)amino)piperidine-1-carbonyl)phenyl)acrylamide

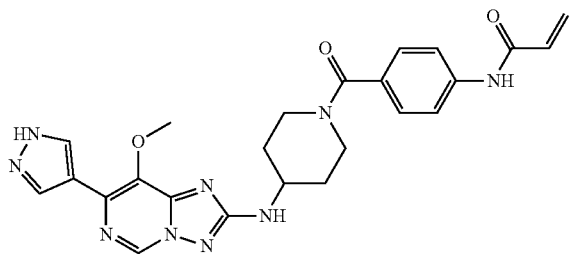 [SMILES: C=CC(=O)Nc1ccc(C(=O)N2CCC(Nc3nc4c(OC)c(-c5cn[nH]c5)ncn4n3)CC2)cc1]

Step 1. 7-Chloro-8-methoxy-[1,2,4]triazolo[1,5-c]pyrimidin-2-amine

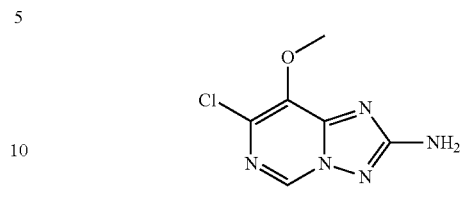

This compound was prepared according to the procedure described in Example 1, Step 2, using 6-chloro-5-methoxy-pyrimidin-4-amine instead of 6-chloro-5-(1-(1-ethoxyethyl)-1H-pyrazol-4-yl)pyrazin-2-amine as starting material. LC-MS calculated for $C_6H_7ClN_5O$ (M+H)$^+$: m/z=200.0; found 200.0.

Step 2. 7-(1-(1-Ethoxyethyl)-1H-pyrazol-4-yl)-8-methoxy-[1,2,4]triazolo[1,5-c]pyrimidin-2-amine

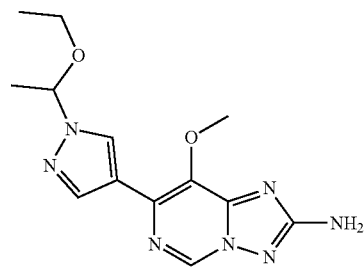 [SMILES: CCOC(C)n1cc(-c2ncn3nc(N)nc3c2OC)cn1]

This compound was prepared according to the procedure described in Example 1, Step 1, using 7-chloro-8-methoxy-[1,2,4]triazolo[1,5-c]pyrimidin-2-amine instead of 5-bromo-6-chloropyrazin-2-amine as starting material. LC-MS calculated for $C_{13}H_{18}N_7O_2$ (M+H)$^+$: m/z=304.1; found 304.1.

Step 3. 2-Bromo-7-(1-(1-ethoxyethyl)-1H-pyrazol-4-yl)-8-methoxy-[1,2,4]triazolo[1,5-c]pyrimidine

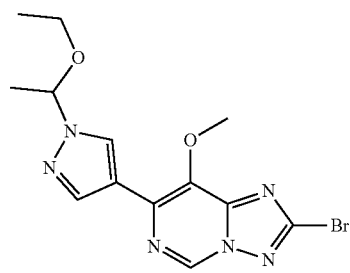 [SMILES: CCOC(C)n1cc(-c2ncn3nc(Br)nc3c2OC)cn1]

This compound was prepared according to the procedure described in Example 1, Step 3, using 7-(1-(1-ethoxyethyl)-1H-pyrazol-4-yl)-8-methoxy-[1,2,4]triazolo[1,5-c]pyrimidin-2-amine instead of 5-chloro-6-(1-(1-ethoxyethyl)-1H-pyrazol-4-yl)-[1,2,4]triazolo[1,5-a]pyrazin-2-amine as starting material. LC-MS calculated for $C_{13}H_{16}BrN_6O_2$(M+H)$^+$: m/z=367.0; found 367.0.

Step 4. 8-Methoxy-N-(piperidin-4-yl)-7-(1H-pyrazol-4-yl)-[1,2,4]triazolo[1,5-c]pyrimidin-2-amine

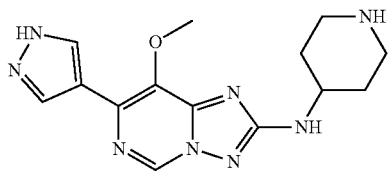 [SMILES: COc1c(-c2cn[nH]c2)ncn2nc(NC3CCNCC3)nc12]

This compound was prepared according to the procedure described in Example 1, Step 5, using tert-butyl 4-aminopiperidine-1-carboxylate and 2-bromo-7-(1-(1-ethoxyethyl)-1H-pyrazol-4-yl)-8-methoxy-[1,2,4]triazolo[1,5-c]pyrimidine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{14}H_{19}N_8O$ $(M+H)^+$: m/z=315.2; found 315.2.

Step 5. N-(4-(4-((8-methoxy-7-(1H-pyrazol-4-yl)-[1,2,4]triazolo[1,5-c]pyrimidin-2-yl)amino)piperidine-1-carbonyl)phenyl)acrylamide This compound was prepared according to the procedures described in Example 1, Step 7, using 8-methoxy-N-(piperidin-4-yl)-7-(1H-pyrazol-4-yl)-[1,2,4]triazolo[1,5-c]pyrimidin-2-amine instead of N-(azetidin-3-yl)-5-isopropoxy-6-(1H-pyrazol-4-yl)-[1,2,4]triazolo[1,5-a]pyrazin-2-amine as starting material. LC-MS calculated for $C_{24}H_{26}N_9O_3(M+H)^+$: m/z=488.2; found 488.3.

Example 3. N-(4-(3-((8-Methoxy-7-(1H-pyrazol-4-yl)-[1,2,4]triazolo[1,5-c]pyrimidin-2-yl)amino)azetidine-1-carbonyl)phenyl)acrylamide

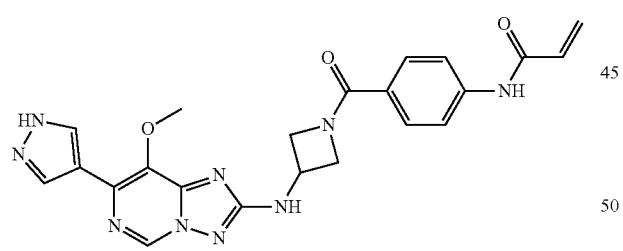

Step 1. N-(Azetidin-3-yl)-8-methoxy-7-(1H-pyrazol-4-yl)-[1,2,4]triazolo[1,5-c]pyrimidin-2-amine

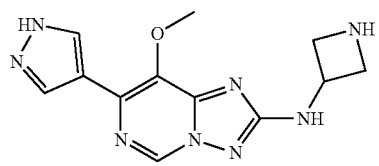 [SMILES: COc1c(-c2cn[nH]c2)ncn2nc(NC3CNC3)nc12]

This compound was prepared according to the procedure described in Example 1, Step 5, using 2-bromo-7-(1-(1-ethoxyethyl)-1H-pyrazol-4-yl)-8-methoxy-[1,2,4]triazolo[1,5-c]pyrimidine instead of 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{12}H_{15}N_8O(M+H)^+$: m/z=287.1; found 287.1.

Step 2. N-(4-(3-((8-Methoxy-7-(1H-pyrazol-4-yl)-[1,2,4]triazolo[1,5-c]pyrimidin-2-yl)amino)azetidine-1-carbonyl)phenyl)acrylamide This compound was prepared according to the procedure described in Example 1, Step 7, using N-(azetidin-3-yl)-8-methoxy-7-(1H-pyrazol-4-yl)-[1,2,4]triazolo[1,5-c]pyrimidin-2-amine instead of N-(azetidin-3-yl)-5-isopropoxy-6-(1H-pyrazol-4-yl)-[1,2,4]triazolo[1,5-a]pyrazin-2-amine as starting material. LC-MS calculated for $C_{22}H_{22}N_9O_3(M+H)^+$: m/z=460.2; found 460.2.

Example 4. (R)-N-(3-Fluoro-4-(3-((5-isopropoxy-6-(1H-pyrazol-4-yl)-[1,2,4]triazolo[1,5-a]pyrazin-2-yl)amino)piperidine-1-carbonyl)phenyl)acrylamide

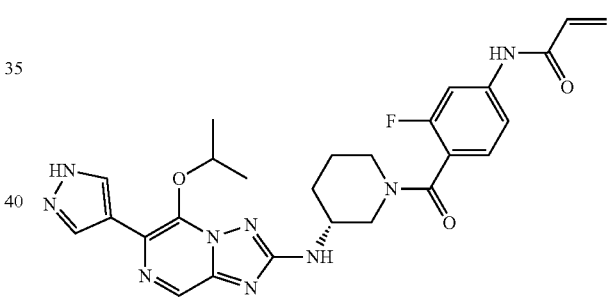

Step 1. (R)-5-Isopropoxy-N-(piperidin-3-yl)-6-(1H-pyrazol-4-yl)-[1,2,4]triazolo[1,5-a]pyrazin-2-amine

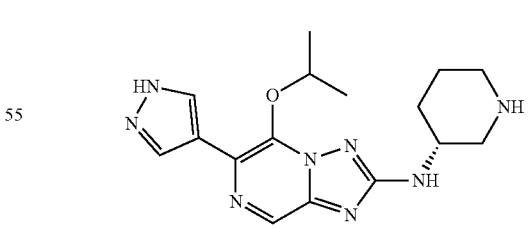

This compound was prepared according to the procedure described in Example 1, Step 5, using tert-butyl (R)-3-aminopiperidine-1-carboxylate instead of tert-butyl 3-aminoazetidine-1-carboxylate as starting material. LC-MS calculated for $C_{16}H_{23}N_8O$ $(M+H)^+$: m/z=343.2; found 343.1.

Step 2. 4-Acrylamido-2-fluorobenzoic acid

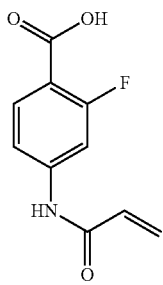

To a solution of methyl 4-amino-2-fluorobenzoate (0.80 g, 4.73 mmol) and DIPEA (1.65 mL, 9.46 mmol) in 1,4-dioxane (10 mL) at 0° C. was added acryloyl chloride (0.42 mL, 5.20 mmol) slowly. The mixture was stirred at r.t. for 0.5 h. The reaction mixture was then diluted with EtOAC, and the organic layer was washed with water and brine, dried, and concentrated. The residue was purified by Biotage Isolera. The obtained intermediate was dissolved in THF (10 mL) and acetonitrile (10 mL). To the mixture was added aqueous sodium hydroxide (1N, 10 mL). The reaction was stirred at r.t. for 2 h. The volatile was removed, the residue was adjusted to pH=4-5 with aqueous HCl (1N). The solid formed was filtered, washed with water, air-dried to give the desired product. LC-MS calculated for $C_{10}H_9FNO_3$ (M+H)$^+$: m/z=210.1; found 210.1.

Step 3. (R)-N-(3-Fluoro-4-(3-((5-isopropoxy-6-(1H-pyrazol-4-yl)-[1,2,4]triazolo[1,5-a]pyrazin-2-yl)amino)piperidine-1-carbonyl)phenyl)acrylamide This compound was prepared according to the procedure described in Example 1, Step 7, using (R)-5-isopropoxy-N-(piperidin-3-yl)-6-(1H-pyrazol-4-yl)-[1,2,4]triazolo[1,5-a]pyrazin-2-amine and 4-acrylamido-2-fluorobenzoic acid instead of N-(azetidin-3-yl)-5-isopropoxy-6-(1H-pyrazol-4-yl)-[1,2,4]triazolo[1,5-a]pyrazin-2-amine and 4-acrylamidobenzoic acid as starting material. LC-MS calculated for $C_{26}H_{29}FN_9O_3$ (M+H)$^+$: m/z=534.2; found 534.3.

Example 5. (R)-N-(4-(3-((8-Methoxy-7-(1H-pyrazol-4-yl)-[1,2,4]triazolo[1,5-c]pyrimidin-2-yl)amino)piperidine-1-carbonyl)phenyl)acrylamide

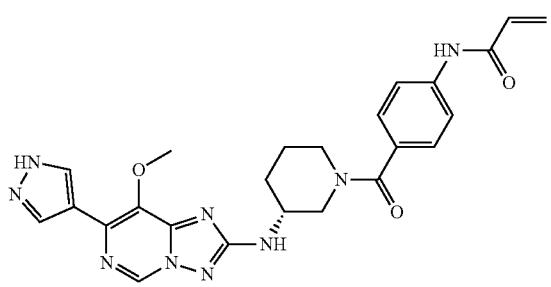 [SMILES: C=CC(=O)Nc1ccc(C(=O)N2CCC[C@@H](Nc3nc4c(OC)c(-c5cn[nH]c5)ncn4n3)C2)cc1]

Step 1. (R)-8-Methoxy-N-(piperidin-3-yl)-7-(1H-pyrazol-4-yl)-[1,2,4]triazolo[1,5-c]pyrimidin-2-amine

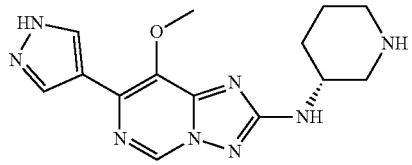 [SMILES: COc1c(-c2cn[nH]c2)ncn2nc(N[C@@H]3CCCNC3)nc12]

This compound was prepared according to the procedure described in Example 1, Step 5, using tert-butyl (R)-3-aminopiperidine-1-carboxylate and 2-bromo-7-(1-(1-ethoxyethyl)-1H-pyrazol-4-yl)-8-methoxy-[1,2,4]triazolo[1,5-c]pyrimidine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{14}H_{19}N_8O$ (M+H)$^+$: m/z=315.2; found 315.1.

Step 2. (R)-N-(4-(3-((8-methoxy-7-(1H-pyrazol-4-yl)-[1,2,4]triazolo[1,5-c]pyrimidin-2-yl)amino)piperidine-1-carbonyl)phenyl)acrylamide This compound was prepared according to the procedure described in Example 1, Step 7, using (R)-8-methoxy-N-(piperidin-3-yl)-7-(1H-pyrazol-4-yl)-[1,2,4]triazolo[1,5-c]pyrimidin-2-amine instead of N-(azetidin-3-yl)-5-isopropoxy-6-(1H-pyrazol-4-yl)-[1,2,4]triazolo[1,5-a]pyrazin-2-amine as starting material. LC-MS calculated for $C_{24}H_{26}N_9O_3$ (M+H)$^+$: m/z=488.2; found 488.3.

Example 6. (R)-N-(4-(3-((5-(Piperidin-1-yl)-6-(1H-pyrazol-4-yl)-[1,2,4]triazolo[1,5-a]pyridin-2-yl)amino)piperidine-1-carbonyl)phenyl)acrylamide

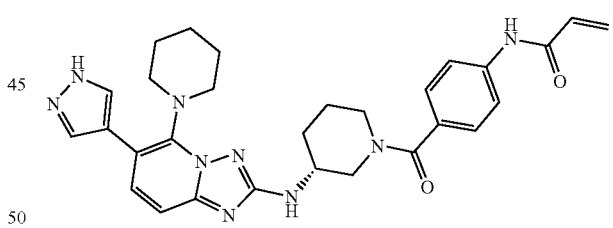

Step 1. 6-Bromo-5-chloro-[1,2,4]triazolo[1,5-a]pyridin-2-amine

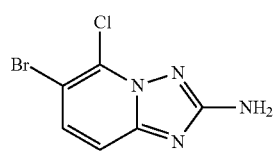 [SMILES: Nc1nc2ccc(Br)c(Cl)n2n1]

To a mixture of 5-bromo-6-chloropyridin-2-amine (5.0 g, 24.10 mmol) in MeCN (100 mL) was added ethoxycarbonyl isothiocyanate (3.27 mL, 28.9 mmol) and the mixture was stirred at 90° C. for 2 h. The mixture was then concentrated, and to the residue was added hydroxylammonium chloride (5.02 g, 72.3 mmol), N,N-diisopropylethylamine (12.63 mL, 72.3 mmol), MeOH (50 mL) and EtOH (50 mL). The reaction mixture was then heated to 90° C. for 2 h. The reaction mixture was then cooled to r.t, and MeCN (100 mL) was added. The precipitated solid was filtered, washed with MeCN, and air-dried to obtain clean product as an off-white solid. LCMS calculated for $C_6H_5BrClN_4$ $(M+H)^+$: m/z=246.9; found 246.9.

Step 2. 5-Chloro-6-(1-(1-ethoxyethyl)-1H-pyrazol-4-yl)-[1,2,4]triazolo[1,5-a]pyridin-2-amine

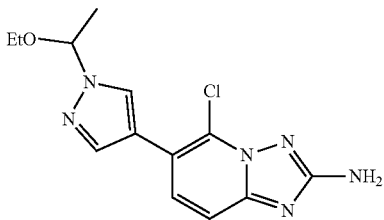 [SMILES: CCOC(C)n1cc(-c2ccc3nc(N)nn3c2Cl)cn1]

A mixture of 6-bromo-5-chloro-[1,2,4]triazolo[1,5-a]pyridin-2-amine (2.0 g, 8.08 mmol), 1-(1-ethoxyethyl)-4-(4,4,5,5-tetramethyl-1,3,2-dioxaborolan-2-yl)-1H-pyrazole (2.15 g, 8.08 mmol), Pd(dppf)Cl$_2$*DCM (0.66 g, 0.808 mmol), and tripotassium phosphate (5.15 g, 24.24 mmol) in dioxane (30 mL) and water (3 mL) was heated at 90° C. for 20 h. The reaction mixture was then cooled to r.t. and diluted with DCM and water. Organic layer was then extracted with DCM, washed with brine, dried with Na$_2$SO$_4$, filtered and concentrated. The crude was then purified by CombiFlash Rf+ Lumen to obtain product as an off-white solid (2.45 g, 8 mmol, 99% yield). LCMS calculated for $C_{13}H_{16}ClN_6O$ $(M+H)^+$: m/z=307.1; found 307.1.

Step 3. 2-Bromo-5-chloro-6-(1-(1-ethoxyethyl)-1H-pyrazol-4-yl)-[1,2,4]triazolo[1,5-a]pyridine

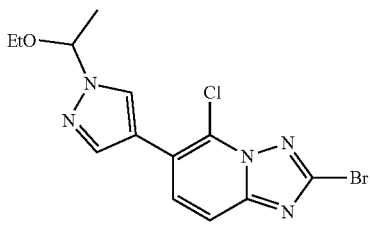 [SMILES: CCOC(C)n1cc(-c2ccc3nc(Br)nn3c2Cl)cn1]

To a mixture of 5-chloro-6-(1-(1-ethoxyethyl)-1H-pyrazol-4-yl)-[1,2,4]triazolo[1,5-a]pyridin-2-amine (2.45 g, 7.99 mmol) and copper(II) bromide (1.78 g, 7.99 mmol) in MeCN (40 mL) was added tert-butyl nitrite (90%, 2.64 mL, 19.97 mmol), and the resulting mixture was stirred at r.t. for 20 h. The reaction was then diluted with DCM and water. The organic layer was extracted with DCM, washed with brine and concentrated. The crude was then purified by CombiFlash Rf+ Lumen to obtain desired product (0.78 g, 2.1 mmol, 26% yield). LCMS calculated for $C_{13}H_{14}BrClN_5O$ $(M+H)^+$: m/z=370.0; found 369.9.

Step 4. 2-Bromo-6-(1-(1-ethoxyethyl)-1H-pyrazol-4-yl)-5-(piperidin-1-yl)-[1,2,4]triazolo[1,5-a]pyridine

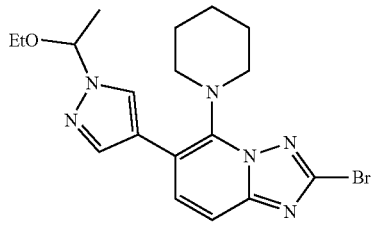 [SMILES: CCOC(C)n1cc(-c2ccc3nc(Br)nn3c2N2CCCCC2)cn1]

A mixture of 2-bromo-5-chloro-6-(1-(1-ethoxyethyl)-1H-pyrazol-4-yl)-[1,2,4]triazolo[1,5-a]pyridine (450 mg, 1.214 mmol), piperidine (126 µL, 1.275 mmol), cesium fluoride (369 mg, 2.428 mmol), and N,N-diisopropylethylamine (424 µL, 2.428 mmol) in DMSO (5 mL) was heated to 150° C. for 3 h. The reaction mixture was then cooled to r.t. and diluted with water and EtOAc. The organic layer was separated, washed with brine, dried with Na$_2$SO$_4$, filtered, and concentrated. The crude product was purified by CombiFlash Rf+ Lumen to obtain desired product (300 mg, 0.715 mmol, 59% yield). LCMS calculated for $C_{18}H_{24}BrN_6O$ $(M+H)^+$: m/z=419.1; found 419.1.

Step 5. (R)-5-(Piperidin-1-yl)-N-(piperidin-3-yl)-6-(1H-pyrazol-4-yl)-[1,2,4]triazolo[1,5-a]pyridin-2-amine

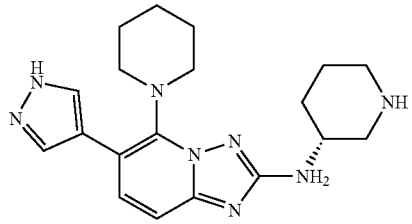 [SMILES: c1n[nH]cc1-c1ccc2nc(N[C@@H]3CCCNC3)nn2c1N1CCCCC1]

A mixture of 2-bromo-6-(1-(1-ethoxyethyl)-1H-pyrazol-4-yl)-5-(piperidin-1-yl)-[1,2,4]triazolo[1,5-a]pyridine (73 mg, 0.174 mmol), tert-butyl (R)-3-aminopiperidine-1-carboxylate (52 mg, 0.261 mmol), sodium tert-butoxide (33 mg, 0.348 mmol), and tBuBrettPhos Pd G3 (15 mg, 0.017 mmol) in dioxane (1.5 mL) was heated to 100° C. for 2 h. The reaction mixture was then cooled to r.t., diluted with EtOAc and water. The organic layer was separated, washed with brine, dried with Na$_2$SO$_4$, filtered and concentrated. The crude was purified by Combi-Flash (EtOAc/Hex then MeOH/DCM) to obtain tert-butyl (3R)-3-((6-(1-(1-ethoxyethyl)-1H-pyrazol-4-yl)-5-(piperidin-1-yl)-[1,2,4]triazolo[1,5-a]pyridin-2-yl)amino)piperidine-1-carboxylate (80 mg, 0.149 mmol, 85% yield). The above compound was then taken up in 1 mL DCM and 1 mL TFA was added. The reaction was stirred at r.t. for 1 hr. The solvent was then removed and the crude product was purified by CombiFlash Rf+ Lumen to obtain desired product. LCMS calculated for $C_{19}H_{27}N_8$ $(M+H)^+$: m/z=367.2; found 367.2.

Step 6. (R)-N-(4-(3-((5-(Piperidin-1-yl)-6-(1H-pyrazol-4-yl)-[1,2,4]triazolo[1,5-a]pyridin-2-yl)amino)piperidine-1-carbonyl)phenyl)acrylamide A mixture of (R)-5-(piperidin-1-yl)-N-(piperidin-3-yl)-6-(1H-pyrazol-4-yl)-[1,2,4]triazolo[1,5-a]pyridin-2-amine (30 mg, 0.082 mmol), 4-acrylamidobenzoic acid (17 mg, 0.090 mmol), HATU (41 mg, 0.106 mmol), and N,N-diisopropylethylamine (43 μL, 0.246 mmol) in DMF (1 mL) was stirred at r.t. for 1 h. The resulting mixture was diluted with MeCN and purified with prep-LCMS (XBridge C18 column, eluting with a gradient of acetonitrile/water containing 0.1% TFA, at flow rate of 60 mL/min). LCMS calculated for $C_{29}H_{34}N_9O_2$ (M+H)+: m/z=540.3; found 540.3.

Example 7. (R)-N-(4-(3-((6-(1H-Pyrazol-4-yl)-5-(pyrrolidin-1-yl)-[1,2,4]triazolo[1,5-a]pyridin-2-yl)amino)piperidine-1-carbonyl)phenyl)acrylamide

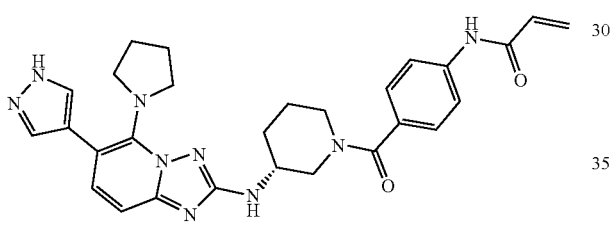

This compound was prepared according to the procedures described in Example 6, using pyrrolidine instead of piperidine as starting material. LCMS calculated for $C_{28}H_{32}N_9O_2$ (M+H)+: m/z=526.3; found: 526.3.

Example 8. (R)-N-(4-(3-((5-Morpholino-6-(1H-pyrazol-4-yl)-[1,2,4]triazolo[1,5-a]pyridin-2-yl)amino)piperidine-1-carbonyl)phenyl)acrylamide

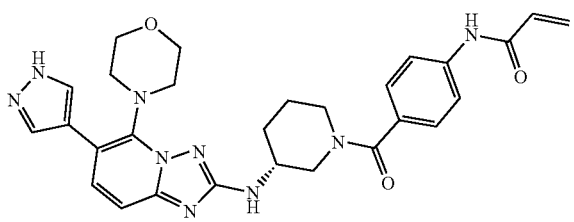 [SMILES: C=CC(=O)Nc1ccc(C(=O)N2CCC[C@@H](Nc3nc4ccc(-c5cn[nH]c5)c(N5CCOCC5)n4n3)C2)cc1]

This compound was prepared according to the procedures described in Example 6, using morpholine instead of piperidine as starting material. LCMS calculated for $C_{28}H_{32}N_9O_3$ (M+H)+: m/z=542.3; found: 542.1.

Example 9. N-(4-(3-((6-(3-Methyl-1H-pyrazol-4-yl)-5-morpholino-[1,2,4]triazolo[1,5-a]pyridin-2-yl)amino)piperidine-1-carbonyl)phenyl)acrylamide

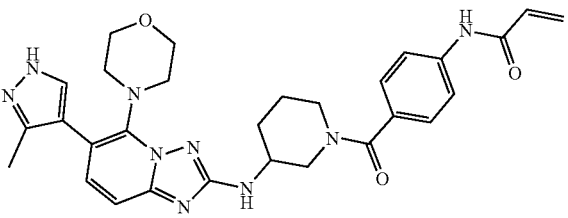 [SMILES: C=CC(=O)Nc1ccc(C(=O)N2CCCC(Nc3nc4ccc(-c5c[nH]nc5C)c(N5CCOCC5)n4n3)C2)cc1]

Step 1. 6-Bromo-5-morpholino-[1,2,4]triazolo[1,5-a]pyridin-2-amine

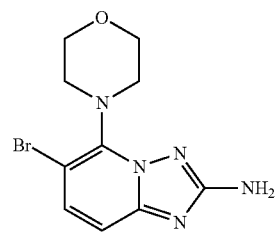 [SMILES: Nc1nc2ccc(Br)c(N3CCOCC3)n2n1]

A mixture of 6-bromo-5-chloro-[1,2,4]triazolo[1,5-a]pyridin-2-amine (1.0 g, 4.04 mmol), morpholine (0.4 mL, 4.44 mmol), cesium fluoride (1.2 g, 8.08 mmol), and N,N-diisopropylethylamine (1.4 mL, 8.08 mmol) in DMSO (5 mL) was irradiated in a microwave at 150° C. for 3 h. The reaction mixture was cooled to r.t. and water was added. The precipitated solid was filtered, washed with water and air-dried overnight to obtain the desired product, which was used directly in the next step. LCMS calculated for $C_{10}H_{13}BrN_5O$(M+H)+: m/z=298.0; found 298.0.

Step 2. Benzyl 3-((6-bromo-5-morpholino-[1,2,4]triazolo[1,5-a]pyridin-2-yl)amino)piperidine-1-carboxylate

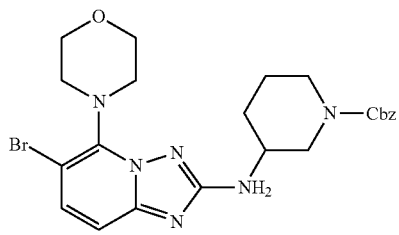 [SMILES: O=C(OCc1ccccc1)N1CCCC(Nc2nc3ccc(Br)c(N4CCOCC4)n3n2)C1]

A mixture of 6-bromo-5-morpholino-[1,2,4]triazolo[1,5-a]pyridin-2-amine (0.87 g, 2.92 mmol), benzyl 3-oxopiperidine-1-carboxylate (2 g, 8.75 mmol) in DMF (7.30 mL) and TFA (7.30 mL) was stirred at r.t. After 2 days, sodium triacetoxyborohydride (1.9 g, 8.75 mmol) was added and the resulting mixture was stirred overnight. The solvent was removed and the reaction crude was then diluted with DCM, water and sat. aq. NaHCO₃. The organic layer was extracted with DCM, washed with brine, dried with Na$_2$SO$_4$, filtered and concentrated. The crude product was purified by CombiFlash Rf+ Lumen to obtain desired product. LCMS calculated for C$_{23}$H$_{28}$BrN$_6$O$_3$(M+H)$^+$: m/z=515.1; found 515.1.

Step 3. Benzyl 3-((6-(3-methyl-1H-pyrazol-4-yl)-5-morpholino-[1,2,4]triazolo[1,5-a]pyridin-2-yl)amino)piperidine-1-carboxylate

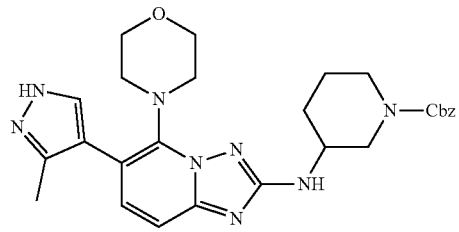 [SMILES: Cc1n[nH]cc1-c1ccc2nc(NC3CCCN(C(=O)OCc4ccccc4)C3)nn2c1N1CCOCC1]

A mixture of benzyl 3-((6-bromo-5-morpholino-[1,2,4]triazolo[1,5-a]pyridin-2-yl)amino)piperidine-1-carboxylate (100 mg, 0.194 mmol), 3-methyl-4-(4,4,5,5-tetramethyl-1,3,2-dioxaborolan-2-yl)-1H-pyrazole (81 mg, 0.388 mmol), potassium phosphate, tribasic (82 mg, 0.388 mmol), and XPhos Pd G2 (46 mg, 0.058 mmol) in dioxane (2 mL) and water (0.4 mL) was heated to 85° C. for 3 h. The reaction was then diluted with DCM and water. The organic layer was extracted with DCM, washed with brine and concentrated. The crude was then purified by CombiFlash Rf+ Lumen to obtain desired product. LCMS calculated for C$_{27}$H$_{33}$N$_8$O$_3$ (M+H)$^+$: m/z=517.3; found 517.3.

Step 4. 6-(3-Methyl-1H-pyrazol-4-yl)-5-morpholino-N-(piperidin-3-yl)-[1,2,4]triazolo[1,5-a]pyridin-2-amine

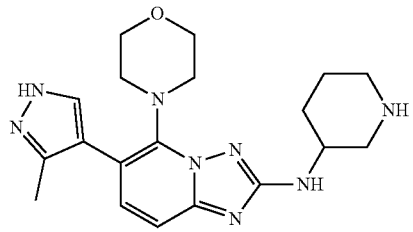 [SMILES: Cc1n[nH]cc1-c1ccc2nc(NC3CCCNC3)nn2c1N1CCOCC1]

A mixture of benzyl 3-((6-(3-methyl-1H-pyrazol-4-yl)-5-morpholino-[1,2,4]triazolo[1,5-a]pyridin-2-yl)amino)piperidine-1-carboxylate (47 mg, 0.091 mmol), Pd on carbon (10%, 19 mg, 0.018 mmol) in MeOH (3 mL) and dioxane (0.5 mL) was stirred under a hydrogen balloon for 20 h. The reaction mixture was then diluted with MeOH, filtered through celite and concentrated. The obtained product was used directly in the next step. LCMS calculated for C$_{19}$H$_{27}$N$_8$O (M+H)$^+$: m/z=383.2; found 383.2.

Step 5. N-(4-(3-((6-(3-Methyl-1H-pyrazol-4-yl)-5-morpholino-[1,2,4]triazolo[1,5-a]pyridin-2-yl)amino)piperidine-1-carbonyl)phenyl)acrylamide A mixture of 6-(3-methyl-1H-pyrazol-4-yl)-5-morpholino-N-(piperidin-3-yl)-[1,2,4]triazolo[1,5-a]pyridin-2-amine (25 mg, 0.065 mmol), HATU (32 mg, 0.085 mmol), 4-acrylamidobenzoic acid (14 mg, 0.072 mmol), and N,N-diisopropylethylamine (34 μL, 0.2 mmol) in DMF (1 mL) was stirred at r.t. for 1 hr. The resulting mixture was diluted with MeCN and purified with prep-LCMS (XBridge C18 column, eluting with a gradient of acetonitrile/water containing 0.1% TFA, at flow rate of 60 mL/min). LCMS calculated for C$_{29}$H$_{34}$N$_9$O$_3$ (M+H)$^+$: m/z=556.3; found 556.3.

Example 10. (R)-N-(4-(3-((5-(3,3-Difluorocyclobutoxy)-6-(1H-pyrazol-4-yl)-[1,2,4]triazolo[1,5-a]pyrazin-2-yl)amino)piperidine-1-carbonyl)phenyl)acrylamide

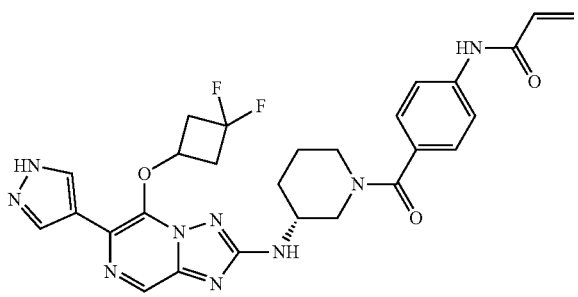 [SMILES: C=CC(=O)Nc1ccc(C(=O)N2CCC[C@@H](Nc3nc4cnc(-c5cn[nH]c5)c(OC5CC(F)(F)C5)n4n3)C2)cc1]

Step 1. 2-Bromo-5-(3,3-difluorocyclobutoxy)-6-(1-(1-ethoxyethyl)-1H-pyrazol-4-yl)-[1,2,4]triazolo[1,5-a]pyrazine

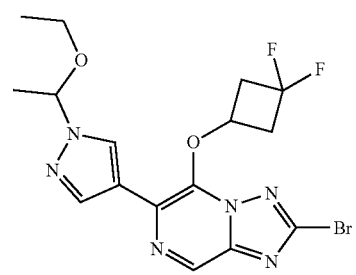 [SMILES: CCOC(C)n1cc(-c2ncc3nc(Br)nn3c2OC2CC(F)(F)C2)cn1]

To a mixture of 3,3-difluorocyclobutan-1-ol (29 mg, 0.269 mmol) in 1,4-dioxane (0.54 mL) was added NaH (60%, 11 mg, 0.269 mmol) portionwise. The reaction mixture was stirred under nitrogen at r.t. After 15 min, 2-bromo-5-chloro-6-(1-(1-ethoxyethyl)-1H-pyrazol-4-yl)-[1,2,4]triazolo[1,5-a]pyrazine (100 mg, 0.269 mmol, Example 1, Step 3) was added and the reaction mixture was stirred under nitrogen at r.t. for 15 min before the mixture was stirred at 130° C. for 4 h. After cooling to r.t., the reaction mixture was diluted with DCM. The organic layer was washed with water, brine, dried over Na$_2$SO$_4$, filtered, and concentrated. The crude material was purified by Biotage Isolera. The purification gave 82 mg (69%) of desired product. LC-MS calculated for C$_{16}$H$_{18}$BrF$_2$N$_6$O$_2$ (M+H)$^+$: m/z=443.1; found 443.1.

Step 2. (R)-5-(3,3-Difluorocyclobutoxy)-N-(piperidin-3-yl)-6-(1H-pyrazol-4-yl)-[1,2,4]triazolo[1,5-a]pyrazin-2-amine

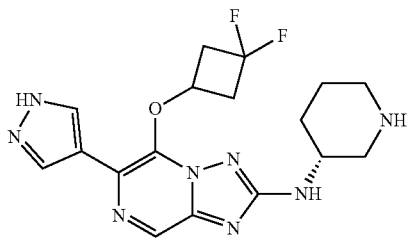 [SMILES: FC1(F)CC(Oc2c(-c3cn[nH]c3)ncc3nc(N[C@@H]4CCCNC4)nn23)C1]

This compound was prepared according to the procedure described in Example 1, Step 5, using tert-butyl (R)-3-aminopiperidine-1-carboxylate and 2-bromo-5-(3,3-difluorocyclobutoxy)-6-(1-(1-ethoxyethyl)-1H-pyrazol-4-yl)-[1,2,4]triazolo[1,5-a]pyrazine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{17}H_{21}F_2N_8O$ $(M+H)^+$: m/z=391.2; found 391.2.

Step 3. (R)-N-(4-(3-((5-(3,3-Difluorocyclobutoxy)-6-(1H-pyrazol-4-yl)-[1,2,4]triazolo[1,5-a]pyrazin-2-yl)amino)piperidine-1-carbonyl)phenyl)acrylamide This compound was prepared according to the procedure described in Example 1, Step 7, using (R)-5-(3,3-difluorocyclobutoxy)-N-(piperidin-3-yl)-6-(1H-pyrazol-4-yl)-[1,2,4]triazolo[1,5-a]pyrazin-2-amine instead of N-(azetidin-3-yl)-5-isopropoxy-6-(1H-pyrazol-4-yl)-[1,2,4]triazolo[1,5-a]pyrazin-2-amine as starting material. LC-MS calculated for $C_{27}H_{28}F_2N_9O_3$ $(M+H)^+$: m/z=564.2; found 564.1.

Example 11. (R)-N-(4-(3-((6-(1H-Pyrazol-4-yl)-[1,2,4]triazolo[1,5-a]pyridin-2-yl)amino)pyrrolidine-1-carbonyl)phenyl)acrylamide

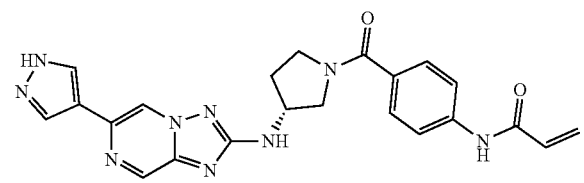 [SMILES: C=CC(=O)Nc1ccc(C(=O)N2CC[C@@H](Nc3nc4cnc(-c5cn[nH]c5)cn4n3)C2)cc1]

Step 1. 6-(1-(1-Ethoxyethyl)-1H-pyrazol-4-yl)-[1,2,4]triazolo[1,5-a]pyridin-2-amine

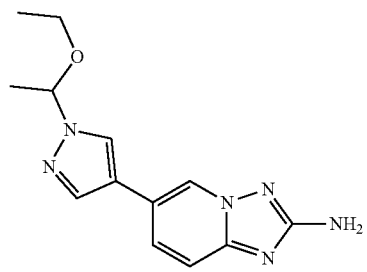 [SMILES: CCOC(C)n1cc(-c2ccc3nc(N)nn3c2)cn1]

A mixture of 6-bromo-[1,2,4]triazolo[1,5-a]pyridin-2-amine (2 g, 9.39 mmol, purchased from Asta Tech, Inc., catalog #51342), 1-(1-ethoxyethyl)-4-(4,4,5,5-tetramethyl-1,3,2-dioxaborolan-2-yl)-1H-pyrazole (3.25 g, 12.20 mmol), chloro(2-dicyclohexylphosphino-2',4',6'-tri-1-propyl-1,1'-biphenyl)(2'-amino-1,1'-biphenyl-2-yl) palladium (II) (0.74 g, 0.939 mmol) and potassium phosphate tribasic (4 g, 18.78 mmol) in 1,4-dioxane (20 mL) and water (4 mL) was sparged with nitrogen and stirred at 80° C. for 2 h. After cooling to r.t., the reaction mixture was diluted with water and extracted with $CH_2Cl_2$. The organic layer was dried over $MgSO_4$, filtered, and concentrated. The crude material was purified by Biotage Isolera. LC-MS calculated for $C_{13}H_{17}N_6O$ $(M+H)^+$: m/z=273.1; found 273.1.

Step 2. 2-Bromo-6-(1-(1-ethoxyethyl)-1H-pyrazol-4-yl)-[1,2,4]triazolo[1,5-a]pyridine

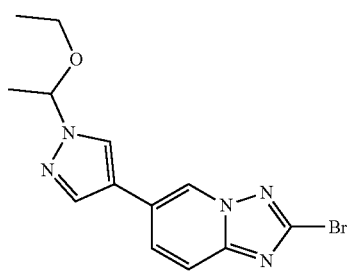 [SMILES: CCOC(C)n1cc(-c2ccc3nc(Br)nn3c2)cn1]

This compound was prepared according to the procedure described in Example 1, Step 3, using 6-(1-(1-ethoxyethyl)-1H-pyrazol-4-yl)-[1,2,4]triazolo[1,5-a]pyridin-2-amine instead of 5-chloro-6-(1-(1-ethoxyethyl)-1H-pyrazol-4-yl)-[1,2,4]triazolo[1,5-a]pyrazin-2-amine as starting material. LC-MS calculated for $C_{13}H_{15}BrN_5O$ $(M+H)^+$: m/z=336.0; found 336.0.

Step 3. (R)-6-(1H-Pyrazol-4-yl)-N-(pyrrolidin-3-yl)-[1,2,4]triazolo[1,5-a]pyridin-2-amine

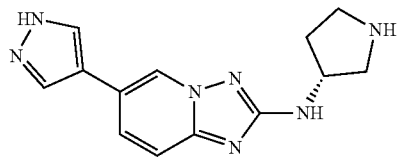 [SMILES: c1cc2nc(N[C@@H]3CCNC3)nn2cc1-c1cn[nH]c1]

This compound was prepared according to the procedure described in Example 1, Step 5, using tert-butyl (R)-3-aminopyrrolidine-1-carboxylate and 2-bromo-6-(1-(1-ethoxyethyl)-1H-pyrazol-4-yl)-[1,2,4]triazolo[1,5-a]pyridine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{13}H_{16}N_7$ $(M+H)^+$: m/z=270.1; found 270.1.

Step 4. (R)-N-(4-(3-((6-(1H-Pyrazol-4-yl)-[1,2,4]triazolo[1,5-a]pyridin-2-yl)amino)pyrrolidine-1-carbonyl)phenyl)acrylamide This compound was prepared according to the procedure described in Example 1, Step 7, using (R)-6-(1H-pyrazol- 4-yl)-N-(pyrrolidin-3-yl)-[1,2,4]triazolo[1,5-a]pyridin-2-amine instead of N-(azetidin-3-yl)-5-isopropoxy-6-(1H-pyrazol-4-yl)-[1,2,4]triazolo[1,5-a]pyrazin-2-amine as starting material. LC-MS calculated for $C_{23}H_{23}N_8O_2$ $(M+H)^+$: m/z=443.2; found 443.2.

Example 12. (R)-N-(4-(3-((5-Methyl-6-(1H-pyrazol-4-yl)-[1,2,4]triazolo[1,5-a]pyridin-2-yl)amino)pyrrolidine-1-carbonyl)phenyl)acrylamide

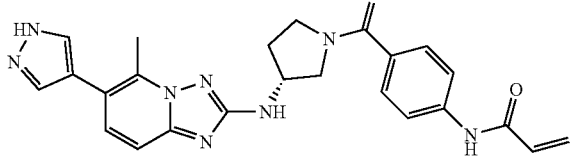

Step 1. 6-(1-(1-Ethoxyethyl)-1H-pyrazol-4-yl)-5-methyl-[1,2,4]triazolo[1,5-a]pyridin-2-amine

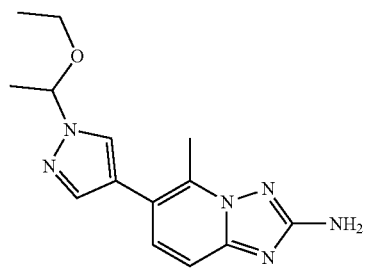 [SMILES: CCOC(C)n1cc(-c2ccc3nc(N)nn3c2C)cn1]

This compound was prepared according to the procedure described in Example 11, Step 1, using 6-bromo-5-methyl-[1,2,4]triazolo[1,5-a]pyridin-2-amine (purchased from Affinity Research Chemicals, Inc., catalog #AZ-0884) instead of 6-bromo-[1,2,4]triazolo[1,5-a]pyridin-2-amine as starting material. LC-MS calculated for $C_{14}H_{19}N_6O$ $(M+H)^+$: m/z=287.2; found 287.2.

Step 2. 2-Bromo-6-(1-(1-ethoxyethyl)-1H-pyrazol-4-yl)-5-methyl-[1,2,4]triazolo[1,5-a]pyridine

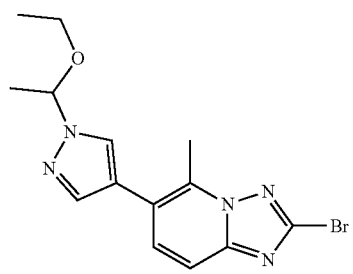 [SMILES: CCOC(C)n1cc(-c2ccc3nc(Br)nn3c2C)cn1]

This compound was prepared according to the procedure described in Example 1, Step 3, using 6-(1-(1-ethoxyethyl)-1H-pyrazol-4-yl)-5-methyl-[1,2,4]triazolo[1,5-a]pyridin-2-amine instead of 5-chloro-6-(1-(1-ethoxyethyl)-1H-pyrazol-4-yl)-[1,2,4]triazolo[1,5-a]pyrazin-2-amine as starting material. LC-MS calculated for $C_{14}H_{17}BrN_5O$ $(M+H)^+$: m/z=350.0; found 350.0.

Step 3. (R)-5-Methyl-6-(1H-pyrazol-4-yl)-N-(pyrrolidin-3-yl)-[1,2,4]triazolo[1,5-a]pyridin-2-amine

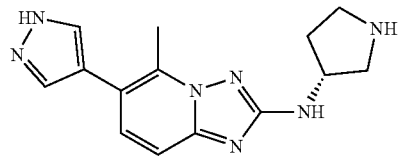

This compound was prepared according to the procedure described in Example 1, Step 5, using tert-butyl (R)-3-aminopyrrolidine-1-carboxylate and 2-bromo-6-(1-(1-ethoxyethyl)-1H-pyrazol-4-yl)-5-methyl-[1,2,4]triazolo[1,5-a]pyridine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{14}H_{18}N_7(M+H)^+$: m/z=284.2; found 284.2.

Step 4. (R)-N-(4-(3-((5-Methyl-6-(1H-pyrazol-4-yl)-[1,2,4]triazolo[1,5-a]pyridin-2-yl)amino)pyrrolidine-1-carbonyl)phenyl)acrylamide This compound was prepared according to the procedure described in Example 1, Step 7, using (R)-5-methyl-6-(1H-pyrazol-4-yl)-N-(pyrrolidin-3-yl)-[1,2,4]triazolo[1,5-a]pyridin-2-amine instead of N-(azetidin-3-yl)-5-isopropoxy-6-(1H-pyrazol-4-yl)-[1,2,4]triazolo[1,5-a]pyrazin-2-amine as starting material. LC-MS calculated for $C_{24}H_{25}N_8O_2$ $(M+H)^+$: m/z=457.2; found 457.3.

Example 13. (R)-N-(4-(3-((5-(4,4-Difluoropiperidin-1-yl)-6-(1H-pyrazol-4-yl)-[1,2,4]triazolo[1,5-a]pyridin-2-yl)amino)piperidine-1-carbonyl)phenyl)acrylamide

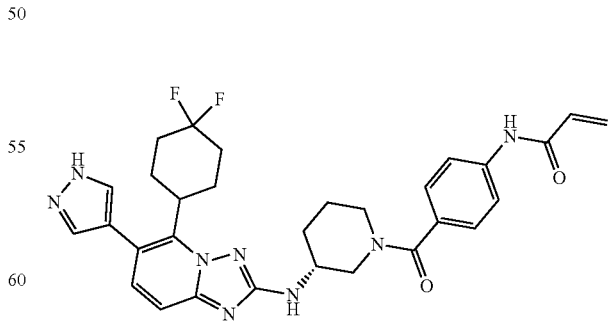

This compound was prepared according to the procedures described in Example 6, using 4,4-difluoropiperidine instead of piperidine as starting material. LCMS calculated for $C_{29}H_{32}F_2N_9O_2(M+H)^+$: m/z=576.3; found: 576.2.

Example 14. N-(4-((R)-3-((6-(1H-Pyrazol-4-yl)-5-(((S)-tetrahydrofuran-3-yl)oxy)-[1,2,4]triazolo[1,5-a]pyridin-2-yl)amino)piperidin-1-carbonyl)phenyl)acrylamide

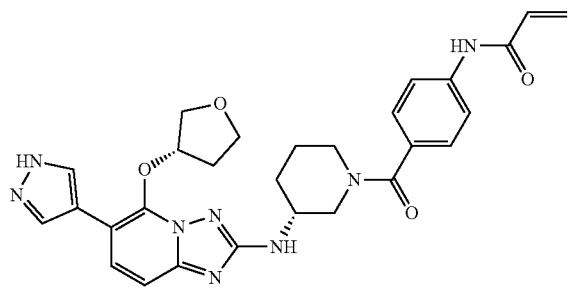 [SMILES: C=CC(=O)Nc1ccc(C(=O)N2CCC[C@@H](Nc3nc4ccc(-c5cn[nH]c5)c(O[C@H]5CCOC5)n4n3)C2)cc1]

Step 1. 2-Bromo-6-(1-(1-ethoxyethyl)-1H-pyrazol-4-yl)-5-(((S)-tetrahydrofuran-3-yl)oxy)-[1,2,4]triazolo[1,5-a]pyridine

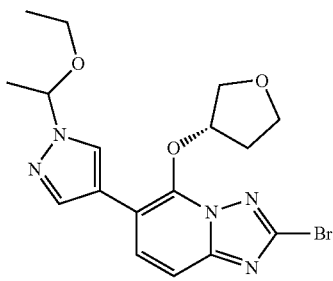 [SMILES: CCOC(C)n1cc(-c2ccc3nc(Br)nn3c2O[C@H]2CCOC2)cn1]

This compound was prepared according to the procedure described in Example 10, Step 1, using (S)-tetrahydrofuran-3-ol and 2-bromo-5-chloro-6-(1-(1-ethoxyethyl)-1H-pyrazol-4-yl)-[1,2,4]triazolo[1,5-a]pyridine (Example 6, Step 3) instead of 3,3-difluorocyclobutan-1-ol and 2-bromo-5-chloro-6-(1-(1-ethoxyethyl)-1H-pyrazol-4-yl)-[1,2,4]triazolo[1,5-a]pyrazine as starting material. LC-MS calculated for $C_{17}H_{21}BrN_5O_3$ (M+H)$^+$: m/z=422.1; found 422.1.

Step 2. N-((R)-Piperidin-3-yl)-6-(1H-pyrazol-4-yl)-5-(((S)-tetrahydrofuran-3-yl)oxy)-[1,2,4]triazolo[1,5-a]pyridin-2-amine

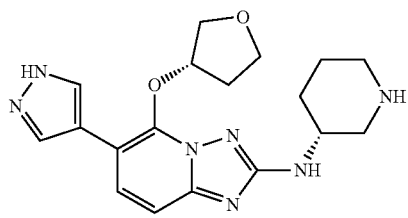 [SMILES: c1n[nH]cc1-c1ccc2nc(N[C@@H]3CCCNC3)nn2c1O[C@H]1CCOC1]

This compound was prepared according to the procedure described in Example 1, Step 5, using tert-butyl (R)-3-aminopiperidine-1-carboxylate and 2-bromo-6-(1-(1-ethoxyethyl)-1H-pyrazol-4-yl)-5-(((S)-tetrahydrofuran-3-yl)oxy)-[1,2,4]triazolo[1,5-a]pyridine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{18}H_{24}N_7O_2$ (M+H)$^+$: m/z=370.2; found 370.1.

Step 3. N-(4-((R)-3-((6-(1H-Pyrazol-4-yl)-5-(((S)-tetrahydrofuran-3-yl)oxy)-[1,2,4]triazolo[1,5-a]pyridin-2-yl)amino)piperidin-1-carbonyl)phenyl)acrylamide This compound was prepared according to the procedure described in Example 1, Step 7, using N-((R)-piperidin-3-yl)-6-(1H-pyrazol-4-yl)-5-(((S)-tetrahydrofuran-3-yl)oxy)-[1,2,4]triazolo[1,5-a]pyridin-2-amine instead of N-(azetidin-3-yl)-5-isopropoxy-6-(1H-pyrazol-4-yl)-[1,2,4]triazolo[1,5-a]pyrazin-2-amine as starting material. LC-MS calculated for $C_{28}H_{31}N_8O_4$ (M+H)$^+$: m/z=543.2; found 543.2.

Example 15. (R)-N-(4-(3-((6-(1H-Pyrazol-4-yl)-5-((tetrahydro-2H-pyran-4-yl)oxy)-[1,2,4]triazolo[1,5-a]pyridin-2-yl)amino)piperidin-1-carbonyl)phenyl)acrylamide

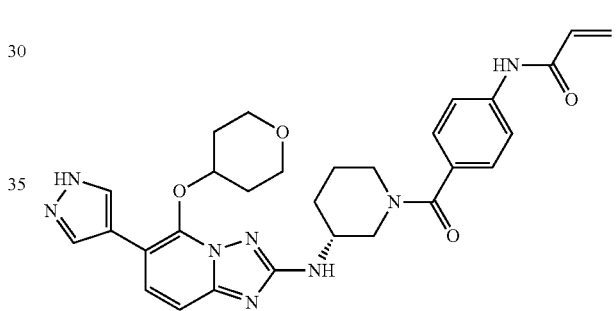

This compound was prepared according to the procedure described in Example 14, using tetrahydro-2H-pyran-4-ol instead of (S)-tetrahydrofuran-3-ol as starting material. LCMS calculated for $C_{29}H_{33}N_8O_4$ (M+H)+: m/z=557.3; found 557.2.

Example 16. N-(4-(((1S,3R)-3-((5-(Piperidin-1-yl)-6-(1H-pyrazol-4-yl)-[1,2,4]triazolo[1,5-a]pyridin-2-yl)amino)cyclohexyl)oxy)phenyl)acrylamide

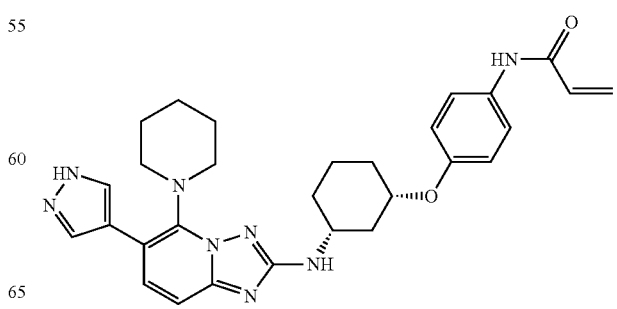

Step 1. (1S,3R)-3-((6-(1-(1-Ethoxyethyl)-1H-pyrazol-4-yl)-5-(piperidin-1-yl)-[1,2,4]triazolo[1,5-a]pyridin-2-yl)amino)cyclohexan-1-ol

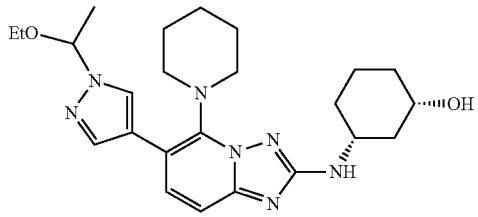 [SMILES: CCOC(C)n1cc(-c2ccc3nc(N[C@@H]4CCC[C@H](O)C4)nn3c2N2CCCCC2)cn1]

A mixture of 2-bromo-6-(1-(1-ethoxyethyl)-1H-pyrazol-4-yl)-5-(piperidin-1-yl)-[1,2,4]triazolo[1,5-a]pyridine (100 mg, 0.238 mmol, Example 6, Step 4), (1S,3R)-3-aminocyclohexan-1-ol hydrochloride (54 mg, 0.358 mmol), tBu-BrettPhos Pd G3 (20 mg, 0.024 mmol), and sodium tert-butoxide (69 mg, 0.715 mmol) in dioxane (2 mL) was heated at 100° C. for 2 h. The reaction mixture was then cooled to r.t., diluted with EtOAc and water. The organic layer was extracted with EtOAc, washed with brine, dried with $Na_2SO_4$, filtered and concentrated. The crude product was purified by CombiFlash Rf+ Lumen to obtain desired product. LCMS calculated for $C_{24}H_{36}N_7O_2$ $(M+H)^+$: m/z=454.3; found 454.3.

Step 2. 6-(1-(1-Ethoxyethyl)-1H-pyrazol-4-yl)-N-((1R,3S)-3-(4-nitrophenoxy)cyclohexyl)-5-(piperidin-1-yl)-[1,2,4]triazolo[1,5-a]pyridin-2-amine

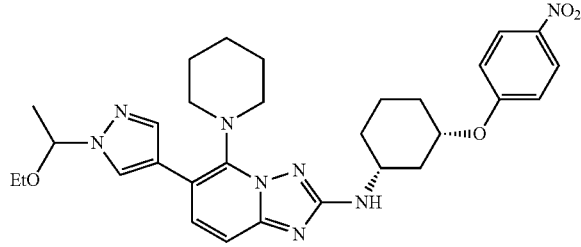 [SMILES: CCOC(C)n1cc(-c2ccc3nc(N[C@@H]4CCC[C@H](Oc5ccc([N+](=O)[O-])cc5)C4)nn3c2N2CCCCC2)cn1]

To a solution of (1S,3R)-3-((6-(1-(1-ethoxyethyl)-1H-pyrazol-4-yl)-5-(piperidin-1-yl)-[1,2,4]triazolo[1,5-a]pyridin-2-yl)amino)cyclohexan-1-ol (40 mg, 0.088 mmol) in DMF (2 mL) was added sodium hydride (60%, 5.3 mg, 0.132 mmol) and the resulting mixture was stirred at r.t. After 20 min, 1-fluoro-4-nitrobenzene (18.7 µL, 0.176 mmol) was then added and the mixture was stirred at r.t. for 4 h. The reaction was then quenched with water and DCM. The organic layer was extracted with DCM, washed with brine, dried with $Na_2SO_4$, filtered, and concentrated. The crude product was purified by CombiFlash Rf+ Lumen to obtain desired product. LCMS calculated for $C_{30}H_{39}N_8O_4$ $(M+H)^+$: m/z=575.3; found 575.2.

Step 3. N-((1R,3S)-3-(4-Aminophenoxy)cyclohexyl)-6-(1-(1-ethoxyethyl)-1H-pyrazol-4-yl)-5-(piperidin-1-yl)-[1,2,4]triazolo[1,5-a]pyridin-2-amine

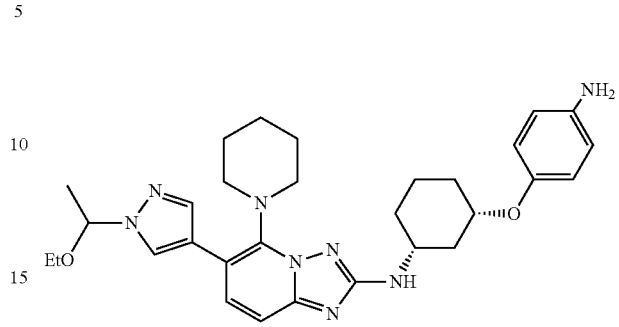

A mixture of 6-(1-(1-ethoxyethyl)-1H-pyrazol-4-yl)-N-((1R,3S)-3-(4-nitrophenoxy)cyclohexyl)-5-(piperidin-1-yl)-[1,2,4]triazolo[1,5-a]pyridin-2-amine (42 mg, 0.073 mmol), zinc (48 mg, 0.731 mmol), and ammonium chloride (78 mg, 1.462 mmol) in MeOH (1 mL), THF (0.5 mL) and water (0.5 mL) was stirred at 40° C. for 1 h. The reaction mixture was then cooled to r.t., diluted with MeOH and filtered through celite. The solvent was removed and the crude was then purified by CombiFlash Rf+ Lumen to obtain desired product. LCMS calculated for $C_{30}H_{41}N_8O_2(M+H)^+$: m/z=545.3; found 545.3.

Step 4. N-(4-(((1S,3R)-3-((5-(Piperidin-1-yl)-6-(1H-pyrazol-4-yl)-[1,2,4]triazolo[1,5-a]pyridin-2-yl)amino)cyclohexyl)oxy)phenyl)acrylamide To a solution of N-((1R,3S)-3-(4-aminophenoxy)cyclohexyl)-6-(1-(1-ethoxyethyl)-1H-pyrazol-4-yl)-5-(piperidin-1-yl)-[1,2,4]triazolo[1,5-a]pyridin-2-amine (23 mg, 0.042 mmol) and triethylamine (17.7 µL, 0.127 mmol) in DCM (1 mL) at 0° C. was added acryloyl chloride (5.1 µL, 0.063 mmol) and the resulting solution was stirred at 0° C. After 1 h, the reaction was quenched with water and diluted with DCM. The organic layer was extracted and concentrated. The crude product was taken up in 2 mL DCM and 2 mL TFA was added, and the resulting solution was stirred at r.t. for 1 h. Solvent was then removed and the crude was dissolved in MeCN and purified with prep-LCMS (XBridge C18 column, eluting with a gradient of acetonitrile/water containing 0.1% TFA, at flow rate of 60 mL/min). LCMS calculated for $C_{29}H_{35}N_8O_2$ (M+H)+: m/z=527.3; found 527.2.

Example 17. (R)-N-(4-(3-((5-Cyano-6-(1H-pyrazol-4-yl)-[1,2,4]triazolo[1,5-a]pyridin-2-yl)amino)pyrrolidine-1-carbonyl)phenyl)acrylamide

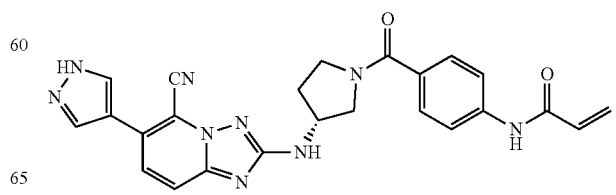

Step 1. 2-Amino-6-(1-(1-ethoxyethyl)-1H-pyrazol-4-yl)-[1,2,4]triazolo[1,5-a]pyridine-5-carbonitrile

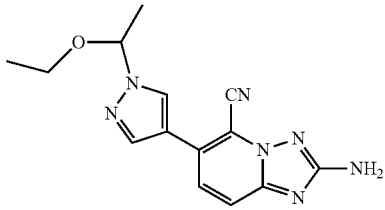 [SMILES: CCOC(C)n1cc(-c2ccc3nc(N)nn3c2C#N)cn1]

A mixture of 5-chloro-6-(1-(1-ethoxyethyl)-1H-pyrazol-4-yl)-[1,2,4]triazolo[1,5-a]pyridin-2-amine (0.70 g, 2.282 mmol, Example 6, Step 2), tBuXPhos Pd G3 (0.181 g, 0.228 mmol), potassium hexacyanoferrate(II) trihydrate (1.16 g, 2.74 mmol) and potassium acetate (0.029 mL, 0.456 mmol) in 1,4-dioxane (1 mL) and water (1 mL) was irradiated in microwave at 120° C. for 0.5 h. After cooling to r.t., the reaction mixture was diluted with EtOAc and water, and the organic layer was extracted with EtOAc. The combined organic layer was dried over MgSO$_4$, filtered and concentrated. The crude material was purified by Biotage Isolera. LC-MS calculated for $C_{14}H_{16}N_7O$ (M+H)$^+$: m/z=298.1; found 298.1.

Step 2. 2-Bromo-6-(1-(1-ethoxyethyl)-1H-pyrazol-4-yl)-[1,2,4]triazolo[1,5-a]pyridine-5-carbonitrile

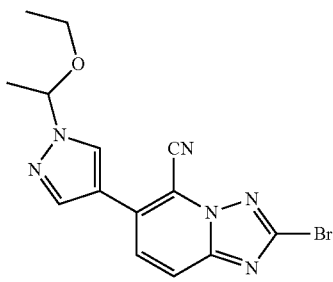 [SMILES: CCOC(C)n1cc(-c2ccc3nc(Br)nn3c2C#N)cn1]

This compound was prepared according to the procedure described in Example 1, Step 3, using 2-amino-6-(1-(1-ethoxyethyl)-1H-pyrazol-4-yl)-[1,2,4]triazolo[1,5-a]pyridine-5-carbonitrile instead of 5-chloro-6-(1-(1-ethoxyethyl)-1H-pyrazol-4-yl)-[1,2,4]triazolo[1,5-a]pyrazin-2-amine as starting material. LC-MS calculated for $C_{14}H_{14}BrN_6O$ (M+H)$^+$: m/z=361.0; found 361.0.

Step 3. (R)-6-(1H-Pyrazol-4-yl)-2-(pyrrolidin-3-ylamino)-[1,2,4]triazolo[1,5-a]pyridine-5-carbonitrile

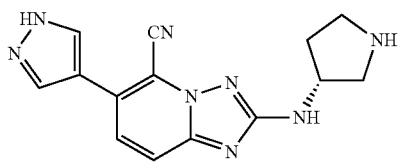 [SMILES: N#Cc1c(-c2cn[nH]c2)ccc2nc(N[C@@H]3CCNC3)nn12]

This compound was prepared according to the procedure described in Example 1, Step 5, using tert-butyl (R)-3-aminopyrrolidine-1-carboxylate and 2-bromo-6-(1-(1-ethoxyethyl)-1H-pyrazol-4-yl)-[1,2,4]triazolo[1,5-a]pyridine-5-carbonitrile instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{14}H_{15}N_8$(M+H)$^+$: m/z=295.1; found 295.1.

Step 4. (R)-N-(4-(3-((5-Cyano-6-(1H-pyrazol-4-yl)-[1,2,4]triazolo[1,5-a]pyridin-2-yl)amino)pyrrolidine-1-carbonyl)phenyl)acrylamide This compound was prepared according to the procedure described in Example 1, Step 7, using (R)-6-(1H-pyrazol-4-yl)-2-(pyrrolidin-3-ylamino)-[1,2,4]triazolo[1,5-a]pyridine-5-carbonitrile instead of N-(azetidin-3-yl)-5-isopropoxy-6-(1H-pyrazol-4-yl)-[1,2,4]triazolo[1,5-a]pyrazin-2-amine. LC-MS calculated for $C_{24}H_{22}N_9O_2$ (M+H)$^+$: m/z=468.2; found 468.2. $^1$H NMR (600 MHz, DMSO) δ 10.34 (d, J=15.4 Hz, 1H), 8.25-8.16 (m, 2H), 7.85-7.67 (m, 4H), 7.58-7.49 (m, 2H), 6.45 (td, J=16.0, 10.0 Hz, 1H), 6.32-6.24 (m, 1H), 5.78 (t, J=9.9 Hz, 1H), 4.38-4.25 (m, 1H), 3.87-3.45 (m, 4H), 2.26-1.91 (m, 2H).

Example 18. (R)-N-(4-(3-((5-Isopropyl-6-(1H-pyrazol-4-yl)-[1,2,4]triazolo[1,5-a]pyridin-2-yl)amino)pyrrolidine-1-carbonyl)phenyl)acrylamide

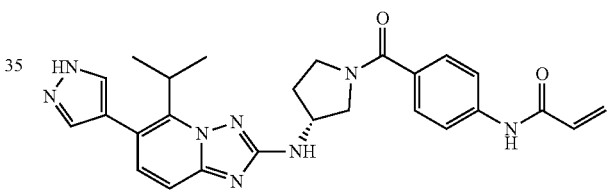

Step 1. 6-(1-(1-Ethoxyethyl)-1H-pyrazol-4-yl)-5-(prop-1-en-2-yl)-[1,2,4]triazolo[1,5-a]pyridin-2-amine

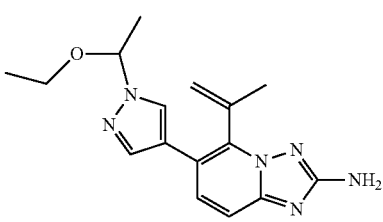 [SMILES: C=C(C)c1c(-c2cnn(C(C)OCC)c2)ccc2nc(N)nn12]

A mixture of 5-chloro-6-(1-(1-ethoxyethyl)-1H-pyrazol-4-yl)-[1,2,4]triazolo[1,5-a]pyridin-2-amine (1.50 g, 4.89 mmol, Example 6, Step 2), 4,4,5,5-tetramethyl-2-(prop-1-en-2-yl)-1,3,2-dioxaborolane (1.068 g, 6.36 mmol), tripotassium phosphate (2.076 g, 9.78 mmol), chloro(2-dicyclohexylphosphino-2',4',6'-tri-1-propyl-1,1'-biphenyl)(2'-amino-1,1'-biphenyl-2-yl) palladium(II) (0.385 g, 0.489 mmol) in 1,4-dioxane (15 mL) and water (3 mL) was purged with nitrogen and stirred at 120° C. for 2 h. After cooling to r.t., the reaction mixture was diluted with water and extracted with CH₂Cl₂. The organic layer was dried over MgSO₄, filtered, and concentrated. The crude material was purified by Biotage Isolera. LC-MS calculated for $C_{16}H_{21}N_6O$ (M+H)⁺: m/z=313.2; found 313.2.

Step 2. 6-(1-(1-Ethoxyethyl)-1H-pyrazol-4-yl)-5-isopropyl-[1,2,4]triazolo[1,5-a]pyridin-2-amine

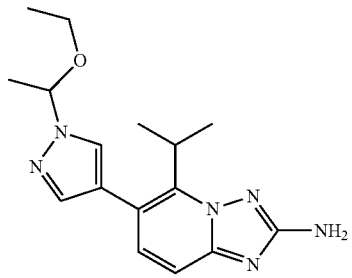 [SMILES: CCOC(C)n1cc(-c2ccc3nc(N)nn3c2C(C)C)cn1]

A mixture of 6-(1-(1-ethoxyethyl)-1H-pyrazol-4-yl)-5-(prop-1-en-2-yl)-[1,2,4]triazolo[1,5-a]pyridin-2-amine (1 g, 3.20 mmol), palladium hydroxide on carbon (20%, 0.225 g, 0.320 mmol) in MeOH (10 mL) and EtOAc (10 mL) was stirred at r.t. under a balloon of H₂ overnight. The reaction mixture was filtered through a pad of celite, rinsed with MeOH. The filtrate was concentrated, and the crude material was purified by Biotage Isolera. LC-MS calculated for $C_{16}H_{23}N_6O$ (M+H)⁺: m/z=315.2; found 315.2.

Step 3. 2-Bromo-6-(1-(1-ethoxyethyl)-1H-pyrazol-4-yl)-5-isopropyl-[1,2,4]triazolo[1,5-a]pyridine

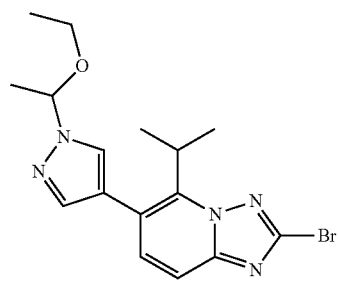 [SMILES: CCOC(C)n1cc(-c2ccc3nc(Br)nn3c2C(C)C)cn1]

This compound was prepared according to the procedure described in Example 1, Step 3, using 6-(1-(1-ethoxyethyl)-1H-pyrazol-4-yl)-5-isopropyl-[1,2,4]triazolo[1,5-a]pyridin-2-amine instead of 5-chloro-6-(1-(1-ethoxyethyl)-1H-pyrazol-4-yl)-[1,2,4]triazolo[1,5-a]pyrazin-2-amine as starting material. LC-MS calculated for $C_{16}H_{21}BrN_5O$ (M+H)⁺: m/z=378.1; found 378.1.

Step 4. (R)-5-Isopropyl-6-(1H-pyrazol-4-yl)-N-(pyrrolidin-3-yl)-[1,2,4]triazolo[1,5-a]pyridin-2-amine

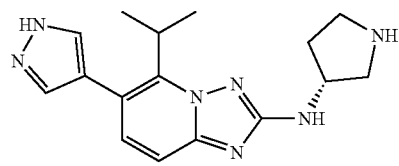 [SMILES: CC(C)c1c(-c2cn[nH]c2)ccc2nc(N[C@@H]3CCNC3)nn12]

This compound was prepared according to the procedure described in Example 1, Step 5, using tert-butyl (R)-3-aminopyrrolidine-1-carboxylate and 2-bromo-6-(1-(1-ethoxyethyl)-1H-pyrazol-4-yl)-5-isopropyl-[1,2,4]triazolo[1,5-a]pyridine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{16}H_{22}N_7$(M+H)⁺: m/z=312.2; found 312.2.

Step 5. (R)-N-(4-(3-((5-Isopropyl-6-(1H-pyrazol-4-yl)-[1,2,4]triazolo[1,5-a]pyridin-2-yl)amino)pyrrolidine-1-carbonyl)phenyl)acrylamide This compound was prepared according to the procedure described in Example 1, Step 7, using (R)-5-isopropyl-6-(1H-pyrazol-4-yl)-N-(pyrrolidin-3-yl)-[1,2,4]triazolo[1,5-a]pyridin-2-amine instead of N-(azetidin-3-yl)-5-isopropoxy-6-(1H-pyrazol-4-yl)-[1,2,4]triazolo[1,5-a]pyrazin-2-amine. LC-MS calculated for $C_{26}H_{29}N_8O_2$(M+H)⁺: m/z=485.2; found 485.2. ¹H NMR (600 MHz, DMSO) δ 10.32 (s, 1H), 7.75-7.68 (m, 4H), 7.59-7.31 (m, 4H), 6.46 (ddd, J=16.7, 14.5, 10.0 Hz, 1H), 6.32-6.24 (m, 1H), 5.81-5.74 (m, 1H), 4.37-4.14 (m, 1H), 3.92-3.81 (m, 1H), 3.69 (tp, J=13.8, 7.3 Hz, 1H), 3.58 (dtt, J=15.4, 10.9, 4.6 Hz, 3H), 2.27-1.99 (m, 2H), 1.51 (dd, J=7.1, 4.3 Hz, 2H), 1.43 (d, J=7.1 Hz, 2H), 1.33 (d, J=7.1 Hz, 2H).

Example 19. (R)-N-(2-Fluoro-4-(3-((5-isopropyl-6-(1H-pyrazol-4-yl)-[1,2,4]triazolo[1,5-a]pyridin-2-yl)amino)pyrrolidine-1-carbonyl)phenyl)acrylamide

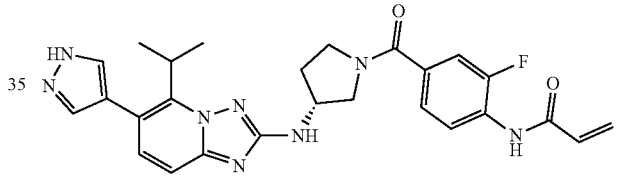

Step 1. 4-Acrylamido-3-Fluorobenzoic Acid

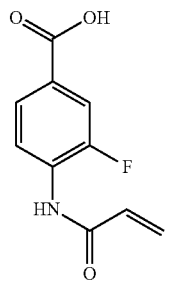

This compound was prepared according to the procedure described in Example 4, Step 2, using methyl 4-amino-3-fluorobenzoate instead of methyl 4-amino-2-fluorobenzoate as starting material. LC-MS calculated for $C_{10}H_9FNO_3$ (M+H)⁺: m/z=210.1; found 210.1.

Step 2. (R)-N-(2-Fluoro-4-(3-((5-isopropyl-6-(1H-pyrazol-4-yl)-[1,2,4]triazolo[1,5-a]pyridin-2-yl)amino)pyrrolidine-1-carbonyl)phenyl)acrylamide This compound was prepared according to the procedure described in Example 18, Step 5, using 4-acrylamido-3- fluorobenzoic acid instead of 4-acrylamidobenzoic acid as starting material. LCMS calculated for $C_{26}H_{28}FN_8O_2$ (M+H)$^+$: m/z=503.2; found 503.2.

Example 20. (R)-N-(4-(3-((6-(Oxazol-5-yl)-[1,2,4]triazolo[1,5-a]pyridin-2-yl)amino)pyrrolidine-1-carbonyl)phenyl)acrylamide

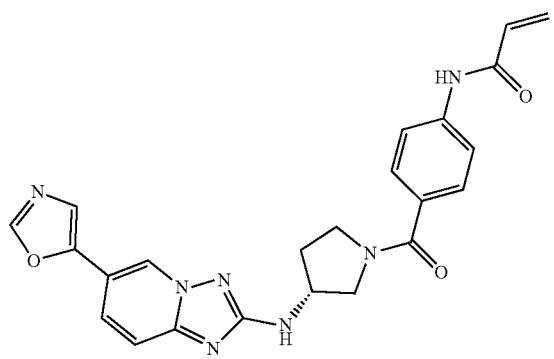 [SMILES: C=CC(=O)Nc1ccc(C(=O)N2CC[C@@H](Nc3nc4ccc(-c5cnco5)cn4n3)C2)cc1]

Step 1. 6-(Oxazol-5-yl)-[1,2,4]triazolo[1,5-a]pyridin-2-amine

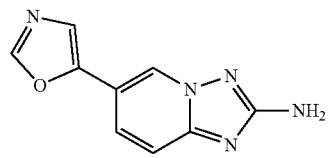 [SMILES: Nc1nc2ccc(-c3cnco3)cn2n1]

A mixture of 6-bromo-[1,2,4]triazolo[1,5-a]pyridin-2-amine (0.52 g, 2.441 mmol), 5-(4,4,5,5-tetramethyl-1,3,2-dioxaborolan-2-yl)oxazole (0.524 g, 2.68 mmol), tripotassium phosphate (1.554 g, 7.32 mmol), and XPhos Pd G2 (0.192 g, 0.244 mmol) in dioxane (15 mL) and water (3 mL) was heated at 90° C. for 20 h. The reaction mixture was then cooled to r.t., diluted with DCM and water. The organic layer was extracted with DCM, washed with brine, dried over Na$_2$SO$_4$, filtered, and concentrated. The crude product was purified by CombiFlash Rf+ Lumen to obtain desired product. LCMS calculated for $C_9H_8N_5O$ (M+H)$^+$: m/z=202.1; found 202.0.

Step 2. 5-(2-Bromo-[1,2,4]triazolo[1,5-a]pyridin-6-yl)oxazole

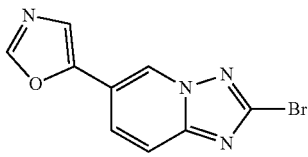 [SMILES: Brc1nc2ccc(-c3cnco3)cn2n1]

A mixture of copper(II) bromide (200 mg, 0.895 mmol) and tert-butyl nitrite (90%, 197 µL, 1.491 mmol) in 3 mL MeCN was stirred at 60° C. for 30 min. The above solution was then added into another flask containing a suspension of 6-(oxazol-5-yl)-[1,2,4]triazolo[1,5-a]pyridin-2-amine (120 mg, 0.596 mmol) pre-stirred in 2 mL MeCN for 30 min at r.t. Another portion of tert-butyl nitrite (90%, 197 µL, 1.491 mmol) was then added. The resulting mixture was then stirred at r.t. After 2 h, the solution was then quenched with sat. aq. NaHCO$_3$ and diluted with DCM. The organic layer was extracted with DCM, washed with brined, dried with MgSO$_4$, filtered and concentrated. The crude product was purified by CombiFlash Rf+ Lumen to obtain desired product. LCMS calculated for $C_9H_6BrN_4O$ (M+H)$^+$: m/z=265.0; found 265.0.

Step 3. (R)-6-(oxazol-5-yl)-N-(pyrrolidin-3-yl)-[1,2,4]triazolo[1,5-a]pyridin-2-amine

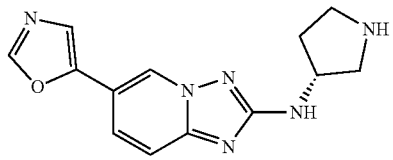 [SMILES: c1ncc(-c2ccc3nc(N[C@@H]4CCNC4)nn3c2)o1]

A mixture of 5-(2-bromo-[1,2,4]triazolo[1,5-a]pyridin-6-yl)oxazole (43 mg, 0.162 mmol), tert-butyl (R)-3-aminopyrrolidine-1-carboxylate (45 mg, 0.243 mmol), sodium tert-butoxide (31 mg, 0.324 mmol), and tBuBrettPhos Pd G3 (14 mg, 0.016 mmol) in dioxane (2 mL) was stirred at 100° C. for 2 h. The reaction mixture was then cooled to r.t., diluted with EtOAc and water. The organic layer was extracted with EtOAc, washed with brine, dried with Na$_2$SO$_4$, filtered and concentrated. The crude product was purified by CombiFlash Rf+ Lumen to obtain tert-butyl (R)-3-((6-(oxazol-5-yl)-[1,2,4]triazolo[1,5-a]pyridin-2-yl)amino)pyrrolidine-1-carboxylate (13 mg, 0.035 mmol, 21.63% yield). The above product was taken up in 1 mL DCM and TFA (0.5 mL) was added. The reaction was stirred at r.t. for 1 h. The solvent was then removed and the crude product was purified by CombiFlash Rf+ Lumen to obtain desired product. LCMS calculated for $C_{13}H_{15}N_6O$ (M+H)$^+$: m/z=271.1; found 271.1.

Step 4. (R)-N-(4-(3-((6-(Oxazol-5-yl)-[1,2,4]triazolo[1,5-a]pyridin-2-yl)amino)pyrrolidine-1-carbonyl)phenyl)acrylamide A mixture of (R)-6-(oxazol-5-yl)-N-(pyrrolidin-3-yl)-[1,2,4]triazolo[1,5-a]pyridin-2-amine (4 mg, 0.015 mmol), 4-acrylamidobenzoic acid (3 mg, 0.016 mmol), HATU (6 mg, 0.016 mmol), and N,N-diisopropylethylamine (7.8 µL, 0.044 mmol) in DMF (1 mL) was stirred at r.t. for 1 h. The resulting mixture was diluted with MeCN and purified with prep-LCMS (XBridge C18 column, eluting with a gradient of acetonitrile/water containing 0.1% TFA, at flow rate of 60 mL/min). LCMS calculated for $C_{23}H_{22}N_7O_3$ (M+H)+: m/z=444.2; found 444.2.

Example 21. N-(3-Oxo-2-((1S,3R)-3-((5-(piperidin-1-yl)-6-(1H-pyrazol-4-yl)-[1,2,4]triazolo[1,5-a]pyridin-2-yl)amino)cyclohexyl)isoindolin-5-yl)acrylamide

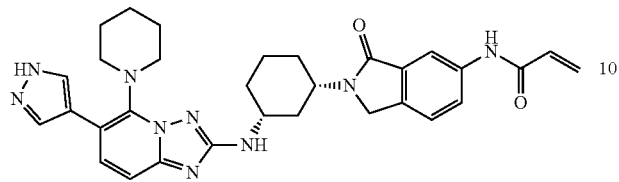

Step 1. tert-Butyl ((1R,3S)-3-(6-nitro-1-oxoisoindolin-2-yl)cyclohexyl)carbamate

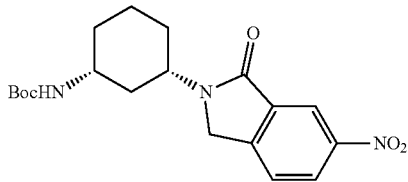 [SMILES: CC(C)(C)OC(=O)N[C@@H]1CCC[C@H](N2Cc3ccc(N)cc3C2=O)C1]

A mixture of tert-butyl ((1R,3S)-3-aminocyclohexyl)carbamate (0.782 g, 3.65 mmol), methyl 2-(bromomethyl)-5-nitrobenzoate (1 g, 3.65 mmol), and N,N-diisopropylethylamine (1.3 mL, 7.66 mmol) in DMF (10 mL) was stirred at 80° C. for 3 h. The reaction mixture was then cooled to r.t., diluted with DCM and water. The organic layer was extracted with DCM, washed with brine, dried with $Na_2SO_4$, filtered, and concentrated. The crude product was purified by CombiFlash Rf+ Lumen to obtain desired product (0.96 g, 2.56 mmol, 70% yield). LCMS calculated for $C_{14}H_{18}N_3O_3$ $(M-C_5H_7O_2)^+$: m/z=276.1; found 276.1.

Step 2. tert-Butyl ((1R,3S)-3-(6-amino-1-oxoisoindolin-2-yl)cyclohexyl)carbamate

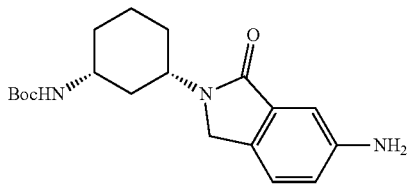

A mixture of tert-butyl ((1R,3S)-3-(6-nitro-1-oxoisoindolin-2-yl)cyclohexyl)carbamate (0.96 g, 2.56 mmol), zinc (1.672 g, 25.6 mmol), and ammonium chloride (2.74 g, 51.1 mmol) in MeOH (30 mL), THF (15 mL) and water (15 mL) was heated at 40° C. for 1 h. The reaction mixture was then cooled to r.t., diluted with MeOH and filtered through celite. The solvent was evaporated and the crude was taken up in DCM. The precipitated white solid was filtered and washed with DCM. The filtrate containing desired product was concentrated and used directly in the next step. LCMS calculated for $C_{14}H_{20}N_3O$ $(M-C_5H_7O_2)+$: m/z=246.2; found 246.1.

Step 3. Benzyl (2-((1S,3R)-3-aminocyclohexyl)-3-oxoisoindolin-5-yl)carbamate

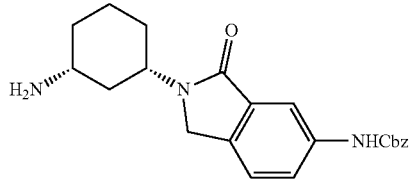 [SMILES: N[C@@H]1CCC[C@H](N2Cc3ccc(NC(=O)OCc4ccccc4)cc3C2=O)C1]

To a solution of tert-butyl ((1R,3S)-3-6-amino-1-oxoisoindolin-2-yl)cyclohexyl)carbamate (0.883 g, 2.56 mmol) and N,N-diisopropylethylamine (0.893 mL, 5.11 mmol) in DCM (25.6 mL) was added benzyl carbonochloridate (0.401 mL, 2.81 mmol) and the resulting solution was stirred at r.t. for 20 h. The reaction was quenched with water, diluted with DCM. Organic layer was extracted with DCM, washed with brine, dried with $Na_2SO_4$, filtered, and concentrated. The crude product was then taken up in 10 mL DCM and 5 mL TFA was added. The mixture was then stirred at r.t. for 1 h. The solvent was then removed and the crude product was purified by CombiFlash Rf+ Lumen to obtain desired product. LCMS calculated for $C_{22}H_{26}N_3O_3$ $(M+H)^+$: m/z=380.2; found 380.3.

Step 4. Benzyl (2-((1S,3R)-3-((6-(1-(1-ethoxyethyl)-1H-pyrazol-4-yl)-5-(piperidin-1-yl)-[1,2,4]triazolo[1,5-a]pyridin-2-yl)amino)cyclohexyl)-3-oxoisoindolin-5-yl)carbamate

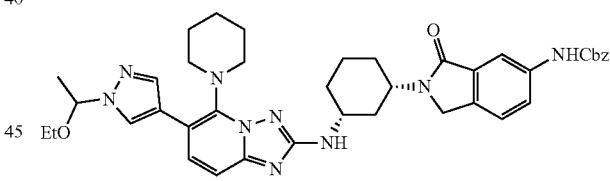

A mixture of 2-bromo-6-(1-(1-ethoxyethyl)-1H-pyrazol-4-yl)-5-(piperidin-1-yl)-[1,2,4]triazolo[1,5-a]pyridine (100 mg, 0.238 mmol, Example 6, Step 4), benzyl (2-((1S,3R)-3-aminocyclohexyl)-3-oxoisoindolin-5-yl)carbamate (136 mg, 0.358 mmol), sodium tert-butoxide (46 mg, 0.477 mmol), and tBuBrettPhos Pd G3 (20 mg, 0.024 mmol) in dioxane (2 mL) was heated at 100° C. for 1 h. The reaction mixture was then cooled to r.t. and diluted with DCM and water. The organic layer was extracted with DCM, washed with brine, dried over $Na_2SO_4$, filtered, and concentrated. The crude product was purified by CombiFlash Rf+ Lumen to obtain desired product (0.09 g, 0.125 mmol, 53% yield). LCMS calculated for $C_{40}H_{48}N_9O_4$ (M+H)+: m/z=718.4; found 718.4.

Step 5. 6-Amino-2-((1S,3R)-3-((6-(1-(1-ethoxyethyl)-1H-pyrazol-4-yl)-5-(piperidin-1-yl)-[1,2,4]triazolo[1,5-a]pyridin-2-yl)amino)cyclohexyl)isoindolin-1-one

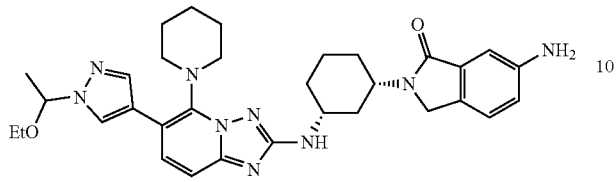

A mixture of benzyl (2-((1S,3R)-3-((6-(1-(1-ethoxyethyl)-1H-pyrazol-4-yl)-5-(piperidin-1-yl)-[1,2,4]triazolo[1,5-a]pyridin-2-yl)amino)cyclohexyl)-3-oxoisoindolin-5-yl)carbamate (90 mg, 0.125 mmol) and Pd on carbon (10%, 13 mg, 0.013 mmol) in MeOH (3 mL) and dioxane (0.5 mL) was stirred at r.t. under a hydrogen balloon for 20 h. The reaction mixture was then diluted with MeOH, filtered through celite and concentrated. The obtained product was used directly in the next step. LCMS calculated for $C_{32}H_{42}N_9O_2$ (M+H)⁺: m/z=584.3; found 584.4.

Step 6. N-(3-Oxo-2-((1S,3R)-3-((5-(piperidin-1-yl)-6-(1H-pyrazol-4-yl)-[1,2,4]triazolo[1,5-a]pyridin-2-yl)amino)cyclohexyl)isoindolin-5-yl)acrylamide To a solution of 6-amino-2-((1S,3R)-3-((6-(1-(1-ethoxyethyl)-1H-pyrazol-4-yl)-5-(piperidin-1-yl)-[1,2,4]triazolo[1,5-a]pyridin-2-yl)amino)cyclohexyl)isoindolin-1-one (38 mg, 0.065 mmol) and triethylamine (27 μL, 0.195 mmol) in DCM (2 mL) at 0° C. was added acryloyl chloride (8 μL, 0.098 mmol) and the resulting solution was stirred at 0° C. After 1 h, the reaction was quenched with water and diluted with DCM. The organic layer was extracted and concentrated. The crude product was taken up in 2 mL DCM and 2 mL TFA was added, and the resulting solution was stirred at r.t. for 1 h. Solvent was then removed and the crude was dissolved in MeCN and purified with prep-LCMS (XBridge C18 column, eluting with a gradient of acetonitrile/water containing 0.1% TFA, at flow rate of 60 mL/min). LCMS calculated for $C_{31}H_{36}N_9O_2$ (M+H)+: m/z=566.3; found 566.2.

Example 22. N-(2-((1S,3R)-3-((5-Methyl-6-(1H-pyrazol-4-yl)-[1,2,4]triazolo[1,5-a]pyridin-2-yl)amino)cyclohexyl)-3-oxoisoindolin-5-yl)acrylamide

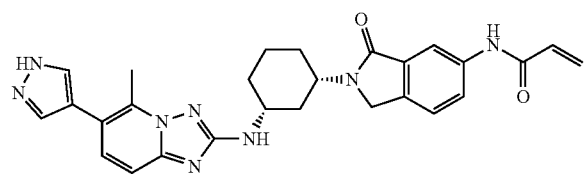 [SMILES: C=CC(=O)Nc1ccc2c(c1)C(=O)N([C@H]1CCC[C@@H](Nc3nc4ccc(-c5cn[nH]c5)c(C)n4n3)C1)C2]

Step 1. 6-(1-(1-Ethoxyethyl)-1H-pyrazol-4-yl)-5-methyl-[1,2,4]triazolo[1,5-a]pyridin-2-amine

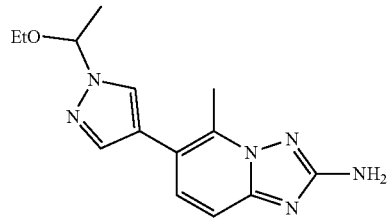 [SMILES: CCOC(C)n1cc(-c2ccc3nc(N)nn3c2C)cn1]

A mixture of 6-bromo-5-methyl-[1,2,4]triazolo[1,5-a]pyridin-2-amine (1.0 g, 4.40 mmol, purchased from Affinity Research Chemicals, Inc., catalog #AZ-0884), 1-(1-ethoxyethyl)-4-(4,4,5,5-tetramethyl-1,3,2-dioxaborolan-2-yl)-1H-pyrazole (1.4 g, 5.28 mmol), tripotassium phosphate (2.80 g, 13.21 mmol) and XPhos Pd G2 (0.35 g, 0.440 mmol) in dioxane (20 mL) and water (4 mL) was stirred at 90° C. for 20 h. The reaction mixture was then cooled to r.t., diluted with DCM and water. The organic layer was extracted with DCM, washed with brine, dried with $Na_2SO_4$, filtered and concentrated. The crude product was purified by Combi-Flash Rf+ Lumen to obtain desired product (1.1 g, 3.84 mmol, 87% yield). LCMS calculated for $C_{14}H_{19}N_6O$ (M+H)⁺: m/z=287.2; found 287.1.

Step 2. 2-Bromo-6-(1-(1-ethoxyethyl)-1H-pyrazol-4-yl)-5-methyl-[1,2,4]triazolo[1,5-a]pyridine

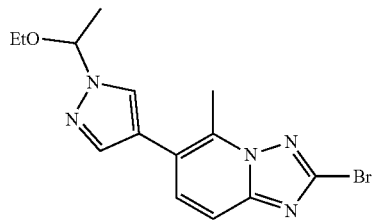 [SMILES: CCOC(C)n1cc(-c2ccc3nc(Br)nn3c2C)cn1]

A mixture of copper(II) bromide (1.29 g, 5.76 mmol) and tert-butyl nitrite (90%, 1.27 mL, 9.60 mmol) in 20 mL MeCN was stirred at 60° C. for 30 min. The above solution was then added into another flask containing a suspension of 6-(1-(1-ethoxyethyl)-1H-pyrazol-4-yl)-5-methyl-[1,2,4]triazolo[1,5-a]pyridin-2-amine (1.1 g, 3.84 mmol) pre-stirred in 15 mL MeCN for 30 min at r.t. Another portion of tert-butyl nitrite (90%, 1.27 mL, 9.60 mmol) was added. The resulting mixture was then stirred at r.t. After 2 h, the solution was then quenched with sat. aq. $NaHCO_3$ and diluted with DCM. The organic layer was extracted with DCM, washed with brined, dried with MgSO4, filtered and concentrated. The crude product was purified by Combi-Flash Rf+ Lumen to obtain desired product (0.57 g, 1.628 mmol, 42% yield). LCMS calculated for $C_{14}H_{17}BrN_5O$ (M+H)⁺: m/z=350.1; found 350.1.

Step 3. N-(2-((1S,3R)-3-((5-Methyl-6-(1H-pyrazol-4-yl)-[1,2,4]triazolo[1,5-a]pyridin-2-yl)amino)cyclohexyl)-3-oxoisoindolin-5-yl)acrylamide This compound was prepared according to the procedures described in Example 21, using 2-bromo-6-(1-(1-ethoxyethyl)-1H-pyrazol-4-yl)-5-methyl-[1,2,4]triazolo[1,5-a]pyridine instead of 2-bromo-6-(1-(1-ethoxyethyl)-1H-pyrazol-4-yl)-5-(piperidin-1-yl)-[1,2,4]triazolo[1,5-a]pyridine as starting material. LCMS calculated for $C_{27}H_{29}N_8O_2$ (M+H)$^+$: m/z=497.2; found: 497.2. $^1$H NMR (500 MHz, DMSO) δ 10.35 (s, 1H), 8.13 (d, J=2.0 Hz, 1H), 7.92 (s, 2H), 7.75 (dd, J=8.3, 2.1 Hz, 1H), 7.66 (d, J=9.0 Hz, 1H), 7.54 (d, J=8.2 Hz, 1H), 7.43 (d, J=9.0 Hz, 1H), 6.45 (dd, J=17.0, 10.1 Hz, 1H), 6.29 (dd, J=16.9, 2.0 Hz, 1H), 5.79 (dd, J=10.1, 2.0 Hz, 1H), 4.41 (q, J=17.5 Hz, 2H), 4.17 (tt, J=12.0, 3.8 Hz, 1H), 3.73 (tt, J=11.7, 3.5 Hz, 1H), 2.72 (s, 3H), 2.19 (d, J=11.6 Hz, 1H), 2.04 (d, J=12.2 Hz, 1H), 1.90-1.84 (m, 1H), 1.77 (d, J=10.3 Hz, 1H), 1.65-1.44 (m, 3H), 1.36-1.25 (m, 1H).

Example 23. N-(2-((1S,3R)-3-((5-Isopropyl-6-(1H-pyrazol-4-yl)-[1,2,4]triazolo[1,5-a]pyridin-2-yl)amino)cyclohexyl)-3-oxoisoindolin-5-yl)acrylamide

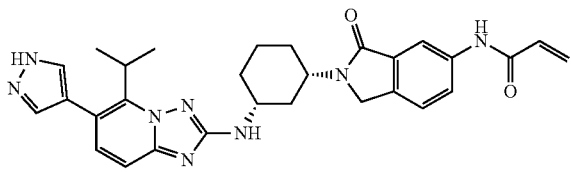 [SMILES: C=CC(=O)Nc1ccc2c(c1)C(=O)N([C@H]1CCC[C@@H](Nc3nc4ccc(-c5cn[nH]c5)c(C(C)C)n4n3)C1)C2]

Step 1. Benzyl (2-((1S,3R)-3-((6-(1-(1-ethoxyethyl)-1H-pyrazol-4-yl)-5-isopropyl-[1,2,4]triazolo[1,5-a]pyridin-2-yl)amino)cyclohexyl)-3-oxoisoindolin-5-yl)carbamate

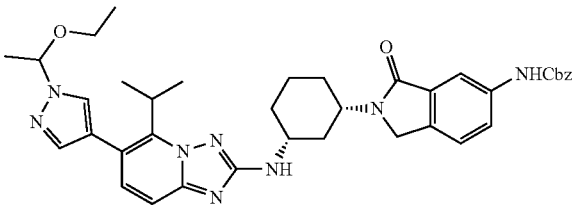 [SMILES: CCOC(C)n1cc(-c2ccc3nc(N[C@@H]4CCC[C@H](N5Cc6ccc(NC(=O)OCc7ccccc7)cc6C5=O)C4)nn3c2C(C)C)cn1]

A mixture of benzyl (2-((1S,3R)-3-aminocyclohexyl)-3-oxoisoindolin-5-yl)carbamate (100 mg, 0.264 mmol, Example 21, Step 3), 2-bromo-6-(1-(1-ethoxyethyl)-1H-pyrazol-4-yl)-5-isopropyl-[1,2,4]triazolo[1,5-a]pyridine (100 mg, 0.264 mmol, Example 18, Step 3), AdBrettPhos Pd G3 (53.5 mg, 0.053 mmol) and sodium tert-butoxide (50.8 mg, 0.529 mmol) in 1,4-dioxane (1 mL) was sparged with nitrogen and heated to 110° C. for 2 hours. After cooling to r.t., the solution was diluted with sat. aq. NaHCO$_3$ and extracted with CH$_2$Cl$_2$. The organic layer was dried over MgSO$_4$ and concentrated. The crude material was purified by Biotage Isolera. The purification gave 70 mg (39%) of desired product. LC-MS calculated for $C_{38}H_{45}N_8O_4$ (M+H)$^+$: m/z=677.4; found 677.3.

Step 2. 6-Amino-2-((1S,3R)-3-((6-(1-(1-ethoxyethyl)-1H-pyrazol-4-yl)-5-isopropyl-[1,2,4]triazolo[1,5-a]pyridin-2-yl)amino)cyclohexyl)isoindolin-1-one

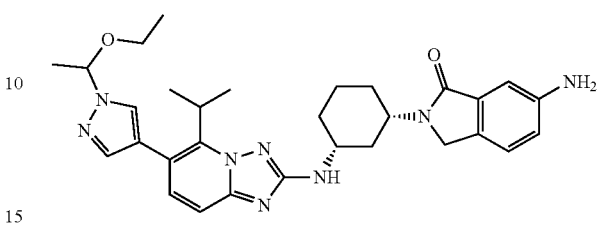

A mixture of benzyl (2-((1S,3R)-3-((6-(1-(1-ethoxyethyl)-1H-pyrazol-4-yl)-5-isopropyl-[1,2,4]triazolo[1,5-a]pyridin-2-yl)amino)cyclohexyl)-3-oxoisoindolin-5-yl)carbamate (70 mg, 0.103 mmol) and Pd on carbon (10%, 16 mg, 0.016 mmol) in MeOH (2 mL) was stirred under a balloon of H$_2$ overnight. The reaction mixture was filtered through a pad of celite, washed with MeOH. The filtrate was concentrated to give 54 mg (96%) of the desired product. LC-MS calculated for $C_{30}H_{39}N_8O_2$ (M+H)$^+$: m/z=543.3; found 543.3.

Step 3. N-(2-((1S,3R)-3-((5-Isopropyl-6-(1H-pyrazol-4-yl)-[1,2,4]triazolo[1,5-a]pyridin-2-yl)amino)cyclohexyl)-3-oxoisoindolin-5-yl)acrylamide To a solution of 6-amino-2-((1S,3R)-3-((6-(1-(1-ethoxyethyl)-1H-pyrazol-4-yl)-5-isopropyl-[1,2,4]triazolo[1,5-a]pyridin-2-yl)amino)cyclohexyl)isoindolin-1-one (54 mg, 0.10 mmol) and triethylamine (42 µL, 0.299 mmol) in DCM (1 mL) at 0° C. was added acryloyl chloride (12 µL, 0.149 mmol) and the resulting solution was stirred at 0° C. The reaction was quenched with water, extracted with DCM and concentrated. The crude was taken up in 2 mL DCM and 2 mL TFA. The resulting solution was stirred at r.t. for 1 h. Solvent was then removed and the crude was dissolved in MeCN and purified with prep-LCMS (XBridge C18 column, eluting with a gradient of acetonitrile/water containing 0.1% TFA, at flow rate of 60 mL/min). LC-MS calculated for $C_{29}H_{33}N_8O_2$ (M+H)$^+$: m/z=525.3; found 525.2.

Example 24. (R)-N-(4-(3-((7-Methyl-6-(1H-pyrazol-4-yl)-[1,2,4]triazolo[1,5-a]pyridin-2-yl)amino)pyrrolidine-1-carbonyl)phenyl)acrylamide

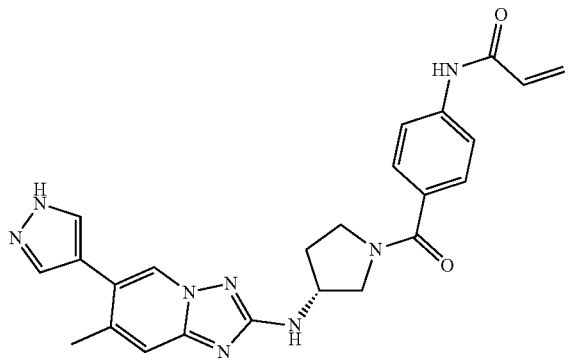 [SMILES: C=CC(=O)Nc1ccc(C(=O)N2CC[C@@H](Nc3nc4cc(C)c(-c5cn[nH]c5)cn4n3)C2)cc1]

Step 1. 6-(1-(1-Ethoxyethyl)-1H-pyrazol-4-yl)-7-methyl-[1,2,4]triazolo[1,5-a]pyridin-2-amine

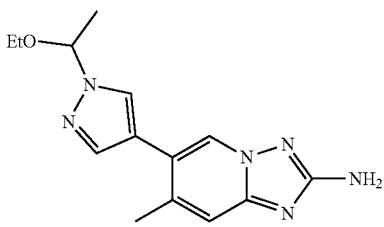 [SMILES: CCOC(C)n1cc(-c2cn3nc(N)nc3cc2C)cn1]

A mixture of 6-bromo-7-methyl-[1,2,4]triazolo[1,5-a]pyridin-2-amine (1.0 g, 14.40 mmol), 1-(1-ethoxyethyl)-4-(4,4,5,5-tetramethyl-1,3,2-dioxaborolan-2-yl)-1H-pyrazole (1.407 g, 5.28 mmol), tripotassium phosphate (2.80 g, 13.21 mmol), and XPhos Pd G2 (0.347 g, 0.440 mmol) in dioxane (20 mL) and water (4 mL) was heated at 90° C. for 2 h. The reaction mixture was then cooled to r.t., diluted with DCM and water. The organic layer was extracted with DCM, washed with brine, dried with $Na_2SO_4$, filtered and concentrated. The crude product was taken up in 50 mL MeCN. The precipitated solid was filtered, washed with MeCN, and air-dried to obtain the desired product (1.1 g, 3.84 mmol, 87% yield). LCMS calculated for $C_{14}H_{19}N_6O$ (M+H)$^+$: m/z=287.2; found 287.1.

Step 2. 2-Bromo-6-(1-(1-ethoxyethyl)-1H-pyrazol-4-yl)-7-methyl-[1,2,4]triazolo[1,5-a]pyridine

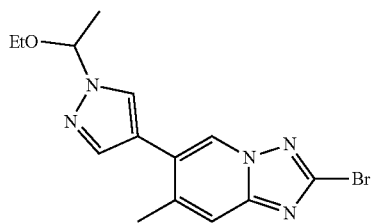 [SMILES: CCOC(C)n1cc(-c2cn3nc(Br)nc3cc2C)cn1]

A mixture of copper(II) bromide (1.287 g, 5.76 mmol) and tert-butyl nitrite (90%, 1.27 mL, 9.60 mmol) in 20 mL MeCN was stirred at 60° C. for 30 min. The above solution was then added into another flask containing a suspension of 6-(1-(1-ethoxyethyl)-1H-pyrazol-4-yl)-7-methyl-[1,2,4]triazolo[1,5-a]pyridin-2-amine (1.1 g, 3.84 mmol) pre-stirred in 15 mL MeCN for 30 min at r.t. Another portion of tert-butyl nitrite (90%, 1.27 mL, 9.60 mmol) was added. The resulting mixture was then stirred at r.t. After 2 h, the solution was then quenched with sat. aq. $NaHCO_3$ and diluted with DCM. The organic layer was extracted with DCM, washed with brined, dried with $MgSO_4$, filtered and concentrated. The crude product was purified by CombiFlash Rf+ Lumen to obtain desired product (145 mg, 0.414 mmol, 11% yield). LCMS calculated for $C_{14}H_{17}BrN_5O$ (M+H)$^+$: m/z=350.1; found 350.0.

Step 3. (R)-7-Methyl-6-(1H-pyrazol-4-yl)-N-(pyrrolidin-3-yl)-[1,2,4]triazolo[1,5-a]pyridin-2-amine

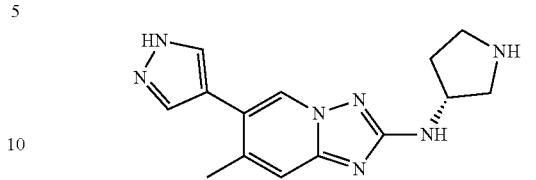

A mixture of 2-bromo-6-(1-(1-ethoxyethyl)-1H-pyrazol-4-yl)-7-methyl-[1,2,4]triazolo[1,5-a]pyridine (60 mg, 0.171 mmol), tert-butyl (R)-3-aminopyrrolidine-1-carboxylate (48 mg, 0.257 mmol), sodium tert-butoxide (33 mg, 0.343 mmol), and tBuBrettPhos Pd G3 (15 mg, 0.017 mmol) in dioxane (2 mL) was heated at 100° C. for 2 h. The reaction mixture was then cooled to r.t., diluted with EtOAc and water. The organic layer was extracted with EtOAc, washed with brine, dried with $Na_2SO_4$, filtered and concentrated. The crude product was purified by CombiFlash Rf+ Lumen to obtain tert-butyl (3R)-3-((6-(1-(1-ethoxyethyl)-1H-pyrazol-4-yl)-7-methyl-[1,2,4]triazolo[1,5-a]pyridin-2-yl)amino)pyrrolidine-1-carboxylate. The above product was taken up in 1 mL DCM and TFA (0.5 mL) was added. The reaction was stirred at r.t. for 1 hr. The solvent was then removed and the crude product was purified by CombiFlash Rf+ Lumen to obtain desired product. LCMS calculated for $C_{14}H_{18}N_7$ (M+H)$^+$: m/z=284.2; found 284.1.

Step 4. (R)-N-(4-(3-((7-Methyl-6-(1H-pyrazol-4-yl)-[1,2,4]triazolo[1,5-a]pyridin-2-yl)amino)pyrrolidine-1-carbonyl)phenyl)acrylamide A mixture of (R)-7-methyl-6-(1H-pyrazol-4-yl)-N-(pyrrolidin-3-yl)-[1,2,4]triazolo[1,5-a]pyridin-2-amine (20 mg, 0.071 mmol), 4-acrylamidobenzoic acid (15 mg, 0.078 mmol), HATU (29.5 mg, 0.078 mmol), and N,N-diisopropylethylamine (37 µL, 0.212 mmol) in DMF (1 mL) was stirred at r.t. for 1 h. The resulting mixture was diluted with MeCN and purified with prep-LCMS (XBridge C18 column, eluting with a gradient of acetonitrile/water containing 0.1% TFA, at flow rate of 60 mL/min). LCMS calculated for $C_{24}H_{25}N_8O_2$ (M+H)+: m/z=457.2; found 457.1.

Example 25. (R)-N-(4-(3-((5-Isopropyl-6-(1H-pyrazol-4-yl)-[1,2,4]triazolo[1,5-a]pyridin-2-yl)amino)pyrrolidine-1-carbonyl)phenyl)-N-methylacrylamide

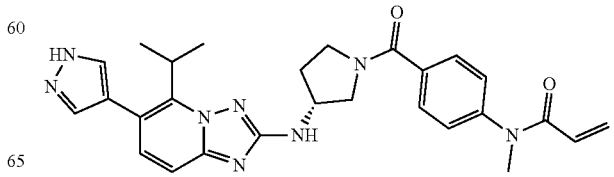

Step 1. 4-(N-methylacrylamido)benzoic acid

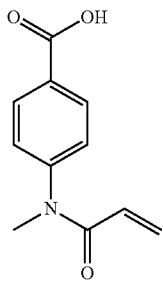

A solution of methyl 4-(methylamino)benzoate (1.00 g, 6.05 mmol) and potassium carbonate (2.5 g, 18.16 mmol) in THF (10 mL) at 0° C. was added acryloyl chloride (0.541 mL, 6.66 mmol) slowly. The reaction was stirred at r.t. for 0.5 h. The reaction was then quenched with water, extracted with EtOAc. The organic layer was washed with brine, dried with MgSO$_4$ and concentrated. The obtained intermediate was dissolved in THF (10 mL) and MeCN (8 mL). The solution was added aqueous sodium hydroxide (1N, 12 mL). The mixture was stirred at r.t. for 1 h. The volatile was removed, the residue was neutralized to pH=4-5 with aqueous HCl (1N). The solid formed was filtered, washed with water and air-dried to give desired product. LC-MS calculated for $C_{11}H_{12}NO_3$ (M+H)$^+$: m/z=206.1; found 206.0.

Step 2. (R)-N-(4-(3-((5-Isopropyl-6-(1H-pyrazol-4-yl)-[1,2,4]triazolo[1,5-a]pyridin-2-yl)amino)pyrrolidine-1-carbonyl)phenyl)-N-methylacrylamide This compound was prepared according to the procedure described in Example 1, Step 7, using (R)-5-isopropyl-6-(1H-pyrazol-4-yl)-N-(pyrrolidin-3-yl)-[1,2,4]triazolo[1,5-a]pyridin-2-amine (Example 18, Step 4) and 4-(N-methylacrylamido)benzoic acid instead of N-(azetidin-3-yl)-5-isopropoxy-6-(1H-pyrazol-4-yl)-[1,2,4]triazolo[1,5-a]pyrazin-2-amine and 4-acrylamidobenzoic acid as starting material. LC-MS calculated for $C_{27}H_{31}N_8O_2$ (M+H)$^+$: m/z=499.2; found 499.3.

Example 26. (R)-2-Fluoro-N-(4-(3-((5-isopropyl-6-(1H-pyrazol-4-yl)-[1,2,4]triazolo[1,5-a]pyridin-2-yl)amino)pyrrolidine-1-carbonyl)phenyl)acrylamide

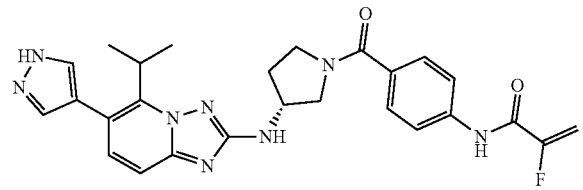 [SMILES: C=C(F)C(=O)Nc1ccc(C(=O)N2CC[C@@H](Nc3nc4ccc(-c5cn[nH]c5)c(C(C)C)n4n3)C2)cc1]

Step 1. 4-(2-Fluoroacrylamido)benzoic acid

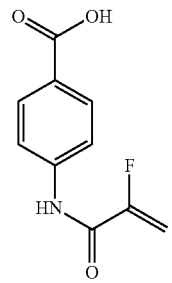

A solution of methyl 4-aminobenzoate (1.00 g, 6.62 mmol) in MeCN (10 mL) at 0° C. was added DIPEA (3.5 mL, 19.85 mmol), 2-fluoroacrylic acid (0.9 g, 9.92 mmol) and T3P (1-propanephosphonic anhydride solution, ca. 50% in EtOAc, 16.35 mL, 26.5 mmol). After stirring at 0° C. for 10 minutes, the reaction was quenched with NaHCO$_3$, extracted with EtOAc, washed with NH$_4$Cl. The organic layer was concentrated and the crude was purified by Biotage Isolera. The obtained intermediate was dissolved in THF (10 mL) and MeCN (10 mL). To the solution was added aqueous sodium hydroxide (1N, 13 mL). The mixture was stirred at r.t. for 1 h. The volatiles were removed, and the residue was neutralized to pH=4-5 with aqueous HCl (1N). The solid formed was filtered, washed with water, and air-dried to give desired product. LC-MS calculated for $C_{10}H_9FNO_3$ (M+H)$^+$: m/z=210.0; found 210.0.

Step 2. (R)-2-Fluoro-N-(4-(3-((5-isopropyl-6-(1H-pyrazol-4-yl)-[1,2,4]triazolo[1,5-a]pyridin-2-yl)amino)pyrrolidine-1-carbonyl)phenyl)acrylamide This compound was prepared according to the procedure described in Example 1, Step 7, using (R)-5-isopropyl-6-(1H-pyrazol-4-yl)-N-(pyrrolidin-3-yl)-[1,2,4]triazolo[1,5-a]pyridin-2-amine (Example 18, Step 4) and 4-(2-fluoroacrylamido)benzoic acid instead of N-(azetidin-3-yl)-5-isopropoxy-6-(1H-pyrazol-4-yl)-[1,2,4]triazolo[1,5-a]pyrazin-2-amine and 4-acrylamidobenzoic acid as starting material. LC-MS calculated for $C_{26}H_{28}FN_8O_2$(M+H)$^+$: m/z=503.2; found 503.2.

Example 27. (R)-N-(2-(3-((5-Isopropyl-6-(1H-pyrazol-4-yl)-[1,2,4]triazolo[1,5-a]pyridin-2-yl)amino)piperidin-1-yl)benzo[d]thiazol-5-yl)acrylamide

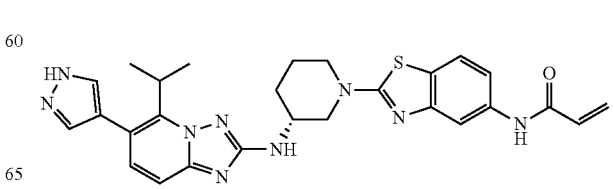

Step 1. Benzyl (2-chlorobenzo[d]thiazol-5-yl)carbamate

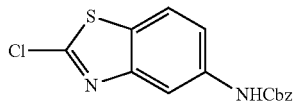 [SMILES: O=C(Nc1ccc2sc(Cl)nc2c1)OCc1ccccc1]

To a solution of 2-chlorobenzo[d]thiazol-5-amine (1.50 g, 8.12 mmol) in acetonitrile (20 mL) was added 10 mL aqueous saturated $K_2CO_3$, followed by benzyl chloroformate (2.3 mL, 16.25 mmol). The reaction was stirred at r.t. for 1 h, followed by addition of EtOAc. The organic layer was washed with brine, dried over $Na_2SO_4$, filtered and concentrated. The crude was purified by Biotage Isolera. LC-MS calculated for $C_{15}H_{12}ClN_2O_2S$ (M+H)$^+$: m/z=319.0; found 318.9.

Step 2. Benzyl (R)-(2-(3-aminopiperidin-1-yl)benzo[d]thiazol-5-yl)carbamate

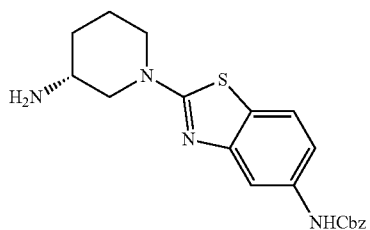 [SMILES: N[C@@H]1CCCN(c2nc3cc(NC(=O)OCc4ccccc4)ccc3s2)C1]

A mixture of tert-butyl (R)-piperidin-3-ylcarbamate (1 g, 5.02 mmol), benzyl (2-chlorobenzo[d]thiazol-5-yl)carbamate (1.60 g, 5.02 mmol), N,N-diisopropylethylamine (2.63 mL, 15.06 mmol) in DMF (30 mL) was heated to 100° C. for 1 h. The reaction mixture was cooled to r.t., diluted with EtOAc. The organic layer was then washed with brine, dried over $Na_2SO_4$. The obtained intermediate was then taken up in 5 mL DCM and 5 mL TFA was added. The reaction was stirred at r.t. for 1 h. The solvent was then removed and the crude product was purified by Biotage Isolera. LC-MS calculated for $C_{20}H_{23}N_4O_2S$ (M+H)$^+$: m/z=383.2; found 383.1.

Step 3. Benzyl (2-((3R)-3-((6-(1-(1-ethoxyethyl)-1H-pyrazol-4-yl)-5-isopropyl-[1,2,4]triazolo[1,5-a]pyridin-2-yl)amino)piperidin-1-yl)benzo[d]thiazol-5-yl)carbamate

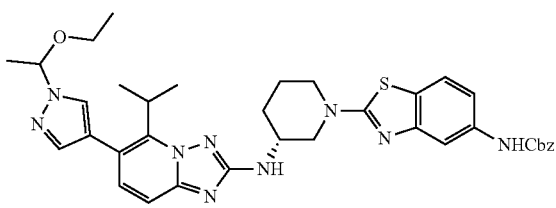 [SMILES: CCOC(C)n1cc(-c2ccc3nc(N[C@@H]4CCCN(c5nc6cc(NC(=O)OCc7ccccc7)ccc6s5)C4)nn3c2C(C)C)cn1]

This compound was prepared according to the procedure described in Example 23, Step 1, using benzyl (R)-(2-(3-aminopiperidin-1-yl)benzo[d]thiazol-5-yl)carbamate instead of benzyl (2-((1S,3R)-3-aminocyclohexyl)-3-oxoisoindolin-5-yl)carbamate as starting material. LC-MS calculated for $C_{36}H_{42}N_9O_3S$ (M+H)$^+$: m/z=680.3; found 680.3.

Step 4. 2-((3R)-3-((6-(1-(1-Ethoxyethyl)-1H-pyrazol-4-yl)-5-isopropyl-[1,2,4]triazolo[1,5-a]pyridin-2-yl)amino)piperidin-1-yl)benzo[d]thiazol-5-amine

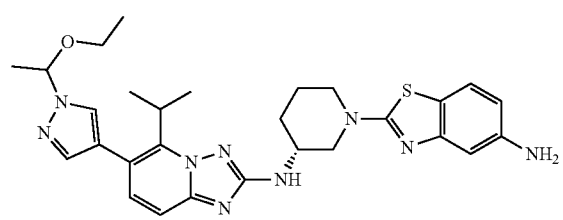 [SMILES: CCOC(C)n1cc(-c2ccc3nc(N[C@@H]4CCCN(c5nc6cc(N)ccc6s5)C4)nn3c2C(C)C)cn1]

This compound was prepared according to the procedures described in Example 23, Step 2, using benzyl (2-((3R)-3-((6-(1-(1-ethoxyethyl)-1H-pyrazol-4-yl)-5-isopropyl-[1,2,4]triazolo[1,5-a]pyridin-2-yl)amino)piperidin-1-yl)benzo[d]thiazol-5-yl)carbamate instead of benzyl (2-((1S,3R)-3-((6-(1-(1-ethoxyethyl)-1H-pyrazol-4-yl)-5-isopropyl-[1,2,4]triazolo[1,5-a]pyridin-2-yl)amino)cyclohexyl)-3-oxoisoindolin-5-yl)carbamate as starting material. LC-MS calculated for $C_{28}H_{36}N_9OS$ (M+H)$^+$: m/z=546.3; found 546.2.

Step 5. (R)-N-(2-(3-((5-Isopropyl-6-(1H-pyrazol-4-yl)-[1,2,4]triazolo[1,5-a]pyridin-2-yl)amino)piperidin-1-yl)benzo[d]thiazol-5-yl)acrylamide This compound was prepared according to the procedure described in Example 23, Step 3, using 2-((3R)-3-((6-(1-(1-ethoxyethyl)-1H-pyrazol-4-yl)-5-isopropyl-[1,2,4]triazolo[1,5-a]pyridin-2-yl)amino)piperidin-1-yl)benzo[d]thiazol-5-amine instead of 6-amino-2-((1S,3R)-3-((6-(1-(1-ethoxyethyl)-1H-pyrazol-4-yl)-5-isopropyl-[1,2,4]triazolo[1,5-a]pyridin-2-yl)amino)cyclohexyl)isoindolin-1-one as starting material. LC-MS calculated for $C_{27}H_{30}N_9OS$ (M+H)$^+$: m/z=528.2; found 528.2.

Example 28. (R)-N-(2-(3-((5-Isopropyl-6-(1H-pyrazol-4-yl)-[1,2,4]triazolo[1,5-a]pyridin-2-yl)amino)piperidin-1-yl)-1-methyl-1H-benzo[d]imidazol-5-yl)acrylamide

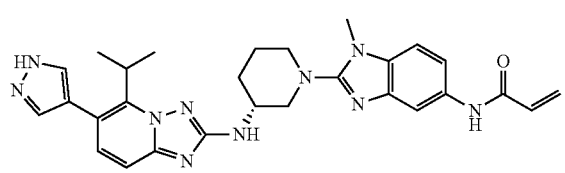 [SMILES: C=CC(=O)Nc1ccc2c(c1)nc(N1CCC[C@@H](Nc3nc4ccc(-c5cn[nH]c5)c(C(C)C)n4n3)C1)n2C]

Step 1. tert-Butyl (R)-(1-(I-methyl-5-nitro-1H-benzo[d]imidazol-2-yl)piperidin-3-yl)carbamate

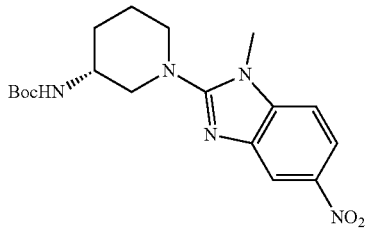 [SMILES: Cn1c(N2CCC[C@@H](NC(=O)OC(C)(C)C)C2)nc2cc([N+](=O)[O-])ccc21]

A mixture of 2-chloro-1-methyl-5-nitro-1H-benzo[d]imidazole (1.00 g, 4.73 mmol), tert-butyl (R)-piperidin-3-ylcarbamate (0.946 g, 4.73 mmol) and N,N-diisopropylethylamine (2.47 mL, 14.18 mmol) in DMF (30 mL) was heated to 100° C. for 1 h. The reaction mixture was cooled to r.t., diluted with EtOAc. The organic layer was then washed with brine, dried over Na$_2$SO$_4$. The solvent was then removed and the crude product was used directly in the next step. LC-MS calculated for C$_{18}$H$_{26}$N$_5$O$_4$ (M+H)$^+$: m/z=376.2; found 376.2.

Step 2. tert-Butyl (R)-(1-(5-amino-1-methyl-1H-benzo[d]imidazol-2-yl)piperidin-3-yl)carbamate

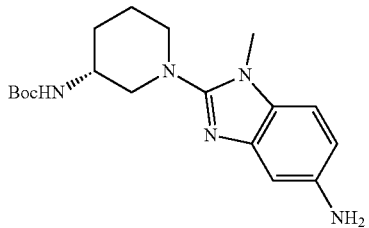

A mixture of tert-butyl (R)-(1-(1-methyl-5-nitro-1H-benzo[d]imidazol-2-yl)piperidin-3-yl)carbamate (1.76 g, 4.69 mmol), zinc (3.06 g, 46.9 mmol) and ammonium chloride (5.02 g, 94 mmol) in MeOH (10 mL), THF (5 mL) and water (5 mL) was stirred at 40° C. for 1 h. The mixture was cooled to r.t., diluted with MeOH and filtered through celite. Solvent was evaporated, and the crude was purified by Biotage Isolera. LC-MS calculated for C$_{18}$H$_{28}$N$_5$O$_2$ (M+H)$^+$: m/z=346.2; found 346.2.

Step 3. Benzyl (R)-(2-(3-aminopiperidin-1-yl)-1-methyl-1H-benzo[d]imidazol-5-yl)carbamate

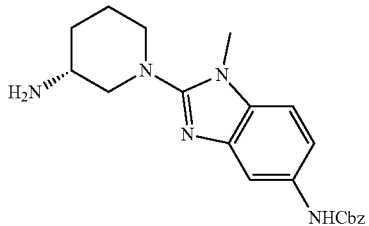 [SMILES: Cn1c(N2CCC[C@@H](N)C2)nc2cc(NC(=O)OCc3ccccc3)ccc21]

A mixture of tert-butyl (R)-(1-5-amino-1-methyl-1H-benzo[d]imidazol-2-yl)piperidin-3-yl)carbamate (1.60 g, 4.63 mmol) in acetonitrile (20 mL) was added 10 mL saturated aqueous K$_2$CO$_3$, then benzyl chloroformate (1.32 mL, 9.26 mmol), and the resulting mixture was stirred at r.t. for 1 hr. The reaction mixture was diluted with EtOAc. The organic layer was extracted and dried over Na$_2$SO$_4$, filtered and concentrated. The crude material was purified by Biotage Isolera. The obtained intermediate was then taken up in 5 mL DCM and 5 mL TFA was added. The reaction was stirred at r.t. for 1 h. The reaction mixture was then concentrated, the residue was partitioned between DCM and sat. aq. NaHCO$_3$ solution. The organic layer was washed with brine, dried over Na$_2$SO$_4$, and concentrated to give desired product. LC-MS calculated for C$_{21}$H$_{26}$N$_5$O$_2$ (M+H)$^+$: m/z=380.2; found 380.2.

Step 4. Benzyl (2-((3R)-3-((6-(1-(1-ethoxyethyl)-1H-pyrazol-4-yl)-5-isopropyl-[1,2,4]triazolo[1,5-a]pyridin-2-yl)amino)piperidin-1-yl)-1-methyl-1H-benzo[d]imidazol-5-yl)carbamate

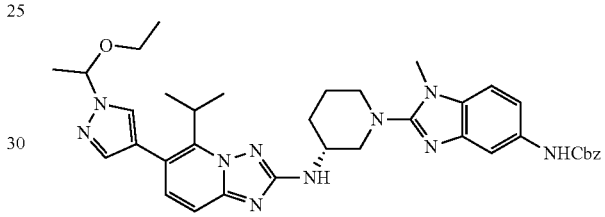

This compound was prepared according to the procedure described in Example 23, Step 1, using benzyl (R)-(2-(3-aminopiperidin-1-yl)-1-methyl-1H-benzo[d]imidazol-5-yl)carbamate instead of benzyl (2-((1S,3R)-3-aminocyclohexyl)-3-oxoisoindolin-5-yl)carbamate as starting material. LC-MS calculated for C$_{37}$H$_{45}$N$_{10}$O$_3$ (M+H)$^+$: m/z=677.4; found 677.5.

Step 5. N-((R)-1-(5-Amino-1-methyl-1H-benzo[d]imidazol-2-yl)piperidin-3-yl)-6-(1-(1-ethoxyethyl)-1H-pyrazol-4-yl)-5-isopropyl-[1,2,4]triazolo[1,5-a]pyridin-2-amine

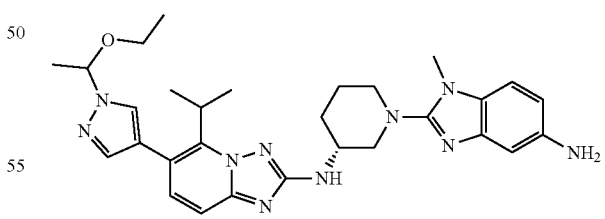

This compound was prepared according to the procedure described in Example 23, Step 2, using (2-((3R)-3-((6-(1-(1-ethoxyethyl)-1H-pyrazol-4-yl)-5-isopropyl-[1,2,4]triazolo[1,5-a]pyridin-2-yl)amino)piperidin-1-yl)-1-methyl-1H-benzo[d]imidazol-5-yl)carbamate instead of (2-((1S,3R)-3-((6-(1-(1-ethoxyethyl)-1H-pyrazol-4-yl)-5-isopropyl-[1,2,4]triazolo[1,5-a]pyridin-2-yl)amino)cyclohexyl)-3-oxoisoindolin-5-yl)carbamate. LC-MS calculated for C$_{29}$H$_{39}$N$_{10}$O (M+H)$^+$: m/z=543.3; found 543.4.

151

Step 6. (R)-N-(2-(3-((5-Isopropyl-6-(1H-pyrazol-4-yl)-[1,2,4]triazolo[1,5-a]pyridin-2-yl)amino)piperidin-1-yl)-1-methyl-1H-benzo[d]imidazol-5-yl)acrylamide This compound was prepared according to the procedure described in Example 23, Step 3, using N-((R)-1-(5-amino-1-methyl-1H-benzo[d]imidazol-2-yl)piperidin-3-yl)-6-(1-(1-ethoxyethyl)-1H-pyrazol-4-yl)-5-isopropyl-[1,2,4]triazolo[1,5-a]pyridin-2-amine instead of 6-amino-2-((1S,3R)-3-((6-(1-(1-ethoxyethyl)-1H-pyrazol-4-yl)-5-isopropyl-[1,2,4]triazolo[1,5-a]pyridin-2-yl)amino)cyclohexyl)isoindolin-1-one as starting material. LC-MS calculated for $C_{28}H_{33}N_{10}O$ (M+H)+: m/z=525.3; found 525.2. $^1$H NMR (600 MHz, DMSO) δ 10.44 (s, 1H), 8.12 (d, J=1.9 Hz, 1H), 7.75 (s, 2H), 7.57 (d, J=8.8 Hz, 1H), 7.50 (dd, J=8.8, 1.9 Hz, 1H), 7.38 (d, J=9.0 Hz, 1H), 7.32 (d, J=9.0 Hz, 1H), 6.99 (s, 1H), 6.46 (dd, J=16.9, 10.2 Hz, 1H), 6.29 (dd, J=17.0, 1.8 Hz, 1H), 5.79 (dd, J=10.2, 1.9 Hz, 1H), 4.02 (dd, J=12.6, 3.7 Hz, 1H), 3.94 (s, 1H), 3.74 (s, 3H), 3.78-3.60 (m, 2H), 3.45-3.36 (m, 2H), 2.12-1.99 (m, 2H), 1.85-1.74 (m, 2H), 1.45 (dd, J=12.0, 7.0 Hz, 6H).

Example 29. (R)-N-(2-(3-((5-Methyl-6-(1H-pyrazol-4-yl)-[1,2,4]triazolo[1,5-a]pyridin-2-yl)amino)piperidin-1-yl)benzo[d]thiazol-5-yl)acrylamide

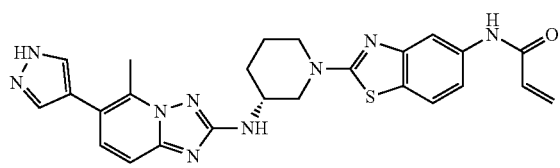 [SMILES: C=CC(=O)Nc1ccc2sc(N3CCC[C@@H](Nc4nc5ccc(-c6cn[nH]c6)c(C)n5n4)C3)nc2c1]

Step 1. Benzyl (2-((3R)-3-((6-(1-(1-ethoxyethyl)-1H-pyrazol-4-yl)-5-methyl-[1,2,4]triazolo[1,5-a]pyridin-2-yl)amino)piperidin-1-yl)benzo[d]thiazol-5-yl)carbamate

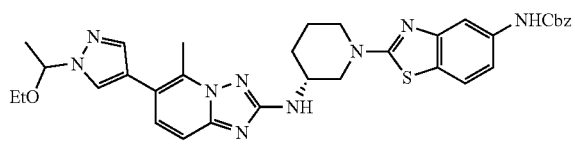 [SMILES: CCOC(C)n1cc(-c2ccc3nc(N[C@@H]4CCCN(c5nc6cc(NC(=O)OCc7ccccc7)ccc6s5)C4)nn3c2C)cn1]

A mixture of 2-bromo-6-(1-(1-ethoxyethyl)-1H-pyrazol-4-yl)-5-methyl-[1,2,4]triazolo[1,5-a]pyridine (100 mg, 0.286 mmol, Example 22, Step 2), benzyl (R)-(2-(3-aminopiperidin-1-yl)benzo[d]thiazol-5-yl)carbamate (164 mg, 0.428 mmol, Example 27, Step 2), sodium tert-butoxide (55 mg, 0.571 mmol), and tBuBrettPhos Pd G3 (24 mg, 0.029 mmol) in dioxane (2 mL) was heated to 100° C. for 1 hr. The reaction mixture was then cooled to r.t., diluted with DCM and water. The organic layer was extracted with DCM,

152 washed with brine, dried with $Na_2SO_4$, filtered and concentrated. The crude product was purified by CombiFlash Rf+ Lumen to obtain desired product (63 mg, 0.097 mmol, 34% yield). LCMS calculated for $C_{34}H_{38}N_9O_3S$ (M+H)+: m/z=652.3; found 652.2.

Step 2. 2-((3R)-3-((6-(1-(1-Ethoxyethyl)-1H-pyrazol-4-yl)-5-methyl-[1,2,4]triazolo[1,5-a]pyridin-2-yl)amino)piperidin-1-yl)benzo[d]thiazol-5-amine

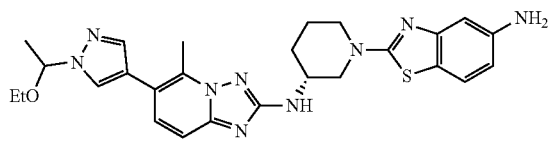 [SMILES: CCOC(C)n1cc(-c2ccc3nc(N[C@@H]4CCCN(c5nc6cc(N)ccc6s5)C4)nn3c2C)cn1]

A mixture of benzyl (2-((3R)-3-((6-(1-(1-ethoxyethyl)-1H-pyrazol-4-yl)-5-methyl-[1,2,4]triazolo[1,5-a]pyridin-2-yl)amino)piperidin-1-yl)benzo[d]thiazol-5-yl)carbamate (63 mg, 0.097 mmol), Pd on carbon (10%, 10 mg, 9.67 μmol) in dioxane (0.5 mL) and MeOH (3 mL) was stirred at r.t. under a hydrogen balloon for 20 h. The reaction mixture was then diluted with MeOH, filtered through celite and concentrated. The obtained product was used directly in the next step. LCMS calculated for $C_{26}H_{32}N_9OS$ (M+H)+: m/z=518.2; found 518.2.

Step 3. (R)-N-(2-(3-((5-Methyl-6-(1H-pyrazol-4-yl)-[1,2,4]triazolo[1,5-a]pyridin-2-yl)amino)piperidin-1-yl)benzo[d]thiazol-5-yl)acrylamide To a solution of 2-((3R)-3-((6-(1-(1-ethoxyethyl)-1H-pyrazol-4-yl)-5-methyl-[1,2,4]triazolo[1,5-a]pyridin-2-yl)amino)piperidin-1-yl)benzo[d]thiazol-5-amine (22 mg, 0.042 mmol) and triethylamine (18 μL, 0.127 mmol) in DCM (2 mL) at 0° C. was added acryloyl chloride (5.2 μL, 0.064 mmol) and the reaction mixture was stirred at r.t. for 1 h. The reaction was quenched with water and diluted with DCM. The organic layer was extracted and concentrated. The crude product was taken up in 2 mL DCM and 2 mL TFA was added, and the resulting solution was stirred at r.t. for 1 h. Solvent was then removed and the crude was dissolved in MeCN and purified with prep-LCMS (XBridge C18 column, eluting with a gradient of acetonitrile/water containing 0.1% TFA, at flow rate of 60 mL/min). LCMS calculated for $C_{25}H_{26}N_9OS$ (M+H)+: m/z=500.2; found 500.1. $^1$H NMR (500 MHz, DMSO) δ 10.17 (s, 1H), 7.93 (d, J=4.5 Hz, 3H), 7.69-7.58 (m, 2H), 7.41 (d, J=9.0 Hz, 1H), 7.31 (dd, J=8.6, 2.0 Hz, 1H), 6.45 (dd, J=16.9, 10.1 Hz, 1H), 6.27 (dd, J=17.0, 2.0 Hz, 1H), 5.76 (dd, J=10.1, 2.0 Hz, 1H), 4.21 (dd, J=12.7, 4.0 Hz, 1H), 3.89 (d, J=12.3 Hz, 1H), 3.83 (dp, J=8.8, 4.1 Hz, 1H), 3.36 (ddd, J=13.1, 9.7, 3.6 Hz, 1H), 3.26 (dd, J=12.7, 8.9 Hz, 1H), 2.75 (s, 3H), 2.09 (p, J=5.4 Hz, 1H), 1.93 (dt, J=9.6, 5.3 Hz, 1H), 1.74-1.62 (m, 2H).

Example 30. (R)-N-(4-(3-((6-(1H-Pyrazol-4-yl)-5-(trifluoromethyl)-[1,2,4]triazolo[1,5-a]pyridin-2-yl)amino)pyrrolidine-1-carbonyl)phenyl)acrylamide

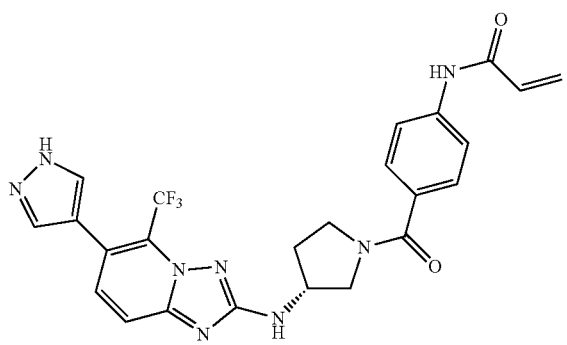 [SMILES: C=CC(=O)Nc1ccc(C(=O)N2CC[C@@H](Nc3nc4ccc(-c5cn[nH]c5)c(C(F)(F)F)n4n3)C2)cc1]

Step 1. 6-Bromo-5-(trifluoromethyl)-[1,2,4]triazolo[1,5-a]pyridin-2-amine

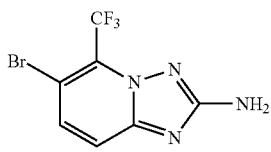 [SMILES: Nc1nc2ccc(Br)c(C(F)(F)F)n2n1]

To a mixture of 5-bromo-6-(trifluoromethyl)pyridin-2-amine (5.18 g, 21.49 mmol) in MeCN (100 mL) was added ethoxycarbonyl isothiocyanate (2.92 mL, 25.8 mmol) and the mixture was stirred at 90° C. for 2 h. The mixture was then concentrated, and to the residue was added hydroxylamine hydrochloride (4.48 g, 64.5 mmol), N,N-diisopropylethylamine (11.26 mL, 64.5 mmol), MeOH (50 mL) and EtOH (50 mL). The reaction was then heated to 90° C. for 2 h. The reaction mixture was then cooled to r.t, and MeCN (100 mL) was added. The precipitated solid was filtered, washed with MeCN, and air-dried to obtain the product as yellow solid. LCMS calculated for $C_7H_5BrF_3N_4$ $(M+H)^+$: m/z=281.0; found 280.9.

Step 2. 6-(1-(1-Ethoxyethyl)-1H-pyrazol-4-yl)-5-(trifluoromethyl)-[1,2,4]triazolo[1,5-a]pyridin-2-amine

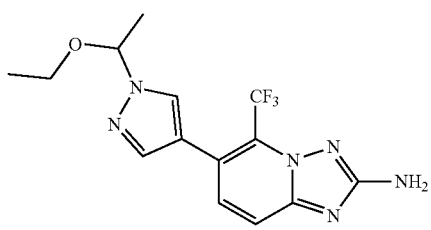 [SMILES: CCOC(C)n1cc(-c2ccc3nc(N)nn3c2C(F)(F)F)cn1]

A mixture of 6-bromo-5-(trifluoromethyl)-[1,2,4]triazolo[1,5-a]pyridin-2-amine (3.0 g, 10.67 mmol), 1-(1-ethoxyethyl)-4-(4,4,5,5-tetramethyl-1,3,2-dioxaborolan-2-yl)-1H-pyrazole (4.26 g, 16.01 mmol), tripotassium phosphate (6.80 g, 32.0 mmol) and XPhos Pd G2 (2.52 g, 3.20 mmol) was heated at 90° C. for 40 h. The reaction mixture was then cooled to r.t., diluted with DCM and water. The organic layer was extracted with DCM, washed with brine, dried with $Na_2SO_4$, filtered, and concentrated. The crude product was purified by CombiFlash Rf+ Lumen to obtain desired product. LCMS calculated for $C_{14}H_{16}F_3N_6O$ $(M+H)^+$: m/z=341.1; found 341.1.

Step 3. 2-Bromo-6-(1-(1-ethoxyethyl)-1H-pyrazol-4-yl)-5-(trifluoromethyl)-[1,2,4]triazolo[1,5-a]pyridine

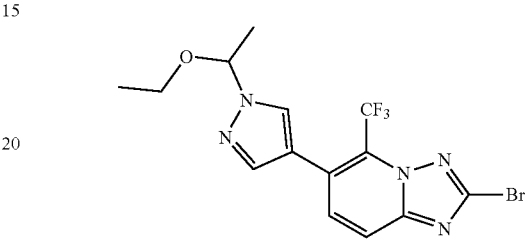

A mixture of copper(II) bromide (4.23 g, 18.95 mmol) and tert-butyl nitrite (90%, 4.17 mL, 31.6 mmol) in 50 mL MeCN was stirred at 60° C. for 30 min. The above solution was then added into another flask containing a suspension of 6-(1-(1-ethoxyethyl)-1H-pyrazol-4-yl)-5-(trifluoromethyl)-[1,2,4]triazolo[1,5-a]pyridin-2-amine (4.3 g, 12.64 mmol) pre-stirred in 40 mL MeCN for 30 min at r.t. Another portion of tert-butyl nitrite (90%, 4.17 mL, 31.6 mmol) was added. The resulting mixture was then stirred at r.t. After 2 h, the solution was then quenched with sat. aq. $NaHCO_3$ and diluted with DCM. The organic layer was extracted with DCM, washed with brined, dried over $MgSO_4$, filtered and concentrated. The crude product was purified by CombiFlash Rf+ Lumen to obtain desired product (2.6 g, 6.43 mmol, 51% yield). LCMS calculated for $C_{14}H_{14}BrF_3N_5O$ $(M+H)^+$: m/z=404.0; found 404.0.

Step 4. (R)-N-(4-(3-((6-(1H-Pyrazol-4-yl)-5-(trifluoromethyl)-[1,2,4]triazolo[1,5-a]pyridin-2-yl)amino)pyrrolidine-1-carbonyl)phenyl)acrylamide This compound was prepared according to the procedures described in Example 24, using 2-bromo-6-(1-(1-ethoxyethyl)-1H-pyrazol-4-yl)-5-(trifluoromethyl)-[1,2,4]triazolo[1,5-a]pyridine instead of 2-bromo-6-(1-(1-ethoxyethyl)-1H-pyrazol-4-yl)-7-methyl-[1,2,4]triazolo[1,5-a]pyridine as starting material. LCMS calculated for $C_{24}H_{22}F_3N_8O_2$ $(M+H)^+$: m/z=511.2; found 511.1. $^1$H NMR (500 MHz, DMSO) δ 10.31 (d, J=13.0 Hz, 1H), 7.83-7.66 (m, 5H), 7.63-7.35 (m, 3H), 6.45 (dt, J=16.8, 10.0 Hz, 1H), 6.28 (ddd, J=17.1, 8.5, 2.1 Hz, 1H), 5.82-5.74 (m, 1H), 4.35-4.22 (m, 1H), 3.87-3.44 (m, 4H), 2.21-1.96 (m, 2H).

Example 31. (R)-N-(4-(3-((7-(1H-Pyrazol-4-yl)-[1,2,4]triazolo[1,5-a]pyridin-2-yl)amino)pyrrolidine-1-carbonyl)phenyl)-2-fluoroacrylamide

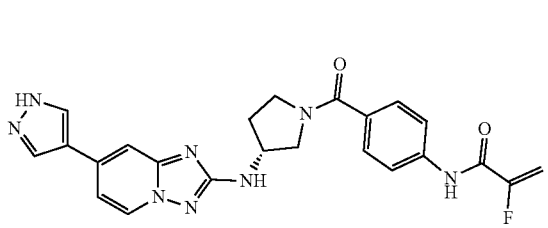 [SMILES: C=C(F)C(=O)Nc1ccc(C(=O)N2CC[C@@H](Nc3nc4cc(-c5cn[nH]c5)ccn4n3)C2)cc1]

Step 1. 7-(1-(1-Ethoxyethyl)-1H-pyrazol-4-yl)-[1,2,4]triazolo[1,5-a]pyridin-2-amine

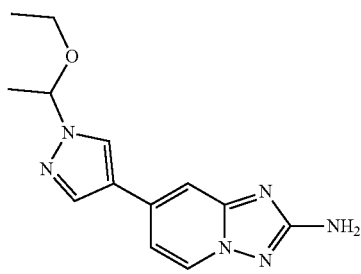 [SMILES: CCOC(C)n1cc(-c2ccn3nc(N)nc3c2)cn1]

This compound was prepared according to the procedure described in Example 11, Step 1, using 7-bromo-[1,2,4]triazolo[1,5-a]pyridin-2-amine instead of 6-bromo-[1,2,4]triazolo[1,5-a]pyridin-2-amine as starting material. LC-MS calculated for $C_{13}H_{17}N_6O$ (M+H)$^+$: m/z=273.1; found 273.2.

Step 2. 2-Bromo-7-(1-(1-ethoxyethyl)-1H-pyrazol-4-yl)-[1,2,4]triazolo[1,5-a]pyridine

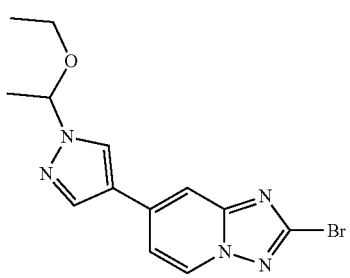 [SMILES: CCOC(C)n1cc(-c2ccn3nc(Br)nc3c2)cn1]

This compound was prepared according to the procedure described in Example 1, Step 3, using 7-(1-(1-ethoxyethyl)-1H-pyrazol-4-yl)-[1,2,4]triazolo[1,5-a]pyridin-2-amine instead of 5-chloro-6-(1-(1-ethoxyethyl)-1H-pyrazol-4-yl)-[1,2,4]triazolo[1,5-α]pyrazin-2-amine as starting material. LC-MS calculated for $C_{13}H_{15}BrN_5O$ (M+H)$^+$: m/z=336.0; found 336.0.

Step 3. (R)-7-(1H-pyrazol-4-yl)-N-(pyrrolidin-3-yl)-[1,2,4]triazolo[1,5-a]pyridin-2-amine

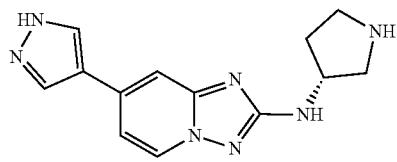 [SMILES: c1cn2nc(N[C@@H]3CCNC3)nc2cc1-c1cn[nH]c1]

This compound was prepared according to the procedures described in Example 1, Step 5, using tert-butyl (R)-3-aminopyrrolidine-1-carboxylate and 2-bromo-7-(1-(1-ethoxyethyl)-1H-pyrazol-4-yl)-[1,2,4]triazolo[1,5-a]pyridine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{13}H_{16}N_7$(M+H)$^+$: m/z=270.1; found 270.3.

Step 4. (R)-N-(4-(3-((7-(1H-Pyrazol-4-yl)-[1,2,4]triazolo[1,5-a]pyridin-2-yl)amino)pyrrolidine-1-carbonyl)phenyl)-2-fluoroacrylamide This compound was prepared according to the procedure described in Example 1, Step 7, using (R)-7-(1H-pyrazol-4-yl)-N-(pyrrolidin-3-yl)-[1,2,4]triazolo[1,5-a]pyridin-2-amine and 4-(2-fluoroacrylamido)benzoic acid instead of N-(azetidin-3-yl)-5-isopropoxy-6-(1H-pyrazol-4-yl)-[1,2,4]triazolo[1,5-a]pyrazin-2-amine and 4-acrylamidobenzoic acid as starting material. LC-MS calculated for $C_{23}H_{22}FN_8O_2$(M+H)$^+$: m/z=461.2; found 461.2.

Example 32. (R)-2-Fluoro-N-(4-(3-((8-methyl-7-(1H-pyrazol-4-yl)-[1,2,4]triazolo[1,5-a]pyridin-2-yl)amino)pyrrolidine-1-carbonyl)phenyl)acrylamide

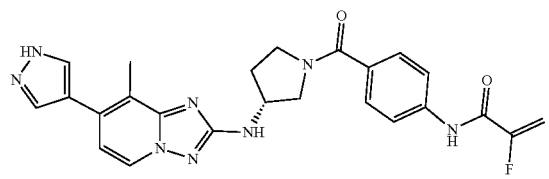 [SMILES: C=C(F)C(=O)Nc1ccc(C(=O)N2CC[C@@H](Nc3nc4c(C)c(-c5cn[nH]c5)ccn4n3)C2)cc1]

Step 1. 4-(1-(1-Ethoxyethyl)-1H-pyrazol-4-yl)-3-methylpyridin-2-amine

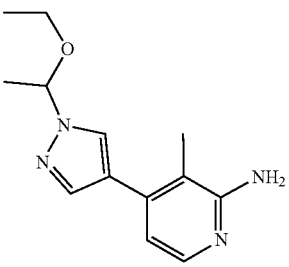 [SMILES: CCOC(C)n1cc(-c2ccnc(N)c2C)cn1]

This compound was prepared according to the procedure described in Example 1, Step 1, using 4-chloro-3-methylpyridin-2-amine instead of 5-bromo-6-chloropyrazin-2-amine as starting material. LC-MS calculated for $C_{13}H_{19}N_4O$ (M+H)$^+$: m/z=247.2; found 247.2.

Step 2. 7-(1-(1-Ethoxyethyl)-1H-pyrazol-4-yl)-8-methyl-[1,2,4]triazolo[1,5-a]pyridin-2-amine

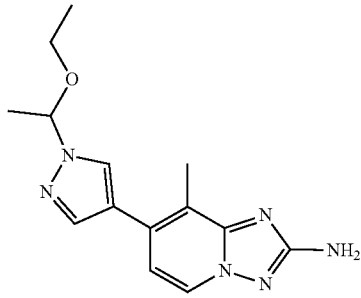 [SMILES: CCOC(C)n1cc(-c2ccn3nc(N)nc3c2C)cn1]

This compound was prepared according to the procedure described in Example 1, Step 2, using 4-(1-(1-ethoxyethyl)-1H-pyrazol-4-yl)-3-methylpyridin-2-amine instead of 6-chloro-5-(1-(1-ethoxyethyl)-1H-pyrazol-4-yl)pyrazin-2-amine as starting material. LC-MS calculated for $C_{14}H_{19}N_6O$ (M+H)$^+$: m/z=287.2; found 287.1.

Step 3. 2-Bromo-7-(1-(1-ethoxyethyl)-1H-pyrazol-4-yl)-8-methyl-[1,2,4]triazolo[1,5-a]pyridine

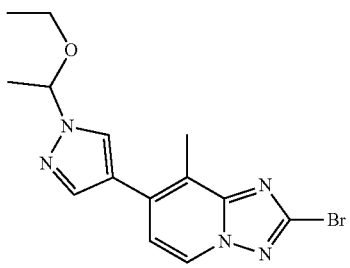 [SMILES: CCOC(C)n1cc(-c2ccn3nc(Br)nc3c2C)cn1]

This compound was prepared according to the procedure described in Example 1, Step 3, using 7-(1-(1-ethoxyethyl)-1H-pyrazol-4-yl)-8-methyl-[1,2,4]triazolo[1,5-a]pyridin-2-amine instead of 5-chloro-6-(1-(1-ethoxyethyl)-1H-pyrazol-4-yl)-[1,2,4]triazolo[1,5-a]pyrazin-2-amine as starting material. LC-MS calculated for $C_{14}H_{17}BrN_5O$ (M+H)$^+$: m/z=350.1; found 350.0.

Step 4. (R)-8-Methyl-7-(1H-pyrazol-4-yl)-N-(pyrrolidin-3-yl)-[1,2,4]triazolo[1,5-a]pyridin-2-amine

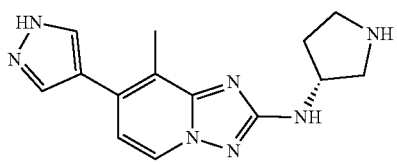 [SMILES: Cc1c(-c2cn[nH]c2)ccn2nc(N[C@@H]3CCNC3)nc12]

This compound was prepared according to the procedure described in Example 1, Step 5, using tert-butyl (R)-3-aminopyrrolidine-1-carboxylate and 2-bromo-7-(1-(1-ethoxyethyl)-1H-pyrazol-4-yl)-8-methyl-[1,2,4]triazolo[1,5-a]pyridine instead of tert-butyl 3-aminoazetidine-1-carboxylate and 2-bromo-6-(1-(1-ethoxyethyl)-1H-pyrazol-4-yl)-5-isopropoxy-[1,2,4]triazolo[1,5-a]pyrazine as starting material. LC-MS calculated for $C_{14}H_{18}N_7$(M+H)$^+$: m/z=284.2; found 284.1.

Step 5. (R)-2-Fluoro-N-(4-(3-((8-methyl-7-(1H-pyrazol-4-yl)-[1,2,4]triazolo[1,5-a]pyridin-2-yl)amino)pyrrolidine-1-carbonyl)phenyl)acrylamide This compound was prepared according to the procedure described in Example 1, Step 7, using (R)-8-methyl-7-(1H-pyrazol-4-yl)-N-(pyrrolidin-3-yl)-[1,2,4]triazolo[1,5-a]pyridin-2-amine and 4-(2-fluoroacrylamido)benzoic acid instead of N-(azetidin-3-yl)-5-isopropoxy-6-(1H-pyrazol-4-yl)-[1,2,4]triazolo[1,5-a]pyrazin-2-amine and 4-acrylamidobenzoic acid as starting material. LC-MS calculated for $C_{24}H_{24}FN_8O_2$ (M+H)$^+$: m/z=475.2; found 475.2.

Example 33. (R)-N-(4-(3-((8-Methyl-7-(1H-pyrazol-4-yl)-[1,2,4]triazolo[1,5-a]pyridin-2-yl)amino)pyrrolidine-1-carbonyl)phenyl)but-2-ynamide

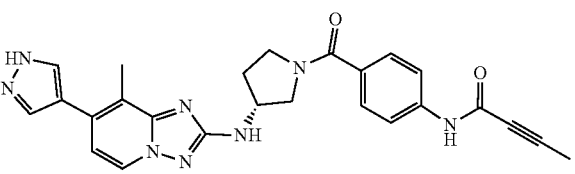 [SMILES: CC#CC(=O)Nc1ccc(C(=O)N2CC[C@@H](Nc3nc4c(C)c(-c5cn[nH]c5)ccn4n3)C2)cc1]

This compound was prepared according to the procedure described in Example 1, Step 7, using (R)-8-methyl-7-(1H-pyrazol-4-yl)-N-(pyrrolidin-3-yl)-[1,2,4]triazolo[1,5-a]pyridin-2-amine and 4-(but-2-ynamido)benzoic acid instead of N-(azetidin-3-yl)-5-isopropoxy-6-(1H-pyrazol-4-yl)-[1,2,4]triazolo[1,5-a]pyrazin-2-amine and 4-acrylamidobenzoic acid as starting material. LC-MS calculated for $C_{25}H_{25}N_8O_2$ (M+H)$^+$: m/z=469.2; found 469.2.

Example 34. N-(2-((1S,3R)-3-((6-(1H-pyrazol-4-yl)-5-(trifluoromethyl)-[1,2,4]triazolo[1,5-a]pyridin-2-yl)amino)cyclohexyl)-3-oxoisoindolin-5-yl)acrylamide

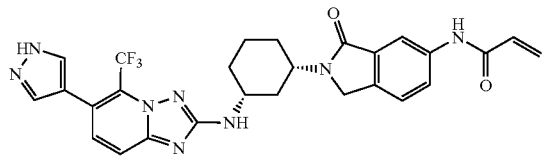 [SMILES: C=CC(=O)Nc1ccc2c(c1)C(=O)N([C@H]1CCC[C@@H](Nc3nc4ccc(-c5cn[nH]c5)c(C(F)(F)F)n4n3)C1)C2]

This compound was prepared according to the procedure described in Example 21, using 2-bromo-6-(1-(1-ethoxyethyl)-1H-pyrazol-4-yl)-5-(trifluoromethyl)-[1,2,4]triazolo[1,5-a]pyridine instead of 2-bromo-6-(1-(1-ethoxyethyl)-1H-pyrazol-4-yl)-5-(piperidin-1-yl)-[1,2,4]triazolo[1,5-a]pyridine. LC-MS calculated for $C_{27}H_{26}F_3N_8O_2$ (M+H)$^+$: m/z=551.2; found 551.2.

Example 35. (R)-N-(2-(3-((6-(1H-pyrazol-4-yl)-5-(trifluoromethyl)-[1,2,4]triazolo[1,5-a]pyridin-2-yl)amino)piperidin-1-yl)benzo[d]thiazol-5-yl)acrylamide

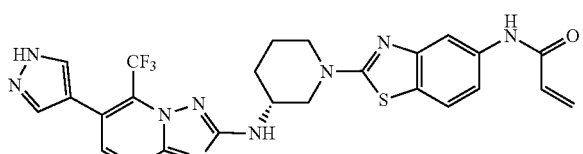

This compound was prepared according to the procedure described in Example 29, using 2-bromo-6-(1-(1-ethoxyethyl)-1H-pyrazol-4-yl)-5-(trifluoromethyl)-[1,2,4]triazolo[1,5-a]pyridine instead of 2-bromo-6-(1-(1-ethoxyethyl)-1H-pyrazol-4-yl)-5-methyl-[1,2,4]triazolo[1,5-a]pyridine. LC-MS calculated for $C_{25}H_{23}F_3N_9OS$ (M+H)$^+$: m/z=554.2; found 554.1.

Example 36. (R)-N-(2-(3-((6-(1H-pyrazol-4-yl)-5-(trifluoromethyl)-[1,2,4]triazolo[1,5-a]pyridin-2-yl)amino)piperidin-1-yl)-1-methyl-1H-benzo[d]imidazol-5-yl)acrylamide

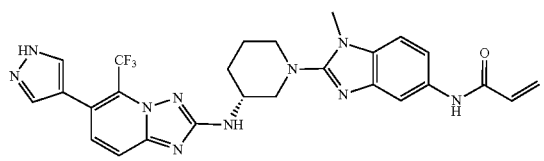 [SMILES: C=CC(=O)Nc1ccc2c(c1)nc(N1CCC[C@@H](Nc3nc4ccc(-c5cn[nH]c5)c(C(F)(F)F)n4n3)C1)n2C]

This compound was prepared according to the procedure described in Example 28, using 2-bromo-6-(1-(1-ethoxyethyl)-1H-pyrazol-4-yl)-5-(trifluoromethyl)-[1,2,4]triazolo[1,5-a]pyridine instead of 2-bromo-6-(1-(1-ethoxyethyl)-1H-pyrazol-4-yl)-5-isopropyl-[1,2,4]triazolo[1,5-a]pyridine. LC-MS calculated for $C_{26}H_{26}F_3N_{10}O$ (M+H)$^+$: m/z=551.2; found 551.1.

Example 37. (R)-N-(6-(3-((5-isopropyl-6-(1H-pyrazol-4-yl)-[1,2,4]triazolo[1,5-a]pyridin-2-yl)amino)piperidin-1-yl)-5-methylpyridin-3-yl)acrylamide

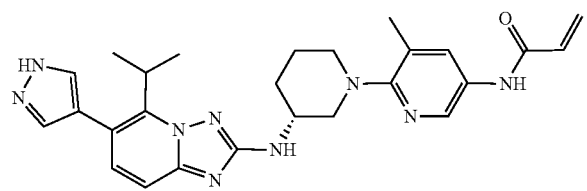 [SMILES: C=CC(=O)Nc1cnc(N2CCC[C@@H](Nc3nc4ccc(-c5cn[nH]c5)c(C(C)C)n4n3)C2)c(C)c1]

This compound was prepared according to the procedure described in Example 28, using 2-chloro-3-methyl-5-nitropyridine instead of 2-chloro-1-methyl-5-nitro-1H-benzo[d]imidazole. LC-MS calculated for $C_{26}H_{32}N_9O$ (M+H)$^+$: m/z=486.3; found 486.2.

Example 38. (R)-N-(6-(3-((6-(1H-pyrazol-4-yl)-5-(trifluoromethyl)-[1,2,4]triazolo[1,5-a]pyridin-2-yl)amino)piperidin-1-yl)-5-methylpyridin-3-yl)acrylamide

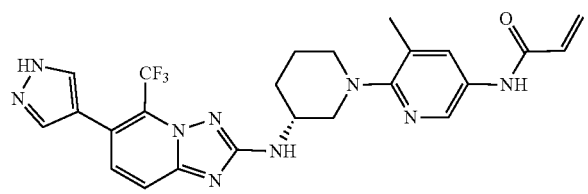 [SMILES: C=CC(=O)Nc1cnc(N2CCC[C@@H](Nc3nc4ccc(-c5cn[nH]c5)c(C(F)(F)F)n4n3)C2)c(C)c1]

This compound was prepared according to the procedure described in Example 28, using 2-chloro-3-methyl-5-nitropyridine and 2-bromo-6-(1-(1-ethoxyethyl)-1H-pyrazol-4-yl)-5-(trifluoromethyl)-[1,2,4]triazolo[1,5-a]pyridine instead of 2-chloro-1-methyl-5-nitro-1H-benzo[d]imidazole and 2-bromo-6-(1-(1-ethoxyethyl)-1H-pyrazol-4-yl)-5-isopropyl-[1,2,4]triazolo[1,5-a]pyridine. LC-MS calculated for $C_{24}H_{25}F_3N_9O$ (M+H)$^+$: m/z=512.2; found 512.2.

Example A. CDK Enzymatic Assays

The following activity of the CDK enzymes in complex with their respective cyclins we assayed: CDK1 complexed with Cyclin B1; CDK2 complexed with Cyclin E1; CDK4 complexed with Cyclin D1; CDK6 complexed with Cyclin D1; CDK6 complexed with Cyclin D3; CDK9 complexed with Cyclin T1; CDK7 complexed with Cyclin H/MAT1; CDK2 complexed with Cyclin A2; CDK5 complexed with p35; CDK12 complexed with Cyclin K; CDK13 complexed with Cyclin K. These in vitro enzyme activity are assayed using homogeneous time-resolved energy transfer (HTRF), which measures phosphorylation of a peptide substrate. The LANCE® Ultra kinase assay (PerkinElmer) uses a ULight™-labeled EIF4E-binding protein 1 (THR37/46) peptide (DYSTTPGGTLFSTTPGTRI (SEQ ID NO: 1)) substrate and a Europium-labeled anti-phospho-4E-BP1 antibody (CDK2, CDK1, CDK4, CDK6, CDK9, CDK12, CDK13) or ULight™-labeled Myelin Basic Protein peptide (VTPRTPPP (SEQ ID NO: 2)) substrate and a Europium-labeled anti-phospho-MBP antibody (CDK7). Each CDK enzyme activity assays utilized human CDK co-expressed as N-terminal GST-tagged protein with its full length cyclin partner using a baculovirus expression system.

Enzyme was pre-incubated with compounds for 30 minutes (CDK1,2,4,6,9) or 60 minutes (CDK7, CDK12, CDK13) prior to addition of ATP and Ulight-peptide (1 mM and 50 nM final, respectively), in assay buffer containing 50 mM HEPES pH 7.5, 1 mM EGTA, 10 mM $MgCl_2$, 2 mM DTT, 0.05 mg/mL BSA, and 0.01% Tween 20. The reaction was then incubated for 60-90 minutes at room temperature. The reactions were stopped by the addition of EDTA and Europium labeled antibody, for a final concentration of 15 mM and 1.0-1.5 nM, respectively. HTRF signals were read after 15-120 minutes. A ratio of fluorescence transferred to the labeled substrate (665 nm) relative to fluorescence of the Europium donor (620 nm) represents the extent of phosphorylation. Ratios for treated wells were normalized to DMSO only (100% activity) and no enzyme (0% activity) controls. Normalized data was analyzed using a three or four parameter dose response curve to determine $IC_{50}$ for each compound and are shown in Table A. Control reference inhibitors were included on each plate.

TABLE A

| Ex. No. | CDK12 $IC_{50}$ (nM) |
|---|---|
| 1 | + |
| 2 | + |
| 3 | + |
| 4 | + |
| 5 | + |
| 6 | + |
| 7 | + |
| 8 | + |
| 9 | +++ |
| 10 | + |
| 11 | + |
| 12 | + |
| 13 | ++ |
| 14 | + |
| 15 | + |
| 16 | + |

TABLE A-continued

| Ex. No. | CDK12 IC$_{50}$ (nM) |
|---|---|
| 17 | + |
| 18 | + |
| 19 | + |
| 20 | + |
| 21 | + |
| 22 | + |
| 23 | + |
| 24 | ++ |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |

+ refers to IC$_{50}$ of <50 nM
++ refers to IC$_{50}$ of ≥50 nM to ≤500 nM
+++ refers to >500 nM Example B. CDK Cellular Activity Assays A. HTRF Assay The following signals were detected using an HTRF assay from Cisbio: CDK12/13 activity (RNA POL II pser2 HTRF assay in multiple cell lines); CDK2 activity (pRbS780 HTRF assay in COV318 cells); CDK4 (pRbS780 HTRF assay in JEKO-1 cells); CDK6 activity (pRbS780 HTRF assay in MV4-11 cells); CDK12 specific activity (RNA POL II pser2 in CDK13$^{-/-}$ isogenic THP1 cells); CDK13 specific activity (RNA POL II pser2 in CDK12$^{-/-}$ isogenic THP1 cells); Gamma H2AX for DNA damage (HTRF assay in multiple cell lines).

All HTRF assays were performed following the following standard protocol. First, cells were plated in a 96 well plate and treated with 3 fold dilution series of compound for 6 hours (CDK2, CDK4, CDK6, CDK12, CDK13) or 48 hours (Gamma H2AX). Then, 4× Cisbio lysis buffer was diluted 4 fold with distilled water supplemented with 100× blocking buffer and a 1:10,000 dilution of Benzonase Nuclease (Sigma Cat #E1014-5KU). Next, 50 μL of the prepared 1× Cisbio lysis buffer was added to each well of cells. The plates were gently shaken at room temperature for 30-45 minutes to lyse. The lysates were then used immediately or stored at −80° C. and processed at a later date. To process, the 96 well plates were centrifuged at 1400 rpm for 5 minutes at 4° C. Then, acceptor D2 and donor K antibody mixes were made up as follows: 50 μL of antibody+950 μL detection buffer per one 384 plate (equal to 4×96 well plates). 2 μL acceptor D2 and 2 μL of donor K antibody mixes were added to enough wells of a 384 well Greiner white plate (Greiner cat #784075) to accommodate the number of cell samples from the 96 well plate. Lastly, 16 μL of each cell lysate from the 96 well plate was transferred to the wells in the 384 well plate containing the 4 μL of acceptor D2+ donor K antibody mixes (final volume of 20 μL per well). The 384 well plate was then incubated overnight at room temperature covered in foil. HTRF signal was measured on the Pherastar microplate reader the next morning.

B. In Cell Western Blotting Assay

The following signals were detected using an in cell western blotting assay: CDK1 activity (pNPM-T199 signal); CDK7 activity (RNA POL II pser5 signal).

Cells were plated at 25,000 cells per well in a 96 well plate at 37° C. and allowed to attach overnight. The next day, cells were treated with a 3 fold dilution series of compound for 6 hours. Next, media was removed and the cells were washed once with 140 μL/well of 1×PBS. The cells were then fixed with freshly diluted 3.7% paraformaldehyde/PBS for 20 minutes at room temperature. The fixing solution was removed and the cells were washed 3 times with 1×PBS containing 0.1% TX-100 for 5-10 minutes per wash with gentle shaking for permeabilization. Next, the plates were blocked by adding 50 μL/well of Odyssey blocking buffer with 0.1% TX-100 followed by rocking gently for 1 hour at room temperature. The blocking buffer was then removed and replaced with 40 μL/well of primary antibody diluted in Odyssey blocking buffer (1:200-1:500) with 0.1% TX-100 and the plates were incubated overnight with moderate shaking at 4° C. Next, the primary antibody was removed and the plates were washed 3 times with 140 μL of 1×PBS containing 0.1% Tween-20 for 10 minutes per wash with gentle shaking. Then 40 μL/well of secondary antibody (IRDye® 800CW Goat anti-Rabbit, 1:2000) and CellTag 700 (1:600) in Odyssey blocking buffer with 0.1% TX-100 was added and the plates were covered in foil and rocked gently for 2 hours at room temperature. Next, secondary antibody was removed and washed 3 times with 140 μL of 1×PBS containing 0.1% Tween-20 for 10 minutes per wash with gentle shaking. The plates were protected from light during washing. After the final wash, the washing solution was completely removed from wells and the bottom plate surface and the scanning bed were cleaned with lint-free paper. The plate was scanned with detection in both 700 and 800 nm channels using an Odyssey CLx. (scanning parameters: Odyssey CLx 169 m resolution at 3.5 mm focus offset).

C. Standard Western Blotting

The following signal was detected using standard western blotting: CDK5 activity (pFAKT732); CDK9 activity (MCL-1 protein level).

Cells were plated overnight in a 6 well plate and treated with a 3 fold dilution of compound. Cells were then washed with ice cold PBS and then lysed using the standard Cell Signaling Lysis Protocol (Cat #9803). Cell lysates were then quantified using the standard BCA protein assay protocol from Pierce (Cat #23225) and equal amounts of protein were then run on a 4 to 12% NuPAGE gel (Cat #NPO322). Expression as analyzed following standard western blotting procedure. Briefly, membranes were blocked with 5% milk in TBST for 1 hour and then incubated with primary antibody (GET CAT #) at 1:2000 overnight. Membranes were then washed 3 times with TBST and incubated (1:4000 dilution) with secondary antibody (Cell Signaling Cat #7074). For imaging, membranes were in incubated in HRP substrate and imaged on a gel-doc imager.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

SEQUENCE LISTING

```
Sequence total quantity: 2
SEQ ID NO: 1              moltype = AA  length = 19
FEATURE                   Location/Qualifiers
source                    1..19
                          mol_type = protein
                          organism = synthetic construct
SEQUENCE: 1
DYSTTPGGTL FSTTPGTRI                                              19

SEQ ID NO: 2              moltype = AA  length = 8
FEATURE                   Location/Qualifiers
source                    1..8
                          mol_type = protein
                          organism = synthetic construct
SEQUENCE: 2
VTPRTPPP                                                           8
```

What is claimed is:

1. A compound of Formula (I):

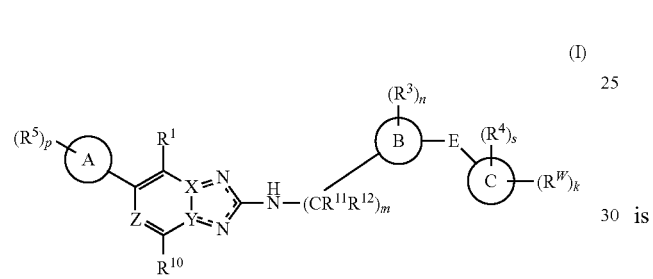

(I)

or a pharmaceutically acceptable salt thereof, wherein:

k is 1 or 2;

m is 0 or 1;

n is 0, 1, 2, 3, 4, 5, or 6;

p is 0, 1, 2, 3, 4, 5, or 6;

s is 0, 1, 2, 3, 4, 5, or 6;

each ≡ is independently a single or a double bond;

X is N, Y is C, and Ring

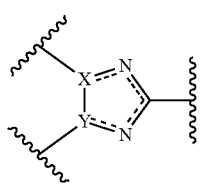

is

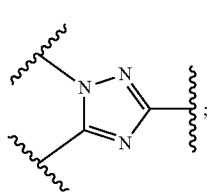 [SMILES: *c1nc(*)n(*)n1]

or

X is C, Y is N, and Ring

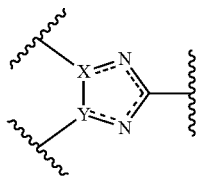

is

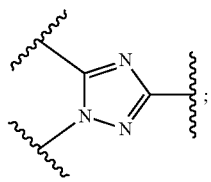 [SMILES: *c1nc(*)n(*)n1]

Z is $CR^2$ or N;

Ring moiety A is a 5-10 membered heteroaryl;

Ring moiety B is $C_{3-10}$ membered cycloalkyl or 4-10 membered heterocycloalkyl;

Ring moiety C is $C_{6-10}$ aryl, 5-10 membered heteroaryl, $C_{5-12}$ partially unsaturated cycloalkyl, or 5-12 membered partially unsaturated heterocycloalkyl;

E is a bond, —C(O)—, —CH$_2$—, —CHR$^6$—, —CR$^6$R$^7$—, or —O—, wherein R$^6$ and R$^7$ are each independently selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^W$, attached to the C ring, is independently:

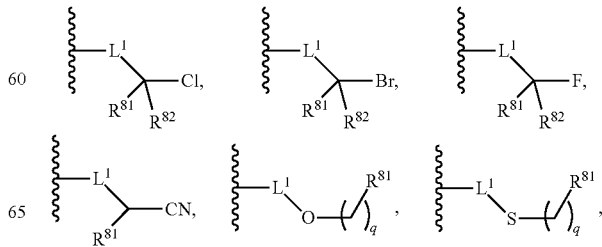

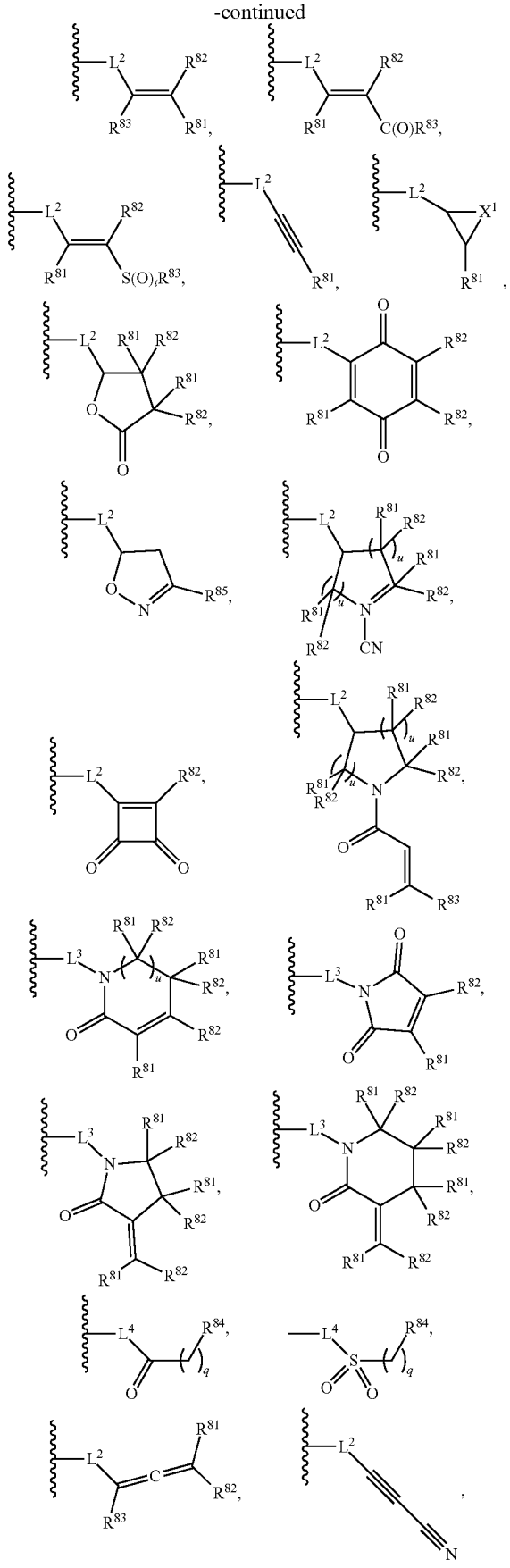

or $L^1$-Ar;

each $L^1$ is independently -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$— or -L-OS(O)$_2$—, wherein $L^1$ is attached to Ring moiety C through the L linking group;

each $L^2$ is independently -L-, -L-O—, -L-NR$^9$—, -L-S—, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)NR$^9$—, -L-NR$^9$S(O)O—, -L-OS(O)NR$^9$—, -L-NR$^9$S(O)$_2$—, -L-OS(O)$_2$—, -L-NR$^9$S(O)$_2$NR$^9$—, -L-NR$^9$S(O)$_2$O—, -L-S(O)(NR$^9$)—, -L-S(O)$_2$(N$^9$)—, or -L-OS(O)$_2$NR$^9$—, wherein $L^2$ is attached to Ring moiety C through the L linking group;

each $L^3$ is independently -L-, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$—, or -L-OS(O)$_2$—, wherein $L^3$ is attached to Ring moiety C through the L linking group;

each $L^4$ is independently -L-, -L-O—, L-S—, -L-NR$^9$—, wherein $L^4$ is attached to Ring moiety C through the L linking group;

each $L^5$ is independently -L-O-L$^x$-, -L-NR$^9$-L$^x$-, -L-S-L$^x$-, -L-C(O)-L$^x$-, -L-NR$^9$C(O)-L$^x$-, -L-OC(O)-L$^x$-, -L-S(O)-L$^x$-, -L-S(O)$_2$-L$^x$-, -L-NR$^9$S(O)-L$^x$-, -L-OS(O)-L$^x$-, -L-NR$^9$S(O)NR$^9$-L$^x$-, -L-NR$^9$S(O)O-L$^x$-, -L-OS(O)NR$^9$-L$^x$-, -L-NR$^9$S(O)$_2$-L$^x$-, -L-OS(O)$_2$-L$^x$-, -L-NR$^9$S(O)$_2$NR$^9$-L$^x$-, -L-NR$^9$S(O)$_2$O-L$^x$-, -L-S(O)(NR$^9$)-L$^x$-, -L-S(O)$_2$(NR$^9$)-L$^x$-, or -L-OS(O)$_2$NR$^9$-L$^x$-, wherein $L^5$ is attached to Ring moiety C through the L linking group;

each L is independently is a bond or $C_{1-6}$ alkylene, wherein said $C_{1-6}$ alkylene is optionally substituted by 1, 2, 3 or 4 independently selected R$^G$ substituents;

each LU is independently is a $C_{1-6}$ alkylene, wherein said $C_{1-6}$ alkylene is optionally substituted by 1, 2, 3 or 4 independently selected R$^G$ substituents;

each $X^1$ independently is O or $NR^9$;
each q is independently 0, 1, 2, or 3;
each t is independently 0, 1, 2, or 3;
each u is independently 0, 1, 2, or 3;
each Ar is independently $C_{6-10}$ aryl or 5-10 membered heteroaryl, which are each optionally substituted with 1, 2, 3, or 4 independently selected $R^{9A}$ substituents;
each $R^{81}$, $R^{82}$, and $R^{83}$ is independently selected from HD, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a8}$, $SR^{a8}$, $NHOR^{a8}$, $C(O)R^{b8}$, $C(O)NR^{c8}R^{d8}$, $C(O)NR^{c8}(OR^{a8})$, $C(O)OR^{a8}$, $OC(O)R^{bB}$, $OC(O)NR^{c8}R^{d8}$, $NR^{c8}R^{d8}$ $NR^{c8}NR^{c8}R^{d8}$ $NR^{c8}C(O)R^{b8}$ $NR^{c8}C(O)OR^{a8}$ $NR^{c8}C(O)NR^{c8}R^{d8}$, $C(=NR^{e8})R^{b8}$, $C(=NR^{e8})R^{c8}R^{d8}$ $NR^{c8}C(=NR^{e8})NR^{c8}R^{d8}$ $NR^{c8}C(=NR^{e8})R^{b8}$, $NR^{c8}S(O)NR^{c8}R^{d8}$ $NR^{c8}S(O)R^{b8}$, $NR^{c8}S(O)_2R^{b8}$, $NR^{c8}S(O)(=NR^{e8})R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$, $OS(O)R^{b8}$, $OS(O)(=NR^{e8})R^{b8}$, $OS(O)_2R^{b8}$, $S(O)(=NR^{e8})R^{b8}$, $SF_5$, $P(O)R^{f8}R^{g8}$, $OP(O)(OR^{h8})(OR^{i8})$, $P(O)(OR^{h8})(OR^{i8})$, and $BR^{j8}R^{k8}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ substituents;
each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^G$ substituents;
or, any $R^{c8}$ and $R^{d8}$ attached to the same N atom, together with the N atom to which they are attached, form a 4-10 membered heterocycloalkyl group, which is optionally substituted with 1, 2, 3, or 4 independently selected $R^G$ substituents;
each $R^{b8}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^G$ substituents;
each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;
each $R^{f8}$ and $R^{g8}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;
each $R^{h8}$ and $R^{i8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;
each $R^{j8}$ and $R^{k8}$ is independently selected from OH, $C_{1-6}$ alkoxy, and $C_{1-6}$ haloalkoxy;
or any $R^{j8}$ and $R^{k8}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;
or any two $R^{81}$ and $R^{82}$ together with the atoms to which they are attached, form $C_{3-7}$ cycloalkyl, 4-7 membered heterocycloalkyl, phenyl, or 5-6-membered heteroaryl ring, each of which is optionally substituted with 1, 2, 3, or 4 independently selected $R^G$ substitutents;
each $R^{84}$ is independently selected from H, D, halo, CN, OH, $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-3}$ alkoxy, $C_{1-3}$ haloalkoxy, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^G$ substituents;
each $R^{85}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl, wherein said $C_{1-6}$ alkyl, $C_{1-6}$ haloalkyl, $C_{3-10}$ cycloalkyl, 4-10 membered heterocycloalkyl, and $C_{3-10}$ cycloalkyl-$C_{1-4}$ alkyl are each optionally substituted by 1, 2, 3, or 4 independently selected $R^G$ substituents;
each $R^9$ is independently selected from H, halo, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a9}$, $SR^{a9}$, $NHOR^{a9}$, $C(O)R^{b9}$, $C(O)NR^{c9}R^{d9}$, $C(O)NR^{c9}(OR^{a9})$, $C(O)OR^{a9}$, $OC(O)R^{b9}$, $OC(O)NR^{c9}R^{d9}$, $NR^{c9}R^{d9}$ $NR^{c9}C(O)R^{b9}$, $NR^{c9}C(O)OR^{a9}$ $NR^{c9}C(O)NR^{c9}R^{d9}$, $C(=NR^{e9})R^{b9}$, $C(=NR^{e9})NR^{c9}R^{d9}$ $NR^{c9}C(=NR^{e9})NR^{c9}R^{d9}$, $NR^{c9}C(=NR^{e9})R^{b9}$ $NR^{c9}S(O)NR^{c9}R^{d9}$ $NR^{c9}S(O)R^{b9}$, $NR^{c9}S(O)_2R^{b9}$, $NR^{c9}S(O)(=NR^{e9})R^{b9}$, $NR^{c9}S(O)_2NR^{c9}R^{d9}$ $S(O)R^{b9}$, $S(O)NR^{c9}R^{d9}$, $S(O)_2R^{b9}$, $S(O)_2NR^{c9}R^{d9}$, $OS(O)(=NR^{e9})R^{b9}$, $OS(O)_2R^{b9}$, and S(O)(=NR$^{e9}$)R$^{b9}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^{9A}$ substituents;

each R$^{a9}$, R$^{c9}$, and R$^{d9}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{9A}$ substituents;

or, any R$^{c9}$ and R$^{d9}$ attached to the same N atom, together with the N atom to which they are attached, form a 4-10 membered heterocycloalkyl group, which is optionally substituted with 1, 2, 3, or 4 independently selected R$^{9A}$ substituents;

each R$^{b9}$ is independently selected from C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, which are each optionally substituted with 1, 2, 3, or 4 independently selected R$^{9A}$ substituents;

each R$^{e9}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{9A}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a91}$, SR$^{a91}$, NHOR$^{a91}$, C(O)R$^{b91}$, C(O)NR$^{c91}$R$^{d91}$, C(O)NR$^{c91}$(OR$^{a91}$), C(O)OR$^{a91}$, OC(O)R$^{b91}$, OC(O)NR$^{c91}$R$^{d91}$, NR$^{c91}$R$^{d91}$, NR$^{c91}$NR$^{c91}$R$^{d91}$, NR$^{c91}$C(O)R$^{b91}$, NR$^{c91}$C(O)OR$^{a91}$, NR$^{c91}$C(O)NR$^{c91}$R$^{d91}$, C(=NR$^{e91}$)R$^{b91}$, C(=NR$^{e91}$)NR$^{c91}$R$^{d91}$, NR$^{c91}$C(=NR$^{e91}$)NR$^{c91}$R$^{d91}$, NR$^{c91}$C(=NR$^{e91}$)R$^{b91}$, NR$^{c91}$S(O)NR$^{c91}$R$^{d91}$, NR$^{c91}$S(O)R$^{b91}$, NR$^{c91}$S(O)$_2$R$^{b91}$, NR$^{c91}$S(O)(=NR$^{e91}$)R$^{b91}$, NR$^{c91}$S(O)$_2$NR$^{c91}$R$^{d91}$, S(O)R$^{b91}$, S(O)NR$^{c91}$R$^{d91}$, S(O)$_2$R$^{b91}$, S(O)$_2$NR$^{c91}$R$^{d91}$, OS(O)(=NR$^{e91}$)R$^{b91}$, OS(O)$_2$R$^{b91}$, S(O)(=NR$^{e91}$)R$^{b91}$, SF$_5$, P(O)R$^{f91}$R$^{g91}$, OP(O)(OR$h^{h91}$)(OR$^{i91}$), P(O)(OR$^{h91}$)(OR$^{i91}$), and BR$^{j91}$R$^{k91}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{9B}$ substituents;

each R$^{a91}$, R$^{c91}$, and R$^{d91}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{9B}$ substituents;

or, any R$^{c91}$ and R$^{d91}$ attached to the same N atom, together with the N atom to which they are attached, form a 4-7 membered heterocycloalkyl group, which is optionally substituted with 1, 2, 3, or 4 independently selected R$^{9B}$ substituents;

each R$^{b91}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^{9B}$ substituents;

each R$^{e91}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl;

each R$^{f91}$ and R$^{g91}$ are independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl;

each R$^{h91}$ and R$^{i91}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl;

each R$^{j91}$ and R$^{k91}$ is independently selected from OH, C$_{1-6}$ alkoxy, and C$_{1-6}$ haloalkoxy;

or any R$^{j91}$ and R$^{k91}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{9B}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a92}$, SR$^{a92}$, NHOR$^{a92}$, C(O)R$^{b92}$, C(O)NR$^{c92}$R$^{d92}$, C(O)NR$^{c92}$(OR$^{a92}$), C(O)OR$^{a92}$, OC(O)R$^{b92}$, OC(O)NR$^{c92}$R$^{d92}$, NR$^{c92}$R$^{d92}$ NR$^{c92}$NR$^{c92}$R$^{d92}$, NR$^{c92}$C(O)R$^{b92}$, NR$^{c92}$C(O)OR$^{a92}$, NR$^{c92}$C(O)NR$^{c92}$R$^{d92}$, C(=NR$^{e92}$)R$^{b92}$, C(=NR$^{e92}$)NR$^{c92}$R$^{d92}$, $NR^{c92}C(=NR^{e92})NR^{c92}R^{d92}$, $NR^{c92}C(=NR^{e92})R^{b92}$, $NR^{c92}S(O)NR^{c92}R^{d92}$, $NR^{c92}S(O)R^{b92}$, $NR^{c92}S(O)_2R^{b92}$, $NR^{c92}S(O)(=NR^{e92})R^{b92}$, $NR^{c92}S(O)_2NR^{c92}R^{d92}$, $S(O)R^{b92}$, $S(O)-NR^{c92}R^{d92}$, $S(O)_2R^{b92}$, $S(O)_2NR^{c92}R^{d92}$, $OS(O)(=NR^{e92})R^{b92}$, $OS(O)_2R^{b92}$, $S(O)(=NR^{e92})R^{b92}$, $SF_5$, $P(O)R^{f92}R^{g92}$, $OP(O)(OR^{h92})(OR^{i92})$, $P(O)(OR^{h92})(OR^{i92})$, and $BR^{j92}R^{k92}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a92}$, $R^{c92}$, and $R^{d92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c92}$ and $R^{d92}$ attached to the same N atom, together with the N atom to which they are attached, form a 4-7 membered heterocycloalkyl group, which is optionally substituted with 1, 2, 3, or 4 independently selected $R^G$ substituents;

each $R^{b92}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e92}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f92}$ and $R^{g92}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h92}$ and $R^{i92}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j92}$ and $R^{k92}$ is independently selected from OH, $C_{1-6}$ alkoxy, and $C_{1-6}$ haloalkoxy;

or any $R^{j92}$ and $R^{k92}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{14}$ substituents;

or, any $R^{c1}$ and $R^{d1}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{14}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{14}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f1}$ and $R^{g1}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)NR^{c11}R^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, $OS(O)_2R^{b11}$, $S(O)(=NR^{e11})R^{b11}$, $SF_5$, $P(O)R^{f11}R^{g11}$, $OP(O)(OR^{h11})(OR^{i11})$, $P(O)(OR^{h11})(OR^{i11})$, and $BR^{j11}R^{k11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1'}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1}$ substituents;

or, any $R^{c11}$ and $R^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f11}$ and $R^{g11}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h11}$ and $R^{i11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$ $NR^{c12}R^{d12}$ $NR^{c12}NR^{c12}R^{d12}$ $NR^{c12}C(O)R^{b12}$ $NR^{c12}C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$ $NR^{c12}C(=NR^{e12})R^{b12}$, $NR^{c12}S(O)NR^{c12}R^{d12}$, $NR^{c12}S(O)R^{b12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$ $S(O)_2R^{b12}$, $S(O)_2NR^{c12}R^{d12}$, $OS(O)(=NR^{e12})R^{b12}$, $OS(O)_2R^{b12}$, $S(O)(=NR^{e12})R^{b12}$, $SF_5$, $P(O)R^{f12}R^{g12}$, $OP(O)(OR^{h12})(OR^{i12})$, $P(O)(OR^{h12})(OR^{i12})$, and $BR^{j12}R^{k12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{G}$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f12}$ and $R^{g12}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h12}$ and $R^{i12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j12}$ and $R^{k12}$ is independently selected from OH, $C_{1-6}$ alkoxy, and $C_{1-6}$ haloalkoxy;

or any $R^{j12}$ and $R^{k12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^2$ is selected from H, D, halo, CN, OH, $NO_2$, $C_{1-4}$ alkyl, $C_{1-4}$ haloalkyl, $C_{2-4}$ alkenyl, $C_{2-4}$ alkynyl, $C_{1-4}$ alkoxy, $C_{1-4}$ haloalkoxy, amino, $C_{1-4}$ alkylamino, di($C_{1-4}$ alkyl)amino, cyano-$C_{1-4}$ alkyl, HO—$C_{1-4}$ alkyl, $C_{1-4}$ alkoxy-$C_{1-4}$ alkyl, $C_{3-4}$ cycloalkyl, thio, $C_{1-4}$ alkylthio, $C_{1-4}$ alkylsulfinyl, $C_{1-4}$ alkylsulfonyl, carbamyl, $C_{1-4}$ alkylcarbamyl, di($C_{1-4}$ alkyl)carbamyl, carboxy, $C_{1-4}$ alkylcarbonyl, $C_{1-4}$ alkoxycarbonyl, $C_{1-4}$ alkylcarbonyloxy, $C_{1-4}$ alkylcarbonylamino, $C_{1-4}$ alkoxycarbonylamino, $C_{1-4}$ alkylaminocarbonyloxy, $C_{1-4}$alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino;

each $R^3$ is independently selected from D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^4$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)NR^{c4}R^{d4}$, $NR^{c4}S(O)R^{b4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $S(O)(=NR^{e4})R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4A}$ substituents;

or, any $R^{c4}$ and $R^{d4}$ attached to the same N atom, together with the N atom to which they are attached, form a 4-10 membered heterocycloalkyl group, wherein the 4-10 membered heterocycloalkyl group is optionally substituted with 1, 2, 3, or 4 independently selected $R^{4A}$ substituents;

each $R^{b4}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f4}$ and $R^{g4}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j4}$ and $R^{k4}$ is independently selected from OH, $C_{1-6}$ alkoxy, and $C_{1-6}$ haloalkoxy;

or any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}C(=NR^{e41})R^{b41}$, $NR^{c41}S(O)NR^{c41}R^{d41}$, $NR^{c41}S(O)R^{b41}$, $NR^{c41}S(O)_2R^{b41}$, $NR^{c41}S(O)(=NR^{e41})R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, $OS(O)(=NR^{e41})R^{b41}$, $OS(O)_2R^{b41}$, $S(O)(=NR^{e41})R^{b41}$, $SF_5$, $P(O)R^{f41}R^{g41}$, $OP(O)(OR^{h41})(OR^{i41})$, $P(O)(OR^{h41})(OR^{i41})$, and $BR^{j41}R^{k41}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

or, any $R^{c41}$ and $R^{d41}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{4B}$ substituents;

each $R^{b41}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f41}$ and $R^{g41}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h41}$ and $R^{i41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j41}$ and $R^{k41}$ is independently selected from OH, $C_{1-6}$ alkoxy, and $C_{1-6}$ haloalkoxy;

or any $R^{j41}$ and $R^{k41}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{4B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a42}$, $SR^{a42}$, $NHOR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}NR^{c42}R^{d42}$, $NR^{c42}C(O)R^{b42}$, $NR^{c42}C(O)OR^{a42}$, $NR^{c42}C(O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}C(=NR^{e42})R^{b42}$, $NR^{c42}S(O)NR^{c42}R^{d42}$, $NR^{c42}S(O)R^{b42}$, $NR^{c42}S(O)_2R^{b42}$, $NR^{c42}S(O)(=NR^{e42})R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, $OS(O)(=NR^{e42})R^{b42}$, $OS(O)_2R^{b42}$, $S(O)(=NR^{e42})R^{b42}$, $SF_5$, $P(O)R^{f42}R^{g42}$, $OP(O)(OR^{h42})(OR^{i42})$, $P(O)(OR^{h42})(OR^{i42})$, and $BR^{j42}R^{k42}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c42}$ and $R^{d42}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b42}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e42}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f42}$ and $R^{g42}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h42}$ and $R^{i42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j42}$ and $R^{k42}$ is independently selected from OH, $C_{1-6}$ alkoxy, and $C_{1-6}$ haloalkoxy;

or any $R^{j42}$ and $R^{k42}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^5$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$ $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$ $NR^{c5}NR^{c5}R^{d5}$ $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$ $NR^{5C}(=NR^{e5})NR^{c5}R^{d5}$ $NR^{c5}C(=NR^{e5})R^{b5}$, $NR^{c5}S(O)NR^{c5}R^{d5}$ $NR^{c5}S(O)R^{b5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $S(O)(=NR^{e5})R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-10 membered heterocycloalkyl group, which is optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{14}$ alkyl, 4-10 membered heterocycloalkyl-$C_{1-4}$ alkyl, and 5-10 membered heteroaryl-$C_{1-4}$ alkyl;

each $R^{f5}$ and $R^{g5}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j5}$ and $R^{k5}$ is independently selected from OH, $C_{1-6}$ alkoxy, and $C_{1-6}$ haloalkoxy;

or any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a51}$, $SR^{a51}$ $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$ $NR^{c51}C(O)OR^{a51}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}C(=NR^{e51})R^{b51}$ $NR^{c51}S(O)NR^{c51}R^{d51}$, $NR^{c51}S(O)R^{b51}$, $NR^{c51}S(O)_2R^{b51}$ $NR^{c51}S(O)(=NR^{e51})R^{b51}$ $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)(=NR^{e51})R^{b51}$, $OS(O)_2R^{b51}$, $S(O)(=NR^{e51})R^{b51}$, $SF_5$, $P(O)R^{f51}R^{g51}$, $OP(O)(OR^{h51})(OR^{i51})$, $P(O)(OR^{h51})(OR^{i51})$, and $BR^{j51}R^{k51}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

or, any $R^{c51}$ and $R^{d51}$ attached to the same N atom, together with the N atom to which they are attached, form a 4-7 membered heterocycloalkyl group, which is optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f51}$ and $R^{g51}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{14}$ alkyl;

each $R^{h51}$ and $R^{i51}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j51}$ and $R^{k51}$ is independently selected from OH, $C_{1-6}$ alkoxy, and $C_{1-6}$ haloalkoxy;

or any $R^{j51}$ and $R^{k51}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{c52}C(=NR^{e52})NR^{c52}R^{d52}$, $NR^{c52}C(=NR^{e52})R^{b52}$, $NR^{c52}S(O)NR^{c52}R^{d52}$, $NR^{c52}S(O)R^{b52}$ $NR^{c52}S(O)_2R^{b52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, $OS(O)_2R^{b52}$, $S(O)(=NR^{e52})R^{b52}$, $SF_5$, $P(O)R^{f52}R^{g52}$, $OP(O)(OR^{h52})(OR^{i52})$, $P(O)(OR^{h52})(OR^{i52})$, and $BR^{j52}R^{k52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

or, any $R^{c52}$ and $R^{d52}$ attached to the same N atom, together with the N atom to which they are attached, form a 4-7 membered heterocycloalkyl group, which is optionally substituted with 1, 2, 3, or 4 independently selected $R^{5C}$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5C}$ substituents;

each $R^{e52}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f52}$ and $R^{g52}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h52}$ and $R^{i52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j52}$ and $R^{k52}$ is independently selected from OH, $C_{1-6}$ alkoxy, and $C_{1-6}$ haloalkoxy;

or any $R^{j52}$ and $R^{k52}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{5C}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a53}$, $SR^{a53}$, $NHOR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}NR^{c53}R^{d53}$, $NR^{c53}C(OR^{b53}$, $NR^{c53}C(O)OR^{a53}$, $NR^{c53}C(O)NR^{c53}R^{d53}$, $C(=NR^{e53})R^{b53}$, $C(=NR^{e53})NR^{c53}R^{d53}$, $NR^{c53}C(=NR^{e53})NR^{c53}R^{d53}$, $NR^{c53}C(=NR^{e53})R^{b53}$, $NR^{c53}S(O)NR^{c53}R^{d53}$, $NR^{c53}S(O)R^{b53}$, $NR^{c53}S(O)_2R^{b53}$, $NR^{c53}S(O)(=NR^{e53})R^{b53}$, $NR^{c53}S(O)_2NR^{c53}R^{d53}$, $S(O)R^{b53}$, $S(O)NR^{c53}R^{d53}$, $S(O)_2R^{b53}$, $S(O)_2NR^{c53}R^{d53}$, $OS(O)(=NR^{e53})R^{b53}$, $OS(O)_2R^{b53}$, $S(O)(=NR^{e53})R^{b53}$, $SF_5$, $P(O)R^{f53}R^{g53}$, $OP(O)(OR^{h53})(OR^{i53})$, $P(O)(OR^{h53})(OR^{i53})$, and $BR^{j53}R^{k53}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c53}$ and $R^{d53}$ attached to the same N atom, together with the N atom to which they are attached, form a 4-7 membered heterocycloalkyl group, which is optionally substituted with 1, 2, 3, or 4 independently selected $R^G$ substituents;

each $R^{b53}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e53}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f53}$ and $R^{g53}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h53}$ and $R^{i53}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j53}$ and $R^{k53}$ is independently selected from OH, $C_{1-6}$ alkoxy, and $C_{1-6}$ haloalkoxy;

or any $R^{j53}$ and $R^{k53}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

$R^{10}$, $R^{11}$, and $R^{12}$ are each independently selected from H, D, halo, CN, $C_{1-4}$ alkyl, $C_{1-4}$ haloalkyl, $C_{1-3}$ alkoxy, $C_{1-3}$ haloalkoxy, cyano-$C_{1-4}$ alkyl, HO—$C_{1-4}$ alkyl, $C_{1-3}$ alkoxy-$C_{1-4}$ alkyl, and $C_{3-4}$ cycloalkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

2. The compound of claim 1, or a pharmaceutically acceptable salt thereof, wherein X is N, Y is C, and Ring

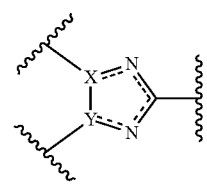

is

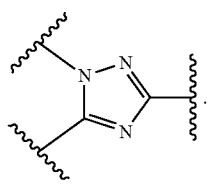 [SMILES: *c1nc(*)n(*)n1]

3. The compound of claim 1, or a pharmaceutically acceptable salt thereof, wherein X is C, Y is N, and Ring is

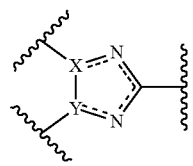

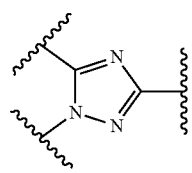

4. The compound of claim 1, or a pharmaceutically acceptable salt thereof, wherein:
  $R^1$ is independently selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $NHOR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2 NR^{c1}R^{d1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents;
  each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents;
  or, any $R^{c1}$ and $R^{d1}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1A}$ substituents; and
  each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1A}$ substituents.

5. The compound of claim 1, or a pharmaceutically acceptable salt thereof, wherein $R^1$ is selected from H, D, halo, CN, $C_{1-6}$ alkyl, $C_{2-6}$ alkenyl, $C_{2-6}$ alkynyl, $C_1$-6 haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $NR^{c1}R^{d1}$, and $OR^{a1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents; and
  each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, and 5-6 membered heteroaryl are each optionally substituted with 1, 2, 3, or 4 independently selected $R^{1A}$ substituents.

6. The compound of claim 1, or a pharmaceutically acceptable salt thereof, wherein $R^1$ is selected from H, CN, $C_{1-6}$ alkyl, $C_{1-6}$ haloalkyl, 4-7 membered heterocycloalkyl, and $OR^{a1}$, wherein said $C_{1-6}$ alkyl and 4-7 membered heterocycloalkyl are each optionally substituted with 1, 2, 3, or 4 independently selected $R^{1A}$ substituents;
  each $R^{a1}$ is independently selected from H, $C_{1-6}$ alkyl, $C_{3-7}$ cycloalkyl, and 4-7 membered heterocycloalkyl, wherein said $C_{1-6}$ alkyl, $C_{3-7}$ cycloalkyl, and 4-7 membered heterocycloalkyl are each optionally substituted with 1, 2, 3, or 4 independently selected $R^{1A}$ substituents.

7. The compound of claim 1, or a pharmaceutically acceptable salt thereof, wherein each $R^{1A}$ is independently selected from H, D, halo, CN, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{1B}$ substituents; and
  each $R^{1B}$ is independently selected from H, D, halo, CN, $C_{1-6}$ alkyl, $C_{2-6}$ alkenyl, $C_{2-6}$ alkynyl, and $C_{1-6}$ haloalkyl.

8. The compound of claim 1, or a pharmaceutically acceptable salt thereof, wherein each $R^{1A}$ is independently selected from halo, $C_{1-6}$ alkyl, and $C_{1-6}$ haloalkyl.

9. The compound of claim 1, or a pharmaceutically acceptable salt thereof, wherein Z is $CR^2$.

10. The compound of claim 1, or a pharmaceutically acceptable salt thereof, wherein Z is N.

11. The compound of claim 1, or a pharmaceutically acceptable salt thereof, wherein $R^2$ is selected from H and $C_{1-3}$ alkyl.

12. The compound of claim 1, or a pharmaceutically acceptable salt thereof, wherein $R^2$ is H or methyl.

13. The compound of claim 1, or a pharmaceutically acceptable salt thereof, wherein Ring moiety A is a monocyclic 5-membered heteroaryl.

14. The compound of claim 1, or a pharmaceutically acceptable salt thereof, wherein Ring moiety A is selected from pyrazolyl and oxazolyl.

15. The compound of claim 1, or a pharmaceutically acceptable salt thereof, wherein Ring moiety B is monocyclic $C_{3-7}$ cycloalkyl or monocyclic 4-7 membered heterocycloalkyl.

16. The compound of claim 1, or a pharmaceutically acceptable salt thereof, wherein Ring moiety B is cyclohexyl, azetidinyl, pyrrolidinyl, or piperidinyl.

17. The compound of claim 1, or a pharmaceutically acceptable salt thereof, wherein Ring moiety C is $C_{6-10}$ aryl, 5-10 membered heteroaryl, or 5-12 membered partially unsaturated heterocycloalkyl.

18. The compound of claim 1, or a pharmaceutically acceptable salt thereof, wherein Ring moiety C is phenyl, pyridinyl, benzothiazolyl, isoindolinonyl, or benzoimidazolyl.

19. The compound of claim 1, or a pharmaceutically acceptable salt thereof, wherein n is 0 or 1.

20. The compound of claim 1, or a pharmaceutically acceptable salt thereof, wherein each $R^3$ is independently selected from D, halo, and $C_{1-4}$ alkyl.

21. The compound of claim 1, or a pharmaceutically acceptable salt thereof, wherein s is 0 or 1.

22. The compound of claim 1, or a pharmaceutically acceptable salt thereof, wherein each $R^4$ is independently selected from H, D, halo, CN, $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, 5-6 membered heteroaryl-$C_{1-3}$ alkyl, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl are each optionally substituted by 1, 2, 3, or 4 independently selected $R^{4A}$ substituents;

each $R^{a4}$, $R^{c4}$, and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl are each optionally substituted with 1, 2, 3, or 4 independently selected $R^{4A}$ substituents;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl, which are each optionally substituted with 1, 2, 3, or 4 independently selected $R^{4A}$ substituents;

each $R^{4A}$ is independently selected from H, D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)NR^{c41}R^{d41}$, $NR^{c41}S(O)R^{b41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{b41}$, and $S(O)_2NR^{c41}R^{d41}$, wherein said $C_{1-6}$ alkyl, $C_{2-6}$ alkenyl, $C_{2-6}$ alkynyl, $C_{1-6}$ haloalkyl, $C_{3-6}$ cycloalkyl, phenyl, 4-6 membered heterocycloalkyl, 5-6 membered heteroaryl, $C_{3-6}$ cycloalkyl-$C_{1-3}$ alkyl, phenyl-$C_{1-3}$ alkyl, 4-6 membered heterocycloalkyl-$C_{1-3}$ alkyl, and 5-6 membered heteroaryl-$C_{1-3}$ alkyl are each optionally substituted with 1, 2, 3, or 4 independently selected $R^G$ substituents;

each $R^{a41}$, $R^{c4}$, and $R^{d41}$ is independently selected from H, $C_{1-6}$ alkyl, $C_{2-6}$ alkenyl, $C_{2-6}$ alkynyl, $C_{1-6}$ haloalkyl, and $C_{3-4}$ cycloalkyl, wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted with 1, 2, 3, or 4 independently selected $R^G$ substituents; and each $R^{b41}$ is independently selected from $C_{1-6}$ alkyl, $C_{2-6}$ alkenyl, $C_{2-6}$ alkynyl, $C_{1-6}$ haloalkyl, and $C_{3-4}$ cycloalkyl, which are each optionally substituted with 1, 2, 3, or 4 independently selected $R^G$ substituents.

23. The compound of claim 1, or a pharmaceutically acceptable salt thereof, wherein each $R^4$ is independently selected from H, D, halo, CN, $C_{1-6}$ alkyl, $C_{2-6}$ alkenyl, $C_{2-6}$ alkynyl, $C_{1-6}$ haloalkyl, $C_{3-4}$ cycloalkyl, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^{4A}$ substituents;

each $R^{a4}$, $R^{c4}$, and $R^{d4}$ is independently selected from H, $C_{1-6}$ alkyl and $C_{1-6}$ haloalkyl, wherein said $C_{1-6}$ alkyl and $C_{1-6}$ haloalkyl; and each $R^{b4}$ is independently selected from $C_{1-6}$ alkyl and $C_{1-6}$ haloalkyl.

24. The compound of claim 1, or a pharmaceutically acceptable salt thereof, wherein each $R^4$ is independently selected from D, halo, $C_{1-3}$ alkyl, and $C_{1-3}$ haloalkyl.

25. The compound of claim 1, or a pharmaceutically acceptable salt thereof, wherein each $R^4$ is independently selected from halo and $C_{1-3}$ alkyl.

26. The compound of claim 1, or a pharmaceutically acceptable salt thereof, wherein p is 0 or 1.

27. The compound of claim 1, or a pharmaceutically acceptable salt thereof, wherein:

each $R^5$ is independently selected from H, D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $NHOR^{a5}$, $C(O)R^{b5}$, $C(O)$ $NR^{c5}R^{d5}$, $C(O)OR^{a5}$, $OC(O)R^{b5}$, $OC(O)NR^{c5}R^{d5}$ $NR^{c5}R^{d5}$, $NR^{c5}C(O)R^{b5}$, $NR^{c5}C(O)OR^{a5}$, $NR^{c5}C(O)NR^{c5}R^{d5}$ $NR^{c5}S(O)NR^{c5}R^{d5}$ $NR^{c5}S(O)R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents; and each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5A}$ substituents.

28. The compound of claim 1, or a pharmaceutically acceptable salt thereof, wherein:

each $R^5$ is independently selected from H, D, halo, $NO_2$, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, and $NR^{c5}R^{d5}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{5A}$ substituents; and each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents.

29. The compound of claim 1, or a pharmaceutically acceptable salt thereof, wherein:

each $R^{5A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, and 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ substituents; and each $R^{5B}$ is independently selected from H, D, halo, CN, $NO_2$, $C_{1-3}$ alkyl, $C_{2-3}$ alkenyl, $C_2$-3 alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

30. The compound of claim 1, or a pharmaceutically acceptable salt thereof, wherein each $R^{5A}$ is independently selected from H, D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl) carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

31. The compound of claim 1, or a pharmaceutically acceptable salt thereof, wherein each $R^5$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

32. The compound of claim 1, or a pharmaceutically acceptable salt thereof, wherein each $R^5$ is independently selected from halo, CN, $C_{1-3}$ alkyl, and $C_{1-3}$ haloalkyl.

33. The compound of claim 1, or a pharmaceutically acceptable salt thereof, wherein E is a bond, —C(O)—, or —O—.

34. The compound of claim 1, or a pharmaceutically acceptable salt thereof, wherein k is 1.

35. The compound of claim 1, or a pharmaceutically acceptable salt thereof, wherein each $R^W$ is independently.

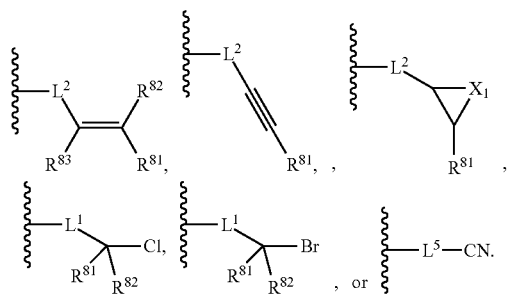

36. The compound of claim 1, or a pharmaceutically acceptable salt thereof, wherein each $L^1$ is independently -L-C(O)— or -L-$NR^9$C(O)—, wherein $L^1$ is attached to Ring moiety C through the L linking group.

37. The compound of claim 1, or a pharmaceutically acceptable salt thereof, wherein each $L^2$ is independently -L-C(O)— or -L-$NR^9$C(O)—, wherein $L^2$ is attached to Ring moiety C through the L linking group.

38. The compound of claim 1, or a pharmaceutically acceptable salt thereof, wherein each $L^3$ is independently -L-C(O)— or -L-$NR^9$C(O)—, wherein $L^3$ is attached to Ring moiety C through the L linking group.

39. The compound of claim 1, or a pharmaceutically acceptable salt thereof, wherein each $L^4$ is -L-$NR^9$—, wherein $L^4$ is attached to Ring moiety C through the L linking group.

40. The compound of claim 1, or a pharmaceutically acceptable salt thereof, wherein each $L^5$ is independently -L-O-$L^x$-, -L-$NR^9$-$L^x$-, -L-S-$L^x$-, -L-C(O)-$L^x$-, —$NR^9$C(O)-$L^x$-, -L-OC(O)-$L^x$-, -L-S(O)-$L^x$-, -L-$S(O)_2$-$L^x$-, —$NR^9$S(O)-$L^x$-, -L-OS(O)-$L^x$-, -L-$NR^9$S(O)$NR^9$-$L^x$-, -L-$NR^9$S(O)O-$L^x$-, -L-OS(O)$NR^9$-$L^x$-, —$NR^9$S(O)$_2$-$L^x$-, -L-OS(O)$_2$-$L^x$-, -L-$NR^9$S(O)$_2$$NR^9$-$L^x$-, -L-$NR^9$S(O)$_2$O-$L^x$-, -L-S(O)($NR^9$)-$L^x$-, -L-S(O)$_2$($NR^9$)-$L^x$-, or -L-OS(O)$_2$$NR^9$-$L^x$-, wherein $L^5$ is attached to Ring C through the L linking group.

41. The compound of claim 1, or a pharmaceutically acceptable salt thereof, wherein each $R^W$ is independently:

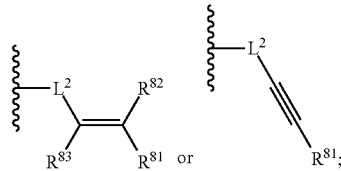

and
each $L^2$ is independently -L-$NR^9$C(O)—, wherein $L^2$ is attached to Ring moiety C through the L linking group.

42. The compound of claim 1, or a pharmaceutically acceptable salt thereof, wherein each L is a bond.

43. The compound of claim 1, or a pharmaceutically acceptable salt thereof, wherein each $L^2$ is independently NHC(O) or N(CH$_3$)C(O).

44. The compound of claim 1, or a pharmaceutically acceptable salt thereof, wherein:
each $R^{81}$, $R^{82}$, and $R^{83}$ is independently selected from H, D, halo, CN, C(O)H, $OR^{a8}$, C(O)$OR^{a8}$, $C_{1-6}$ alkyl, $C_{2-6}$ alkenyl, $C_{2-6}$ alkynyl, $C_{1-6}$ haloalkyl, and $C_{3-4}$ cycloalkyl; wherein said $C_{1-6}$ alkyl, $C_{2-6}$ alkenyl, $C_{2-6}$ alkynyl, $C_{1-6}$ haloalkyl, and $C_{3-4}$ cycloalkyl are each optionally substituted by 1, 2, 3, or 4 independently selected $R^G$ substituents;
each $R^{a8}$ is independently selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^G$ substituents.

45. The compound of claim 1, or a pharmaceutically acceptable salt thereof, wherein $R^{10}$ is H, D, halo, or $C_{1-4}$ alkyl.

46. The compound of claim 1, or a pharmaceutically acceptable salt thereof, wherein:
k is 1 or 2;
m is 0 or 1;
n is 0, 1, 2, 3, or 4;
p is 0, 1, 2, 3, or 4;
s is 0, 1, 2, 3, or 4;
each ==== is independently a single or a double bond;
X is N, Y is C, and Ring

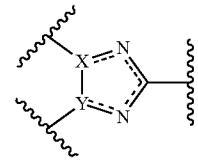

is

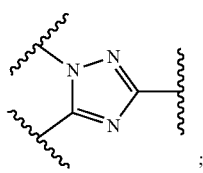

or

X is C, Y is N, and Ring

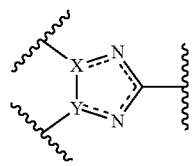

is;

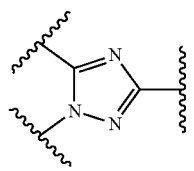

Z is CR² or N;
Ring moiety A is a 5-10 membered heteroaryl;
Ring moiety B is $C_{3-10}$ membered cycloalkyl or 4-10 membered heterocycloalkyl;
Ring moiety C is $C_{6-10}$ aryl, 5-10 membered heteroaryl, $C_{5-12}$ partially unsaturated cycloalkyl, or 5-12 membered partially unsaturated heterocycloalkyl;
E is a bond, —C(O)—, —CH₂—, —CHR⁶—, —CR⁶R⁷—, or —O—, wherein R⁶ and R⁷ are each independently selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;
each $R^W$, attached to the C ring, is independently:

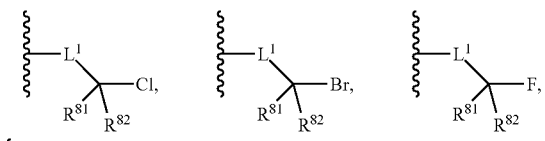

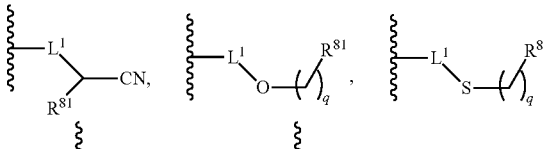

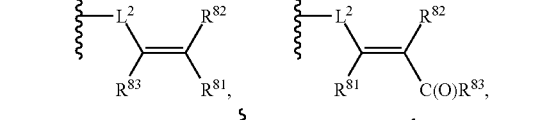

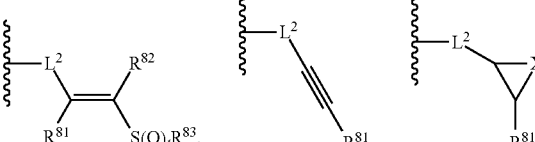

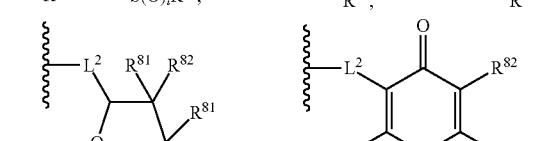

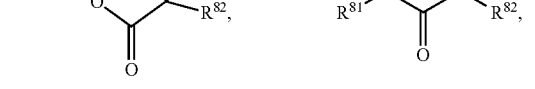

-continued

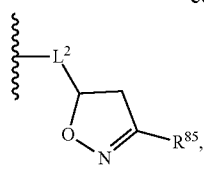

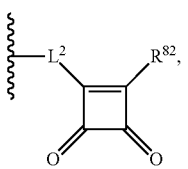

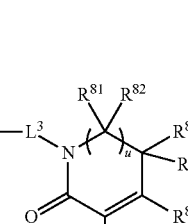

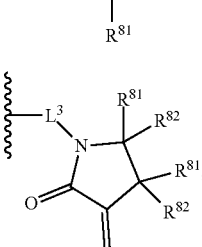

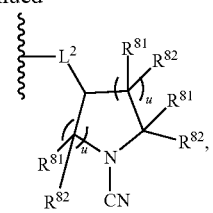

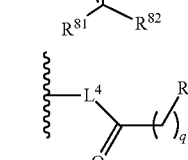

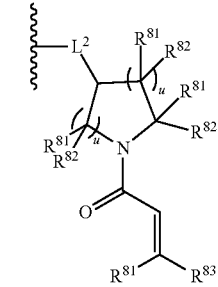

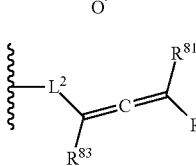

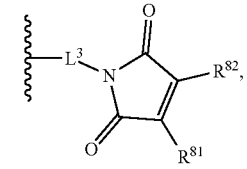

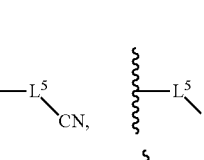

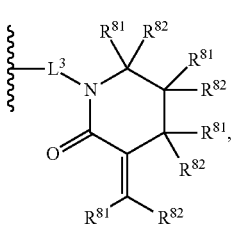

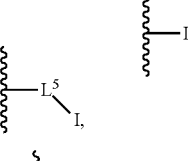

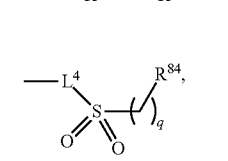

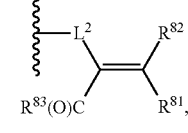

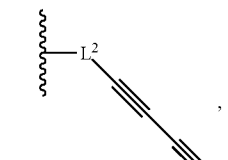

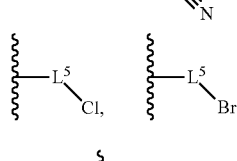

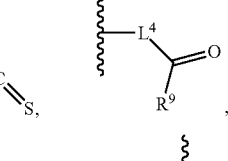

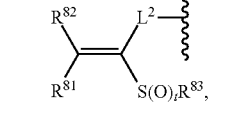

-continued

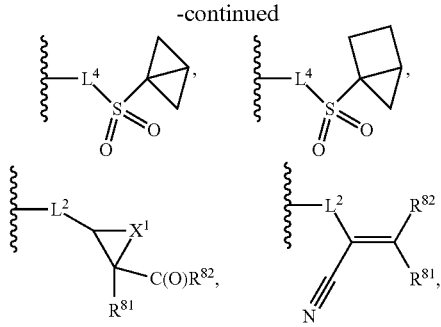

each L is independently -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$— or -L-OS(O)$_2$—, wherein L$^1$ is attached to Ring moiety C through the L linking group;

each L$^2$ is independently -L-, -L-O—, -L-NR$^9$—, -L-S—, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)NR$^9$—, -L-NR$^9$S(O)O—, -L-OS(O)NR$^9$—, -L-NR$^9$S(O)$_2$—, -L-OS(O)$_2$—, -L-NR$^9$S(O)$_2$NR$^9$—, -L-NR$^9$S(O)$_2$O—, -L-S(O)(NR$^9$)—, -L-S(O)$_2$N$^9$)—, or -L-OS(O)$_2$NR$^9$—, wherein L$^2$ is attached to Ring moiety C through the L linking group;

each L$^3$ is independently -L-, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$—, or -L-OS(O)$_2$—, wherein L$^3$ is attached to Ring moiety C through the L linking group;

each L$^4$ is independently -L-, -L-O—, L-S—, -L-NR$^9$—, wherein L$^4$ is attached to Ring moiety C through the L linking group;

each L$^5$ is independently -L-O-L$^x$-, -L-NR$^9$-L$^x$-, -L-S-L$^x$-, -L-C(O)-L$^x$-, -L-NR$^9$C(O)-L$^x$-, -L-OC(O)-L$^x$-, -L-S(O)-L$^x$-, -L-S(O)$_2$-L-, -L-NR$^9$S(O)-L$^x$-, -L-OS(O)-L$^x$-, -L-NR$^9$S(O)NR$^9$-L$^x$-, -L-NR$^9$S(O)O-L$^x$-, -L-OS(O)NR$^9$-L$^x$-, -L-NR$^9$S(O)$_2$-L$^x$-, -L-OS(O)$_2$-L$^x$-, -L-NR$^9$S(O)$_2$NR$^9$-L$^x$-, -L-NR$^9$S(O)$_2$O-L$^x$-, -L-S(O)(NR$^9$)-L$^x$-, -L-S(O)$_2$(NR$^9$)-L$^x$-, or -L-OS(O)$_2$NR$^9$-L$^x$-, wherein L$^5$ is attached to Ring moiety C through the L linking group;

each L is independently is a bond or C$_{1-6}$ alkylene, wherein said C$_{1-6}$ alkylene is optionally substituted by 1, 2, 3 or 4 independently selected R$^G$ substituents;

each LU is independently is a C$_{1-6}$ alkylene, wherein said C$_{1-6}$ alkylene is optionally substituted by 1, 2, 3 or 4 independently selected R$^G$ substituents;

each X$^1$ is independently 0 or NR$^9$;

each q is independently 0, 1, or 2;

each t is independently 0, 1, or 2;

each u is independently 0, 1, or 2;

each Ar is independently C$_{6-10}$ aryl or 5-10 membered heteroaryl, which are each optionally substituted with 1, 2, 3, or 4 independently selected R$^{9A}$ substituents;

each R$^{81}$, R$^{82}$, and R$^{83}$ is independently selected from H, D, halo, CN, C(O)H, OH, C$_{1-3}$ alkoxy, C$_{1-3}$ haloalkoxy, amino, C$_{1-6}$ alkyl, C$_{1-6}$ haloalkyl, C$_{3-10}$ cycloalkyl, 4-10 membered heterocycloalkyl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, wherein said C$_{1-6}$ alkyl, C$_{1-6}$ haloalkyl, C$_{3-10}$ cycloalkyl, 4-10 membered heterocycloalkyl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^G$ substituents;

each R$^{84}$ is independently selected from H, D, halo, CN, OH, C$_{1-3}$ alkoxy, C$_{1-3}$ haloalkoxy, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, each of which is optionally substituted by 1, 2, 3, or 4 independently selected R$^G$ substituents;

each R$^{85}$ is independently selected from H, D, halo, CN, C(O)H, OH, C$_{1-3}$ alkoxy, C$_{1-3}$ haloalkoxy, amino, C$_{1-6}$ alkyl, C$_{1-6}$ haloalkyl, C$_{3-10}$ cycloalkyl, 4-10 membered heterocycloalkyl, and C$_{3-10}$ cycloalkyl-C$_{1-4}$ alkyl, wherein said C$_{1-6}$ alkyl, C$_{1-6}$ haloalkyl, C$_{3-10}$ cycloalkyl, 4-10 membered heterocycloalkyl, and C$_{3-10}$ cycloalkyl-C$_{1-4}$ alkyl are each optionally substituted by 1, 2, 3, or 4 independently selected R$^G$ substituents;

each R$^9$ is independently H, C$_{1-4}$ alkyl, or C$_{1-4}$ haloalkyl;

R$^1$ is selected from H, D, halo, CN, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, 5-10 membered heteroaryl-C$_{1-4}$ alkyl, OR$^{a1}$, SR$^{a1}$, NHOR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{14}$ substituents;

each R$^{a1}$, R$^{c1}$, and R$^{d1}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{14}$ substituents;

or, any R$^{c1}$ and R$^{d1}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected R$^{14}$ substituents;

each R$^{b1}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-$C_{1-4}$ alkyl, which are each optionally substituted with 1, 2, 3, or 4 independently selected $R^{1A}$ substituents;

each $R^{1A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{b11}$, $S(O)_2R^{b11}$, and $S(O)_2NR^{c11}R^{b11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^1$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^1$ substituents;

or, any $R^{c11}$ and $R^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^2$ is selected from H, D, halo, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-4}$ cycloalkyl, $C_{1-3}$ alkoxy, $C_{1-3}$ haloalkoxy, amino, $C_{1-3}$ alkylamino, and di($C_{1-3}$ alkyl)amino;

each $R^3$ is independently selected from D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^4$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$, $NR^{c4}C(O)OR^{a4}$, $NR^{c4}C(O)NR^{c4}R^{d4}$, $NR^{c4}S(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4A}$ substituents;

or, any $R^{c4}$ and $R^{d4}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{4A}$ substituents;

each $R^{b4}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4A}$ substituents;

each $R^{4A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a41}$, $SR^{a41}$, $NHOR^{a41}$, $C(O)R^{b41}$, $C(O)NR^{c41}R^{d41}$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)NR^{c41}R^{d41}$, $NR^{c41}S(O)R^{b41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{b41}$, and $S(O)_2NR^{c41}R^{d41}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{4B}$ substituents;

or, any $R^{c41}$ and $R^{d41}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{4B}$ substituents;

each $R^{b41}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{4B}$ substituents;

each $R^{4B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a42}$, $SR^{a42}$, $NHOR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)OR^{a42}$, $NR^{c42}C(O)NR^{c42}R^{d42}$, $NR^{c42}S(O)NR^{c42}R^{d42}$, $NR^{c42}S(O)R^{b42}$, $NR^{c42}S(O)_2R^{b42}$, $NR^{c42}S(O)_2NR^{c42}R^{d42}$, $S(O)R^{b42}$, $S(O)NR^{c42}R^{d42}$, $S(O)_2R^{b42}$, and $S(O)_2NR^{c42}R^{d42}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c42}$ and $R^{d42}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b42}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^5$ is independently selected from D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$ $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents;

or, any $R^{c5}$ and $R^{d5}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5A}$ substituents;

each $R^{5A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a1}$, $SR^{a1}$, $NHOR^{a5}$, $C(O)R^{b51}$, $C(O)NR^{c51}R^{d51}$, $C(O)OR^{a5}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a5}$, $NR^{c51}C(O)NR^{c51}R^{d51}$, $NR^{c51}S(O)NR^{c51}R^{d51}$, $NR^{c51}S(O)R^{b51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, and $S(O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

or, any $R^{c51}$ and $R^{d51}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{5B}$ substituents;

each $R^{b51}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5B}$ substituents;

each $R^{5B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $NHOR^{a52}$, $C(O)R^{b52}$, $C(O)NR^{c52}R^{d52}$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)NR^{c52}R^{d52}$, $NR^{c52}S(O)R^{b52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, and $S(O)_2NR^{c52}R^{d52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5C}$ substituents;

or, any $R^{c52}$ and $R^{d52}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{5C}$ substituents;

each $R^{b52}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{5C}$ substituents;

each $R^{5C}$ is independently selected from D, halo, CN, $NO_2$, $C_{1-6}$ alkyl, $C_{2-6}$ alkenyl, $C_{2-6}$ alkynyl, $C_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a53}$, SR$^{a53}$, NHOR$^{a53}$, C(O)R$^{b53}$, C(O)NR$^{c53}$R$^{d53}$, C(O)OR$^{a53}$, OC(O)R$^{b53}$, OC(O)NR$^{c53}$R$^{d53}$, NR$^{c53}$R$^{d53}$, NR$^{c53}$C(O)R$^{b53}$, NR$^{c53}$C(O)OR$^{a53}$, NR$^{c53}$C(O)NR$^{c53}$R$^{d53}$, NR$^{c53}$S(O)NR$^{c53}$R$^{d53}$, NR$^{c53}$S(O)R$^{b53}$, NR$^{c53}$S(O)$_2$R$^{b53}$, NR$^{c53}$S(O)$_2$NR$^{c53}$R$^{d53}$, S(O)R$^{b53}$, S(O)NR$^{c53}$R$^{d53}$, S(O)$_2$R$^{b53}$, and S(O)$_2$NR$^{c53}$R$^{d53}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{a53}$, R$^{c53}$, and R$^{d53}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

or, any R$^{c53}$ and R$^{d53}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected R$^G$ substituents;

each R$^{b53}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^G$ substituents;

R$^{10}$, R$^{11}$, and R$^{12}$ are each independently selected from H, D, halo, CN, C$_{1-4}$ alkyl, C$_{1-4}$ haloalkyl, C$_{1-3}$ alkoxy, C$_{1-3}$ haloalkoxy, cyano-C$_{1-4}$ alkyl, HO—C$_{1-4}$ alkyl, C$_{1-3}$ alkoxy-C$_{1-4}$ alkyl, and C$_{3-4}$ cycloalkyl; and each R$^G$ is independently selected from OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-3}$ alkoxycarbonyl, C$_{1-3}$ alkylcarbonyloxy, C$_{1-3}$ alkylcarbonylamino, C$_{1-3}$ alkoxycarbonylamino, C$_{1-3}$ alkylaminocarbonyloxy, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino.

47. The compound of claim 1, or a pharmaceutically acceptable salt thereof, wherein:

k is 1 or 2;
m is 0 or 1;
n is 0, 1, or 2;
p is 0, 1, or 2;
s is 0, 1, or 2;
each ≡≡≡ is independently a single or a double bond;
X is N, Y is C, and Ring

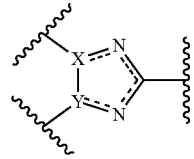

is

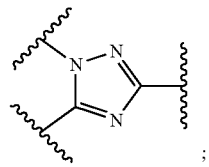 [SMILES: *c1nc(*)n(*)n1]

;

or

X is C, Y is N, and Ring

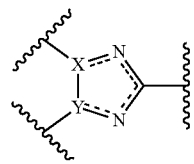

is

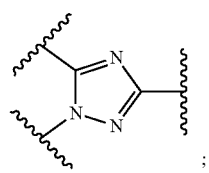 [SMILES: *c1nc(*)n(*)n1]

;

Z is CR$^2$ or N;
Ring moiety A is a 5-10 membered heteroaryl;
Ring moiety B is C$_{3-10}$ membered cycloalkyl or 4-10 membered heterocycloalkyl;
Ring moiety C is C$_{6-10}$ aryl, 5-10 membered heteroaryl, C$_{5-12}$ partially unsaturated cycloalkyl, or 5-12 membered partially unsaturated heterocycloalkyl;
E is a bond, —C(O)—, —CH$_2$—, —CHR$^6$—, —CR$^6$R$^7$—, or —O—, wherein R$^6$ and R$^7$ are each independently selected from H, D, halo, CN, C$_{1-4}$ alkyl, C$_{1-4}$ haloalkyl, C$_{2-4}$ alkenyl, C$_{2-4}$ alkynyl, OH, C$_{1-3}$ alkoxy, C$_{1-3}$ haloalkoxy, amino, C$_{1-3}$ alkylamino, di(C$_{1-3}$ alkyl)amino, cyano-C$_{1-4}$ alkyl, HO—C$_{1-4}$ alkyl, C$_{1-3}$ alkoxy-C$_{1-4}$ alkyl, and C$_{3-4}$ cycloalkyl;

each $R^w$, attached to the C ring, is independently:

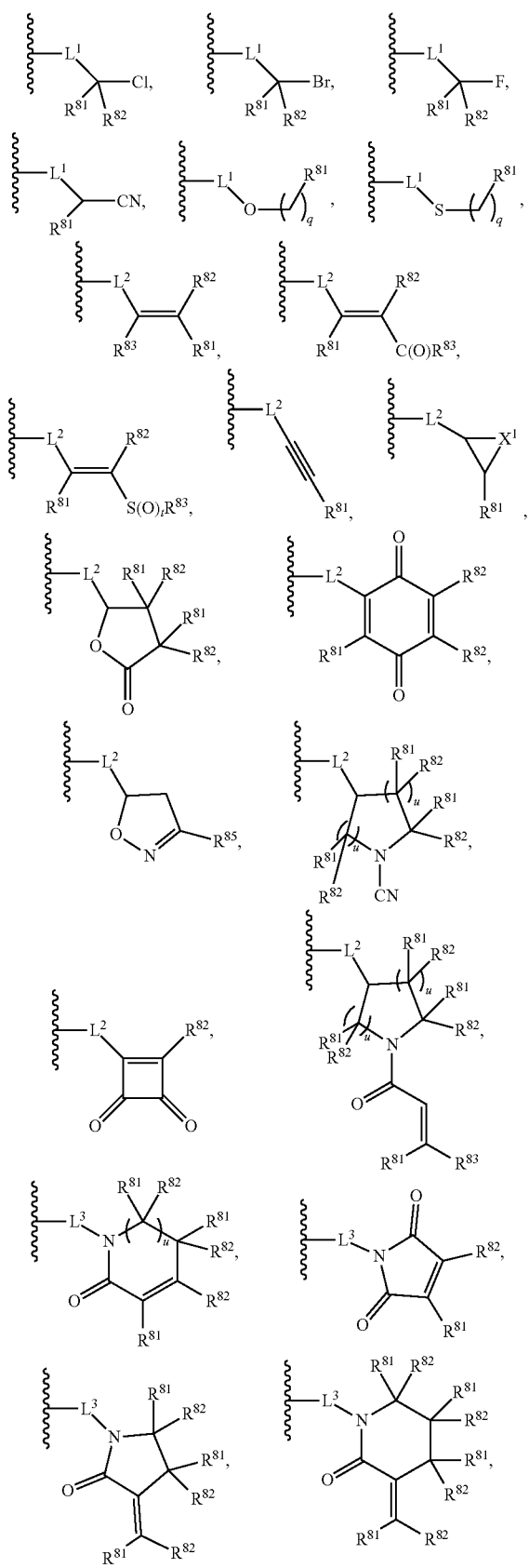

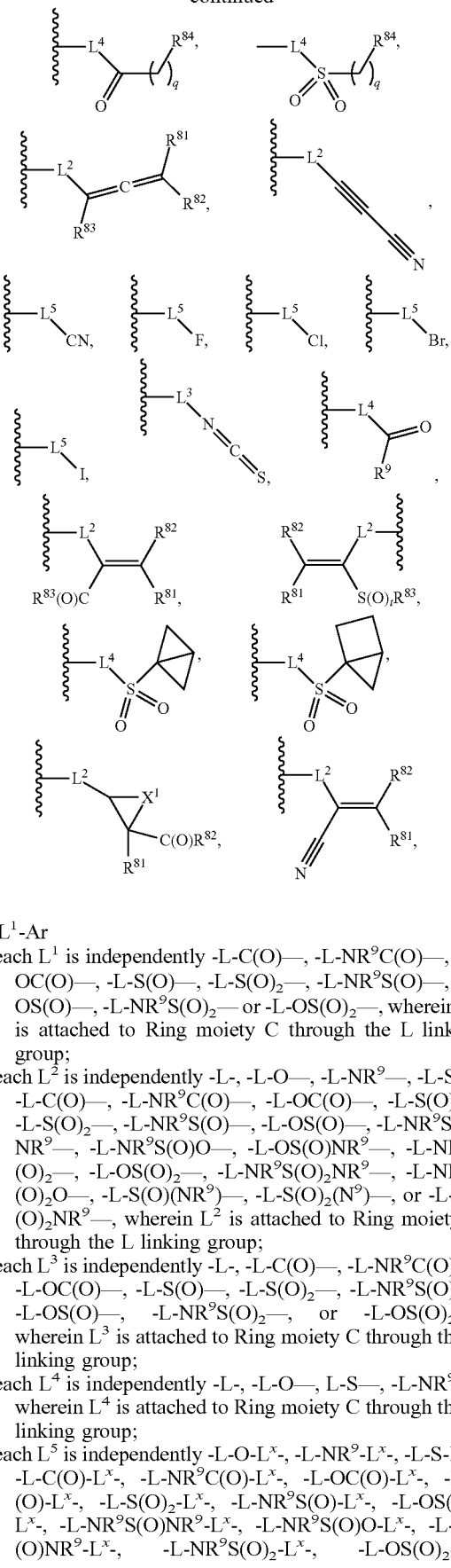

or $L^1$-Ar each $L^1$ is independently -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$— or -L-OS(O)$_2$—, wherein $L^1$ is attached to Ring moiety C through the L linking group;

each $L^2$ is independently -L-, -L-O—, -L-NR$^9$—, -L-S—, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)NR$^9$—, -L-NR$^9$S(O)O—, -L-OS(O)NR$^9$—, -L-NR$^9$S(O)$_2$—, -L-OS(O)$_2$—, -L-NR$^9$S(O)$_2$NR$^9$—, -L-NR$^9$S(O)$_2$O—, -L-S(O)(NR$^9$)—, -L-S(O)$_2$(N$^9$)—, or -L-OS(O)$_2$NR$^9$—, wherein $L^2$ is attached to Ring moiety C through the L linking group;

each $L^3$ is independently -L-, -L-C(O)—, -L-NR$^9$C(O)—, -L-OC(O)—, -L-S(O)—, -L-S(O)$_2$—, -L-NR$^9$S(O)—, -L-OS(O)—, -L-NR$^9$S(O)$_2$—, or -L-OS(O)$_2$—, wherein $L^3$ is attached to Ring moiety C through the L linking group;

each $L^4$ is independently -L-, -L-O—, L-S—, -L-NR$^9$—, wherein $L^4$ is attached to Ring moiety C through the L linking group;

each $L^5$ is independently -L-O-L$^x$-, -L-NR$^9$-L$^x$-, -L-S-L$^x$-, -L-C(O)-L$^x$-, -L-NR$^9$C(O)-L$^x$-, -L-OC(O)-L$^x$-, -L-S(O)-L$^x$-, -L-S(O)$_2$-L$^x$-, -L-NR$^9$S(O)-L$^x$-, -L-OS(O)-L$^x$-, -L-NR$^9$S(O)NR$^9$-L$^x$-, -L-NR$^9$S(O)O-L$^x$-, -L-OS(O)NR$^9$-L$^x$-, -L-NR$^9$S(O)$_2$-L$^x$-, -L-OS(O)$_2$-L-, -L-NR$^9$S(O)$_2$NR$^9$-L$^x$-, -L-NR$^9$S(O)$_2$O-L$^x$-, -L-S(O)(NR$^9$)-L$^x$-, -L-S(O)$_2$(NR$^9$)-L$^x$-, or -L-OS(O)$_2$NR$^9$-L$^x$-, wherein L$^5$ is attached to Ring moiety C through the L linking group;

each L is independently is a bond or C$_{1-6}$ alkylene, wherein said C$_{1-6}$ alkylene is optionally substituted by 1, 2, 3 or 4 independently selected R$^G$ substituents;

each L$^x$ is independently is a C$_{1-6}$ alkylene, wherein said C$_{1-6}$ alkylene is optionally substituted by 1, 2, 3 or 4 independently selected R$^G$ substituents;

each X$^1$ is independently O or NR$^9$;

each q is independently 0, 1, or 2;

each t is independently 0, 1, or 2;

each u is independently 0, 1, or 2;

each Ar is independently C$_{6-10}$ aryl or 5-10 membered heteroaryl, which are each optionally substituted with 1, 2, 3, or 4 independently selected R$^{9A}$ substituents;

each R$^{81}$, R$^{82}$, and R$^{83}$ is independently selected from H, D, halo, CN, C(O)H, OH, C$_{1-3}$ alkoxy, C$_{1-3}$ haloalkoxy, amino, C$_{1-6}$ alkyl, C$_{1-6}$ haloalkyl, C$_{3-10}$ cycloalkyl, 4-10 membered heterocycloalkyl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, wherein said C$_{1-6}$ alkyl, C$_{1-6}$ haloalkyl, C$_{3-10}$ cycloalkyl, 4-10 membered heterocycloalkyl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^G$ substituents;

each R$^{84}$ is independently selected from H, D, halo, CN, OH, C$_{1-3}$ alkoxy, C$_{1-3}$ haloalkoxy, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, each of which is optionally substituted by 1, 2, 3, or 4 independently selected R$^G$ substituents;

each R$^{85}$ is independently selected from H, C(O)H, OH, C$_{1-3}$ alkoxy, C$_{1-3}$ haloalkoxy, amino, C$_{1-6}$ alkyl, C$_{1-6}$ haloalkyl, C$_{3-10}$ cycloalkyl, 4-10 membered heterocycloalkyl, and C$_{3-10}$ cycloalkyl-C$_{1-4}$ alkyl, wherein said C$_{1-6}$ alkyl, C$_{1-6}$ haloalkyl, C$_{3-10}$ cycloalkyl, 4-10 membered heterocycloalkyl, and C$_{3-10}$ cycloalkyl-C$_{1-4}$ alkyl are each optionally substituted by 1, 2, 3, or 4 independently selected R$^G$ substituents;

each R$^9$ is independently H, C$_{1-4}$ alkyl, or C$_{1-4}$ haloalkyl;

R$^1$ is selected from H, D, halo, CN, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, 5-10 membered heteroaryl-C$_{1-4}$ alkyl, OR$^{a1}$, SR$^{a1}$, NHOR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{1A}$ substituents;

each R$^{a1}$, R$^{c1}$, and R$^{d1}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{1A}$ substituents;

or, any R$^{c1}$ and R$^{d1}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected R$^{1A}$ substituents;

each R$^{b1}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected R$^{1A}$ substituents;

each R$^{1A}$ is independently selected from H, D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a11}$, SR$^{a11}$, NHOR$^{a11}$, C(O)R$^{b11}$, C(O)NR$^{c11}$R$^{d11}$, C(O)OR$^{a11}$, OC(O)R$^{b11}$, OC(O)NR$^{c11}$R$^{d11}$, NR$^{c11}$R$^{d11}$, NR$^{c11}$C(O)R$^{b11}$, NR$^{c11}$C(O)OR$^{a11}$, NR$^{c11}$C(O)NR$^{c11}$R$^{d11}$, NR$^{c11}$S(O)NR$^{c11}$R$^{d11}$, NR$^{c11}$S(O)R$^{b11}$, NR$^{c11}$S(O)$_2$R$^{b11}$, NR$^{c11}$S(O)$_2$NR$^{c11}$R$^{d11}$, S(O)R$^{b11}$, S(O)NR$^{c11}$R$^{b11}$, S(O)$_2$R$^{b11}$, and S(O)$_2$NR$^{c11}$R$^{b11}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^1$ substituents;

each R$^{a11}$, R$^{c11}$, and R$^{d11}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-10}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^1$ substituents;

or, any R$^{c11}$ and R$^{d11}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c11}R^{d12}$, $C(O)OR^{a12}$, $OC(O)R^{b12}$, $OC(O)NR^{c12}R^{d12}$, $R^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, and $S(O)_2NR^{c12}R^{d12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c12}$ and $R^{d12}$ attached to the same N atom, together with the N atom to which they are attached, form a 4-7 membered heterocycloalkyl group, wherein the 4-7 membered heterocycloalkyl group is optionally substituted with 1, 2, 3, or 4 independently selected $R^G$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

$R^2$ is selected from H, D, halo, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-4}$ cycloalkyl, $C_{1-3}$ alkoxy, $C_{1-3}$ haloalkoxy, amino, $C_{1-3}$ alkylamino, and di($C_{1-3}$ alkyl)amino;

each $R^3$ is independently selected from D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^4$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^5$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^{10}$ is H, D, halo, or $C_{1-4}$ alkyl;

$R^{11}$ and $R^{12}$ are each independently selected from H, D, halo, CN, $C_{1-4}$ alkyl, $C_{1-4}$ haloalkyl, $C_{1-3}$ alkoxy, $C_{1-3}$ haloalkoxy, cyano-$C_{1-4}$ alkyl, HO—$C_{1-4}$ alkyl, $C_{1-3}$ alkoxy-$C_{1-4}$ alkyl, and $C_{3-4}$ cycloalkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

48. The compound of claim 1, or a pharmaceutically acceptable salt thereof, wherein:

k is 1 or 2;

m is 0 or 1;

n is 0, 1, or 2;

p is 0, 1, or 2;

s is 0, 1, or 2;

each ═══ is independently a single or a double bond;

X is N, Y is C, and Ring

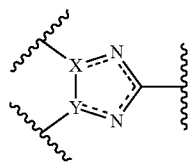

is

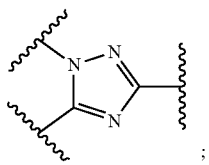 [SMILES: *c1nc(*)n(*)n1]

or

X is C, Y is N, and Ring

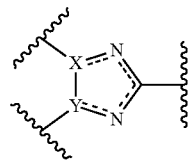

is

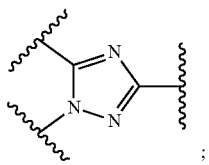 [SMILES: *c1nc(*)n(*)n1]

Z is $CR^2$ or N;

Ring moiety A is a monocyclic 5-6 membered heteroaryl;

Ring moiety B is monocyclic $C_{3-7}$ cycloalkyl or monocyclic 4-7 membered heterocycloalkyl;

Ring moiety C is $C_{6-10}$ aryl, 5-10 membered heteroaryl, or 5-12 membered partially unsaturated heterocycloalkyl;

E is a bond, —C(O)—, or —O—;

each $R^W$, attached to the C ring, is independently:

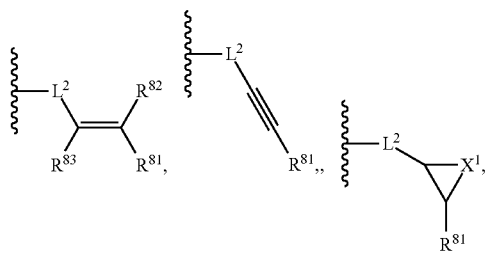

-continued

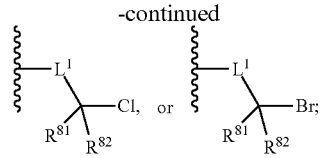

each $L^1$ is independently -L-C(O)— or -L-NR$^9$C(O)—, wherein each $L^1$ is attached to Ring moiety C through the L linking group;

each $L^2$ is independently -L-C(O)— or -L-NR$^9$C(O)—, wherein $L^2$ is attached to Ring moiety C through the L linking group;

each L is independently a bond or $C_{1-6}$ alkylene;

each $X^1$ is independently O or $NR^9$;

each $R^{81}$, $R^{82}$, and $R^{83}$ is independently selected from H, D, halo, CN, C(O)H, OH, $C_{1-3}$ alkoxy, $C_{1-3}$ haloalkoxy, amino, $C_{1-6}$ alkyl, $C_{1-6}$ haloalkyl;

each $R^9$ is independently H, $C_{1-4}$ alkyl, or $C_{1-4}$ haloalkyl;

$R^1$ is selected from H, D, halo, CN, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, and $OR^{a1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-10}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents;

each $R^{a1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, and 5-6 membered heteroaryl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, and 5-6 membered heteroaryl are each optionally substituted with 1, 2, 3, or 4 independently selected $R^{1A}$ substituents;

each $R^{1A}$ is independently selected from H, D, halo, CN, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^1$ substituents;

each $R^{1B}$ is independently selected from H, D, halo, CN, $C_{1-6}$ alkyl, $C_{2-6}$ alkenyl, $C_{2-6}$ alkynyl, and $C_{1-6}$ haloalkyl;

$R^2$ is selected from H, D, halo, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-4}$ cycloalkyl, $C_{1-3}$ alkoxy, $C_{1-3}$ haloalkoxy, amino, $C_{1-3}$ alkylamino, and di($C_{1-3}$ alkyl)amino;

each $R^3$ is independently selected from D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-4}$ alkyl, HO—$C_{1-4}$ alkyl, $C_{1-3}$ alkoxy-$C_{1-4}$ alkyl, and $C_{3-4}$ cycloalkyl;

each $R^4$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^5$ is independently selected from D, halo, CN, $NO_2$, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^{10}$ is H, D, halo, or $C_{1-4}$ alkyl; and $R^{11}$ and $R^{12}$ are each independently selected from H, D, halo, CN, $C_{1-4}$ alkyl, $C_{1-4}$ haloalkyl, $C_{1-3}$ alkoxy, $C_{1-3}$ haloalkoxy, cyano-$C_{1-4}$ alkyl, HO—$C_{1-4}$ alkyl, $C_{1-3}$ alkoxy-$C_{1-4}$ alkyl, and $C_{3-4}$ cycloalkyl.

49. The compound of claim 1, or a pharmaceutically acceptable salt thereof, wherein:

k is 1;

m is 0;

n is 0 or 1;

p is 0 or 1;

s is 0 or 1;

each ==== is independently a single or a double bond;

X is N, Y is C, and Ring is or

X is C, Y is N, and Ring is

Z is $CR^2$ or N;

Ring moiety A is a monocyclic 5-membered heteroaryl;

Ring moiety B is monocyclic $C_{4-6}$ cycloalkyl or monocyclic 4-6 membered heterocycloalkyl;

Ring moiety C is phenyl, 5-10 membered heteroaryl, or 5-10 membered partially unsaturated heterocycloalkyl;

E is a bond, —C(O)—, or —O—;

$R^W$, attached to the C ring, is:

$L^2$ is -L-$NR^9C(O)$—, wherein $L^2$ is attached to Ring moiety C through the L linking group;

L is a bond;

$R^{81}$, $R^{82}$, and $R^{83}$ are each independently selected from H, halo, and $C_{1-6}$ alkyl;

$R^9$ is H or $C_{1-4}$ alkyl;

$R^1$ is selected from H, CN, $C_{1-6}$ alkyl, $C_{1-6}$ haloalkyl, and $OR^{a1}$, wherein said $C_{1-6}$ alkyl and $C_{1-6}$ haloalkyl are each optionally substituted with 1 or 2 independently selected $R^{1A}$ substituents;

each $R^{a1}$ is independently selected from $C_{1-6}$ alkyl, $C_{3-7}$ cycloalkyl, and 4-7 membered heterocycloalkyl, wherein each of which is optionally substituted with 1 or 2 independently selected $R^{1A}$ substituents;

each $R^{1A}$ is independently selected from halo and $C_{1-6}$ alkyl;

$R^2$ is selected from H and $C_{1-3}$ alkyl;

each $R^3$ is independently selected from halo and $C_{1-4}$ alkyl;

each $R^4$ is independently selected from halo and $C_{1-4}$ alkyl;

each $R^5$ is independently selected from halo and $C_{1-4}$ alkyl; and $R^{10}$ is H.

50. The compound of claim 1, having Formula (V), (VI), (VII), or (VIII):

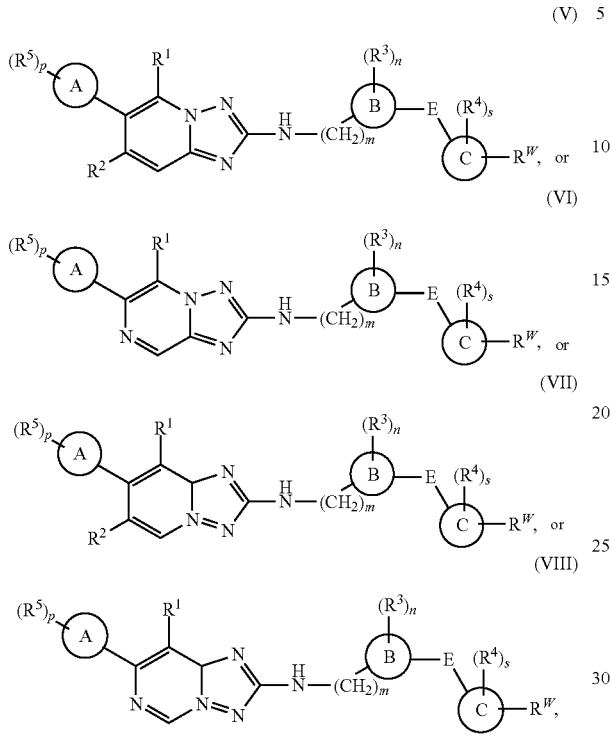

or a pharmaceutically acceptable salt of any of the aforementioned.

51. The compound of claim 1, selected from:
N-(4-(3-((5-isopropoxy-6-(1H-pyrazol-4-yl)-[1,2,4]triazolo[1,5-a]pyrazin-2-yl)amino)azetidine-1-carbonyl)phenyl)acrylamide;
N-(4-(4-((8-methoxy-7-(1H-pyrazol-4-yl)-[1,2,4]triazolo[1,5-c]pyrimidin-2-yl)amino)piperidine-1-carbonyl)phenyl)acrylamide;
N-(4-(3-((8-methoxy-7-(1H-pyrazol-4-yl)-[1,2,4]triazolo[1,5-c]pyrimidin-2-yl)amino)azetidine-1-carbonyl)phenyl)acrylamide;
(R)-N-(3-fluoro-4-(3-((5-isopropoxy-6-(1H-pyrazol-4-yl)-[1,2,4]triazolo[1,5-a]pyrazin-2-yl)amino)piperidine-1-carbonyl)phenyl)acrylamide;
(R)-N-(4-(3-((8-methoxy-7-(1H-pyrazol-4-yl)-[1,2,4]triazolo[1,5-c]pyrimidin-2-yl)amino)piperidine-1-carbonyl)phenyl)acrylamide;
(R)-N-(4-(3-((5-(piperidin-1-yl)-6-(1H-pyrazol-4-yl)-[1,2,4]triazolo[1,5-a]pyridin-2-yl)amino)piperidine-1-carbonyl)phenyl)acrylamide;
(R)-N-(4-(3-((6-(1H-pyrazol-4-yl)-5-(pyrrolidin-1-yl)-[1,2,4]triazolo[1,5-a]pyridin-2-yl)amino)piperidine-1-carbonyl)phenyl)acrylamide;
(R)-N-(4-(3-((5-morpholino-6-(1H-pyrazol-4-yl)-[1,2,4]triazolo[1,5-a]pyridin-2-yl)amino)piperidine-1-carbonyl)phenyl)acrylamide;
N-(4-(3-((6-(3-methyl-1H-pyrazol-4-yl)-5-morpholino-[1,2,4]triazolo[1,5-a]pyridin-2-yl)amino)piperidine-1-carbonyl)phenyl)acrylamide;
(R)-N-(4-(3-((5-(3,3-difluorocyclobutoxy)-6-(1H-pyrazol-4-yl)-[1,2,4]triazolo[1,5-a]pyrazin-2-yl)amino)piperidine-1-carbonyl)phenyl)acrylamide;
(R)-N-(4-(3-((6-(1H-pyrazol-4-yl)-[1,2,4]triazolo[1,5-a]pyridin-2-yl)amino)pyrrolidine-1-carbonyl)phenyl)acrylamide;
(R)-N-(4-(3-((5-methyl-6-(1H-pyrazol-4-yl)-[1,2,4]triazolo[1,5-a]pyridin-2-yl)amino)pyrrolidine-1-carbonyl)phenyl)acrylamide;
(R)-N-(4-(3-((5-(4,4-difluoropiperidin-1-yl)-6-(1H-pyrazol-4-yl)-[1,2,4]triazolo[1,5-a]pyridin-2-yl)amino)piperidine-1-carbonyl)phenyl)acrylamide;
N-(4-((R)-3-((6-(1H-pyrazol-4-yl)-5-(((S)-tetrahydrofuran-3-yl)oxy)-[1,2,4]triazolo[1,5-a]pyridin-2-yl)amino)piperidine-1-carbonyl)phenyl)acrylamide;
(R)-N-(4-(3-((6-(1H-pyrazol-4-yl)-5-((tetrahydro-2H-pyran-4-yl)oxy)-[1,2,4]triazolo[1,5-a]pyridin-2-yl)amino)piperidine-1-carbonyl)phenyl)acrylamide;
N-(4-(((1S,3R)-3-((5-(piperidin-1-yl)-6-(1H-pyrazol-4-yl)-[1,2,4]triazolo[1,5-a]pyridin-2-yl)amino)cyclohexyl)oxy)phenyl)acrylamide;
(R)-N-(4-(3-((5-cyano-6-(1H-pyrazol-4-yl)-[1,2,4]triazolo[1,5-a]pyridin-2-yl)amino)pyrrolidine-1-carbonyl)phenyl)acrylamide;
(R)-N-(4-(3-((5-isopropyl-6-(1H-pyrazol-4-yl)-[1,2,4]triazolo[1,5-a]pyridin-2-yl)amino)pyrrolidine-1-carbonyl)phenyl)acrylamide;
(R)-N-(2-fluoro-4-(3-((5-isopropyl-6-(1H-pyrazol-4-yl)-[1,2,4]triazolo[1,5-a]pyridin-2-yl)amino)pyrrolidine-1-carbonyl)phenyl)acrylamide;
(R)-N-(4-(3-((6-(oxazol-5-yl)-[1,2,4]triazolo[1,5-a]pyridin-2-yl)amino)pyrrolidine-1-carbonyl)phenyl)acrylamide;
N-(3-oxo-2-((1S,3R)-3-((5-(piperidin-1-yl)-6-(1H-pyrazol-4-yl)-[1,2,4]triazolo[1,5-a]pyridin-2-yl)amino)cyclohexyl)isoindolin-5-yl)acrylamide;
N-(2-((1S,3R)-3-((5-methyl-6-(1H-pyrazol-4-yl)-[1,2,4]triazolo[1,5-a]pyridin-2-yl)amino)cyclohexyl)-3-oxoisoindolin-5-yl)acrylamide;
N-(2-((1S,3R)-3-((5-isopropyl-6-(1H-pyrazol-4-yl)-[1,2,4]triazolo[1,5-a]pyridin-2-yl)amino)cyclohexyl)-3-oxoisoindolin-5-yl)acrylamide;
(R)-N-(4-(3-((7-methyl-6-(1H-pyrazol-4-yl)-[1,2,4]triazolo[1,5-a]pyridin-2-yl)amino)pyrrolidine-1-carbonyl)phenyl)acrylamide;
(R)-N-(4-(3-((5-isopropyl-6-(1H-pyrazol-4-yl)-[1,2,4]triazolo[1,5-a]pyridin-2-yl)amino)pyrrolidine-1-carbonyl)phenyl)-N-methylacrylamide;
(R)-2-fluoro-N-(4-(3-((5-isopropyl-6-(1H-pyrazol-4-yl)-[1,2,4]triazolo[1,5-a]pyridin-2-yl)amino)pyrrolidine-1-carbonyl)phenyl)acrylamide;
(R)-N-(2-(3-((5-isopropyl-6-(1H-pyrazol-4-yl)-[1,2,4]triazolo[1,5-a]pyridin-2-yl)amino)piperidin-1-yl)benzo[d]thiazol-5-yl)acrylamide;
(R)-N-(2-(3-((5-isopropyl-6-(1H-pyrazol-4-yl)-[1,2,4]triazolo[1,5-a]pyridin-2-yl)amino)piperidin-1-yl)-1-methyl-1H-benzo[d]imidazol-5-yl)acrylamide;
(R)-N-(2-(3-((5-methyl-6-(1H-pyrazol-4-yl)-[1,2,4]triazolo[1,5-a]pyridin-2-yl)amino)piperidin-1-yl)benzo[d]thiazol-5-yl)acrylamide;
(R)-N-(4-(3-((6-(1H-pyrazol-4-yl)-5-(trifluoromethyl)-[1,2,4]triazolo[1,5-a]pyridin-2-yl)amino)pyrrolidine-1-carbonyl)phenyl)acrylamide;
(R)-N-(4-(3-((7-(1H-pyrazol-4-yl)-[1,2,4]triazolo[1,5-a]pyridin-2-yl)amino)pyrrolidine-1-carbonyl)phenyl)-2-fluoroacrylamide;
(R)-2-fluoro-N-(4-(3-((8-methyl-7-(1H-pyrazol-4-yl)-[1,2,4]triazolo[1,5-a]pyridin-2-yl)amino)pyrrolidine-1-carbonyl)phenyl)acrylamide; and (R)-N-(4-(3-((8-methyl-7-(1H-pyrazol-4-yl)-[1,2,4]triazolo[1,5-a]pyridin-2-yl)amino)pyrrolidine-1-carbonyl)phenyl)but-2-ynamide;

or a pharmaceutically acceptable salt thereof.

52. The compound of claim 1, selected from:

N-(2-((1S,3R)-3-((6-(1H-pyrazol-4-yl)-5-(trifluoromethyl)-[1,2,4]triazolo[1,5-a]pyridin-2-yl)amino)cyclohexyl)-3-oxoisoindolin-5-yl)acrylamide;

(R)-N-(2-(3-((6-(1H-pyrazol-4-yl)-5-(trifluoromethyl)-[1,2,4]triazolo[1,5-a]pyridin-2-yl)amino)piperidin-1-yl)benzo[d]thiazol-5-yl)acrylamide;

(R)-N-(2-(3-((6-(1H-pyrazol-4-yl)-5-(trifluoromethyl)-[1,2,4]triazolo[1,5-a]pyridin-2-yl)amino)piperidin-1-yl)-1-methyl-1H-benzo[d]imidazol-5-yl)acrylamide;

(R)-N-(6-(3-((5-isopropyl-6-(1H-pyrazol-4-yl)-[1,2,4]triazolo[1,5-a]pyridin-2-yl)amino)piperidin-1-yl)-5-methylpyridin-3-yl)acrylamide; and (R)-N-(6-(3-((6-(1H-pyrazol-4-yl)-5-(trifluoromethyl)-[1,2,4]triazolo[1,5-a]pyridin-2-yl)amino)piperidin-1-yl)-5-methylpyridin-3-yl)acrylamide;

or a pharmaceutically acceptable salt thereof.

53. A pharmaceutical composition comprising the compound of claim 1, or a pharmaceutically acceptable salt thereof, and a pharmaceutically acceptable carrier.

54. A method of inhibiting CDK12, comprising contacting the CDK12 with the compound of claim 1, or a pharmaceutically acceptable salt thereof.

55. A method of inhibiting CDK12 in a patient, comprising administering to the patient the compound of claim 1, or a pharmaceutically acceptable salt thereof.

56. A method of treating a disease or disorder associated with CDK12 in a patient, comprising administering to the patient a therapeutically effective amount of the compound of claim 1, or pharmaceutically acceptable salt thereof.

57. The method of claim 56, wherein the disease or disorder is cancer.

58. The method of claim 56, wherein the disease or disorder is a cancer which has been previously identified as homologous recombination deficiency (HRD) high.

59. The method of claim 57, wherein the cancer is ovarian cancer, breast cancer, Ewing's sarcoma, osteosarcoma, liver cancer, hepatocellular carcinoma, or colorectal cancer.

* * * * *

UNITED STATES PATENT AND TRADEMARK OFFICE
CERTIFICATE OF CORRECTION

PATENT NO. : 12,084,453 B2
APPLICATION NO. : 18/064173
DATED : September 10, 2024
INVENTOR(S) : Minh Nguyen et al.

It is certified that error appears in the above-identified patent and that said Letters Patent is hereby corrected as shown below:

In the Claims

Column 166, Line 41: In Claim 1, delete "-L-S(O)$_2$(N$^9$)—," and insert -- -L-S(O)$_2$(NR$^9$)—, --.

Column 166, Line 49: In Claim 1, delete "L-S—," and insert -- -L-S—, or --.

Column 166, Line 65: In Claim 1, delete "LU" and insert -- L$^x$ --.

Column 166, Line 62: In Claim 1, delete "independently is" and insert -- independently --.

Column 166, Line 65: In Claim 1, delete "independently is" and insert -- independently --.

Column 167, Line 1: In Claim 1, delete "independently is" and insert -- is independently --.

Column 167, Line 9: In Claim 1, delete "HD," and insert -- H, D, --.

Column 167, Line 16: In Claim 1, delete "OC(O)R$^{bB}$," and insert -- OC(O)R$^{b8}$, --.

Column 167, Line 17: In Claim 1, after "NR$^{c8}$R$^{d8}$" insert -- , --.

Column 167, Line 17: In Claim 1, after "NR$^{c8}$NR$^{c8}$R$^{d8}$" insert -- , --.

Column 167, Line 17: In Claim 1, after "NR$^{c8}$C(O)R$^{b8}$" insert -- , --.

Column 167, Line 18: In Claim 1, after "NR$^{c8}$C(O)OR$^{a8}$" insert -- , --.

Column 167, Line 19: In Claim 1, delete "C(=NR$^{e8}$)R$^{c8}$R$^{d8}$" and insert -- C(=NR$^{e8}$)NR$^{c8}$R$^{d8}$ , --.

Column 167, Line 19: In Claim 1, after "NR$^{c8}$C(=NR$^{e8}$)NR$^{c8}$R$^{d8}$" insert -- , --.

Signed and Sealed this
Eleventh Day of February, 2025

Coke Morgan Stewart
*Acting Director of the United States Patent and Trademark Office*

Column 167, Line 20: In Claim 1, after "$NR^{c8}S(O)NR^{c8}R^{d8}$" insert -- , --.

Column 168, Line 28: In Claim 1, delete "substitutents;" and insert -- substituents; --.

Column 168, Line 61: In Claim 1, after "$NR^{c9}R^{d9}$" insert -- , --.

Column 168, Line 62: In Claim 1, after "$NR^{c9}C(O)OR^{a9}$" insert -- , --.

Column 168, Line 63: In Claim 1, after "$C(=NR^{e9})NR^{c9}R^{d9}$" insert -- , --.

Column 168, Line 64: In Claim 1, after "$NR^{c9}C(=NR^{e9})R^{b9}$" insert -- , --.

Column 168, Line 64: In Claim 1, after "$NR^{c9}S(O)NR^{c9}R^{d9}$" insert -- , --.

Column 168, Line 66: In Claim 1, after "$NR^{c9}S(O)_2NR^{c9}R^{d9}$" insert -- , --.

Column 169, Line 53: In Claim 1, after "$OC(O)NR^{c91}R^{d91}$" insert -- , --.

Column 169, Line 53: In Claim 1, after "$NR^{c91}R^{d91}$" insert -- , --.

Column 169, Lines 61-62: In Claim 1, delete "$OP(O)(ORh^{91})(OR^{i91})$," and insert -- $OP(O)(OR^{h91})(OR^{i91})$, --.

Column 170, Line 65: In Claim 1, after "$NR^{c92}R^{d92}$" insert -- , --.

Column 171, Line 4: In Claim 1, delete "$S(O)—NR^{c92}R^{d92}$," and insert -- $S(O)NR^{c92}R^{d92}$, --.

Column 172, Lines 11-12: In Claim 1, delete "$NR^{c1}(O)R^{b1}$," and insert -- $NR^{c1}C(O)R^{b1}$, --.

Column 172, Line 14: In Claim 1, delete "$NR^{c1}(O)NR^{c1}R^{d1}$," and insert -- $NR^{c1}C(O)NR^{c1}R^{d1}$, --.

Column 173, Lines 32-33: In Claim 1, delete "$NR^{c11}S(O)_2NR^{c11}R^{d11}$," and insert -- $NR^{c11}S(O)_2NR^{c11}R^{d11}$, --.

Column 173, Line 43: In Claim 1, delete "$R^1$" and insert -- $R^{1B}$ --.

Column 173, Line 56: In Claim 1, delete "$R^1$" and insert -- $R^{1B}$ --.

Column 174, Line 3: In Claim 1, delete "$R^1$" and insert -- $R^{1B}$ --.

Column 174, Line 39: In Claim 1, after "$OC(O)NR^{c12}R^{d12}$" insert -- , --.

Column 174, Line 39: In Claim 1, after "$NR^{c12}R^{d12}$" insert -- , --.

Column 174, Line 39: In Claim 1, after "$NR^{c12}NR^{c12}R^{d12}$" insert -- , --.

CERTIFICATE OF CORRECTION (continued)
U.S. Pat. No. 12,084,453 B2

Column 174, Line 40: In Claim 1, after "$NR^{c12}C(O)R^{b12}$" insert -- , --.

Column 174, Line 42: In Claim 1, after "$NR^{c12}C(=NR^{e12})NR^{c12}R^{d12}$" insert -- , --.

Column 174, Line 45: In Claim 1, after "$S(O)NR^{c12}R^{d12}$" insert -- , --.

Column 175, Line 53: In Claim 1, delete "$C_{1-4}$alkylsulfonylamino," and insert -- $C_{1-4}$ alkylsulfonylamino, --.

Column 176, Line 5: In Claim 1, after "$NR^{c4}R^{d4}$" insert -- , --.

Column 176, Line 6: In Claim 1, after "$NR^{c4}NR^{c4}R^{d4}$" insert -- , --.

Column 176, Line 7: In Claim 1, after "$C(=NR^{e4})NR^{c4}R^{d4}$" insert -- , --.

Column 176, Line 8: In Claim 1, after "$NR^{c4}C(=NR^{e4})NR^{c4}R^{d4}$" insert -- , --.

Column 176, Line 9: In Claim 1, after "$NR^{c4}S(O)NR^{c4}R^{d4}$" insert -- , --.

Column 177, Line 21: In Claim 1, after "$OC(O)NR^{c41}R^{d41}$" insert -- , --.

Column 177, Line 21: In Claim 1, after "$NR^{c41}R^{d41}$" insert -- , --.

Column 177, Line 22: In Claim 1, after "$NR^{c41}C(O)R^{b41}$" insert -- , --.

Column 177, Line 25: In Claim 1, after "$NR^{c41}S(O)NR^{c41}R^{d41}$" insert -- , --.

Column 177, Line 27: In Claim 1, after "$S(O)NR^{c41}R^{d41}$" insert -- , --.

Column 177, Line 66: In Claim 1, delete "$R^{c41}$" and insert -- $R^{e41}$ --.

Column 178, Line 34: In Claim 1, after "$OC(O)NR^{c42}R^{d42}$" insert -- , --.

Column 178, Line 34: In Claim 1, after "$NR^{c42}R^{d42}$" insert -- , --.

Column 178, Line 37: In Claim 1, after "$NR^{c42}C(=NR^{e42})NR^{c42}R^{d42}$" insert -- , --.

Column 178, Line 38: In Claim 1, after "$NR^{c42}S(O)NR^{c42}R^{d42}$" insert -- , --.

Column 179, Line 45: In Claim 1, after "$SR^{a5}$" insert -- , --.

Column 179, Line 47: In Claim 1, after "$NR^{c5}R^{d5}$" insert -- , --.

Column 179, Line 47: In Claim 1, after "$NR^{c5}NR^{c5}R^{d5}$" insert -- , --.

Column 179, Line 49: In Claim 1, after "$C(=NR^{e5})NR^{c5}R^{d5}$" insert -- , --.

Column 179, Lines 49-50: In Claim 1, delete "$NR^{5C}(=NR^{e5})NR^{c5}R^{d5}$" and insert -- $NR^{c5}C(=NR^{e5})NR^{c5}R^{d5}$, --.

Column 179, Line 50: In Claim 1, after "$NR^{c5}S(O)NR^{c5}R^{d5}$" insert -- , --.

Column 180, Line 31: In Claim 1, delete "aryl-$C_{14}$" and insert -- aryl-$C_{1-4}$ --.

Column 180, Line 60: In Claim 1, after "$SR^{a51}$" insert -- , --.

Column 180, Line 63: In Claim 1, after "$NR^{c51}C(O)R^{b51}$" insert -- , --.

Column 180, Line 66: In Claim 1, after "$NR^{c51}C(=NR^{e51})R^{b51}$" insert -- , --.

Column 180, Line 67: In Claim 1, after "$NR^{c51}S(O)_2R^{b51}$" insert -- , --.

Column 180, Line 67: In Claim 1, after "$NR^{c51}S(O)(=NR^{e51})R^{b51}$" insert -- , --.

Column 181, Line 2: In Claim 1, after "$OS(O)(=NR^{e51})R^{b51}$" insert -- , --.

Column 181, Line 4: In Claim 1, delete "$P(O)(OR^{h51})(OR^{j51})$," and insert -- $P(O)(OR^{h51})(OR^{i51})$, --.

Column 181, Line 55: In Claim 1, delete "heteroaryl-$C_{14}$" and insert -- heteroaryl-$C_{1-4}$ --.

Column 182, Line 17 (approx.): In Claim 1, after "$NR^{c52}S(O)R^{b52}$" insert -- , --.

Column 183, Line 27: In Claim 1, delete "$NR^{c53}C(OR^{b53}$," and insert -- $NR^{c53}C(O)R^{b53}$, --.

Column 183, Lines 27-28: In Claim 1, delete "$NR^{c53}C(O)NR^{c53}R^{d53}$," and insert -- $NR^{c53}C(O)NR^{c53}R^{d53}$, --.

Column 185, Line 42: In Claim 4, after "$NR^{c1}C(O)R^{b1}$" insert -- , --.

Column 186, Line 18: In Claim 5, delete "$C_1$-6" and insert -- $C_{1-6}$ --.

Column 187, Line 13: In Claim 15, delete "Bis" and insert -- B is --.

Column 187, Line 45: In Claim 22, after "$NR^{c4}S(O)_2NR^{c4}R^{d4}$" insert -- , --.

Column 188, Line 11: In Claim 22, after "$OC(O)NR^{c41}R^{d41}$" insert -- , --.

Column 188, Line 11: In Claim 22, after "$NR^{c41}R^{d41}$" insert -- , --.

Column 188, Line 12: In Claim 22, after "$NR^{c41}NR^{c41}R^{d41}$" insert -- , --.

Column 188, Line 12: In Claim 22, after "$NR^{c41}C(O)R^{b41}$" insert -- , --.

CERTIFICATE OF CORRECTION (continued)
U.S. Pat. No. 12,084,453 B2

Column 188, Line 13: In Claim 22, after "$NR^{c41}C(O)NR^{c41}R^{d41}$" insert -- , --.

Column 188, Line 13: In Claim 22, after "$NR^{c41}S(O)NR^{c41}R^{d41}$" insert -- , --.

Column 188, Line 24: In Claim 22, delete "$R^{c4}$," and insert -- $R^{c41}$, --.

Column 188, Line 39: In Claim 23, after "$OC(O)NR^{c4}R^{d4}$" insert -- , --.

Column 188, Line 39: In Claim 23, after "$NR^{c4}R^{d4}$" insert -- , --.

Column 188, Line 39: In Claim 23, after "$NR^{c4}NR^{c4}R^{d4}$" insert -- , --.

Column 188, Line 40: In Claim 23, after "$NR^{c4}C(O)NR^{c4}R^{d4}$" insert -- , --.

Column 188, Line 40: In Claim 23, after "$NR^{c4}S(O)NR^{c4}R^{d4}$" insert -- , --.

Column 188, Line 41: In Claim 23, after "$NR^{c4}S(O)R^{b4}$" insert -- , --.

Column 188, Line 41: In Claim 23, after "$NR^{c4}S(O)_2NR^{c4}R^{d4}$" insert -- , --.

Column 189, Line 1: In Claim 27, after "$OC(O)NR^{c5}R^{d5}$" insert -- , --.

Column 189, Line 3: In Claim 27, after "$NR^{c5}C(O)NR^{c5}R^{d5}$" insert -- , --.

Column 189, Line 3: In Claim 27, after "$NR^{c5}S(O)NR^{c5}R^{d5}$" insert -- , --.

Column 190, Line 40: In Claim 29, delete "$C_2$-3" and insert -- $C_{2-3}$ --.

Column 191, Line 30: In Claim 35, delete "independently." and insert -- independently: --.

Column 193, Line 11 (approx.): In Claim 46, delete "is;" and insert -- is --.

Column 195, Line 14: In Claim 46, above "each L is" insert -- or $L^1$-Ar --.

Column 195, Line 15: In Claim 46, delete "L" and insert -- $L^1$ --.

Column 195, Line 25: In Claim 46, delete "-L-S(O)$_2$N$^9$—," and insert -- -L-S(O)$_2$(NR$^9$)—, --.

Column 195, Line 33: In Claim 46, delete "L-S—," and insert -- -L-S—, --.

Column 195, Line 38: In Claim 46, delete "-L-S(O)$_2$-L-," and insert -- -L-S(O)$_2$-L$^x$-, --.

Column 195, Line 48: In Claim 46, delete "LU" and insert -- $L^x$ --.

Column 195, Line 51: In Claim 46, delete "0 or NR$^9$;" and insert -- O or NR$^9$; --.

CERTIFICATE OF CORRECTION (continued)
U.S. Pat. No. 12,084,453 B2

Column 197, Line 15: In Claim 46, delete "S(O)NRc11Rb11," and insert -- S(O)NR$^{c11}$R$^{d11}$, --.

Column 197, Line 16: In Claim 46, delete "S(O)$_2$NR$^{c11}$R$^{b11}$, ," and insert -- S(O)$_2$NR$^{c11}$R$^{d11}$, --.

Column 197, Line 22: In Claim 46, delete "R$^1$" and insert -- R$^{1B}$ --.

Column 197, Line 36: In Claim 46, delete "R$^1$" and insert -- R$^{1B}$ --.

Column 198, Line 51: In Claim 46, after "NR$^{c4}$R$^{d4}$" insert -- , --.

Column 200, Line 58: In Claim 46, after "SR$^{a5}$" insert -- , --.

Column 201, Line 42: In Claim 46, delete "OR$^{a1}$," and insert -- OR$^{a51}$, --.

Column 201, Line 42: In Claim 46, delete "SR$^{a1}$," and insert -- SR$^{a51}$, --.

Column 201, Line 43: In Claim 46, delete "NHOR$^{a5}$," and insert -- NHOR$^{a51}$, --.

Column 201, Line 43: In Claim 46, delete "C(O)OR$^{a5}$," and insert -- C(O)OR$^{a51}$,--.

Column 201, Line 45: In Claim 46, delete "NR$^{c51}$C(O)OR$^{a5}$," and insert -- NR$^{c51}$C(O)OR$^{a51}$,--.

Column 202, Line 52: In Claim 46, delete "R$^{e52}$" and insert -- R$^{c52}$ --.

Column 206, Line 52: In Claim 47, delete "-L-S(O)$_2$(N$^9$)—," and insert -- -L-S(O)$_2$(NR$^9$)—, --.

Column 206, Line 60: In Claim 47, delete "L-S—," and insert -- -L-S—, --.

Column 206, Line 67: In Claim 47, delete "-L-OS(O)$_2$L-," and insert -- -L-OS(O)$_2$L$^x$-, --.

Column 207, Line 11: In Claim 47, delete "0 or NR$^9$;" and insert -- O or NR$^9$; --.

Column 208, Line 43: In Claim 47, delete "S(O)NR$^{c11}$R$^{b11}$," and insert -- S(O)NR$^{c11}$R$^{d11}$, --.

Column 208, Line 44: In Claim 47, delete "S(O)$_2$NR$^{c11}$R$^{b11}$," and insert -- S(O)$_2$NR$^{c11}$R$^{d11}$, --.

Column 208, Line 50: In Claim 47, delete "R$^1$" and insert -- R$^{1B}$ --.

Column 208, Line 64: In Claim 47, delete "R$^1$" and insert -- R$^{1B}$ --.

Column 209, Lines 19-20: In Claim 47, delete "C(O)NR$^{c11}$R$^{d12}$," and insert -- C(O)NR$^{c12}$R$^{d12}$, --.

Column 209, Line 21: In Claim 47, delete "R$^{c12}$R$^{d12}$," and insert -- NR$^{c12}$R$^{d12}$, --.

CERTIFICATE OF CORRECTION (continued)

Column 211, Lines 57-63 (approx.): In Claim 48, delete " 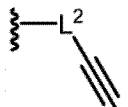 ," and insert 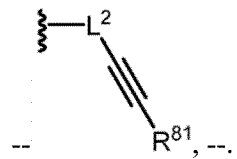 --.

Column 212, Line 27: In Claim 48, delete "$C_1$-6" and insert -- $C_{1-6}$ --.

Column 212, Line 46: In Claim 48, delete "$R_1$" and insert -- $R_{1B}$ --.